US012708440B2

(12) United States Patent
Mayse et al.

(10) Patent No.: US 12,708,440 B2
(45) Date of Patent: Aug. 18, 2026

(54) COMPACT DELIVERY PULMONARY TREATMENT SYSTEMS AND METHODS FOR IMPROVING PULMONARY FUNCTION

(71) Applicant: Nuvaira, Inc., Plymouth, MN (US)

(72) Inventors: Martin L. Mayse, Wayzata, MN (US); Steven Dimmer, Bellevue, WA (US); Mark Deem, Mountain View, CA (US); John Streeter, Redmond, WA (US); Ryan Kaveckis, Minneapolis, MN (US); Edward S. Harshman, Kirkland, WA (US)

(73) Assignee: Nuvaira, Inc., Minneapolis, MN (US)

(*) Notice: Subject to any disclaimer, the term of this patent is extended or adjusted under 35 U.S.C. 154(b) by 346 days.

(21) Appl. No.: 16/260,871

(22) Filed: Jan. 29, 2019

(65) Prior Publication Data

US 2019/0151018 A1 May 23, 2019

Related U.S. Application Data

(63) Continuation of application No. 13/894,920, filed on May 15, 2013, now abandoned.

(Continued)

(51) Int. Cl.

*A61B 18/14* (2006.01)
*A61B 18/00* (2006.01)

(Continued)

(52) U.S. Cl.

CPC ...... *A61B 18/1815* (2013.01); *A61B 18/1492* (2013.01); *A61N 7/022* (2013.01);

(Continued)

(58) Field of Classification Search

CPC .......... A61N 1/403; A61N 1/06; A61B 18/04; A61B 18/12; A61B 18/1492; A61B 18/18;

(Continued)

(56) References Cited

U.S. PATENT DOCUMENTS

| | | | |
|---|---|---|---|
| 612,724 | A | 10/1898 | Hamilton |
| 1,155,169 | A | 9/1915 | Starkweather |

(Continued)

FOREIGN PATENT DOCUMENTS

| | | | |
|---|---|---|---|
| CA | 2419228 | A1 | 8/2004 |
| CN | 1700880 | A | 11/2005 |

(Continued)

OTHER PUBLICATIONS

Abbott., "Present Concepts Relative to Autonomic Nerve Surgery in the Treatment of Pulmonary Disease," American Journal of Surgery, 1955, vol. 90, pp. 479-489.

(Continued)

*Primary Examiner* — Joseph A Stoklosa
*Assistant Examiner* — Adam J Avigan
(74) *Attorney, Agent, or Firm* — Merchant & Gould P.C.

(57) ABSTRACT

A pulmonary treatment system includes a compact configuration for delivery to a first airway of a patient. An energy delivery system of the pulmonary treatment system delivers energy to target tissue in or along an airway wall of the first airway to reduce airway resistance in a second airway distal to the first airway. The pulmonary treatment system protects tissue in the airway wall of the first airway located between the target tissue and the energy delivery system by at least one of thermodynamically cooling, circulating a liquid coolant through the pulmonary treatment system, and shielding a portion of the energy delivery system.

13 Claims, 42 Drawing Sheets

Related U.S. Application Data

(60) Provisional application No. 61/786,203, filed on Mar. 14, 2013, provisional application No. 61/649,154, filed on May 18, 2012.

(51) Int. Cl.
*A61B 18/18* (2006.01)
*A61N 7/02* (2006.01)

(52) U.S. Cl.
CPC .............. *A61B 2018/00017* (2013.01); *A61B 2018/00083* (2013.01); *A61B 2018/00095* (2013.01); *A61B 2018/0022* (2013.01); *A61B 2018/00267* (2013.01); *A61B 2018/00541* (2013.01)

(58) Field of Classification Search
CPC ...... A61B 18/1815; A61B 2018/00214; A61B 2018/0022; A61B 2018/00541; A61B 2018/00577; A61B 2018/0005; A61B 2018/00011; A61B 2018/0023; A61B 2018/00434
See application file for complete search history.

(56) References Cited

U.S. PATENT DOCUMENTS 1,207,479 A 12/1916 Bisgaard
1,216,183 A 2/1917 Swingle
1,695,107 A 12/1928 Kahl
2,072,346 A 3/1937 Smith
2,279,714 A 4/1942 Meyerhof et al.
3,320,957 A 5/1967 Sokolik
3,568,659 A 3/1971 Karnegis
3,667,476 A 6/1972 Muller
3,692,029 A 9/1972 Adair
3,918,449 A 11/1975 Pistor
3,946,745 A 3/1976 Hsiang-Lai et al.
3,949,743 A 4/1976 Shanbrom
3,995,617 A 12/1976 Watkins et al.
4,078,864 A 3/1978 Howell
4,095,602 A 6/1978 Leveen
4,116,589 A 9/1978 Rishton
4,129,129 A 12/1978 Amrine
4,154,246 A 5/1979 LeVeen
4,277,168 A 7/1981 Oku
4,305,402 A 12/1981 Katims
4,351,330 A 9/1982 Scarberry
4,461,283 A 7/1984 Doi
4,502,490 A 3/1985 Evans et al.
4,503,855 A 3/1985 Maslanka
4,503,863 A 3/1985 Katims
4,512,762 A 4/1985 Spears
4,522,212 A 6/1985 Gelinas et al.
4,557,272 A 12/1985 Carr
4,565,200 A 1/1986 Cosman
4,567,882 A 2/1986 Heller
4,573,481 A 3/1986 Bullara
4,584,998 A 4/1986 McGrail
4,612,934 A 9/1986 Borkan
4,621,642 A 11/1986 Chen
4,621,882 A 11/1986 Krumme
4,625,712 A 12/1986 Wampler
4,643,186 A 2/1987 Rosen et al.
4,646,737 A 3/1987 Hussein et al.
4,649,924 A 3/1987 Taccardi
4,649,935 A 3/1987 Charmillot et al.
4,658,836 A 4/1987 Turner
4,674,497 A 6/1987 Ogasawara
4,683,890 A 8/1987 Hewson
4,704,121 A 11/1987 Moise
4,706,688 A 11/1987 Don Michael et al.
4,709,698 A 12/1987 Johnston et al.
4,739,759 A 4/1988 Rexroth et al.
4,754,065 A 6/1988 Levenson et al.
4,754,752 A 7/1988 Ginsburg et al.
4,765,322 A 8/1988 Charmillot et al.
4,765,959 A 8/1988 Fukasawa
4,767,402 A 8/1988 Kost et al.
4,772,112 A 9/1988 Zider et al.
4,773,899 A 9/1988 Spears
4,779,614 A 10/1988 Moise
4,784,135 A 11/1988 Blum et al.
4,790,305 A 12/1988 Zoltan et al.
4,799,479 A 1/1989 Spears
4,802,492 A 2/1989 Grunstein
4,808,164 A 2/1989 Hess
4,817,586 A 4/1989 Wampler
4,825,871 A 5/1989 Cansell
4,827,935 A 5/1989 Geddes et al.
4,846,152 A 7/1989 Wampler et al.
4,862,886 A 9/1989 Clarke et al.
4,881,542 A 11/1989 Schmidt et al.
4,895,557 A 1/1990 Moise et al.
4,902,129 A 2/1990 Siegmund et al.
4,904,472 A 2/1990 Belardinelli et al.
4,906,229 A 3/1990 Wampler
4,907,589 A 3/1990 Cosman
4,908,012 A 3/1990 Moise et al.
4,920,978 A 5/1990 Colvin
4,944,722 A 7/1990 Carriker et al.
4,945,910 A 8/1990 Budyko et al.
4,955,377 A 9/1990 Lennox et al.
4,967,765 A 11/1990 Turner et al.
4,969,865 A 11/1990 Hwang et al.
4,976,709 A 12/1990 Sand
4,976,710 A 12/1990 Mackin
4,985,014 A 1/1991 Orejola
4,989,604 A 2/1991 Fang
4,991,603 A 2/1991 Cohen et al.
4,992,474 A 2/1991 Skidmore et al.
5,005,559 A 4/1991 Blanco et al.
5,007,908 A 4/1991 Rydell
5,009,636 A 4/1991 Wortley et al.
5,009,936 A 4/1991 Yamanaka et al.
5,010,892 A 4/1991 Colvin et al.
5,019,075 A 5/1991 Spears et al.
5,027,829 A 7/1991 Larsen
5,030,645 A 7/1991 Kollonitsch
5,036,848 A 8/1991 Hewson
5,053,033 A 10/1991 Clarke
5,054,486 A 10/1991 Yamada
5,056,519 A 10/1991 Vince
5,056,529 A 10/1991 De Groot
5,057,107 A 10/1991 Parins et al.
5,074,860 A 12/1991 Gregory et al.
5,078,716 A 1/1992 Doll
5,084,044 A 1/1992 Quint
5,096,916 A 3/1992 Skupin
5,100,388 A 3/1992 Behl et al.
5,100,423 A 3/1992 Fearnot
5,103,804 A 4/1992 Abele et al.
5,105,826 A 4/1992 Smits et al.
5,106,360 A 4/1992 Ishiwara et al.
5,107,830 A 4/1992 Younes
5,107,835 A 4/1992 Thomas
5,109,846 A 5/1992 Thomas
5,114,423 A 5/1992 Kasprzyk et al.
5,116,864 A 5/1992 March et al.
5,117,828 A 6/1992 Metzger et al.
5,123,413 A 6/1992 Hasegawa et al.
5,126,375 A 6/1992 Skidmore et al.
5,135,480 A 8/1992 Bannon et al.
5,135,517 A 8/1992 McCoy
5,139,029 A 8/1992 Fishman et al.
5,151,100 A 9/1992 Abele et al.
5,152,286 A 10/1992 Sitko et al.
5,158,536 A 10/1992 Sekins et al.
5,165,420 A 11/1992 Strickland
5,167,223 A 12/1992 Koros et al.
5,170,802 A 12/1992 Mehra
5,170,803 A 12/1992 Hewson et al.
5,174,288 A 12/1992 Bardy et al.
5,188,602 A 2/1993 Nichols

(56) References Cited

U.S. PATENT DOCUMENTS 5,190,540 A 3/1993 Lee
5,191,883 A 3/1993 Lennox et al.
5,213,576 A 5/1993 Abiuso et al.
5,215,103 A 6/1993 Desai
5,224,491 A 7/1993 Mehra
5,225,445 A 7/1993 Skidmore et al.
5,231,996 A 8/1993 Bardy et al.
5,232,444 A 8/1993 Just et al.
5,234,456 A 8/1993 Silvestrini
5,239,982 A 8/1993 Trauthen
5,254,088 A 10/1993 Lundquist et al.
5,255,678 A 10/1993 Deslauriers et al.
5,255,679 A 10/1993 Imran
5,265,604 A 11/1993 Vince
5,269,758 A 12/1993 Taheri
5,271,383 A 12/1993 Wilk
5,281,218 A 1/1994 Imran
5,286,254 A 2/1994 Shapland et al.
5,292,331 A 3/1994 Boneau
5,293,869 A 3/1994 Edwards et al.
5,309,910 A 5/1994 Edwards et al.
5,311,866 A 5/1994 Kagan et al.
5,313,943 A 5/1994 Houser et al.
5,324,255 A 6/1994 Passafaro et al.
5,324,284 A 6/1994 Imran
5,331,947 A 7/1994 Shturman
5,343,936 A 9/1994 Beatenbough et al.
5,344,398 A 9/1994 Hara
5,345,936 A 9/1994 Pomeranz et al.
5,348,554 A 9/1994 Imran et al.
5,366,443 A 11/1994 Eggers et al.
5,368,591 A 11/1994 Lennox et al.
5,370,644 A 12/1994 Langberg
5,370,675 A 12/1994 Edwards et al.
5,370,679 A 12/1994 Atlee, III
5,372,603 A 12/1994 Acker et al.
5,374,287 A 12/1994 Rubin
5,379,765 A 1/1995 Kajiwara et al.
5,383,917 A 1/1995 Desai et al.
5,393,207 A 2/1995 Maher et al.
5,394,880 A 3/1995 Atlee, III
5,396,887 A 3/1995 Imran
5,400,778 A 3/1995 Jonson et al.
5,400,783 A 3/1995 Pomeranz et al.
5,405,362 A 4/1995 Kramer et al.
5,405,366 A 4/1995 Fox et al.
5,409,483 A 4/1995 Campbell et al.
5,409,710 A 4/1995 Leonard
5,411,025 A 5/1995 Webster, Jr.
5,415,166 A 5/1995 Imran
5,415,656 A 5/1995 Tihon et al.
5,417,687 A 5/1995 Nardella et al.
5,422,362 A 6/1995 Vincent et al.
5,423,744 A 6/1995 Gencheff et al.
5,423,811 A 6/1995 Imran et al.
5,425,023 A 6/1995 Haraguchi et al.
5,425,703 A 6/1995 Feiring
5,425,811 A 6/1995 Mashita
5,431,696 A 7/1995 Atlee, III
5,433,730 A 7/1995 Alt
5,437,665 A 8/1995 Munro
5,443,470 A 8/1995 Stern et al.
5,454,782 A 10/1995 Perkins
5,454,840 A 10/1995 Krakovsky et al.
5,456,667 A 10/1995 Ham et al.
5,458,596 A 10/1995 Lax et al.
5,465,717 A 11/1995 Imran et al.
5,470,352 A 11/1995 Rappaport
5,471,982 A 12/1995 Edwards et al.
5,474,530 A 12/1995 Passafaro et al.
5,478,309 A 12/1995 Sweezer et al.
5,478,578 A 12/1995 Arnold et al.
5,496,271 A 3/1996 Burton et al.
5,496,304 A 3/1996 Chasan
5,496,311 A 3/1996 Abele et al.
5,496,312 A 3/1996 Klicek
5,500,011 A 3/1996 Desai
5,505,728 A 4/1996 Ellman et al.
5,505,730 A 4/1996 Edwards
5,507,791 A 4/1996 Sit'ko
5,509,419 A 4/1996 Edwards et al.
5,522,862 A 6/1996 Testerman et al.
5,531,779 A 7/1996 Dahl et al.
5,540,681 A 7/1996 Strul et al.
5,540,730 A 7/1996 Terry, Jr. et al.
5,545,161 A 8/1996 Imran
5,545,193 A 8/1996 Fleischman et al.
5,547,469 A 8/1996 Rowland et al.
5,549,559 A 8/1996 Eshel
5,549,655 A 8/1996 Erickson
5,549,661 A 8/1996 Kordis et al.
RE35,330 E 9/1996 Malone et al.
5,553,611 A 9/1996 Budd et al.
5,558,073 A 9/1996 Pomeranz et al.
5,562,608 A 10/1996 Sekins et al.
5,571,074 A 11/1996 Buckman, Jr. et al.
5,571,088 A 11/1996 Lennox et al.
5,574,059 A 11/1996 Regunathan et al.
5,578,072 A 11/1996 Barone et al.
5,582,609 A 12/1996 Swanson et al.
5,588,432 A 12/1996 Crowley
5,588,812 A 12/1996 Taylor et al.
5,595,183 A 1/1997 Swanson et al.
5,598,848 A 2/1997 Swanson et al.
5,599,345 A 2/1997 Edwards et al.
5,601,088 A 2/1997 Swanson et al.
5,605,157 A 2/1997 Panescu et al.
5,607,419 A 3/1997 Amplatz et al.
5,607,462 A 3/1997 Imran
5,620,438 A 4/1997 Amplatz et al.
5,620,463 A 4/1997 Drolet
5,623,940 A 4/1997 Daikuzono
5,624,392 A 4/1997 Saab
5,624,439 A 4/1997 Edwards et al.
5,626,618 A 5/1997 Ward et al.
5,630,425 A 5/1997 Panescu et al.
5,630,794 A 5/1997 Lax et al.
5,630,813 A 5/1997 Kieturakis
5,634,471 A 6/1997 Fairfax et al.
5,641,326 A 6/1997 Adams
5,647,870 A 7/1997 Kordis et al.
5,658,278 A 8/1997 Imran et al.
5,658,322 A 8/1997 Fleming
5,658,549 A 8/1997 Akehurst et al.
5,660,175 A 8/1997 Dayal
5,662,108 A 9/1997 Budd et al.
5,669,930 A 9/1997 Igarashi
5,669,932 A 9/1997 Fischell et al.
5,674,472 A 10/1997 Akehurst et al.
5,678,535 A 10/1997 DiMarco
5,680,860 A 10/1997 Imran
5,681,280 A 10/1997 Rusk et al.
5,681,308 A 10/1997 Edwards et al.
5,687,723 A 11/1997 Avitall
5,688,267 A 11/1997 Panescu et al.
5,690,692 A 11/1997 Fleming
5,693,078 A 12/1997 Desai et al.
5,694,934 A 12/1997 Edelman
5,695,471 A 12/1997 Wampler
5,699,799 A 12/1997 Xu et al.
5,702,386 A 12/1997 Stern et al.
5,707,218 A 1/1998 Maher et al.
5,707,336 A 1/1998 Rubin
5,707,352 A 1/1998 Sekins et al.
5,707,400 A 1/1998 Terry, Jr. et al.
5,722,401 A 3/1998 Pietroski et al.
5,722,403 A 3/1998 Mcgee et al.
5,722,416 A 3/1998 Swanson et al.
5,725,525 A 3/1998 Kordis
5,727,569 A 3/1998 Benetti et al.
5,728,094 A 3/1998 Edwards
5,730,128 A 3/1998 Pomeranz et al.
5,730,704 A 3/1998 Avitall
5,730,726 A 3/1998 Klingenstein

(56) References Cited

U.S. PATENT DOCUMENTS 5,730,741 A 3/1998 Horzewski et al.
5,733,316 A 3/1998 Tierney et al.
5,733,319 A 3/1998 Neilson et al.
5,735,846 A 4/1998 Panescu et al.
5,740,808 A 4/1998 Panescu et al.
5,741,248 A 4/1998 Stern et al.
5,746,224 A 5/1998 Edwards
5,752,518 A 5/1998 Mcgee et al.
5,755,714 A 5/1998 Murphy-Chutorian
5,755,753 A 5/1998 Knowlton
5,759,158 A 6/1998 Swanson
5,765,568 A 6/1998 Sweezer, Jr. et al.
5,766,605 A 6/1998 Sanders et al.
5,769,846 A 6/1998 Edwards et al.
5,772,590 A 6/1998 Webster, Jr.
5,779,669 A 7/1998 Haissaguerre et al.
5,779,698 A 7/1998 Clayman et al.
5,782,239 A 7/1998 Webster, Jr.
5,782,797 A 7/1998 Schweich, Jr. et al.
5,782,827 A 7/1998 Gough et al.
5,782,848 A 7/1998 Lennox
5,782,899 A 7/1998 Imran
5,792,064 A 8/1998 Panescu et al.
5,795,303 A 8/1998 Swanson et al.
5,800,375 A 9/1998 Sweezer et al.
5,800,486 A 9/1998 Thome et al.
5,807,306 A 9/1998 Shapland et al.
5,810,757 A 9/1998 Sweezer, Jr. et al.
5,810,807 A 9/1998 Ganz et al.
5,814,078 A 9/1998 Zhou et al.
5,817,028 A 10/1998 Anderson
5,817,073 A 10/1998 Krespi
5,820,554 A 10/1998 Davis et al.
5,820,589 A 10/1998 Torgerson et al.
5,823,189 A 10/1998 Kordis
5,827,277 A 10/1998 Edwards
5,833,651 A 11/1998 Donovan et al.
5,836,874 A 11/1998 Swanson et al.
5,836,905 A 11/1998 Lemelson et al.
5,836,947 A 11/1998 Fleischman et al.
5,837,001 A 11/1998 Mackey
5,843,075 A 12/1998 Taylor
5,843,077 A 12/1998 Edwards
5,843,088 A 12/1998 Barra et al.
5,846,238 A 12/1998 Jackson et al.
5,848,969 A 12/1998 Panescu et al.
5,848,972 A 12/1998 Triedman et al.
5,849,026 A 12/1998 Zhou et al.
5,855,577 A 1/1999 Murphy-Chutorian et al.
5,860,974 A 1/1999 Abele
5,863,291 A 1/1999 Schaer
5,865,791 A 2/1999 Whayne et al.
5,868,740 A 2/1999 LeVeen et al.
5,871,443 A 2/1999 Edwards et al.
5,871,483 A 2/1999 Jackson et al.
5,871,523 A 2/1999 Fleischman et al.
5,873,852 A 2/1999 Vigil et al.
5,873,865 A 2/1999 Horzewski et al.
5,876,340 A 3/1999 Tu et al.
5,876,399 A 3/1999 Chia et al.
5,881,727 A 3/1999 Edwards
5,882,346 A 3/1999 Pomeranz et al.
5,891,027 A 4/1999 Tu et al.
5,891,135 A 4/1999 Jackson et al.
5,891,136 A 4/1999 Mcgee et al.
5,891,138 A 4/1999 Tu et al.
5,891,182 A 4/1999 Fleming
5,893,847 A 4/1999 Kordis
5,893,887 A 4/1999 Jayaraman
5,897,554 A 4/1999 Chia et al.
5,899,882 A 5/1999 Waksman et al.
5,902,268 A 5/1999 Saab
5,904,651 A 5/1999 Swanson et al.
5,904,711 A 5/1999 Flom et al.
5,906,636 A 5/1999 Casscells, III et al.
5,908,445 A 6/1999 Whayne et al.
5,908,446 A 6/1999 Imran
5,908,839 A 6/1999 Levitt et al.
5,911,218 A 6/1999 DiMarco
5,916,235 A 6/1999 Guglielmi
5,919,147 A 7/1999 Jain
5,919,172 A 7/1999 Golba, Jr.
5,924,424 A 7/1999 Stevens et al.
5,928,228 A 7/1999 Kordis et al.
5,931,806 A 8/1999 Shimada
5,931,835 A 8/1999 Mackey
5,935,079 A 8/1999 Swanson et al.
5,941,869 A 8/1999 Patterson et al.
5,951,494 A 9/1999 Wang et al.
5,951,546 A 9/1999 Lorentzen
5,954,661 A 9/1999 Greenspon et al.
5,954,662 A 9/1999 Swanson et al.
5,954,717 A 9/1999 Behl et al.
5,956,501 A 9/1999 Brown
5,957,919 A 9/1999 Laufer
5,957,961 A 9/1999 Maguire et al.
5,964,223 A 10/1999 Baran
5,964,753 A 10/1999 Edwards
5,964,796 A 10/1999 Imran
5,971,983 A 10/1999 Lesh
5,972,026 A 10/1999 Laufer et al.
5,976,175 A 11/1999 Hirano et al.
5,976,709 A 11/1999 Kageyama et al.
5,979,456 A 11/1999 Magovern
5,980,563 A 11/1999 Tu et al.
5,984,917 A 11/1999 Fleischman et al.
5,984,971 A 11/1999 Faccioli et al.
5,989,545 A 11/1999 Foster et al.
5,991,650 A 11/1999 Swanson et al.
5,992,419 A 11/1999 Sterzer et al.
5,993,462 A 11/1999 Pomeranz et al.
5,995,873 A 11/1999 Rhodes
5,997,534 A 12/1999 Tu et al.
5,999,855 A 12/1999 DiMarco
6,001,054 A 12/1999 Regulla et al.
6,003,517 A 12/1999 Sheffield et al.
6,004,269 A 12/1999 Crowley et al.
6,006,134 A 12/1999 Hill et al.
6,006,755 A 12/1999 Edwards
6,008,211 A 12/1999 Robinson et al.
6,009,877 A 1/2000 Edwards
6,010,500 A 1/2000 Sherman et al.
6,012,457 A 1/2000 Lesh
6,014,579 A 1/2000 Pomeranz et al.
6,016,437 A 1/2000 Tu et al.
6,023,638 A 2/2000 Swanson
6,024,740 A 2/2000 Lesh et al.
6,029,091 A 2/2000 De La Rama et al.
6,033,397 A 3/2000 Laufer et al.
6,036,687 A 3/2000 Laufer et al.
6,036,689 A 3/2000 Tu et al.
6,039,731 A 3/2000 Taylor et al.
6,043,273 A 3/2000 Duhaylongsod
6,045,549 A 4/2000 Smethers et al.
6,045,550 A 4/2000 Simpson et al.
6,050,992 A 4/2000 Nichols
6,052,607 A 4/2000 Edwards et al.
6,053,172 A 4/2000 Hovda et al.
6,053,909 A 4/2000 Shadduck
6,056,744 A 5/2000 Edwards
6,056,745 A 5/2000 Panescu et al.
6,056,769 A 5/2000 Epstein et al.
6,060,454 A 5/2000 Duhaylongsod
6,063,078 A 5/2000 Wittkampf
6,063,768 A 5/2000 First
6,071,280 A 6/2000 Edwards et al.
6,071,281 A 6/2000 Burnside et al.
6,071,282 A 6/2000 Fleischman
6,081,749 A 6/2000 Ingle et al.
6,083,249 A 7/2000 Familoni
6,083,255 A 7/2000 Laufer et al.
6,087,394 A 7/2000 Duhaylongsod
6,090,104 A 7/2000 Webster, Jr.
6,091,995 A 7/2000 Ingle et al.

(56) References Cited

U.S. PATENT DOCUMENTS 6,092,528 A 7/2000 Edwards
6,097,985 A 8/2000 Kasevich et al.
6,101,412 A 8/2000 Duhaylongsod
6,102,886 A 8/2000 Lundquist et al.
6,106,524 A 8/2000 Eggers et al.
6,117,101 A 9/2000 Diederich et al.
6,123,702 A 9/2000 Swanson et al.
6,123,703 A 9/2000 Tu et al.
6,123,718 A 9/2000 Tu et al.
6,125,301 A 9/2000 Capel
6,127,410 A 10/2000 Duhaylongsod
6,129,726 A 10/2000 Edwards et al.
6,135,997 A 10/2000 Laufer et al.
6,139,527 A 10/2000 Laufer et al.
6,139,571 A 10/2000 Fuller et al.
6,139,845 A 10/2000 Donovan
6,141,589 A 10/2000 Duhaylongsod
6,142,993 A 11/2000 Whayne et al.
6,143,013 A 11/2000 Samson et al.
6,143,277 A 11/2000 Ashurst et al.
6,149,647 A 11/2000 Tu et al.
6,152,143 A 11/2000 Edwards
6,152,899 A 11/2000 Farley et al.
6,152,953 A 11/2000 Hipskind
6,159,194 A 12/2000 Eggers et al.
6,163,716 A 12/2000 Edwards et al.
6,174,323 B1 1/2001 Biggs et al.
6,179,833 B1 1/2001 Taylor
6,183,468 B1 2/2001 Swanson et al.
6,197,013 B1 3/2001 Reed et al.
6,198,970 B1 3/2001 Freed et al.
6,200,311 B1 3/2001 Danek et al.
6,200,332 B1 3/2001 Del Giglio
6,200,333 B1 3/2001 Laufer
6,203,562 B1 3/2001 Ohkubo
6,210,013 B1 4/2001 Bousfield
6,210,355 B1 4/2001 Edwards et al.
6,210,367 B1 4/2001 Carr
6,212,432 B1 4/2001 Matsuura
6,212,433 B1 4/2001 Behl
6,214,002 B1 4/2001 Fleischman et al.
6,216,043 B1 4/2001 Swanson et al.
6,216,044 B1 4/2001 Kordis
6,216,704 B1 4/2001 Ingle et al.
6,217,576 B1 4/2001 Tu et al.
6,226,543 B1 5/2001 Gilboa et al.
6,230,052 B1 5/2001 Wolff et al.
6,231,595 B1 5/2001 Dobak, III
6,235,024 B1 5/2001 Tu
6,238,392 B1 5/2001 Long
6,240,307 B1 5/2001 Beatty et al.
6,241,727 B1 6/2001 Tu et al.
6,245,065 B1 6/2001 Panescu et al.
6,251,368 B1 6/2001 Akehurst et al.
6,253,762 B1 7/2001 Britto
6,254,598 B1 7/2001 Edwards et al.
6,254,599 B1 7/2001 Lesh et al.
6,258,083 B1 7/2001 Daniel et al.
6,258,087 B1 7/2001 Edwards et al.
6,264,653 B1 7/2001 Falwell
6,265,379 B1 7/2001 Donovan
6,269,813 B1 8/2001 Fitzgerald et al.
6,270,476 B1 8/2001 Santoianni et al.
6,273,886 B1 8/2001 Edwards et al.
6,273,907 B1 8/2001 Laufer
6,283,987 B1 9/2001 Laird et al.
6,283,988 B1 9/2001 Laufer et al.
6,283,989 B1 9/2001 Laufer et al.
6,287,304 B1 9/2001 Eggers et al.
6,296,639 B1 10/2001 Truckai et al.
6,299,633 B1 10/2001 Laufer
6,302,870 B1 10/2001 Jacobsen et al.
6,303,509 B1 10/2001 Chen et al.
6,306,423 B1 10/2001 Donovan et al.
6,315,173 B1 11/2001 Di Giovanni et al.
6,315,778 B1 11/2001 Gambale et al.
6,317,615 B1 11/2001 Kenknight et al.
6,322,559 B1 11/2001 Daulton et al.
6,322,584 B2 11/2001 Ingle et al.
6,325,798 B1 12/2001 Edwards et al.
6,327,503 B1 12/2001 Familoni
6,338,727 B1 1/2002 Noda et al.
6,338,836 B1 1/2002 Kuth et al.
6,341,236 B1 1/2002 Osorio et al.
6,346,104 B2 2/2002 Daly et al.
6,355,031 B1 3/2002 Edwards et al.
6,356,786 B1 3/2002 Rezai et al.
6,356,787 B1 3/2002 Rezai et al.
6,357,447 B1 3/2002 Swanson et al.
6,358,245 B1 3/2002 Edwards et al.
6,358,926 B2 3/2002 Donovan
6,361,554 B1 3/2002 Brisken
6,363,937 B1 4/2002 Hovda et al.
6,366,814 B1 4/2002 Boveja et al.
6,379,352 B1 4/2002 Reynolds et al.
6,383,509 B1 5/2002 Donovan et al.
6,394,956 B1 5/2002 Chandrasekaran et al.
6,402,744 B2 6/2002 Edwards et al.
6,405,732 B1 6/2002 Edwards et al.
6,409,723 B1 6/2002 Edwards
6,411,852 B1 6/2002 Danek et al.
6,414,018 B1 7/2002 Duhaylongsod
6,416,511 B1 7/2002 Lesh et al.
6,416,740 B1 7/2002 Unger
6,423,058 B1 7/2002 Edwards et al.
6,423,105 B1 7/2002 Iijima et al.
6,424,864 B1 7/2002 Matsuura
6,425,877 B1 7/2002 Edwards
6,425,887 B1 7/2002 McGuckin et al.
6,425,895 B1 7/2002 Swanson et al.
6,432,092 B2 8/2002 Miller
6,436,130 B1 8/2002 Philips et al.
6,438,423 B1 8/2002 Rezai et al.
6,440,128 B1 8/2002 Edwards et al.
6,440,129 B1 8/2002 Simpson
6,442,435 B2 8/2002 King et al.
6,447,505 B2 9/2002 Mcgovern et al.
6,447,785 B1 9/2002 Donovan
6,448,231 B2 9/2002 Graham
6,451,013 B1 9/2002 Bays et al.
6,458,121 B1 10/2002 Rosenstock et al.
6,460,545 B2 10/2002 Kordis
6,464,680 B1 10/2002 Brisken et al.
6,464,697 B1 10/2002 Edwards et al.
6,475,160 B1 11/2002 Sher
6,480,746 B1 11/2002 Ingle et al.
6,485,416 B1 11/2002 Platt et al.
6,488,673 B1 12/2002 Laufer et al.
6,488,679 B1 12/2002 Swanson et al.
6,491,710 B2 12/2002 Satake
6,493,589 B1 12/2002 Medhkour et al.
6,494,880 B1 12/2002 Swanson et al.
6,496,737 B2 12/2002 Rudie et al.
6,496,738 B2 12/2002 Carr
6,506,399 B2 1/2003 Donovan
6,510,969 B2 1/2003 Di Giovanni et al.
6,514,246 B1 2/2003 Swanson et al.
6,514,290 B1 2/2003 Loomas
6,519,488 B2 2/2003 Kenknight et al.
6,522,913 B2 2/2003 Swanson et al.
6,524,555 B1 2/2003 Ashurst et al.
6,526,320 B2 2/2003 Mitchell
6,526,976 B1 3/2003 Baran
6,529,756 B1 3/2003 Phan et al.
6,532,388 B1 3/2003 Hill et al.
6,533,780 B1 3/2003 Laird et al.
6,536,427 B2 3/2003 Davies et al.
6,544,226 B1 4/2003 Gaiser et al.
6,544,262 B2 4/2003 Fleischman
6,546,928 B1 4/2003 Ashurst et al.
6,546,932 B1 4/2003 Nahon et al.
6,546,934 B1 4/2003 Ingle et al.
6,547,776 B1 4/2003 Gaiser et al.
6,547,788 B1 4/2003 Maguire et al.

(56) References Cited

U.S. PATENT DOCUMENTS 6,549,808 B1 4/2003 Gisel et al.
6,551,274 B2 4/2003 Heiner
6,551,310 B1 4/2003 Ganz et al.
6,558,333 B2 5/2003 Gilboa et al.
6,558,378 B2 5/2003 Sherman et al.
6,558,381 B2 5/2003 Ingle et al.
6,562,034 B2 5/2003 Edwards et al.
6,572,612 B2 6/2003 Stewart et al.
6,575,623 B2 6/2003 Werneth
6,575,969 B1 6/2003 Rittman, III et al.
6,582,427 B1 6/2003 Goble et al.
6,582,430 B2 6/2003 Hall
6,587,718 B2 7/2003 Talpade
6,587,719 B1 7/2003 Barrett et al.
6,587,731 B1 7/2003 Ingle et al.
6,589,235 B2 7/2003 Wong et al.
6,589,238 B2 7/2003 Edwards et al.
6,593,130 B1 7/2003 Sen et al.
6,599,311 B1 7/2003 Biggs et al.
6,601,581 B1 8/2003 Babaev
6,603,996 B1 8/2003 Beatty et al.
6,610,054 B1 8/2003 Edwards et al.
6,610,083 B2 8/2003 Keller et al.
6,610,713 B2 8/2003 Tracey
6,613,002 B1 9/2003 Clark et al.
6,613,045 B1 9/2003 Laufer et al.
6,620,159 B2 9/2003 Hegde
6,620,415 B2 9/2003 Donovan
6,622,047 B2 9/2003 Barrett et al.
6,623,742 B2 9/2003 Voet
6,626,855 B1 9/2003 Weng et al.
6,626,903 B2 9/2003 McGuckin, Jr. et al.
6,629,535 B2 10/2003 Ingle et al.
6,629,951 B2 10/2003 Laufer et al.
6,632,440 B1 10/2003 Quinn et al.
6,633,779 B1 10/2003 Schuler et al.
6,634,363 B1 10/2003 Danek et al.
6,635,054 B2 10/2003 Fjield et al.
6,635,056 B2 10/2003 Kadhiresan et al.
6,638,273 B1 10/2003 Farley et al.
6,640,119 B1 10/2003 Budd et al.
6,640,120 B1 10/2003 Swanson et al.
6,645,200 B1 11/2003 Koblish et al.
6,645,496 B2 11/2003 Aoki et al.
6,647,617 B1 11/2003 Beatty et al.
6,648,881 B2 11/2003 Kenknight et al.
6,649,161 B1 11/2003 Donovan
6,652,517 B1 11/2003 Hall et al.
6,652,548 B2 11/2003 Evans et al.
6,656,960 B2 12/2003 Puskas
6,658,279 B2 12/2003 Swanson et al.
6,663,622 B1 12/2003 Foley et al.
6,666,858 B2 12/2003 Lafontaine
6,669,693 B2 12/2003 Friedman
6,671,533 B2 12/2003 Chen et al.
6,673,068 B1 1/2004 Berube
6,673,070 B2 1/2004 Edwards et al.
6,675,047 B1 1/2004 Konoplev et al.
6,676,686 B2 1/2004 Naganuma
6,681,136 B2 1/2004 Schuler et al.
6,692,492 B2 2/2004 Simpson et al.
6,692,494 B1 2/2004 Cooper et al.
6,699,180 B2 3/2004 Kobayashi
6,699,243 B2 3/2004 West et al.
6,708,064 B2 3/2004 Rezai
6,711,436 B1 3/2004 Duhaylongsod
6,712,074 B2 3/2004 Edwards et al.
6,712,812 B2 3/2004 Roschak et al.
6,712,814 B2 3/2004 Edwards et al.
6,714,822 B2 3/2004 King et al.
6,719,685 B2 4/2004 Fujikura et al.
6,719,694 B2 4/2004 Weng et al.
6,723,053 B2 4/2004 Ackerman et al.
6,723,091 B2 4/2004 Goble et al.
6,728,562 B1 4/2004 Budd et al.
6,735,471 B2 5/2004 Hill et al.
6,735,475 B1 5/2004 Whitehurst et al.
6,740,321 B1 5/2004 Donovan
6,743,197 B1 6/2004 Edwards
6,743,413 B1 6/2004 Schultz et al.
6,749,604 B1 6/2004 Eggers et al.
6,749,606 B2 6/2004 Keast et al.
6,752,765 B1 6/2004 Jensen et al.
6,755,026 B2 6/2004 Wallach
6,755,849 B1 6/2004 Gowda et al.
6,767,347 B2 7/2004 Sharkey et al.
6,767,544 B2 7/2004 Brooks et al.
6,770,070 B1 8/2004 Balbierz
6,772,013 B1 8/2004 Ingle et al.
6,773,711 B2 8/2004 Voet et al.
6,776,991 B2 8/2004 Naumann
6,777,423 B2 8/2004 Banholzer et al.
6,778,854 B2 8/2004 Puskas
6,780,183 B2 8/2004 Jimenez, Jr. et al.
6,786,889 B1 9/2004 Musbach et al.
6,802,843 B2 10/2004 Truckai et al.
6,805,131 B2 10/2004 Kordis
6,819,956 B2 11/2004 DiLorenzo
6,826,420 B1 11/2004 Beatty et al.
6,826,421 B1 11/2004 Beatty et al.
6,827,931 B1 12/2004 Donovan
6,836,688 B2 12/2004 Ingle et al.
6,837,888 B2 1/2005 Ciarrocca et al.
6,838,429 B2 1/2005 Paslin
6,838,434 B2 1/2005 Voet
6,838,471 B2 1/2005 Tracey
6,840,243 B2 1/2005 Deem et al.
6,841,156 B2 1/2005 Aoki et al.
6,843,998 B1 1/2005 Steward et al.
6,846,312 B2 1/2005 Edwards et al.
6,847,849 B2 1/2005 Mamo et al.
6,849,073 B2 2/2005 Hoey et al.
6,852,091 B2 2/2005 Edwards et al.
6,852,110 B2 2/2005 Roy et al.
6,861,058 B2 3/2005 Aoki et al.
6,866,662 B2 3/2005 Fuimaono et al.
6,871,092 B2 3/2005 Piccone
6,872,206 B2 3/2005 Edwards et al.
6,872,397 B2 3/2005 Aoki et al.
6,878,156 B1 4/2005 Noda
6,881,213 B2 4/2005 Ryan et al.
6,885,888 B2 4/2005 Rezai
6,890,347 B2 5/2005 Machold et al.
6,893,436 B2 5/2005 Woodard et al.
6,893,438 B2 5/2005 Hall et al.
6,893,439 B2 5/2005 Fleischman
6,895,267 B2 5/2005 Panescu et al.
6,904,303 B2 6/2005 Phan et al.
6,908,462 B2 6/2005 Joye et al.
6,908,928 B2 6/2005 Banholzer et al.
6,913,616 B2 7/2005 Hamilton et al.
6,917,834 B2 7/2005 Koblish et al.
6,934,583 B2 8/2005 Weinberg et al.
6,937,896 B1 8/2005 Kroll
6,937,903 B2 8/2005 Schuler et al.
6,939,309 B1 9/2005 Beatty et al.
6,939,345 B2 9/2005 Kenknight et al.
6,939,346 B2 9/2005 Kannenberg et al.
6,947,785 B1 9/2005 Beatty et al.
6,954,977 B2 10/2005 Maguire et al.
6,957,106 B2 10/2005 Schuler et al.
6,961,622 B2 11/2005 Gilbert
6,970,742 B2 11/2005 Mann et al.
RE38,912 E 12/2005 Walz et al.
6,971,395 B2 12/2005 Edwards et al.
6,974,224 B2 12/2005 Thomas-Benedict
6,974,456 B2 12/2005 Edwards et al.
6,974,578 B1 12/2005 Aoki et al.
6,978,168 B2 12/2005 Beatty et al.
6,978,174 B2 12/2005 Gelfand et al.
6,990,370 B1 1/2006 Beatty et al.
6,994,706 B2 2/2006 Chornenky et al.
6,997,189 B2 2/2006 Biggs et al.
7,004,942 B2 2/2006 Laird et al.

(56) References Cited

U.S. PATENT DOCUMENTS 7,022,088 B2 4/2006 Keast et al.
7,022,105 B1 4/2006 Edwards
7,027,869 B2 4/2006 Danek et al.
7,043,307 B1 5/2006 Zelickson et al.
7,070,800 B2 7/2006 Bechtold-Peters et al.
7,072,720 B2 7/2006 Puskas
7,083,614 B2 8/2006 Fjield et al.
7,101,368 B2 9/2006 Lafontaine
7,101,387 B2 9/2006 Garabedian et al.
7,104,987 B2 9/2006 Biggs et al.
7,104,990 B2 9/2006 Jenkins et al.
7,112,198 B2 9/2006 Satake
7,118,568 B2 10/2006 Hassett et al.
7,122,031 B2 10/2006 Edwards et al.
7,122,033 B2 10/2006 Wood
7,125,407 B2 10/2006 Edwards et al.
7,131,445 B2 11/2006 Amoah
7,142,910 B2 11/2006 Puskas
7,150,745 B2 12/2006 Stern et al.
7,162,303 B2 1/2007 Levin et al.
7,165,551 B2 1/2007 Edwards et al.
7,167,757 B2 1/2007 Ingle et al.
7,175,644 B2 2/2007 Cooper et al.
7,179,257 B2 2/2007 West et al.
7,186,251 B2 3/2007 Malecki et al.
7,187,964 B2 3/2007 Khoury
7,187,973 B2 3/2007 Hauck
7,189,208 B1 3/2007 Beatty et al.
7,198,635 B2 4/2007 Danek et al.
7,200,445 B1 4/2007 Dalbec et al.
7,229,469 B1 6/2007 Witzel et al.
7,238,357 B2 7/2007 Barron
7,241,295 B2 7/2007 Maguire
7,255,693 B1 8/2007 Johnston et al.
RE39,820 E 9/2007 Banholzer et al.
7,264,002 B2 9/2007 Danek et al.
7,266,414 B2 9/2007 Cornelius et al.
7,273,055 B2 9/2007 Danek et al.
7,289,843 B2 10/2007 Beatty et al.
7,291,146 B2 11/2007 Steinke et al.
7,292,890 B2 11/2007 Whitehurst et al.
7,309,707 B2 12/2007 Bender et al.
7,310,552 B2 12/2007 Puskas
RE40,045 E 2/2008 Palmer
7,326,207 B2 2/2008 Edwards
7,344,535 B2 3/2008 Stern et al.
7,371,231 B2 5/2008 Rioux et al.
7,393,330 B2 7/2008 Keast et al.
7,393,350 B2 7/2008 Maurice
7,394,976 B2 7/2008 Entenman et al.
7,402,172 B2 7/2008 Chin et al.
7,422,563 B2 9/2008 Roschak et al.
7,422,584 B2 9/2008 Loomas et al.
7,425,212 B1 9/2008 Danek et al.
7,430,449 B2 9/2008 Aldrich et al.
7,462,162 B2 12/2008 Phan et al.
7,462,179 B2 12/2008 Edwards et al.
7,473,273 B2 1/2009 Campbell
7,477,945 B2 1/2009 Rezai et al.
7,483,755 B2 1/2009 Ingle et al.
7,493,160 B2 2/2009 Weber et al.
7,494,661 B2 2/2009 Sanders
7,507,234 B2 3/2009 Utley et al.
7,507,238 B2 3/2009 Edwards et al.
7,517,320 B2 4/2009 Wibowo et al.
7,530,979 B2 5/2009 Ganz et al.
7,532,938 B2 5/2009 Machado et al.
7,542,802 B2 6/2009 Danek et al.
7,553,307 B2 6/2009 Bleich et al.
7,556,624 B2 7/2009 Laufer et al.
7,559,890 B2 7/2009 Wallace et al.
7,572,245 B2 8/2009 Herweck et al.
7,585,296 B2 9/2009 Edwards et al.
7,588,549 B2 9/2009 Eccleston
7,594,925 B2 9/2009 Danek et al.
7,608,275 B2 10/2009 Deem et al.
7,613,515 B2 11/2009 Knudson et al.
7,617,005 B2 11/2009 Demarais et al.
7,620,451 B2 11/2009 Demarais et al.
7,628,789 B2 12/2009 Soltesz et al.
7,632,268 B2 12/2009 Edwards et al.
7,641,632 B2 1/2010 Noda et al.
7,641,633 B2 1/2010 Laufer et al.
7,648,500 B2 1/2010 Edwards et al.
7,653,438 B2 1/2010 Deem et al.
7,684,865 B2 3/2010 Aldrich et al.
7,689,290 B2 3/2010 Ingle et al.
7,691,079 B2 4/2010 Gobel et al.
RE41,334 E 5/2010 Beatty et al.
7,708,712 B2 5/2010 Phan et al.
7,708,768 B2 5/2010 Danek et al.
7,711,430 B2 5/2010 Errico et al.
7,717,948 B2 5/2010 Demarais et al.
7,722,538 B2 5/2010 Khoury
7,725,188 B2 5/2010 Errico et al.
7,734,355 B2 6/2010 Cohen et al.
7,734,535 B1 6/2010 Burns
7,740,017 B2 6/2010 Danek et al.
7,740,631 B2 6/2010 Bleich et al.
7,742,795 B2 6/2010 Stone et al.
7,747,324 B2 6/2010 Errico et al.
7,756,583 B2 7/2010 Demarais et al.
7,765,010 B2 7/2010 Chornenky et al.
7,770,584 B2 8/2010 Danek et al.
7,783,358 B2 8/2010 Aldrich et al.
7,815,590 B2 10/2010 Cooper
7,826,881 B1 11/2010 Beatty et al.
7,831,288 B1 11/2010 Beatty et al.
7,837,676 B2 11/2010 Sinelnikov et al.
7,837,679 B2 11/2010 Biggs et al.
7,841,986 B2 11/2010 He et al.
7,844,338 B2 11/2010 Knudson et al.
7,853,331 B2 12/2010 Kaplan et al.
7,854,734 B2 12/2010 Biggs et al.
7,854,740 B2 12/2010 Carney
7,869,879 B2 1/2011 Errico et al.
7,869,880 B2 1/2011 Errico et al.
7,873,417 B2 1/2011 Demarais et al.
7,877,146 B2 1/2011 Rezai et al.
7,904,159 B2 3/2011 Errico et al.
7,906,124 B2 3/2011 Laufer et al.
7,914,448 B2 3/2011 Bob et al.
7,921,855 B2 4/2011 Danek et al.
7,930,012 B2 4/2011 Beatty et al.
7,931,647 B2 4/2011 Wizeman et al.
7,937,143 B2 5/2011 Demarais et al.
7,938,123 B2 5/2011 Danek et al.
7,949,407 B2 5/2011 Kaplan et al.
7,967,782 B2 6/2011 Laufer et al.
7,985,187 B2 7/2011 Wibowo et al.
7,992,572 B2 8/2011 Danek et al.
7,993,336 B2 8/2011 Jackson et al.
8,002,740 B2 8/2011 Willink et al.
8,007,495 B2 8/2011 McDaniel et al.
8,010,197 B2 8/2011 Errico et al.
8,012,149 B2 9/2011 Jackson et al.
8,041,428 B2 10/2011 Errico et al.
8,046,085 B2 10/2011 Knudson et al.
8,052,668 B2 11/2011 Sih
8,088,127 B2 1/2012 Mayse et al.
8,099,167 B1 1/2012 Errico et al.
8,105,817 B2 1/2012 Deem et al.
8,128,595 B2 3/2012 Walker et al.
8,128,617 B2 3/2012 Bencini et al.
8,131,371 B2 3/2012 Demarais et al.
8,133,497 B2 3/2012 Deem et al.
8,152,803 B2 4/2012 Edwards et al.
8,172,827 B2 5/2012 Deem et al.
8,204,598 B2 6/2012 Errico et al.
8,208,998 B2 6/2012 Beatty et al.
8,209,034 B2 6/2012 Simon et al.
8,216,216 B2 7/2012 Warnking et al.
8,226,638 B2 7/2012 Mayse et al.
8,229,564 B2 7/2012 Rezai

(56) References Cited

U.S. PATENT DOCUMENTS 8,231,621 B2 7/2012 Hutchins et al.
8,233,988 B2 7/2012 Errico et al.
8,251,992 B2 8/2012 Utley et al.
8,267,094 B2 9/2012 Danek et al.
8,295,902 B2 10/2012 Salahieh et al.
8,303,581 B2 11/2012 Arts et al.
8,313,484 B2 11/2012 Edwards et al.
8,328,798 B2 12/2012 Witzel et al.
8,338,164 B2 12/2012 Deem et al.
8,347,891 B2 1/2013 Demarais et al.
8,357,118 B2 1/2013 Orr
8,364,237 B2 1/2013 Stone et al.
8,371,303 B2 2/2013 Schaner et al.
8,377,055 B2 2/2013 Jackson et al.
8,483,831 B1 7/2013 Hlavka et al.
8,489,192 B1 7/2013 Hlavka et al.
8,660,647 B2 2/2014 Parnis et al.
8,731,672 B2 5/2014 Hlavka et al.
8,740,895 B2 6/2014 Mayse et al.
8,777,943 B2 7/2014 Mayse et al.
8,808,280 B2 8/2014 Mayse et al.
8,821,489 B2 9/2014 Mayse et al.
8,911,439 B2 12/2014 Mayse et al.
8,932,289 B2 1/2015 Mayse et al.
8,961,391 B2 2/2015 Deem et al.
8,961,507 B2 2/2015 Mayse et al.
8,961,508 B2 2/2015 Mayse et al.
9,005,195 B2 4/2015 Mayse et al.
9,017,324 B2 4/2015 Mayse et al.
9,125,643 B2 9/2015 Hlvaka et al.
9,149,328 B2 10/2015 Dimmer et al.
9,339,618 B2 5/2016 Deem et al.
9,398,933 B2 7/2016 Mayse
9,498,283 B2 11/2016 Deem et al.
9,539,048 B2 1/2017 Hlvaka et al.
9,649,153 B2 5/2017 Mayse et al.
9,649,154 B2 5/2017 Mayse et al.
9,662,171 B2 5/2017 Dimmer et al.
9,668,809 B2 6/2017 Mayse et al.
9,675,412 B2 6/2017 Mayse et al.
9,867,986 B2 1/2018 Hlvaka et al.
9,931,162 B2 4/2018 Mayse et al.
10,022,529 B2 7/2018 Deem et al.
10,149,714 B2 12/2018 Mayse et al.
10,201,386 B2 2/2019 Mayse et al.
10,206,735 B2 2/2019 Kaveckis et al.
10,252,057 B2 4/2019 Hlvaka et al.
10,363,091 B2 7/2019 Dimmer et al.
10,368,937 B2 8/2019 Kaveckis et al.
10,575,893 B2 3/2020 Mayse
10,610,283 B2 4/2020 Mayse et al.
10,729,897 B2 8/2020 Deem et al.
10,869,997 B2 12/2020 Mayse
2001/0014819 A1* 8/2001 Ingle .................. A61B 18/1482
128/898
2001/0020151 A1 9/2001 Reed et al.
2001/0044596 A1 11/2001 Jaafar
2002/0002387 A1 1/2002 Naganuma
2002/0010495 A1 1/2002 Freed et al.
2002/0016344 A1 2/2002 Tracey
2002/0042564 A1 4/2002 Cooper et al.
2002/0042565 A1 4/2002 Cooper et al.
2002/0049370 A1 4/2002 Laufer et al.
2002/0072738 A1 6/2002 Edwards et al.
2002/0082197 A1 6/2002 Aoki et al.
2002/0087153 A1 7/2002 Roschak et al.
2002/0087208 A1 7/2002 Koblish et al.
2002/0091379 A1 7/2002 Danek et al.
2002/0107512 A1 8/2002 Edwards
2002/0107515 A1 8/2002 Edwards et al.
2002/0111386 A1 8/2002 Sekins et al.
2002/0111619 A1 8/2002 Keast et al.
2002/0111620 A1 8/2002 Cooper et al.
2002/0115991 A1 8/2002 Edwards
2002/0116030 A1 8/2002 Rezai
2002/0143302 A1 10/2002 Hinchliffe et al.
2002/0143326 A1 10/2002 Foley et al.
2002/0143373 A1 10/2002 Courtnage et al.
2002/0151888 A1 10/2002 Edwards et al.
2002/0183682 A1 12/2002 Darvish
2002/0198512 A1 12/2002 Seward
2002/0198570 A1 12/2002 Puskas
2002/0198574 A1 12/2002 Gumpert
2003/0018344 A1 1/2003 Kaji et al.
2003/0023287 A1 1/2003 Edwards et al.
2003/0027752 A1 2/2003 Steward et al.
2003/0050591 A1 3/2003 Patrick McHale
2003/0050631 A1 3/2003 Mody et al.
2003/0065371 A1 4/2003 Satake
2003/0069570 A1 4/2003 Witzel et al.
2003/0070676 A1 4/2003 Cooper et al.
2003/0074039 A1 4/2003 Puskas
2003/0093069 A1 5/2003 Panescu et al.
2003/0093128 A1 5/2003 Freed et al.
2003/0100895 A1* 5/2003 Simpson ............ A61B 18/1492
606/41
2003/0125786 A1 7/2003 Gliner et al.
2003/0130657 A1 7/2003 Tom et al.
2003/0144572 A1 7/2003 Oschman et al.
2003/0153905 A1 8/2003 Edwards et al.
2003/0159700 A1 8/2003 Laufer et al.
2003/0181949 A1 9/2003 Whale
2003/0187430 A1 10/2003 Vorisek
2003/0195593 A1 10/2003 Ingle et al.
2003/0195604 A1 10/2003 Ingle et al.
2003/0202990 A1 10/2003 Donovan et al.
2003/0208103 A1 11/2003 Sonnenschein et al.
2003/0211121 A1 11/2003 Donovan
2003/0216791 A1 11/2003 Schuler et al.
2003/0216792 A1 11/2003 Levin et al.
2003/0216891 A1 11/2003 Wegener
2003/0225443 A1 12/2003 Kiran et al.
2003/0233099 A1 12/2003 Danaek et al.
2003/0236455 A1 12/2003 Swanson et al.
2004/0006268 A1 1/2004 Gilboa et al.
2004/0009180 A1 1/2004 Donovan
2004/0010289 A1 1/2004 Biggs et al.
2004/0010290 A1 1/2004 Schroeppel et al.
2004/0028676 A1 2/2004 Klein et al.
2004/0029849 A1 2/2004 Schatzberg et al.
2004/0030368 A1 2/2004 Kemeny et al.
2004/0031494 A1 2/2004 Danek et al.
2004/0044390 A1 3/2004 Szeles
2004/0059383 A1 3/2004 Puskas
2004/0073201 A1 4/2004 Cooper et al.
2004/0073206 A1 4/2004 Foley et al.
2004/0073278 A1 4/2004 Pachys
2004/0086531 A1 5/2004 Barron
2004/0087936 A1 5/2004 Stern et al.
2004/0088030 A1 5/2004 Jung, Jr.
2004/0088036 A1 5/2004 Gilbert
2004/0091880 A1 5/2004 Wiebusch et al.
2004/0106954 A1 6/2004 Whitehurst et al.
2004/0116981 A1 6/2004 Mazar
2004/0122488 A1 6/2004 Mazar et al.
2004/0122489 A1 6/2004 Mazar et al.
2004/0127942 A1 7/2004 Yomtov et al.
2004/0127958 A1 7/2004 Mazar et al.
2004/0142005 A1 7/2004 Brooks et al.
2004/0147921 A1 7/2004 Edwards et al.
2004/0147969 A1 7/2004 Mann et al.
2004/0147988 A1 7/2004 Stephens
2004/0151741 A1 8/2004 Borodic
2004/0153056 A1 8/2004 Muller et al.
2004/0162584 A1 8/2004 Hill et al.
2004/0162597 A1 8/2004 Hamilton et al.
2004/0167509 A1 8/2004 Taimisto
2004/0167580 A1 8/2004 Mann et al.
2004/0172075 A1 9/2004 Shafer et al.
2004/0172080 A1 9/2004 Stadler et al.
2004/0172084 A1 9/2004 Knudson et al.
2004/0175399 A1 9/2004 Schiffman
2004/0176803 A1 9/2004 Whelan et al.
2004/0176805 A1 9/2004 Whelan et al.

(56) References Cited

U.S. PATENT DOCUMENTS

2004/0182399 A1 9/2004 Danek et al.
2004/0186435 A1 9/2004 Seward
2004/0204747 A1 10/2004 Kemeny et al.
2004/0213813 A1 10/2004 Ackerman
2004/0213814 A1 10/2004 Ackerman
2004/0215235 A1 10/2004 Jackson et al.
2004/0215289 A1 10/2004 Fukui
2004/0215296 A1 10/2004 Ganz et al.
2004/0220556 A1 11/2004 Cooper et al.
2004/0220621 A1 11/2004 Zhou et al.
2004/0226556 A1 11/2004 Deem et al.
2004/0230251 A1 11/2004 Schuler et al.
2004/0230252 A1 11/2004 Kullok et al.
2004/0243118 A1 12/2004 Ayers et al.
2004/0243182 A1 12/2004 Cohen et al.
2004/0248188 A1 12/2004 Sanders
2004/0249401 A1 12/2004 Rabiner et al.
2004/0249416 A1 12/2004 Yun et al.
2004/0253274 A1 12/2004 Voet
2005/0004609 A1 1/2005 Stahmann et al.
2005/0004631 A1 1/2005 Benedict
2005/0010263 A1 1/2005 Schauerte
2005/0010270 A1 1/2005 Laufer
2005/0015117 A1 1/2005 Gerber
2005/0019346 A1 1/2005 Boulis
2005/0021092 A1 1/2005 Yun et al.
2005/0049615 A1 3/2005 Cooper et al.
2005/0056292 A1 3/2005 Cooper
2005/0059153 A1 3/2005 George et al.
2005/0060041 A1 3/2005 Phan et al.
2005/0060042 A1 3/2005 Phan et al.
2005/0060044 A1 3/2005 Roschak et al.
2005/0065553 A1 3/2005 Ben Ezra et al.
2005/0065562 A1 3/2005 Rezai
2005/0065567 A1 3/2005 Lee et al.
2005/0065573 A1 3/2005 Rezai
2005/0065574 A1 3/2005 Rezai
2005/0065575 A1 3/2005 Dobak
2005/0065584 A1 3/2005 Schiff et al.
2005/0074461 A1 4/2005 Donovan
2005/0076909 A1 4/2005 Stahmann et al.
2005/0080461 A1 4/2005 Stahmann et al.
2005/0085801 A1 4/2005 Cooper et al.
2005/0090722 A1 4/2005 Perez
2005/0096529 A1 5/2005 Cooper et al.
2005/0096644 A1 5/2005 Hall et al.
2005/0107783 A1 5/2005 Tom et al.
2005/0107829 A1 5/2005 Edwards et al.
2005/0107853 A1 5/2005 Krespi et al.
2005/0125044 A1 6/2005 Tracey
2005/0137518 A1 6/2005 Biggs et al.
2005/0137611 A1 6/2005 Escudero et al.
2005/0137715 A1 6/2005 Phan et al.
2005/0143788 A1 6/2005 Yun et al.
2005/0149146 A1 7/2005 Boveja et al.
2005/0152924 A1 7/2005 Voet
2005/0153885 A1 7/2005 Yun et al.
2005/0159736 A9 7/2005 Danek et al.
2005/0165456 A1 7/2005 Mann et al.
2005/0171396 A1 8/2005 Pankratov et al.
2005/0177144 A1 8/2005 Phan et al.
2005/0177192 A1 8/2005 Rezai et al.
2005/0182288 A1 8/2005 Zabara
2005/0182393 A1 8/2005 Abboud et al.
2005/0183732 A1 8/2005 Edwards
2005/0187579 A1 8/2005 Danek et al.
2005/0193279 A1 9/2005 Daners
2005/0203503 A1 9/2005 Edwards et al.
2005/0222628 A1 10/2005 Krakousky
2005/0222635 A1 10/2005 Krakovsky
2005/0222651 A1 10/2005 Jung
2005/0228054 A1 10/2005 Tatton
2005/0228459 A1 10/2005 Levin et al.
2005/0228460 A1 10/2005 Levin et al.
2005/0234523 A1 10/2005 Levin et al.
2005/0238693 A1 10/2005 Whyte
2005/0240176 A1 10/2005 Oral et al.
2005/0240241 A1 10/2005 Yun et al.
2005/0245926 A1 11/2005 Edwards et al.
2005/0245992 A1 11/2005 Persen et al.
2005/0251128 A1 11/2005 Amoah
2005/0251213 A1 11/2005 Freeman
2005/0255317 A1 11/2005 Bavaro et al.
2005/0256028 A1 11/2005 Yun et al.
2005/0261747 A1 11/2005 Schuler et al.
2005/0267536 A1 12/2005 Freeman et al.
2005/0277993 A1 12/2005 Mower
2005/0283197 A1 12/2005 Daum et al.
2006/0009758 A1 1/2006 Edwards et al.
2006/0015151 A1 1/2006 Aldrich
2006/0058692 A1 3/2006 Beatty et al.
2006/0058693 A1 3/2006 Beatty et al.
2006/0058780 A1 3/2006 Edwards et al.
2006/0062808 A1 3/2006 Laufer et al.
2006/0079887 A1 4/2006 Buysse et al.
2006/0084884 A1 4/2006 Beatty et al.
2006/0084966 A1 4/2006 Maguire et al.
2006/0084970 A1 4/2006 Beatty et al.
2006/0084971 A1 4/2006 Beatty et al.
2006/0084972 A1 4/2006 Beatty et al.
2006/0089637 A1 4/2006 Werneth et al.
2006/0095029 A1 5/2006 Young et al.
2006/0095032 A1 5/2006 Jackson et al.
2006/0100666 A1 5/2006 Wilkinson et al.
2006/0106361 A1 5/2006 Muni et al.
2006/0111755 A1 5/2006 Stone et al.
2006/0116749 A1 6/2006 Willink et al.
2006/0118127 A1 6/2006 Chinn
2006/0135953 A1 6/2006 Kania et al.
2006/0135984 A1 6/2006 Kramer et al.
2006/0135998 A1 6/2006 Libbus et al.
2006/0137698 A1 6/2006 Danek et al.
2006/0142801 A1 6/2006 Demarais et al.
2006/0167498 A1 7/2006 DiLorenzo
2006/0178703 A1 8/2006 Huston et al.
2006/0206150 A1 9/2006 Demarais et al.
2006/0212076 A1 9/2006 Demarais et al.
2006/0212078 A1 9/2006 Demarais et al.
2006/0222667 A1 10/2006 Deem et al.
2006/0225742 A1 10/2006 Deem et al.
2006/0235474 A1 10/2006 Demarais
2006/0241523 A1 10/2006 Sinelnikov et al.
2006/0247617 A1 11/2006 Danek et al.
2006/0247618 A1 11/2006 Kaplan et al.
2006/0247619 A1 11/2006 Kaplan et al.
2006/0247683 A1 11/2006 Danek et al.
2006/0247726 A1 11/2006 Biggs et al.
2006/0247727 A1 11/2006 Biggs et al.
2006/0247746 A1 11/2006 Danek et al.
2006/0254600 A1 11/2006 Danek et al.
2006/0259028 A1 11/2006 Utley et al.
2006/0259029 A1 11/2006 Utley et al.
2006/0259030 A1 11/2006 Utley et al.
2006/0265014 A1 11/2006 Demarais et al.
2006/0265015 A1 11/2006 Demarais et al.
2006/0271111 A1 11/2006 Demarais et al.
2006/0276807 A1 12/2006 Keast et al.
2006/0276852 A1 12/2006 Demarais et al.
2006/0278243 A1 12/2006 Danek et al.
2006/0278244 A1 12/2006 Danek et al.
2006/0280772 A1 12/2006 Roschak et al.
2006/0280773 A1 12/2006 Roschak et al.
2006/0282071 A1 12/2006 Utley et al.
2006/0287679 A1 12/2006 Stone
2007/0021803 A1 1/2007 Deem et al.
2007/0025919 A1 2/2007 Deem et al.
2007/0027496 A1 2/2007 Parnis et al.
2007/0032788 A1 2/2007 Edwards et al.
2007/0043342 A1 2/2007 Kleinberger
2007/0043350 A1 2/2007 Soltesz et al.
2007/0055328 A1 3/2007 Mayse et al.
2007/0060954 A1 3/2007 Cameron et al.
2007/0060990 A1 3/2007 Satake
2007/0062545 A1 3/2007 Danek et al.

(56) References Cited

U.S. PATENT DOCUMENTS

| | | | |
|---|---|---|---|
| 2007/0066957 | A1 | 3/2007 | Demarais et al. |
| 2007/0074719 | A1 | 4/2007 | Danek et al. |
| 2007/0083194 | A1 | 4/2007 | Kunis et al. |
| 2007/0083197 | A1 | 4/2007 | Danek et al. |
| 2007/0083239 | A1 | 4/2007 | Demarais et al. |
| 2007/0093802 | A1 | 4/2007 | Danek et al. |
| 2007/0093809 | A1 | 4/2007 | Edwards et al. |
| 2007/0100390 | A1 | 5/2007 | Danaek et al. |
| 2007/0102011 | A1 | 5/2007 | Danek et al. |
| 2007/0106292 | A1 | 5/2007 | Kaplan et al. |
| 2007/0106296 | A1 | 5/2007 | Laufer et al. |
| 2007/0106337 | A1 | 5/2007 | Errico et al. |
| 2007/0106338 | A1 | 5/2007 | Errico |
| 2007/0106339 | A1 | 5/2007 | Errico et al. |
| 2007/0106348 | A1 | 5/2007 | Laufer |
| 2007/0112349 | A1 | 5/2007 | Danek et al. |
| 2007/0118184 | A1 | 5/2007 | Danek et al. |
| 2007/0118190 | A1 | 5/2007 | Danek et al. |
| 2007/0123922 | A1 | 5/2007 | Cooper et al. |
| 2007/0123958 | A1 | 5/2007 | Laufer |
| 2007/0123961 | A1 | 5/2007 | Danek et al. |
| 2007/0129720 | A1 | 6/2007 | Demarais et al. |
| 2007/0129760 | A1 | 6/2007 | Demarais et al. |
| 2007/0129761 | A1 | 6/2007 | Demarais et al. |
| 2007/0135875 | A1 | 6/2007 | Demarais et al. |
| 2007/0156185 | A1 | 7/2007 | Swanson et al. |
| 2007/0173899 | A1 | 7/2007 | Levin et al. |
| 2007/0191902 | A1 | 8/2007 | Errico et al. |
| 2007/0197896 | A1 | 8/2007 | Moll et al. |
| 2007/0203549 | A1 | 8/2007 | Demarais et al. |
| 2007/0225768 | A1 | 9/2007 | Dobak |
| 2007/0232896 | A1 | 10/2007 | Gilboa et al. |
| 2007/0239256 | A1 | 10/2007 | Weber et al. |
| 2007/0244479 | A1 | 10/2007 | Beatty et al. |
| 2007/0250050 | A1 | 10/2007 | Lafontaine |
| 2007/0255270 | A1 | 11/2007 | Carney |
| 2007/0255304 | A1 | 11/2007 | Roschak et al. |
| 2007/0265639 | A1 | 11/2007 | Danek et al. |
| 2007/0265687 | A1 | 11/2007 | Deem et al. |
| 2007/0267011 | A1 | 11/2007 | Deem et al. |
| 2007/0270794 | A1 | 11/2007 | Anderson et al. |
| 2008/0004596 | A1 | 1/2008 | Yun et al. |
| 2008/0021274 | A1 | 1/2008 | Bayer et al. |
| 2008/0021369 | A1 | 1/2008 | Deem et al. |
| 2008/0051839 | A1 | 2/2008 | Libbus et al. |
| 2008/0086107 | A1 | 4/2008 | Roschak |
| 2008/0097422 | A1 | 4/2008 | Edwards et al. |
| 2008/0097424 | A1 | 4/2008 | Wizeman et al. |
| 2008/0125772 | A1 | 5/2008 | Stone et al. |
| 2008/0147137 | A1 | 6/2008 | Cohen et al. |
| 2008/0154258 | A1 | 6/2008 | Chang et al. |
| 2008/0161801 | A1 | 7/2008 | Steinke et al. |
| 2008/0183248 | A1 | 7/2008 | Rezai et al. |
| 2008/0188912 | A1 | 8/2008 | Stone et al. |
| 2008/0188913 | A1 | 8/2008 | Stone et al. |
| 2008/0194956 | A1 | 8/2008 | Aldrich et al. |
| 2008/0208305 | A1 | 8/2008 | Rezai et al. |
| 2008/0213331 | A1 | 9/2008 | Gelfand et al. |
| 2008/0234564 | A1 | 9/2008 | Beatty et al. |
| 2008/0243112 | A1 | 10/2008 | De Neve |
| 2008/0255449 | A1 | 10/2008 | Warnking et al. |
| 2008/0255642 | A1 | 10/2008 | Zarins et al. |
| 2008/0262489 | A1 | 10/2008 | Steinke |
| 2008/0275445 | A1 | 11/2008 | Kelly et al. |
| 2008/0302359 | A1 | 12/2008 | Loomas et al. |
| 2008/0306570 | A1 | 12/2008 | Rezai et al. |
| 2008/0312543 | A1 | 12/2008 | Laufer et al. |
| 2008/0312725 | A1 | 12/2008 | Penner |
| 2008/0319350 | A1 | 12/2008 | Wallace et al. |
| 2009/0018473 | A1 | 1/2009 | Aldrich et al. |
| 2009/0018538 | A1 | 1/2009 | Webster et al. |
| 2009/0022197 | A1 | 1/2009 | Hisa et al. |
| 2009/0030477 | A1 | 1/2009 | Jarrard |
| 2009/0036948 | A1 | 2/2009 | Levin et al. |
| 2009/0043301 | A1 | 2/2009 | Jarrard et al. |
| 2009/0043302 | A1 | 2/2009 | Ford et al. |
| 2009/0048593 | A1 | 2/2009 | Ganz et al. |
| 2009/0060953 | A1 | 3/2009 | Sandars |
| 2009/0062873 | A1 | 3/2009 | Wu et al. |
| 2009/0069797 | A1 | 3/2009 | Danek et al. |
| 2009/0076409 | A1 | 3/2009 | Wu et al. |
| 2009/0076491 | A1 | 3/2009 | Roschak et al. |
| 2009/0112203 | A1 | 4/2009 | Danek et al. |
| 2009/0124883 | A1 | 5/2009 | Wibowo et al. |
| 2009/0131765 | A1 | 5/2009 | Roschak et al. |
| 2009/0131928 | A1 | 5/2009 | Edwards et al. |
| 2009/0131930 | A1 | 5/2009 | Gelbart et al. |
| 2009/0143678 | A1 | 6/2009 | Keast et al. |
| 2009/0143705 | A1 | 6/2009 | Danek et al. |
| 2009/0143776 | A1 | 6/2009 | Danek et al. |
| 2009/0143831 | A1 | 6/2009 | Huston et al. |
| 2009/0155336 | A1 | 6/2009 | Rezai |
| 2009/0177192 | A1 | 7/2009 | Rioux et al. |
| 2009/0192505 | A1 | 7/2009 | Askew et al. |
| 2009/0192508 | A1 | 7/2009 | Laufer et al. |
| 2009/0204005 | A1 | 8/2009 | Keast et al. |
| 2009/0204119 | A1 | 8/2009 | Bleich et al. |
| 2009/0221997 | A1 | 9/2009 | Arnold et al. |
| 2009/0227885 | A1 | 9/2009 | Lowery et al. |
| 2009/0227980 | A1 | 9/2009 | Kangas et al. |
| 2009/0232850 | A1 | 9/2009 | Manack et al. |
| 2009/0248011 | A1 | 10/2009 | Hlavka et al. |
| 2009/0254079 | A1 | 10/2009 | Edwards et al. |
| 2009/0254142 | A1 | 10/2009 | Edwards et al. |
| 2009/0259274 | A1 | 10/2009 | Simon et al. |
| 2009/0275840 | A1 | 11/2009 | Roschak et al. |
| 2009/0275878 | A1 | 11/2009 | Cambier et al. |
| 2009/0281593 | A9 | 11/2009 | Errico et al. |
| 2009/0287087 | A1 | 11/2009 | Gwerder et al. |
| 2009/0306644 | A1 | 12/2009 | Mayse et al. |
| 2009/0318904 | A9 | 12/2009 | Cooper et al. |
| 2009/0319002 | A1 | 12/2009 | Simon et al. |
| 2010/0003282 | A1 | 1/2010 | Deem et al. |
| 2010/0004648 | A1 | 1/2010 | Edwards et al. |
| 2010/0010564 | A1 | 1/2010 | Simon et al. |
| 2010/0016709 | A1 | 1/2010 | Gilboa et al. |
| 2010/0042089 | A1 | 2/2010 | Soltesz et al. |
| 2010/0049031 | A1 | 2/2010 | Fruland et al. |
| 2010/0049186 | A1 | 2/2010 | Ingle et al. |
| 2010/0049188 | A1 | 2/2010 | Nelson et al. |
| 2010/0057178 | A1 | 3/2010 | Simon |
| 2010/0063495 | A1 | 3/2010 | Edwards et al. |
| 2010/0070004 | A1 | 3/2010 | Hlavka et al. |
| 2010/0076518 | A1 | 3/2010 | Hlavka et al. |
| 2010/0087783 | A1 | 4/2010 | Weber et al. |
| 2010/0087809 | A1 | 4/2010 | Edwards et al. |
| 2010/0094231 | A1 | 4/2010 | Bleich et al. |
| 2010/0114087 | A1 | 5/2010 | Edwards et al. |
| 2010/0116279 | A9 | 5/2010 | Cooper |
| 2010/0125239 | A1 | 5/2010 | Perry et al. |
| 2010/0130892 | A1 | 5/2010 | Warnking |
| 2010/0137860 | A1 | 6/2010 | Demarais et al. |
| 2010/0145427 | A1 | 6/2010 | Gliner et al. |
| 2010/0152835 | A1 | 6/2010 | Orr |
| 2010/0160906 | A1 | 6/2010 | Jarrard |
| 2010/0160996 | A1 | 6/2010 | Simon et al. |
| 2010/0174340 | A1 | 7/2010 | Simon |
| 2010/0179424 | A1 | 7/2010 | Warnking et al. |
| 2010/0185190 | A1 | 7/2010 | Danek et al. |
| 2010/0191089 | A1 | 7/2010 | Stebler et al. |
| 2010/0204689 | A1 | 8/2010 | Danek et al. |
| 2010/0222851 | A1 | 9/2010 | Deem et al. |
| 2010/0228318 | A1 | 9/2010 | Errico et al. |
| 2010/0241188 | A1 | 9/2010 | Errico et al. |
| 2010/0249873 | A1 | 9/2010 | Errico |
| 2010/0256629 | A1 | 10/2010 | Wylie et al. |
| 2010/0256630 | A1 | 10/2010 | Hamilton, Jr. et al. |
| 2010/0268222 | A1 | 10/2010 | Danek et al. |
| 2010/0298905 | A1 | 11/2010 | Simon |
| 2010/0305463 | A1 | 12/2010 | Macklem et al. |
| 2010/0318020 | A1 | 12/2010 | Atanasoska et al. |
| 2010/0331776 | A1 | 12/2010 | Salahieh et al. |
| 2011/0004148 | A1 | 1/2011 | Ishii |
| 2011/0015548 | A1 | 1/2011 | Aldrich et al. |

(56) References Cited

U.S. PATENT DOCUMENTS

2011/0028898 A1 2/2011 Clark, III et al.
2011/0046432 A1 2/2011 Simon et al.
2011/0060380 A1 3/2011 Gelfand et al.
2011/0079230 A1 4/2011 Danek et al.
2011/0093032 A1 4/2011 Boggs et al.
2011/0098762 A1 4/2011 Rezai
2011/0112400 A1 5/2011 Emery et al.
2011/0112521 A1 5/2011 DeLonzor et al.
2011/0118725 A1 5/2011 Mayse et al.
2011/0125203 A1 5/2011 Simon et al.
2011/0125213 A1 5/2011 Simon et al.
2011/0130708 A1 6/2011 Perry et al.
2011/0137284 A1 6/2011 Arora et al.
2011/0144630 A1 6/2011 Loeb
2011/0146673 A1 6/2011 Keast et al.
2011/0146674 A1 6/2011 Roschak
2011/0152855 A1* 6/2011 Mayse ............... A61B 18/1485 606/33
2011/0152967 A1 6/2011 Simon et al.
2011/0152974 A1 6/2011 Rezai et al.
2011/0166499 A1 7/2011 Demarais et al.
2011/0166565 A1 7/2011 Wizeman et al.
2011/0172654 A1 7/2011 Barry et al.
2011/0172655 A1 7/2011 Biggs et al.
2011/0172658 A1 7/2011 Gelbart et al.
2011/0178569 A1 7/2011 Parnis et al.
2011/0184330 A1 7/2011 Laufer et al.
2011/0190569 A1 8/2011 Simon et al.
2011/0196288 A1 8/2011 Kaplan et al.
2011/0202098 A1 8/2011 Demarais et al.
2011/0224768 A1 9/2011 Edwards
2011/0230701 A1 9/2011 Simon et al.
2011/0230938 A1 9/2011 Simon et al.
2011/0245756 A1 10/2011 Arora et al.
2011/0251592 A1 10/2011 Biggs et al.
2011/0257622 A1 10/2011 Salahieh et al.
2011/0257647 A1 10/2011 Mayse et al.
2011/0263960 A1 10/2011 Mitchell
2011/0264086 A1 10/2011 Ingle
2011/0270249 A1 11/2011 Utley et al.
2011/0276107 A1 11/2011 Simon et al.
2011/0276112 A1 11/2011 Simon et al.
2011/0282229 A1 11/2011 Danek et al.
2011/0282418 A1 11/2011 Saunders et al.
2011/0301587 A1 12/2011 Deem et al.
2011/0301664 A1 12/2011 Rezai
2011/0301679 A1 12/2011 Rezai et al.
2011/0306851 A1 12/2011 Wang
2011/0306904 A1 12/2011 Jacobson et al.
2011/0306997 A9 12/2011 Roschak et al.
2011/0319958 A1 12/2011 Simon et al.
2012/0004656 A1 1/2012 Jackson et al.
2012/0015019 A1 1/2012 Pacetti et al.
2012/0016256 A1 1/2012 Mabary et al.
2012/0016358 A1 1/2012 Mayse et al.
2012/0016363 A1 1/2012 Mayse et al.
2012/0016364 A1 1/2012 Mayse et al.
2012/0029261 A1 2/2012 Deem et al.
2012/0029500 A1 2/2012 Jenson
2012/0029512 A1 2/2012 Willard et al.
2012/0029591 A1 2/2012 Simon et al.
2012/0029601 A1 2/2012 Simon et al.
2012/0041412 A1 2/2012 Roth et al.
2012/0041509 A1 2/2012 Knudson et al.
2012/0071870 A1 3/2012 Salahieh et al.
2012/0078096 A1 3/2012 Krolik et al.
2012/0083734 A1 4/2012 Ayres et al.
2012/0089078 A1 4/2012 Deem et al.
2012/0089138 A1 4/2012 Edwards et al.
2012/0101326 A1 4/2012 Simon et al.
2012/0101413 A1 4/2012 Beetel et al.
2012/0109278 A1 5/2012 Sih
2012/0143132 A1 6/2012 Orlowski
2012/0143177 A1 6/2012 Avitall
2012/0143179 A1 6/2012 Avitall
2012/0143181 A1 6/2012 Demarais et al.
2012/0157986 A1 6/2012 Stone et al.
2012/0157987 A1 6/2012 Steinke et al.
2012/0157988 A1 6/2012 Stone et al.
2012/0157989 A1 6/2012 Stone et al.
2012/0158101 A1 6/2012 Stone et al.
2012/0165803 A1 6/2012 Bencini et al.
2012/0184801 A1 7/2012 Simon et al.
2012/0185020 A1 7/2012 Simon et al.
2012/0191081 A1 7/2012 Markowitz
2012/0191082 A1 7/2012 Markowitz
2012/0197100 A1 8/2012 Razavi et al.
2012/0197246 A1 8/2012 Mauch
2012/0197251 A1 8/2012 Edwards et al.
2012/0203067 A1 8/2012 Higgins et al.
2012/0203216 A1 8/2012 Mayse et al.
2012/0203222 A1 8/2012 Mayse et al.
2012/0209118 A1 8/2012 Warnking
2012/0209259 A1 8/2012 Danek et al.
2012/0209261 A1 8/2012 Mayse et al.
2012/0209296 A1 8/2012 Mayse et al.
2012/0221087 A1 8/2012 Parnis et al.
2012/0232436 A1 9/2012 Warnking
2012/0245415 A1 9/2012 Emura et al.
2012/0253442 A1 10/2012 Gliner et al.
2012/0259263 A1 10/2012 Celermajer et al.
2012/0259269 A1 10/2012 Meyer
2012/0259326 A1 10/2012 Brannan et al.
2012/0265280 A1 10/2012 Errico et al.
2012/0289952 A1 11/2012 Utley et al.
2012/0290035 A1 11/2012 Levine et al.
2012/0294424 A1 11/2012 Chin et al.
2012/0296329 A1 11/2012 Ng
2012/0302909 A1 11/2012 Mayse et al.
2012/0310233 A1 12/2012 Dimmer et al.
2012/0316552 A1 12/2012 Mayse et al.
2012/0316559 A1 12/2012 Mayse et al.
2012/0330298 A1 12/2012 Ganz et al.
2013/0012844 A1 1/2013 Demarais et al.
2013/0012866 A1 1/2013 Deem et al.
2013/0012867 A1 1/2013 Demarais et al.
2013/0035576 A1 2/2013 O'Grady et al.
2013/0123751 A1 5/2013 Deem et al.
2013/0289555 A1 10/2013 Mayse et al.
2013/0289556 A1 10/2013 Mayse et al.
2013/0296647 A1 11/2013 Mayse et al.
2013/0303948 A1 11/2013 Deem et al.
2013/0310822 A1 11/2013 Mayse et al.
2013/0345700 A1 12/2013 Hlavka et al.
2014/0018789 A1 1/2014 Kaplan et al.
2014/0018790 A1 1/2014 Kaplan et al.
2014/0025063 A1 1/2014 Kaplan et al.
2014/0186341 A1 7/2014 Mayse
2014/0236148 A1 8/2014 Hlavka et al.
2014/0257271 A1 9/2014 Mayse et al.
2014/0276792 A1 9/2014 Kaveckis et al.
2014/0371809 A1 12/2014 Parnis et al.
2015/0051597 A1 2/2015 Mayse et al.
2016/0220851 A1 8/2016 Mayse et al.
2017/0014571 A1 1/2017 Deem et al.
2018/0028748 A1 2/2018 Deem et al.
2018/0199993 A1 7/2018 Mayse et al.
2019/0105102 A1 4/2019 Mayse et al.
2019/0142510 A1 5/2019 Mayse et al.
2020/0060750 A1 2/2020 Kaveckis et al.
2020/0085495 A1 3/2020 Dimmer et al.
2020/0222114 A1 7/2020 Johnson et al.
2020/0268436 A1 8/2020 Mayse
2020/0360677 A1 11/2020 Deem et al.

FOREIGN PATENT DOCUMENTS

CN 1777396 A 5/2006
CN 101115448 A 1/2008
CN 101209217 A 7/2008
CN 101292897 A 10/2008
CN 101437477 A 5/2009
CN 101448466 A 6/2009
CN 101522106 A 9/2009

(56) References Cited

FOREIGN PATENT DOCUMENTS

| | | | |
|---|---|---|---|
| CN | 101115448 | B | 5/2010 |
| DE | 19529634 | A1 | 2/1997 |
| DE | 19952505 | A1 | 5/2001 |
| EP | 0189329 | A3 | 6/1987 |
| EP | 0286145 | A2 | 10/1988 |
| EP | 0280225 | A3 | 3/1989 |
| EP | 0286145 | A3 | 10/1990 |
| EP | 0282225 | B1 | 6/1992 |
| EP | 0643982 | A1 | 3/1995 |
| EP | 0908713 | A1 | 4/1999 |
| EP | 1064886 | A1 | 1/2001 |
| EP | 1143864 | A2 | 10/2001 |
| EP | 1169972 | A1 | 1/2002 |
| EP | 1271384 | A1 | 1/2003 |
| EP | 1281366 | A2 | 2/2003 |
| EP | 0908150 | B1 | 5/2003 |
| EP | 0768091 | B1 | 7/2003 |
| EP | 1326548 | A1 | 7/2003 |
| EP | 1326549 | A1 | 7/2003 |
| EP | 1400204 | A1 | 3/2004 |
| EP | 1297795 | B1 | 8/2005 |
| EP | 1588662 | A2 | 10/2005 |
| EP | 2320821 | B1 | 10/2012 |
| FR | 2659240 | B1 | 7/1997 |
| GB | 2233293 | A | 1/1991 |
| GB | 2233293 | B | 2/1994 |
| JP | S59167707 | A | 9/1984 |
| JP | H06339453 | A | 12/1994 |
| JP | H07289557 | A | 11/1995 |
| JP | H0947518 | A | 2/1997 |
| JP | H09243837 | A | 9/1997 |
| JP | H1026709 | A | 1/1998 |
| JP | 2001037773 | A | 2/2001 |
| JP | 2002508989 | A | 3/2002 |
| JP | 2002541905 | A | 12/2002 |
| RU | 2053814 | C1 | 2/1996 |
| RU | 2091054 | C1 | 9/1997 |
| SU | 545358 | A1 | 2/1977 |
| WO | WO-8911311 | A1 | 11/1989 |
| WO | WO-9301862 | A1 | 2/1993 |
| WO | WO-9316632 | A1 | 9/1993 |
| WO | WO-9407446 | A1 | 4/1994 |
| WO | WO-9501075 | A1 | 1/1995 |
| WO | WO-9502370 | A2 | 1/1995 |
| WO | WO-9510322 | A1 | 4/1995 |
| WO | WO-9604860 | A1 | 2/1996 |
| WO | WO-9610961 | A1 | 4/1996 |
| WO | WO-9725917 | A1 | 7/1997 |
| WO | WO-9732532 | A1 | 9/1997 |
| WO | WO-9733715 | A1 | 9/1997 |
| WO | WO-9737715 | A1 | 10/1997 |
| WO | WO-9740751 | A1 | 11/1997 |
| WO | WO-9818391 | A1 | 5/1998 |
| WO | WO-9844854 | A1 | 10/1998 |
| WO | WO-9852480 | A1 | 11/1998 |
| WO | WO-9856234 | A1 | 12/1998 |
| WO | WO-9856324 | A1 | 12/1998 |
| WO | WO-9903413 | A1 | 1/1999 |
| WO | WO-9858681 | A3 | 3/1999 |
| WO | WO-9913779 | A2 | 3/1999 |
| WO | WO-9932040 | A1 | 7/1999 |
| WO | WO-9935986 | A1 | 7/1999 |
| WO | WO-9935988 | A1 | 7/1999 |
| WO | WO-9942047 | A1 | 8/1999 |
| WO | WO-9964109 | A1 | 12/1999 |
| WO | WO-0010598 | A2 | 3/2000 |
| WO | WO-0051510 | A1 | 9/2000 |
| WO | WO-0062699 | A2 | 10/2000 |
| WO | WO-0066017 | A1 | 11/2000 |
| WO | WO-0100114 | A1 | 1/2001 |
| WO | WO-0103642 | A1 | 1/2001 |
| WO | WO-0170114 | A1 | 9/2001 |
| WO | WO-0189526 | A1 | 11/2001 |
| WO | WO-0205720 | A1 | 1/2002 |
| WO | WO-0205868 | A2 | 1/2002 |
| WO | WO-0232333 | A1 | 4/2002 |
| WO | WO-0232334 | A1 | 4/2002 |
| WO | WO-03073358 | A2 | 9/2003 |
| WO | WO-03086524 | A1 | 10/2003 |
| WO | WO-03088820 | A2 | 10/2003 |
| WO | WO-2004078252 | A2 | 9/2004 |
| WO | WO-2004082736 | A2 | 9/2004 |
| WO | WO-2004101028 | A2 | 11/2004 |
| WO | WO-2005006963 | A2 | 1/2005 |
| WO | WO-2005006964 | A2 | 1/2005 |
| WO | WO-2006053308 | A2 | 5/2006 |
| WO | WO-2006053309 | A2 | 5/2006 |
| WO | WO-2006116198 | A2 | 11/2006 |
| WO | WO-2007058780 | A2 | 5/2007 |
| WO | WO-2007061982 | A1 | 5/2007 |
| WO | WO-2007092062 | A1 | 8/2007 |
| WO | WO-2007094828 | A2 | 8/2007 |
| WO | WO-2007143665 | A2 | 12/2007 |
| WO | WO-2008005953 | A2 | 1/2008 |
| WO | WO-2008024220 | A1 | 2/2008 |
| WO | WO-2008051706 | A2 | 5/2008 |
| WO | WO-2008063935 | A2 | 5/2008 |
| WO | WO-2008071914 | A2 | 6/2008 |
| WO | WO-2009009236 | A1 | 1/2009 |
| WO | WO-2009015278 | A1 | 1/2009 |
| WO | WO-2009082433 | A2 | 7/2009 |
| WO | WO-2009126383 | A2 | 10/2009 |
| WO | WO-2009137819 | A1 | 11/2009 |
| WO | WO-2010110785 | A1 | 9/2010 |
| WO | WO-2011060200 | A1 | 5/2011 |

OTHER PUBLICATIONS

Accad M., "Single-Step Renal Denervation with the OneShotTM Ablation System," Presentation at the Leipzig Interventional Course 2012 in Leipzig, Germany, Jan. 26, 2012, 11 pages.

Ackrad Labs., "Adult Esophageal Balloon Catheter Set," Device Description Pamphlet, Manufactured by Cooper Surgical, Trumbull, CT, 2 pages.

Ahnert-Hilger., et al., "Introduction of Macromolecules into Bovine Adrenal-Medullary Chromaffin Cells and Rat Pheochromocytoma Cells (PC12) by Permeabilization with Streptolysin O: Inhibitory Effect of Teanus Toxin on Catecholamine Secretion," J. Neurochem, Jun. 1989, vol. 52 (6), pp. 1751-1758.

An S S., et al., "Airway Smooth Muscle Dynamics; A Common Pathway of Airway Obstruction in Asthma," European Respiratory Journal, 2007, vol. 29 (5), pp. 834-860.

Application and File History for U.S. Appl. No. 12/913,702, filed Oct. 27, 2010, Inventor: Martin L. Mayse, et al.

Application and File History for U.S. Appl. No. 13/245,529, filed Sep. 26, 2011, inventors Mayse et al.

Application and File History for U.S. Appl. No. 13/245,537, filed Sep. 26, 2011, issued as U.S. Pat. No. 8,932,289 on Jan. 13, 2015, inventors Mayse et al.

Application and File History for U.S. Appl. No. 13/894,920, filed May 15, 2013, inventors Mayse et al.

Application and File History for U.S. Appl. No. 13/931,208, filed Jun. 28, 2013, issued as U.S. Pat. No. 8,777,943 on Jul. 15, 2014, inventors Mayse et al.

Application and File History for U.S. Appl. No. 13/930,825, filed Jun. 28, 2013, issued as U.S. Pat. No. 8,777,943 on Jul. 15, 2014, inventors Mayse et al.

Application and File History for U.S. Appl. No. 13/931,246, filed Jun. 28, 2013, inventors Mayse et al.

Application and File History for U.S. Appl. No. 15/922,485, filed Mar. 15, 2018, inventors Mayse et al.

Application and File History for U.S. Appl. No. 14/601,717, filed Jan. 21, 2015, inventors Mayse et al.

Awadh N., et al., "Airway Wall Thickness in Patients with Near Fatal Asthma and Control Groups: Assessment with High Resolution Computed Tomographic Scanning," Thorax, 1998, vol. 53, pp. 248-253.

Babichev., et al., "Clinico-Morphological Comparisons in Patients with Bronchial Asthma after Denervation of the Lungs," Sov Med, 1985, vol. 12, pp. 13-16.

(56) References Cited

OTHER PUBLICATIONS

Babichev., et al., "Long-term Results of Surgical Treatment of Bronchial Asthma Based on Adaptive Response," Khirurgiia (Mosk), 1993, vol. 4, pp. 5-11.
Babichev., et al., "Partial Deneration of the Lungs in Bronchial Asthma," Khirurgiia (Mosk), 1985, vol. 4, pp. 31-35.
Barlaw., "Surgical Treatment of Asthma," Postgrad Med. Journal, 1949, vol. 25, pp. 193-196.
Bel E H., "Hot Stuff: Bronchial Thermoplasty for Asthma," American Journal of Respiratory and Critical Care Medicine, 2006, vol. 173, pp. 941-942.
Bertog S., "Covidien-Maya: OneShot.TM.," presentation at the 2012 Congenital & Structural Interventions Congress in Frankfurt, Germany, Jun. 28, 2012, 25 pages.
Bester., et al., "Recovery of C-Fiber-Induced Extravasation Following Peripheral Nerve Injury in the Rat," Experimental Neurology, 1998, vol. 154, pp. 628-636.
Bigalke., et al., "Clostridial Neurotoxins," Handbook of Experimental Pharmacology (Aktories, K., and Just, I., eds), 2000, vol. 145, pp. 407-443.
Bittner., et al., "Isolated Light Chains of Botulinum Neurotoxins Inhibit Exocytosis," The Journal of Biological Chemistry, 1989, vol. 264(18), pp. 10354-10360.
Blindt., et al., "Development of a New Biodegradable Intravascular Polymer Stent with Simultaneous Incorporation of Bioactive Substances," The International Journal of Artificial Organs, 1999, vol. 22 (12), pp. 843-853.
Boxem V Tjm., et al., "Tissue Effects of Bronchoscopic Electrocautery," Chest, Mar. 2000, vol. 117(3), pp. 887-891.
Bradley., et al., "Effect of Vagotomy on the Breathing Pattern and Exercise Ability in Emphysematous Patients," Clinical Science, 1982, vol. 62, pp. 311-319.
Breekveldt-Postma., et al., "Enhanced Persistence with Tiotropium Compared with Other Respiratory Drugs in COPD," Respiratory Medicine, 2007, vol. 101, pp. 1398-1405.
Brody., et al., "Mucociliary Clearance After Lung Denervation and Bronchial Transection," J Applied Physiology, 1972, vol. 32 (2), pp. 160-164.
Brown R H., et al., "Effect of Bronchial Thermoplasty on Airway Distensibility," European Respiratory Journal, Aug. 2005, vol. 26 (2), pp. 277-282.
Brown R H., et al., "In Vivo Evaluation of the Effectiveness of Bronchial Thermoplasty with Computed Tomography," Journal of Applied Physiology, 2005, vol. 98, pp. 1603-1606.
Buzzi., "Diphtheria Toxin Treatment of Human Advanced Cancer," Cancer Research, 1982, vol. 42, pp. 2054-2058.
Canning., et al., "Reflex Mechanisms in Gastroesophageal Reflux Disease and Asthma," The American Journal of Medicine, 2003, vol. 115 (3A), pp. 45S-48S.
Canning., "Reflex Regulation of Airway Smooth Muscle Tone," J Appl. Physiol, 2006, vol. 101, pp. 971-985.
Castro M., et al., "Effectiveness and Safety of Bronchial Thermoplasty in the Treatment of Severe Asthma: a Multicenter, Randomized, Double-Blind, Sham-Controlled Clinical Trial," American Journal of Respiratory and Critical Care Medicine, 2010, vol. 181, pp. 116-124.
Chaddock., et al., "Expression and Purification of Catalytically Active, Non-Toxic Endopeptidase Derivatives of Clostridium Botulinum Toxin Type A," Protein Expression and Purification, Jul. 2002, vol. 25 (2), pp. 219-228.
Chang., "Cell Poration and Cell Fusion Using an Oscillating Electric Field," Biophys. J, 1989, vol. 56 (4), pp. 641-652.
Chernyshova., et al., "The Effect of Low-Energy Laser Radiation in the Infrared Spectrum on Bronchial Patency in Children with Bronchial Asthma," Vopr Kurortol Fizioter Lech Fiz Kult, 1995, vol. 2, pp. 11-14, (6 pages of English translation).
Chhajed P., "Will There be a Role for Bronchoscopic Radiofrequency Ablation," J Bronchol, 2005, vol. 12 (3), p. 184.
Chumakov., et al., "Morphologic Studies of Bronchial Biopsies in Chronic Bronchitis Before and After Treatment," Arkh Patol, 1995, vol. 57 (6), pp. 21-25.(English Abstract and Translation, 8 pages).
Cox G., et al., "Asthma Control During the Year After Bronchial Thermoplasty," The New England Journal of Medicine, Mar. 29, 2007, vol. 356 (13), pp. 1327-1337.
Cox G., et al., "Bronchial Thermoplasty for Asthma," American Journal of Respiratory and Critical Care Medicine, 2006, vol. 173, pp. 965-969.
Cox G., et al., "Bronchial Thermoplasty: Long-Term Follow-up and Patient Satisfaction," 2004, 1 page.
Cox G., et al., "Bronchial Thermoplasty: One-Year Update, American Thoracic Society Annual Meeting," 2004, 1 page.
Cox G., et al., "Clinical Experience with Bronchial Thermoplasty for the Treatment of Asthma," Chest 124, 2003, p. 106S.
Cox G., et al., "Development of a Novel Bronchoscope Therapy for Asthma," Journal of Allergy and Clinical Immunology, 2003, 1 page.
Cox G., et al., "Early Clinical Experience With Bronchial Thermoplasty for the Treatment of Asthma," 2002, p. 1068.
Cox G., et al., "Impact of Bronchial Thermoplasty on Asthma Status: Interim Results From the AIR Trial," European Respiratory Society Annual Meeting, Munich, Germany, 2006, 1 page.
Cox G., et al., "Radiofrequency Ablation of Airway Smooth Muscle for Sustained Treatment of Asthma: Preliminary Investigations," European Respiratory Journal, 2004, vol. 24, pp. 659-663.
Crimi., et al., "Protective Effects of Inhaled Ipratropium Bromide on Bronchoconstriction Induced by Adenosine and Methacholine in Asthma," Eur Respir J, 1992, vol. 5, pp. 560-565.
Danek C J., et al., "Asthma Intervention Research (AIR) Trial Evaluating Bronchial Hermoplasty.TM.; Early Results," American Thoracic Society Annual Meeting, 2002, 1 page.
Danek C J., et al., "Bronchial Thermoplasty Reduces Canine Airway Responsiveness to Local Methacholine Challenge," American Thoracic Society Annual Meeting, 2002, 1 page.
Danek C J., et al., "Reduction in Airway Hyperesponsiveness to Methacholine by the Application of RF Energy in Dogs," J Appl Physiol, 2004, vol. 97, pp. 1946-1953.
De Paiva., et al., "Light Chain of Botulinum Neurotoxin is Active in Mammalian Motor Nerve Terminals When Delivered Via Liposomes," FEBS Lett, Dec. 1990, vol. 17:277(1-2), pp. 171-174.
Dierkesmann., et al., "Indication and Results of Endobronchial Laser Therapy," Lung, 1990, vol. 168, pp. 1095-1102.
Dimitrov-Szokodi., et al., "Lung Denervation in the Therapy of Intractable Bronchial Asthma," J. Thoracic Surg, Feb. 1957, vol. 33 (2), pp. 166-184.
Donohue., et al., "A 6-Month, Placebo-Controlled Study Comparing Lung Function and Health Status Changes in COPD Patients Treated With Tiotropium or Salmeterol," Chest, 2002, vol. 122, pp. 47-55.
Feshenko., et al., "Clinico-Morphological Comparisons in the Laser Therapy of Chronic Bronchitis Patients," Lik Sprava, 1993, vol. 10-12, pp. 75-79.(English abstract, 1 Page).
Friedman., et al., "Healthcare Costs with Tiotropium Plus Usual Care versus Usual Care Alone Following 1 Year of Treatment in Patients with Chronic Obstructive Pulmonary Disorder (COPD)," Pharmacoeconomics, 2004, vol. 22 (11), pp. 741-749.
Gaude., G.S., "Pulmonary Manifestations of Gastroesophageal Reflux Disease," Annals of Thoracic Medicine, Jul.-Sep. 2009, vol. 4 (3), pp. 115-123.
Gelb., et al., "Laser in Treatment of Lung Cancer," American College of Chest Physicians, Nov. 1984, vol. 86 (5), pp. 662-666.
George., et al., "Factors Associated With Medication Nonadherence in Patients With COPD," Chest, 2005, vol. 128, pp. 3198-3204.
Gerasin., et al., "Endobronchial Electrosurgery," Chest, 1988, vol. 93, pp. 270-274.
Gibson., et al., "Gastroesophageal Reflux Treatment for Asthma in Adults and Children," Cochrane Database Syst. Rev. 2:CD001496, 2003. (Abstract only).
Glanville., et al., "Bronchial Responsiveness after Human Heart-Lung Transplantation," Chest, 1990, vol. 97 (6), pp. 1360-1366.

(56) References Cited

OTHER PUBLICATIONS

Glanville., et al., "Bronchial Responsiveness to Exercise after Human Cardiopulmonary Transplantation," Chest, 1989, vol. 96 (2), pp. 281-286.
"Global Strategy for Asthma Management and Prevention," 2002, 192 pages.
Gosens., et al., "Muscarinic Receptor Signaling in the Pathophysiology of Asthma and COPD," Respiratory Research, 2006, vol. 7 (73), pp. 1-15.
Groeben., et al., "High Thoracic Epidural Anesthesia Does Not Alter Airway Resistance and Attenuates the Response to an Inhalational Provocation Test in Patients with Bronchial Hyperreactivity," Anesthesiology, 1994, vol. 81 (4), pp. 868-874.
Guarini., et al., "Efferent Vagal Fibre Stimulation Blunts Nuclear Factor-κB Activation and Protects Against Hypovolemic Hemmorrhagic Shock," Circulation, 2003, vol. 107, pp. 1189-1194.
Guzman., et al., "Bioeffects Caused by Changes in Acoustic Cavitation Bubble Density and Cell Concentration: A Unified Explanation Based on Cell-to-Bubble Ratio and Blast Radius," Ultrasound in medicine & biology, 2003, vol. 29 (8), pp. 1211-1222.
Hainsworth., et al., "Afferent Lung Denervation by Brief Inhalation of Steam," Journal of Applied Physiology, May 1972, vol. 34 (5), pp. 708-714.
Harding., "Pulmonary Manifestations of GERD: Pathophysiology and Management," Division of Pulmonary, Allergy, and Critical Care Medicine—University of Alabama at Birmingham: 4 pages.
Harding., "Recent Clinical Investigations Examining the Association of Asthma and Gastroesophageal Reflux," The American Journal of Medicine, 2003, vol. 115 (Suppl 3A), pp. 39S-44S. (Abstract only).
Hiraga., "Experimental surgical therapy of bronchial asthma. The effect of denervation in dogs," Nihon Kyobu Shikkan Gakkai Zasshi, 1981, vol. 19 (1), pp. 46-56.
Hoffmann., et al., "Inhibition of Histamine-Induced Bronchoconstriction in Guinea Pig and Swine by Pulsed Electrical Vagus Nerve Stimulation," Neuromodulation: Technology at the Neural Interface, 2009, pp. 1-9.
Hogg J.C., et a., "The Pathology of Asthma," APMIS, Oct. 1997, vol. 105 (10), pp. 735-745.
Hooper., et al., "Endobronchial Electrocautery," Chest, 1985, vol. 87 (6), pp. 712-714.
International Preliminary Report on Patentability No. PCT/US2013/041189, mailed on Nov. 27, 2014, 12 pages.
International Search Report and Written Opinion for PCT Application No. PCT/US2013/041189, mailed on Dec. 4, 2013, 16 pages.
Ivanyuta O M., et al., "Effect of Low-Power Laser Irradiation of Bronchia Mucosa on the State of Systemic and Local Immunity in Patients with Chronic Bronchitis," Problemy Tuberkuleza, 1991, vol. 6, pp. 26-29.
James., et al., "The Mechanics of Airway Narrowing in Asthma," The American Review of Respiratory Disease, 1989, vol. 139, pp. 242-246.
Jammes., et al., "Assessment of the Pulmonary Origin of Bronchoconstrictor Vagal Tone," The Journal of physiology, 1979, vol. 291, pp. 305-316.
Janssen L. J., "Asthma therapy: how far have we come, why did we fail and where should we go next?," European Respiratory Journal, 2009, vol. 33, pp. 11-20.
Jiang., et al., "Effects of Antireflux Treatment on Bronchial Hyperresponsiveness and Lung Function in Asthmatic Patients with Gastroesophageal Reflux Disease," World Journal of Gastroenterology, 2003, vol. 9, pp. 1123-1125. (Abstract only).
Johnson S R., et al., "Synthetic Functions of Airway Smooth Muscle in Asthma," Trends in Pharmacological Sciences, Aug. 1997, vol. 18 (8), pp. 288-292.
Karashurov., et al., "Electrostimulation in the Therapy of Bronchial Asthma," Klin Med (Mosk), 2001, vol. 79 (11), pp. 39-41.
Karashurov., et al., "Radiofrequency Electrostimulation of Carotid Sinus Nerves for the treatment of Bronchial Asthma," Khirurgiia (Mosk), 1999, vol. 12, pp. 4-6.
Khmel'Kova et al., "Does laser irridation affect bronchial obstruction?," Probl Tuberk, 1995, vol. 3, pp. 41-42 (Abstract only).
Khoshoo., et al., "Role of Gastroesophageal Reflux in Older Children with Persistent Asthma," Chest, 2003, vol. 123, pp. 1008-1013. (Abstract only).
Kiljander., "The Role of Proton Pump Inhibitors in the Management of Gastroesophageal Reflux Disease-Related Asthma and Chronic Cough," The American Journal of Medicine, 2003, vol. 115 (Suppl 3A), pp. 65S-71S. (Abstract only.).
Kistner., et al., "Reductive Cleavage of Tetanus Toxin and Botulinum Neurotoxin A by the Thioredoxin System from Brain," Naunyn-Schmiedebergs Arch Pharmacal, Feb. 1992, vol. 345 (2), pp. 227-234.
Kitamura S., "Color Atlas of Clinical Application of Fiberoptic Bronchoscopy," 1990, Year Book Medical Publishers, p. 17.
Kletskin., et al., "Value of Assessing the Autonomic Nervous System in Bronchial Asthma in Selecting the Surgical Treatment Method," Khirurgiia (Mosk), 1987, vol. 7, pp. 91-95.
Kliachkin., et al., "Bronchoscopy in the Treatment of Bronchial Asthma of Infectious Allergic Origin," Terapeuticheskil arkhiv, 1982, vol. 54 (4), pp. 76-79.
Korochkin., et al., "Use of a Helium-Neon Laser in Combined Treatment of Bronchial Asthma," New Developments in Diagnostics and Treatment, 1990, 9 pages.
Korpela., et al., "Comparison of Tissue Reactions in the Tracheal Mucosa Surrounding a Bioabsorbable and Silicone Airway Stents," Annals of Thoracic Surgery, 1998, vol. 66, pp. 1772-1776.
Kozaki., et al., "New Surgical Treatment of Bronchial Asthma—Denervation of the Hilus Pulmonis (2)," Nippon Kyobu Geka Gakkai Zasshi, 1974, vol. 22 (5), pp. 465-466.
Kraft M., "The Distal Airways: Are they Important in Asthma?," European Respiratory, 1999, pp. 1403-1417.
Kreitman., "Taming Ricin Toxin," Nature Biotechnology, 2003, vol. 21, pp. 372-374.
Kuntz., "The Autonomic Nervous System in Relation to the Thoracic Viscera," Chest, 1944, vol. 10, pp. 1-18.
Lavioletts et al., "Asthma Intervention Research (AIR) Trial: Early Safety Assessment of Bronchial Thermoplasty," 2004, 1 page.
Leff., et al., "Bronchial Thermoplasty Alters Airway Smooth Muscle and Reduces Responsiveness in Dogs; A Possible Procedure for the Treatment of Asthma," American Thoracic Society Annual Meeting, 2002, 1 page.
Lennerz., et al., "Electrophysiological Characterization of Vagal Afferents Relevant to Mucosal Nociception in the Rat Upper Oesophagus," The Journal of physiology, 2007, vol. 582 (1), pp. 229-242.
Levin., "The Treatment of Bronchial Asthma by Dorsal Sympathectomy," Annals of Surgery, 1935, vol. 102 (2), pp. 161-170.
Lim E E., et al., "Botulinum Toxin: A Novel Therapeutic Option for Bronchial Asthma?," Medical Hypotheses, 2006, vol. 66, pp. 915-919.
Liou., et al., "Causative and Contributive Factors to Asthmas Severity and Patterns of Medication Use in Patients Seeking Specialized Asthma Care," Chest, 2003, vol. 124, pp. 1781-1788. (Abstract only).
Lokke., et al., "Developing COPD: A 25 Year Follow Up Study of the General Population," Thorax, 2006, vol. 61, pp. 935-939.
Lombard., et al., "Histologic Effects of Bronchial Thermoplasty of Canine and Human Airways," American Thoracic Society Annual Meeting, 2002, 1 page.
Macklem P T., "Mechanical Factors Determining Maximum Bronchoconstriction, European Respiratory Journal," Jun. 1989, vol. 6, pp. 516s-519s.
Maesen., et al., "Tiotropium Bromide, A New Long-Acting Antimuscarinic Bronchodilator: A Pharmacodynamic Study in Patients with Chronic Obstructive Pulmonary Disease (COPD)," The European Respiratory Journal, 1995, vol. 8, pp. 1506-1513.
Magnussen., et al., "Effect of Inhaled Ipratropium Bromide on the Airway Response to Methacholine, Histamine, and Exercise in Patients with Mild Bronchial Asthma," Respiration, 1992, vol. 59, pp. 42-47.

(56) References Cited

OTHER PUBLICATIONS

Maltais., et al., "Improvements in Symptom-Limited Exercise Performance Over 8 h With Once-Daily Tiotropium in Patients With COPD," Chest, 2005, vol. 128, pp. 1168-1178.
Martin N., et al., "Bronchial Thermoplasty for the Treatment of Asthma," Current Allergy and Asthma Reports, Jan. 2009, vol. 9 (1), pp. 88-95.
Mathew., et al., "Gastro-Oesophageal Reflux and Bronchial Asthma: Current Status and Future Directions," Postgraduate Medical Journal, 2004, vol. 80, pp. 701-705.
Matthias O., et al., "Fisherman's Pulmonary Diseases and Disorders," Functional Design of the Human Lung for Gas Exchange, McGraw Hill Medical, New York, Edition 4, 2008, Chapter 2(Abstract only).
Mayse M., et al., "Clinical Pearls for Bronchial Thermoplasty," J Bronchol, Apr. 2007, vol. 14 (2), pp. 115-123.
McEvoy C E., et al., "Changing the Landscape: Bronchial Thermoplasty Offers a Novel Approach to Asthma Treatment," Advance for Managers of Respiratory Care, Oct. 24-25, 2007, pp. 22-25.
McKay., et al., "Autocrine Regulation of Asthmatic Airway Inflammation: Role of Airway Smooth Muscle," Respiratory Research, 2002, vol. 3 (11), pp. 1-13.
Mehta., et al., "Effect of Endobronchial Radiation therapy on Malignant Bronchial Obstruction," Chest, Mar. 1990, vol. 97 (3), pp. 662-665.
Meshalkin., et al., "Partial Denervation of the Pulmonary Hilus as One of the Methods of Surgical Treatment of Bronchial Asthma," Grudnaia Khirurgiia, 1975, vol. 1, pp. 109-111.
Michaud G., et al., "Positioned for Success: Interest in Diagnostic and Therapeutic Bronchoscopy is Growing," Advance for Managers of Respiratory Care, Jul.-Aug. 2008, pp. 40, 42-43.
Miller J D., et al., "A Prospective Feasibility Study of Bronchial Thermoplasty in the Human Airway," 2005, vol. 127 (6), pp. 1999-2006.
Miller J D., et al., "Bronchial Thermoplasty is Well Tolerated by Non-Asthmatic Patients Requiring Lobectomy," American Thoracic Society Annual Meeting, 2002, 1 page.
Mitzner W., "Airway Smooth Muscle the appendix of the Lung," American Journal of Respiratory and Critical Care Medicine, 2004, vol. 169, pp. 787-790.
Mitzner W., "Bronchial Thermoplasty in Asthma," Allergology International, 2006, vol. 55, pp. 225-234.
Montaudon M., et al., "Assessment of Bronchial Wall Thickness and Lumen Diameter in Human Adults Using Multi-Detector Computed Tomography: Comparison with Theoretical Models," Journal of Anatomy, 2007, vol. 211, pp. 579-588.
Moore K.L., "Clinically Oriented Anatomy," Williams & Wilkins, Baltimore, 1985, 2nd edition, pp. 85 and 87(Abstract only).
Netter F H., Respiratory System: A Compilation of Paintings Depicting Anatomy and Embryology, Physiology, Pathology, Pathophysiology, and Clinical Features and Treatment of Diseases, In the CIBA Collection of Medical Illustrations M.B. Divertie, ed., Summit: New Jersey, 1979, vol. 7, pp. 119-135.
Netter F H., "The Ciba Collection of Medical Illustrations," Respiratory System, CIBA-GEIGY Corporation, West Caldwell, 1979, vol. 7, p. 23, section 1. (Abstract only).
O'Connor., et al., "Prolonged Effect of Tiotropium Bromide on Methacholine-induced Bronchoconstriction in Asthma," American Journal of Respiratory and Critical Care Medicine, 1996, vol. 154, pp. 876-880.
O'Sullivan M P., et al., "Apoptosis in the Airways: Another Balancing Act in the Epithelial Program," American Journal of Respiratory Cell and Molecular Biology, 2003, vol. 29, pp. 3-7.
Ovcharenko., et al., "Endobronchial Use of Low-Frequency Ultrasound and Ultraviolet Laser Radiation in the Complex Treatment of Patients With Suppurative Bronchial Diseases," Problemy Tuberkuleza, 1997, vol. 3, pp. 40-42. (Abstract only).
Overholt., "Glomectomy for Asthma," Diseases of the Chest, 1961, vol. 40, pp. 605-610.
Patent Examination Report mailed May 1, 2014 for Australian Patent Application No. 2009244058, filed May 8, 2009, 4 pages.
Pavord I D., et al., "Safety and Efficacy of Bronchial Thermoplasty in Symptomatic, Severe Asthma," American Journal of Respiratory and Critical Care Medicine, 2007, vol. 176, pp. 1185-1191.
Peter K. Jeffery, "Remodeling in Asthma and Chronic Obstructive Lung Disease," American Journal of Respiratory and Critical Care Medicine, 2001, vol. 164 (10), pp. S28-S38.
Peters, et al., "Tiotropium Bromide Step-Up Therapy for Adults with Uncontrolled Asthma," New England Journal of Medicine, Oct. 28, 2010, vol. 363 (18), pp. 1715-1726.
Petrou et al., "Bronchoscopic Diathermy Resection and Stent Insertion: a Cost Effective Treatment for Tracheobronchial Obstruction," Thorax, 1993, vol. 48, pp. 1156-1159.
Polosukhin., "Dynamics of the Ultrastructural Changes in Blood and Lymphatic Capillaries of Bronchi in Inflammation and Following Endobronchial Laser Therapy," Virchows Arch, 1997, vol. 431, pp. 283-290.
Polosukhin., "Regeneration of Bronchial Epithelium of Chronic Inflammatory Changes Under Laser Treatment," Pathology, Research and Practice, 1996, vol. 192 (9), pp. 909-918.
Polosukhin., "Ultrastructural Study of the Destructive and Repair Processes in Pulmonary Inflammation and Following Endobronchial Laser Therapy," Virchows Arch, 1999, vol. 435, pp. 13-19.
Polosukhin., "Ultrastructure of the Blood and Lymphatic Capillaries of the Respiratory Tissue During Inflammation and Endobronchial Laser Therapy," Ultrastructural Pathology, 2000, vol. 24, pp. 183-189.
Printout of a Selected List of Reference for Respiratory Development from PubMed Aug. 1999; UNSW Embryo-Respiratory System http://embryology.med.unsw.edu.au/Refer/respire/select.htm; 12 pages, printout dated Oct. 12, 2007.
Provotorov V M., et al., "Clinical Efficacy of Treatment of Patients with Non-Specific Pulmonary Diseases by Using Low-Power Laser Irradiation and Performing Intrapulmonary Drug Administration," Terapevichesky Arkhiv, 1991, vol. 62, pp. 18-23.
Raj., "Editorial," Pain Practice, 2004, vol. 4 (1S), pp. S1-S3.
Ramirez et al., "Sympathetomy in Bronchial Asthma," J. A. M. A., 1925, vol. 84 (26), pp. 2002-2003.
Response to Summons to Attend Oral Proceedings mailed Jun. 2, 2014 from related EP Application No. 10774097.9 filed Oct. 27, 2010, 6 pgs.
Rienhoff., et al., "Treatment of Intractable Bronchial Asthma by Bilateral Resection of the Posterior Pulmonary Plexus," Arch Surg, 1938, vol. 37 (3), pp. 456-469.
Rocha-Singh K J., "Renal Artery Denervation: A Brave New Frontier," Endovascular Today, Feb. 2012, pp. 45-53.
Rubin., et al., "Bronchial Thermoplasty Improves Asthma Status of Moderate to Severe Persistent Asthmatics Over and Above Current Standard-of-Care," American College of Chest Physicians, 2006, 2 pages.
Savchenko., et al., "Adaptation of Regulatory Physiological Systems in Surgical Treatment of Patients with Bronchial Asthma," Klin Med (Mask), 1996, vol. 74 (7), pp. 38-39.
Sengupta., "Part 1 Oral Cavity, Pharynx and Esophagus—Esophageal Sensory Physiology," GI Motility online, 2006, 17 pages.
Seow C Y., et al., "Signal Transduction in Smooth Muscle Historical Perspective on Airway Smooth Muscle: The Saga of a Frustrated Cell," Journal of applied physiology, 2001, vol. 91, pp. 938-952.
Sepulveda., et al., "Treatment of Asthmatic Bronchoconstriction by Percutaneous Low Voltage Vagal Nerve Stimulation: Case Report," Internet Journal of Asthma, Allergy, and Immunology, 2009, vol. 7 (2), 3 pages.
Shaari., et al., "Rhinorrhea is Decreased in Dogs After Nasal Application of Botulinum Toxin," Otolaryngol Head Neck Surgery, Apr. 1995, vol. 112 (4), pp. 566-571.
Sheski F D., et al., "Cryotherapy, Electrocautery, and Brachytherapy," Clinics in Chest Medicine, Mar. 1999, vol. 20 (1), pp. 123-138.
Shesterina M V., et al., "Effect of laser therapy on immunity in patients with bronchial asthma and pulmonary tuberculosis," 1993, pp. 23-26.

(56) References Cited

OTHER PUBLICATIONS

Shore S A., "Airway Smooth Muscle in Asthma—Not Just More of the Same," The New England Journal of Medicine, 2004, vol. 351 (6), pp. 531-532.
Sil'Vestrov., et al., "The Clinico-Pathogenetic Validation and Efficacy of the Use of Low-Energy Laser Irradiation and Glucocorticoids in the Treatment of Bronchial Asthma Patients," Department of Therapy of the Pediatric and Stomatological Faculties of the N.N. Burdenko Voronezh Medical Institute, vol. 63(11), 1991, pp. 87-92.
Simonsson., et al., "Role of Autonomic Nervous System and the Cough Reflex in the Increased Responsiveness of Airways in Patients with Obstructive Airway Disease," The Journal of Clinical Investigation, 1967, vol. 46 (11), pp. 1812-1818.
Simpson., et al., "Isolation and Characterization of the botulinum Neurotoxins," Methods Enzymol, 1988, vol. 165, pp. 76-85.
Smakov., "Denervation of the Lung in the Treatment of Bronchial Asthma," Khirurgiia (Mosk), 1982, vol. 9, pp. 117-120.
Smakov., "Pathogenetic Substantiation of Lung Denervation in Bronchial Asthma and it's Indications," Khirurgiia (Mosk), 1999, vol. 2, pp. 67-69.
Smakov., "Prognostication of the Effect of Therapeutic Bronchoscopy in Patients with Bronchial Asthma According to the State of Local Immunity," Klin Med (Mask), 1995, vol. 73 (5), pp. 76-77.
Solway J., et al., "Airway Smooth Muscle as a Target for Asthma Therapy," The New England Journal of Medicine, Mar. 29, 2007, vol. 356 (13), pp. 1367-1369.
Sontag., et al., "Asthmatics with Gastroesophageal Reflux: Long-term Results of a Randomized Trial of Medical and Surgical Antireflux Therapies," The American Journal of Gastroenterology, 2003, vol. 98, pp. 987-999. (Abstract only.).
Stein., "Possible Mechanisms of Influence of Esophageal Acid on Airway Hyperresponsiveness," The American Journal of Medicine, 2003, vol. 115 (Suppl 3A), pp. 55S-59S. (Abstract only.).
Sterk P J., "Heterogeneity of Airway Hyperresponsiveness: Time for Unconventional, but Traditional Studies," The American Pshychoiogical Society, 2004, pp. 2017-2018.
Sundaram, et al., "An Experimental and Theoretical Analysis of Ultrasound-Induced Permeabilization of Cell Membranes," Biophysical Journal, May 2003, vol. 84 (5), pp. 3087-3101.
Takino., et al., "Surgical Removal of the Carotid Body and its Relation to the Carotid Chemoreceptor and Baroreceptor Reflex in Asthmatics," Dis Chest, 1965, vol. 47, pp. 129-138.
Tashkin., et al., "Long-term Treatment Benefits With Tiotropium in COPD Patients With and Without Short-term Bronchodilator Responses," Chest, 2003, vol. 123, pp. 1441-1449.
Toma T P., "Brave New World for Interventional Bronchoscopy," Thorax, 2005, vol. 60, pp. 180-181.
Trow T., "Clinical Year in Review I, proceedings of the American Thoracic Society," 2006, vol. 3, pp. 553-556.
Tschumperlin D J., et al., "Chronic Effects of Mechanical Force on Airways," Annual Review of Physiology, 2006, vol. 68, pp. 563-583.
Tschumperlin D J., et al., "Mechanical Stimuli to Airway Remodeling," American Journal of Respiratory and Critical Care Medicine, 2001, vol. 164, pp. S90-S94.
Tsugeno., et al., "A Proton-Pump Inhibitor, Rabeprazole, Improves Ventilatory Function in Patients with Asthma Associated with Gastroesophageal Reflux," Scand J Gastroenterol, 2003, vol. (38), pp. 456-461. (Abstract only).
Tsuji., et al., "Biodegradable Stents as a Platform to Drug Loading," International Journal of Cardiovascular Interventions, 2003, vol. 5(1), pp. 13-16.
Unal., et al., "Effect of Botulinum Toxin Type A on Nasal Symptoms in Patients with Allergic Rhinitis: A Double-blind, Placebo-controlled Clinical Trial," Acta Oto-Laryngologica, Dec. 2003, vol. 123 (9), pp. 1060-1063.
Urologix inc., "Cooled Thermo Therapy™" retrieved on Mar. 5, 2013, from http://www.urologix.com/cliinicians/cooled-thermotherapy.php, 2012, 2 pages.
Urologix, Inc, "CTC Advance.TM. Instructions for Use," Targis. RTM. System Manual, 2010, 8 pages.
Vasilotta P I., et al., "I-R Laser: A New Therapy in Rhino-Sino-Nasal Bronchial Syndrome with Asthmatic Component," American Society for Laser medicine and Surgery abstracts, facsimile copy dated, Feb. 8, 2007, p. 74.
Velden V D., et al., "Autonomic Innervation of Human Airways: Structure, Function, and Pathophysiology in Asthma," Neuroimmunomodulation, 1999, vol. 6, pp. 145-159.
Verhein., et al., "Neural Control of Airway Inflammation," Current Allergy and Asthma Reports, 2009, vol. 9, pp. 484-490.
Vincken., et al., "Improved health outcomes in patients with COPD during 1 yr's treatment with tiotropium," Eur. Respir. J., 2002, vol. 19, pp. 209-216.
Vorotnev., et al., "Treatment of Patients with Chronic Obstructive Bronchitis Using Low Energy Laser at a General Rehabilitation Center," Therapeutic Archive, 1997, vol. 3, pp. 17-19.
Wagner., et al., "Methacholine causes reflex bronchoconstriction," J. Appi. Physiol, 1999, vol. 86, pp. 294-297.
Wahidi., et al., "State of the Art: Interventional Pulmonology," American College of Chest Physicians, Jan. 2007, vol. 131 (1), pp. 261-274.
Weaver, "Electroporation: A General Phenomenon for Manipulating Cells and Tissues," Journal of Cellular Biochemistry, Apr. 1993, vol. 51(4), pp. 426-435.
Wechsler M E., "Bronchial Thermoplasty for Asthma: A Critical Review of a New Therapy," Allergy and Asthma Proceedings, Jul.-Aug. 2008, vol. 29 (4), pp. 1-6.
Wiggs B R., et al., On the Mechanism of Mucosal Folding in Normal and Asthmatic Airways, J. Appl. Physiol, Dec. 1997, vol. 83 (6), pp. 1814-1821.
Wilson K C., et al., "Flexible Bronchoscopy: Indications and contraindications," UptoDate, Nov. 12, 2010 (retrieved Sep. 30, 2012 from www.uptodate.com), 15 pages.
Wilson S R., et al., "Global assessment after bronchial thermoplasty: the patient's perspective," Journal of Outcomes Research, 2006, vol. 10, pp. 37-46.
Wirtz., et al., "Bilateral Lung Transplantation for Severe Persistent and Difficult Asthma," The Journal of Heart and Lung Transplantation, 2005, vol. 24 (10), pp. 1700-1703.
Wizeman., et al., "A Computer Model of Thermal Treatment of Airways by Radiofrequency (RF) Energy Delivery," American Thoracic Society Annual Meeting, 2007, 1 page.
European Search Report corresponding to EP 23217542, dated Jun. 6, 2024.

* cited by examiner

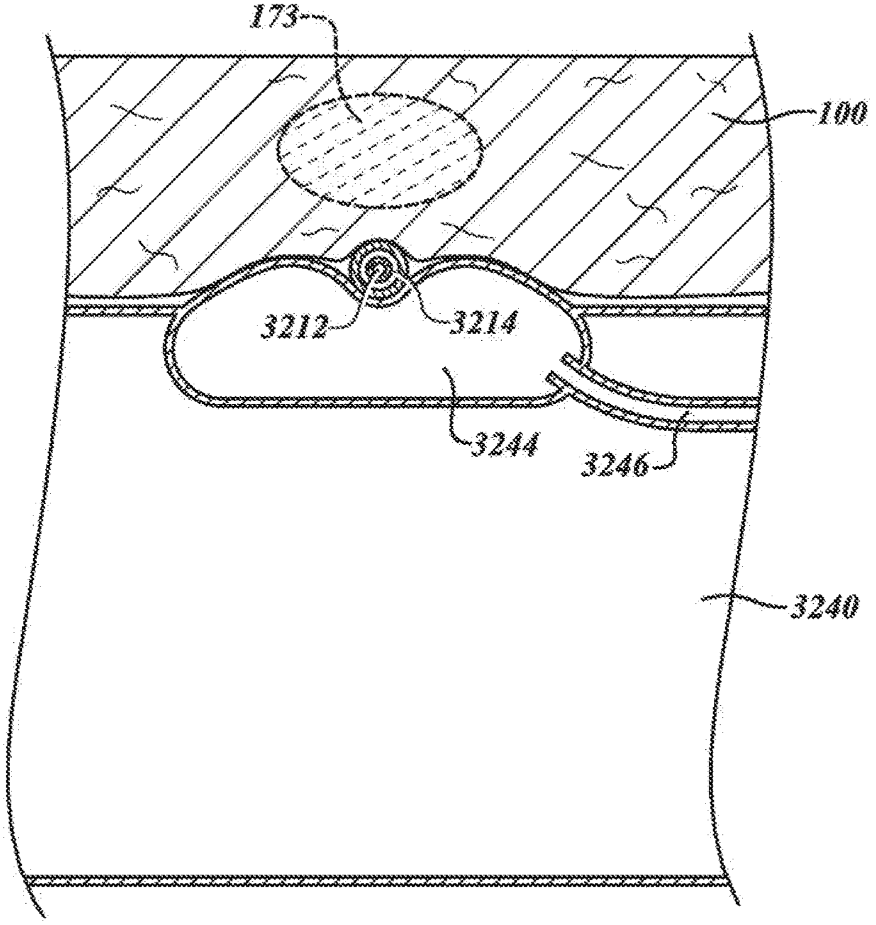
FIG.21B
FIG.21C
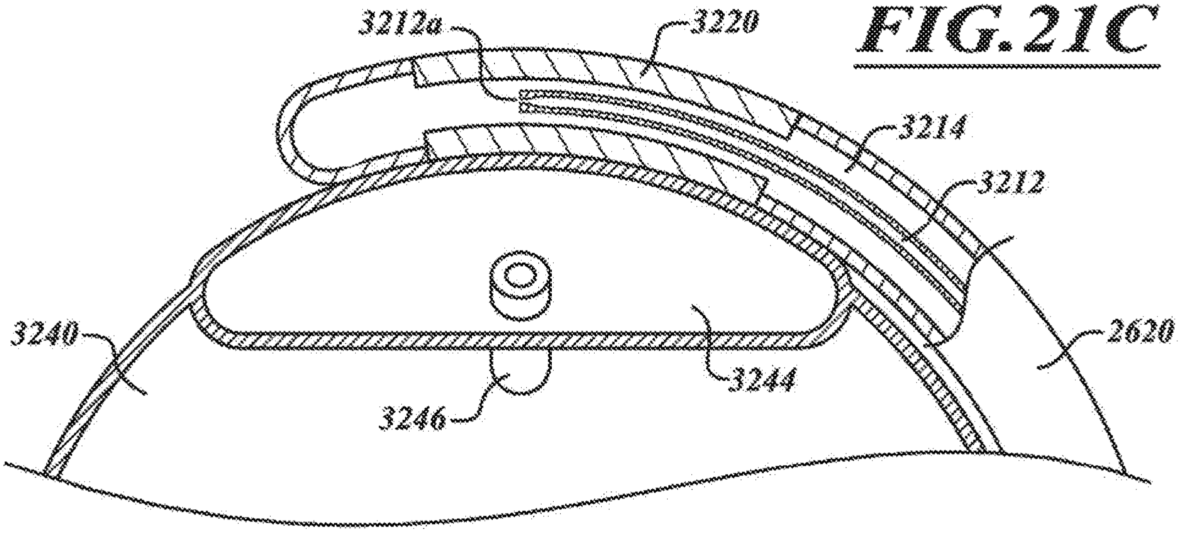

4121
4122
$d_{4120}$
4120
4122a
4126
4129
$D_{4120}$
4124a
4124
$d_{4120}$
4128

4141
4142
$d_{4140}$
4140
4142a
4146
$D_{4140}$
4124a
4144
$d_{4140}$
4148

COMPACT DELIVERY PULMONARY TREATMENT SYSTEMS AND METHODS FOR IMPROVING PULMONARY FUNCTION

RELATED APPLICATIONS

This application is a continuation of application Ser. No. 13/894,920 filed May 15, 2013, which claims the benefit of U.S. Provisional Application No. 61/786,203 filed Mar. 14, 2013 and U.S. Provisional Application No. 61/649,154 filed May 18, 2012, each of which is hereby fully incorporated herein by reference.

BACKGROUND

Technical Field

The present invention generally relates to the field of treatment of the pulmonary diseases.

Description of the Related Art

Pulmonary diseases may cause a wide range of problems that adversely affect performance of the lungs. Pulmonary diseases, such as asthma and chronic obstructive pulmonary disease ("COPD"), may lead to increased airflow resistance in the lungs. Mortality, health-related costs, and the size of the population having adverse effects due to pulmonary diseases are all substantial. These diseases often adversely affect quality of life. Symptoms are varied but often include cough; breathlessness; and wheeze. In COPD, for example, breathlessness may be noticed when performing somewhat strenuous activities, such as running, jogging, brisk walking, etc. As the disease progresses, breathlessness may be noticed when performing non-strenuous activities, such as walking. Over time, symptoms of COPD may occur with less and less effort until they are present all of the time, thereby severely limiting a person's ability to accomplish normal tasks.

Pulmonary diseases are often characterized by airway obstruction associated with blockage of an airway lumen, thickening of an airway wall, alteration of structures within or around the airway wall, or combinations thereof. Airway obstruction can significantly decrease the amount of gas exchanged in the lungs, resulting in breathlessness. Blockage of an airway lumen can be caused by excessive intraluminal mucus or edema fluid, or both. Thickening of the airway wall may be attributable to excessive contraction of the airway smooth muscle, airway smooth muscle hypertrophy, mucous glands hypertrophy, inflammation, edema, or combinations thereof. Alteration of structures around the airway, such as destruction of the lung tissue itself, can lead to a loss of radial traction on the airway wall and subsequent narrowing of the airway.

A variety of solutions have been proposed for addressing pulmonary disorders, including COPD. One conventional treatment for COPD includes delivering the pharmaceutical drug tiotropium to the lungs via an inhaler. Typically, a patient places tiotropium capsules in a specially designed inhaler, and then breathes in dry powder contained in the capsules through the inhaler. This treatment must be administered on a recurring, sometimes daily, basis and its efficacy can be highly dependent on patient compliance.

Another conventional treatment includes maneuvering a catheter with an electrode to an affected area of the lungs and delivering thermal radiofrequency energy directly to the airway wall to directly heat the tissue and thereby reduce airway smooth muscle mass. This treatment, known as bronchial thermoplasty, requires patients to be treated over multiple sessions with each session targeting a different area of the lungs. Possible side-effects over the course of the treatments include asthma attacks, wheezing, chest discomfort, chest pain, partial collapse of the lungs, lower airway bleeding, anxiety, headaches, and nausea.

Several particularly effective treatments for pulmonary disorders are described in, for example, U.S. Pat. No. 8,088,127, titled, "Systems, Assemblies, and Methods for Treating a Bronchial Tree," and U.S. Patent Application Publication No. 2011/0152855, titled, "Delivery Devices With Coolable Energy Emitting Assemblies." In one example treatment described in these documents, a pulmonary treatment system delivers energy to damage a nerve trunk extending along a first airway of a patient, which thereby reduces airway resistance in a second airway distal to the first airway. This treatment provides numerous advantages over other, conventionally available treatments, including being far less invasive and requiring far fewer treatments.

BRIEF SUMMARY

It has been recognized that delivering a pulmonary treatment system to a treatment site in an airway of a patient can present several difficulties to practitioners. For example, if treatment includes positioning a pulmonary treatment system in a main bronchial branch of a patient, a practitioner must navigate the pulmonary treatment system through a tortuous path past the vocal chords, which stretch across the larynx. Successfully steering a pulmonary treatment system past the vocal chords is not only a matter of procedural convenience, but is also highly relevant to patient safety and comfort.

The complexity of positioning a pulmonary treatment system in an airway can be further compounded when a bronchoscope is used in conjunction with the pulmonary treatment system.

Bronchoscopes have become a tool of the trade both for highly trained interventional pulmonologists as well as less specialized physicians trained in the use of a bronchoscope (often referred to as "bronchoscopists") when investigating and treating the lungs. Practitioners typically insert a bronchoscope into the airways, usually through the nose, mouth, an endotracheal tube, or other conduit to guide a variety of treatment processes. In this manner, the bronchoscope can be used to visualize the airway and airway structures to visually guide treatment processes.

Bronchoscopes can be generally sorted into two main groups: flexible bronchoscopes and rigid bronchoscopes. Flexible bronchoscopes are the most common type of bronchoscope used by practitioners. Flexible bronchoscopes typically consist of a flexible sheath that contains cables that allow the tip of the bronchoscope to be flexed and extended, fiberoptic fibers for transmitting endobronchial images, a light source, and a small working channel. Due to their small diameter and flexibility, flexible bronchoscopes can typically be used to visualize the trachea, proximal airways, and segmental airways and can be used to sample and treat lesions in those airways. Flexible bronchoscopy is generally performed in a procedure room with conscious sedation.

In one delivery technique for pulmonary treatment systems, a practitioner utilizes the visualization capabilities of a flexible bronchoscope to guide both the bronchoscope and an independently delivered pulmonary treatment system to a treatment site. This delivery technique can be challenging, as it requires both hands of a single practitioner or two separate practitioners to guide both a delivery catheter for the pulmonary treatment system and the bronchoscope alongside each other.

Pulmonary treatment systems can also be delivered using a rigid bronchoscope. Rigid bronchoscopes typically consist of a large, inflexible tube that encloses a telescope, light source, and working channels. The working channels are generally large enough to allow passage of a variety of instruments related to the treatment of the lungs. A practitioner can first insert the rigid bronchoscope, and then pass the treatment instrument through the working channel. In this way, the rigid bronchoscope shields the passage of treatment instrument past sensitive areas, such as the vocal chords. However, due to their large size and inflexibility, rigid bronchoscopes are limited in their ability to reach smaller and more distal airways. Rigid bronchoscopy is also more invasive than flexible bronchoscopy, and is typically performed in the operating room under general anesthesia.

It has been recognized that one solution that can simplify delivery of a pulmonary treatment system includes securing a suitably sized delivery catheter to the outside of a flexible bronchoscope. The delivery catheter can be secured as an outrider on the flexible bronchoscope with, for example, rubber bands so that the delivery catheter is coextensive with the bronchoscope and flexes jointly together with the bronchoscope to avoid the vocal chords. However, it can be difficult to successfully secure the pulmonary treatment system delivery catheter to the bronchoscope so that the pulmonary treatment system delivery catheter complies with the articulation of the bronchoscope along its length. Such an arrangement would also increase the overall size of the device that must be navigated to the treatment site.

As noted above, flexible bronchoscopes typically include a working channel. Interventional pulmonologists and bronchoscopists use these working channels to deliver various tools, such as biopsy forceps, grasping forceps, retrieval baskets, cytology brushes, aspiration needles, and electrocautery devices, to a treatment site in a patient. It has been recognized that utilizing this channel has numerous benefits, including obviating the need to separately navigate a treatment device to the treatment site and providing a repeatable delivery location for the treatment device with improved visualization. However, these channels are typically limited in size. For example, flexible bronchoscopes include working channels that range in size from as small as 1.2 mm in diameter to as large as 3.2 mm. As will be readily apparent to one of ordinary skill in the art, other sizes of working channels of flexible bronchoscopes will also be applicable to the present disclosure.

Another solution includes sliding a specially designed sheath over a flexible bronchoscope. The sheath includes its own working channel. This solution allows the working channel to move with the bronchoscope. However, the working channels of such sheaths are typically small, in the range of 1.5 mm to 2.5 mm in diameter.

As noted above, U.S. Pat. No. 8,088,127 and U.S. Patent Application Publication No. 2011/0152855 describe several advantageous and effective treatments for pulmonary disease, including delivering energy to damage a nerve trunk extending along a first airway of a patient so as to reduce airway resistance in a second airway distal to the first airway. Some of the example pulmonary treatment systems described in these documents include an energy delivery device configured to be positioned in an airway of the patient to perform the energy delivery, and a cooling system that protects tissue between the nerve trunk and the energy delivery device.

It has been recognized that the cooling requirements of some pulmonary treatment systems can drive the delivery size of the systems. The cooling system of the example pulmonary treatment system noted above can, in some aspects, circulate a liquid coolant to the energy delivery assembly. The liquid coolant is cooled external to the patient's body prior to being supplied to the treatment site via a supply lumen of the pulmonary treatment system, and is then returned via a separate return lumen. Typically, the cooling requirements of the pulmonary treatment system dictate the size of the fluid delivery lumens. It has been recognized that decreasing the size of the supply and return lumens can further limit the flow capacity of such lumens, thereby limiting the ability to achieve both effective cooling and a compact delivery size that is compatibility with the working channel of a flexible bronchoscope.

In one aspect of the present disclosure, it has been recognized that employing a thermodynamically cooled energy delivery system can advantageously increase the cooling efficacy of pulmonary treatment systems while also decreasing delivery size. In the context of the present disclosure, the term "thermodynamic cooling" is intended to encompass temperature drops that are attributable to one or both of (i) a fluid undergoing a phase change from a liquid to a gas; and/or (ii) a rapid transition of a compressible fluid (e.g. gas) from a high pressure to a lower pressure, with or without a phase change, a process known as Joule-Thomson cooling. The apparatus and methods described herein may employ other forms of cooling in addition to thermodynamic cooling, such as heat transfer resulting from convection or conduction caused by simply circulating a fluid at a temperature that is lower than the area to be cooled. The thermodynamic cooling can reduce temperatures of the energy delivery system to less than 20° C. and above −5° C., more preferably to less than 10° C. and above −2° C., and ideally to less than 5° C. and greater than 0° C.

Reducing the temperature of an electrode of the energy delivery system to, for example, 0° C. while delivering energy to tissue of an airway wall can result in, for example, a temperature of about 30° C. at the electrode-tissue interface during the application of power from a radiofrequency electrode.

In one aspect of the present disclosure, a pulmonary treatment system includes a thermodynamically cooled energy delivery system. The energy delivery system is configured to output energy to alter targeted tissue of a bronchial tree. The energy delivery system is thermodynamically cooled so that tissue positioned radially between the targeted tissue and the energy delivery system is maintained at a temperature below which cell death occurs.

In one aspect, a pulmonary treatment system includes a thermodynamically cooled treatment wand. The treatment wand includes an electrode with an exposed contact surface, and a thermodynamic cooling mechanism configured to cool tissue adjacent to the electrode. The wand is configured to assume a delivery configuration in which the wand assumes a reduced profile for passage through a delivery lumen of an elongate device, and a treatment configuration in which at least a portion of the wand that includes the electrode extends in a substantially circumferential direction.

In another aspect of the present disclosure, a method of treating a subject includes positioning an energy delivery system of a pulmonary treatment system at a treatment site within an airway, and delivering energy from the energy delivery system to damage nerve tissue of a nerve trunk such that nervous system signals transmitted to a portion of the bronchial tree are attenuated while thermodynamically cooling the energy delivery system at the treatment site.

Advantageously, thermodynamically cooling the energy delivery system at the treatment site eliminates the need to cool a cooling media outside of the patient's body and then transport it to the treatment site. Accordingly, the size of a supply lumen of a cooling media can be reduced without regard to thermal losses during transport to the treatment site.

In some aspects, thermodynamically cooling the energy delivery system includes a phase transition from a liquid to a gas. In other aspects, thermodynamically cooling the energy delivery system includes delivering a gas at high pressure to an inner tube with an electrode of the energy delivery system and forcing the gas through a throttle into an expansion chamber in the electrode. Advantageously, employing a gas for a cooling media instead of a liquid reduces the size requirements of the supply and return lumens of the cooling system.

In some aspects, thermodynamically cooling the energy delivery system includes cooling the energy delivery system at the treatment site to non-freezing temperatures that are above those typically used to cryogenically injure tissue or cause programmed cell death. Thermodynamically cooling the energy delivery system at the treatment site may include reducing temperatures of the electrode to less than 10° C., more preferably less than 5° C., and greater than −5° C., more preferably greater than −2° C.

Advantageously, thermodynamically cooling the energy delivery system at the treatment site at the distal end of the pulmonary treatment system results in far higher temperature drops than are possible by solely circulating an externally cooled liquid through the pulmonary treatment system. It has been recognized that this increase in cooling efficiency allows for greater flexibility in the size, shape, and treatment role of structures in the energy delivery system such as apposition members and dedicated cooling members.

For example, some embodiments of the pulmonary treatment systems described in U.S. Pat. No. 8,088,127 and U.S. Patent Application Publication No. 2011/0152855 include an expandable member that performs dual functions of apposing an electrode of an energy delivery system to the wall of an airway and cooling tissue of the airway wall that is adjacent to the electrode. In some examples, the expandable member completely fills the airway at a treatment site in order to achieve adequate apposition of the electrode and to ensure that the expandable member cools the airway wall tissue near the electrode. Accordingly, the overall size of the expandable member in these examples not only affects delivery size of the pulmonary treatment system, but also inhibits adequate ventilation of the lungs during treatment.

In one aspect, a pulmonary treatment system includes a thermodynamically cooled treatment wand that is compatible with a working channel of a flexible bronchoscope in a delivery configuration, and that apposes an electrode of an energy delivery portion to an airway wall of treatment site in a deployed configuration without a separate apposition member. The thermodynamically cooled treatment wand in this example cools tissue located radially between the electrode and a target nerve by way of the cooled electrode without the need for a separate cooling member. Advantageously, the thermodynamically cooled treatment wand according to this example decreases the delivery size requirements of the pulmonary treatment system by eliminating the need for a separate apposition or cooling member. As will be readily apparent, a system that does not require a separate apposition or cooling member reduces the device profile substantially for easier delivery through a flexible bronchoscope, and greatly improves ventilation, resulting in increased patient comfort.

In another aspect, the thermodynamically cooled treatment wand includes a partially shielded electrode. A partially shielded electrode includes an exposed portion that is both thermally and electrically conductive, and a shielded portion that includes a layer of electrically insulating, thermally conductive material. Advantageously, partially shielding the electrode can further reduce the need for a dedicated cooling member to cool airway wall tissue immediately adjacent the electrode. For example, when both the exposed portion and the shielded portion are brought into contact with the airway wall, the shielded portion cools the airway wall without delivering energy thereto.

In another aspect, the pulmonary treatment system includes a thermodynamically cooled electrode and a ventilated apposition member. An apposition member is a structural component that brings the electrode into contact with the airway wall. An apposition member can, in some examples, be a balloon, or other deployable member, such as a wire cage or a stent. A ventilated apposition member does not completely obstruct the airway as it holds the thermodynamically cooled electrode in apposition with the airway wall. This configuration allows air to flow through the airway past the pulmonary treatment system during energy delivery. Ventilation can be achieved by an opening or other structural aspect of the apposition member.

In another aspect, a pulmonary treatment system includes an energy delivery system, a cooling member, and a thermodynamic cooling system. The energy delivery system includes an energy delivery portion configured to engage a first tissue region of a bronchial tree to deliver energy to alter targeted tissue of the bronchial tree. The cooling member is in thermal communication with the energy delivery portion and is configured to engage a second tissue region of the bronchial tree adjacent to the first tissue region. The energy delivery portion is cooled using the thermodynamic cooling system. The cooling member need not be independently cooled by circulating coolant or other means. During energy delivery, the cooling member is cooled primarily by heat absorption into the energy delivery portion. The thermodynamic cooling system is arranged within the energy delivery system to cool the energy delivery portion and the cooling member so that: (a) the first tissue region is maintained at a temperature below which cell death occurs, and (b) sufficient heat is absorbed from the cooling member into the electrode to maintain the second tissue region at a temperature below which cell death occurs.

In one example, the cooling member may be connected to only a single inflation lumen arranged to supply an inflation fluid to the interior of the cooling member. By cooling the cooling member by transferring heat to the cooled electrode, the need to circulate coolant through the cooling member is eliminated, thereby obviating the need for both a delivery and a return lumen connected to the cooling member for circulating such a coolant. In some embodiments, however, both a delivery and return lumen may be connected to the cooling member for circulation of fluid in situations where such circulation would be desirable.

Advantageously, the thermodynamic cooling system can be used to passively cool a local cooling member that does not span an entire diameter of an airway. The local cooling member can include an independent supply of cooling fluid. In some aspects, the local cooling member can be actively cooled in addition to the passive cooling from the thermodynamic cooling system. The increase in cooling efficiency achieved by thermodynamic cooling enables the local cooling member to be tailored specifically in size and location on the pulmonary treatment system. For example, the cooling member can be a collapsible and expandable member that is specifically sized to cool an affected area at the treatment site without substantially obstructing ventilation in the airway being treated. This advantageously reduces the delivery size of the pulmonary treatment system.

In another aspect, the pulmonary treatment system includes a thermodynamically cooled energy delivery system and a deployable apposition element that includes a first inflatable chamber and a second inflatable chamber. The first inflatable chamber is in fluid communication with a first fluid supply source, and the second inflatable chamber is in fluid communication with a second fluid supply source. The first inflatable chamber may be inflated independently of the second inflatable chamber. The first inflatable chamber may be arranged at least partially around the energy delivery system and preferably is arranged radially between the second inflatable chamber and the energy delivery system. The first fluid supply may include a liquid coolant and the second fluid supply may include a gas. In this way the first inflatable chamber may be used to urge the energy delivery system against the airway wall, while the second inflatable chamber may used to cool tissue near the energy delivery system. The second inflatable chamber may be cooled passively by transferring heat into the electrode, or actively by circulating a cooled fluid through it.

It has also been recognized that the location of the thermodynamic cooling system relative to an apposition member and/or an expandable cooling member can impair visualization of a treatment site.

In one aspect of the present disclosure, a pulmonary treatment system includes a thermodynamically cooled energy delivery system and a deployable member which may be axially movable relative to each other. In a delivery state, the energy delivery system is extendable axially beyond a distal end of the deployable member. In a deployed state, the energy delivery system extends circumferentially around the deployable member. Preferably the deployable member is at least partially transparent or has an axial channel or opening providing an un-obscured optical path from its proximal end to the energy delivery system. Advantageously, locating the thermodynamically cooled energy delivery system distal of the deployable member during delivery rather than proximal of the deployable member allows a practitioner to optically couple a visualization device, such as a bronchoscope, to the deployable member without the thermodynamically cooled energy delivery system obscuring the view. This configuration also contributes to a compact delivery configuration, as the thermodynamically cooled energy delivery system can be arranged axially in line with the deployable member in the delivery state.

In another aspect of the pulmonary treatment system, the deployable member is an inflatable member. A fluid delivery conduit extends from a proximal end of the deployable member, through the deployable member, out a distal end of the deployable member to the thermodynamically cooled energy delivery system. The fluid delivery conduit includes a supply lumen and return lumen that are each in fluid communication with the thermodynamically cooled energy delivery system.

In one example, the deployable member is coupled to a fluid supply that is independent of the coolant supplied to the thermodynamically cooled energy delivery system. Advantageously, this configuration can decouple actuation of the deployable member from coolant flow. In addition, if the fluid supplied to the deployable member is a coolant, the energy delivery system can act to passively cool the deployable member from two sides: (i) externally from the portion of the energy delivery system that extends circumferentially around the deployable member; and (ii) internally from the return lumen of the fluid delivery conduit which may extend through an interior of the deployable member.

In another example, the deployable member is in fluid communication with the energy system return lumen, and is inflated when fluid is supplied to the thermodynamically cooled energy delivery system. In another example, the deployable member is actively cooled by a first coolant supply that is independent from a second coolant supply associated with the thermodynamically cooled energy delivery system.

It has been further recognized that the size requirements of the energy delivery system in a pulmonary treatment system can also present a barrier to compatibility with the working channel of a flexible bronchoscope. For example, utilizing a rigid electrode to deliver radiofrequency (RF) energy creates competing interests. The efficacy of treatment can be partially dependent on the surface area of the electrode that is available to make contact with airway wall tissue at the treatment site. As such, reducing the size of the rigid electrode in order to achieve size compatibility with the working channel of a flexible bronchoscope can detrimentally reduce the surface area of the electrode that will be available for treatment. In some aspects of the present disclosure, a pulmonary treatment system includes an energy delivery system with an electrode that includes a reduced profile for delivery and deployment and a contact portion that maintains a minimum desired surface area of the electrode at an electrode-tissue interface. This configuration advantageously improves the size of the electrode for delivery, while maintaining a desired electrode surface area available for the electrode-tissue interface during energy delivery.

In other aspect of the present disclosure, a pulmonary treatment system includes an energy delivery system with an electrode that includes a collapsible delivery configuration, and an expanded, deployed configuration that reduces a delivery size of the electrode while maintaining surface area available at an electrode-tissue interface during energy delivery.

In a further aspect of the present disclosure, a pulmonary treatment system includes an energy delivery system with an electrode that includes a collapsed delivery configuration, and an expanded deployed configuration that reduces a delivery size of the electrode while maintaining surface area available at an electrode-tissue interface during energy delivery.

It has been further recognized that pulmonary treatment systems that include inadequate apposition by an expandable cooling member can result, in some cases, in a region of inadequately cooled tissue surrounding the electrode. This inadequate cooling can, in some cases, result in damaged tissue extending immediately along either side of the electrode.

In one aspect of the present disclosure, a pulmonary treatment system includes a highly compliant expandable cooling member and an energy delivery system that includes an electrode with an elongated cross-sectional shape. The compliant cooling member expands so as to surround the electrode in direct contact or very close proximity with the edges thereof. The combination of the highly compliant cooling member and the specially shaped electrode allow for better surface contact for the electrode and also provides better cooling by facilitating better contact with airway wall tissue for the cooling member immediately adjacent the electrode.

In another aspect, the electrode is at least partially shielded to prevent energy delivery to tissue in unprotected regions of airway wall tissue immediately adjacent the electrode. A partially shielded electrode includes an exposed portion that is both thermally and electrically conductive, and a shielded portion that includes a layer of electrically insulating, thermally conductive material. Advantageously, partially shielding the electrode can further reduce the need for a dedicated cooling member to cool airway wall tissue immediately adjacent the electrode. For example, when both the exposed portion and the shielded portion are brought into contact with the airway wall, the shielded portion cools the airway wall without delivering energy thereto.

In another aspect, a pulmonary treatment system includes a flexible bronchoscope and a treatment assembly. The flexible bronchoscope includes a working channel extending from an inlet at a proximal end of the flexible bronchoscope to an outlet at a distal end of the flexible bronchoscope. The working channel of the flexible bronchoscope defines a lumen having a diameter in the range of about 1.0 millimeters to about 6.0 millimeters. The treatment assembly that is movable from a delivery configuration to a treatment configuration. The treatment assembly is sized to be navigable through the working channel of the flexible bronchoscope in the delivery configuration. The treatment assembly includes an energy delivery system configured to delivery energy to an airway wall of a patient to damage nerves extending along the airway wall of the patient, and a cooling system configured to cool and thereby prevent permanent damage to portions of the airway wall located radially between the energy delivery system and the nerves. In other aspects, the flexible bronchoscope defines a lumen having a diameter in the range of about 1.0 millimeters to about 4.0 millimeters. In other aspects, the flexible bronchoscope defines a lumen having a diameter in the range of about 1.2 millimeters to about 3.2 millimeters.

The energy delivery system can include a radio frequency electrode. The energy delivery cooling system includes an expandable member. The pulmonary treatment system can include a plurality of electrodes. The plurality of electrodes can extend around the expandable member in a spiral pattern. The plurality of electrodes can be arranged to create a lesion around an entire circumference with a single energy application. The energy delivery system can include a microwave antenna. The energy delivery system can include at least one transducer operable to alter nerve tissue with ultrasound energy.

In another aspect, a pulmonary treatment system includes an elongate member including a coolant supply lumen and a coolant return lumen, a collapsible and expandable cooling member including a first balloon nested within a second balloon, the first and second balloons defining a collapsible and expandable fluid supply channel therebetween, and a collapsible and expandable electrode at least partially covering a portion of the fluid supply channel. The first balloon defines a cooling chamber in serial fluid communication with the fluid supply channel. The fluid supply channel can be defined by a recess in an external surface of the first balloon and an internal surface of the second balloon. The fluid supply channel can be defined by an internal surface of a raised portion of the second balloon and an external surface of the second balloon.

An overall working length of the pulmonary treatment system can be less than 800 mm, preferably about 760 mm. The pulmonary treatment system can be flexible enough to accommodate a working channel with a bending radius of 3.1 mm or less or, in some examples, 2.7 mm or less.

In one aspect delivering the pulmonary treatment system through the working channel of a flexible bronchoscope is achieved without the assistance of a guide wire. Further, the advancing the pulmonary treatment system can be achieved as a non-percutaneous procedure. As such, the pulmonary treatment system lacks a guide wire lumen, hemostasis valve, or other structure typically associated with percutaneous catheter procedures performed in the vasculature.

In another aspect, a method of delivering a pulmonary treatment assembly to a treatment site in a patient includes advancing a flexible bronchoscope to a treatment location in an airway of a patient, advancing a pulmonary treatment assembly through a working channel of the flexible bronchoscope, deploying the pulmonary treatment assembly from the working channel of the flexible bronchoscope, simultaneously applying energy and cooling to the airway wall of the patient, and withdrawing the pulmonary treatment assembly through the working channel of the flexible bronchoscope. The working channel of the flexible bronchoscope defines a lumen having a diameter in the range of about 1.0 millimeters to about 6.0 millimeters. The pulmonary treatment assembly including an energy delivery system configured to delivery energy to an airway wall of a patient to damage nerves extending along the airway wall of the patient, and a cooling system configured to cool and thereby prevent permanent damage to portions of the airway wall located radially between the energy delivery system and the nerves. In other aspects, the flexible bronchoscope defines a lumen having a diameter in the range of about 1.0 millimeters to about 4.0 millimeters. In other aspects, the flexible bronchoscope defines a lumen having a diameter in the range of about 1.2 millimeters to about 3.2 millimeters.

In another aspect, a method of treating a subject includes positioning an energy delivery system at a treatment site in a first airway and delivering energy from the energy delivery system while thermodynamically cooling the energy delivery system. Delivering the energy damages target nerve tissue of a nerve trunk such that bronchial constriction is reduced in a second airway that is a higher generation airway of the first airway. Thermodynamically cooling the energy delivery system protects tissue of the first airway located radially between the delivery system and the target nerve tissue. The method may further include positioning the energy delivery system through a channel of a flexible bronchoscope having a distal end positioned in the first airway.

In another aspect, a method of treating a subject includes positioning an energy delivery system at a treatment site in a first airway and delivering energy from the energy delivery system to occlude at least one bronchial artery that extends along the first airway to reduce inflammation in a second airway that is a higher generation airway than the first airway. Advantageously, it has been recognized that occluding a bronchial artery along the first airway can result in backfilling the occluded artery and lowering blood pressure in the occluded artery at the second airway. This may result in a decrease in the supply of blood that feeds inflammation at the second airway, thereby reducing inflammation at the second airway. In addition, the decrease in nutrient supply to the mucosa and smooth muscle would result in decreased cellular function. A lower pressure gradient further results in lower interstitial fluid buildup, thereby decreasing the hydrostatic pressure gradient.

In another aspect, a method of treating a subject includes reducing inflammatory cytokines in a first airway by positioning an energy delivery system at a treatment site in a second airway that is a lower generation airway than the first airway and delivering energy such that inflammatory cells, inflammatory cytokines, and other inflammation markers are reduced in the first airway.

In another aspect of the present disclosure, a pulmonary treatment system that is compatible with a working channel of a flexible bronchoscope includes a cooling system that employs an externally chilled, liquid coolant.

In one aspect, an energy delivery portion of the pulmonary treatment system includes a flexible electrode that can be collapsed for delivery and expanded at a treatment site. The electrode is preferably adhered directly to or otherwise thermally and mechanically coupled to a flexible fluid delivery conduit and/or to an expandable member of the cooling system. The electrode can be, for example, a conductive epoxy applied to the flexible fluid delivery conduit or expandable member.

In another aspect, the cooling system includes a differential pressure system that can maintain coolant delivered to the energy delivery system at a different pressure than coolant delivered to a collapsible and expandable cooling member of the system. For example, maintaining the energy delivery system at a higher pressure than the expandable and collapsible cooling member advantageously allows the energy delivery system to be changeable from a flexible, collapsed state during delivery of the pulmonary treatment system to a more rigid, expanded state during treatment.

It has been further recognized that maintaining the coolant delivered to the collapsible and expandable cooling member at a pressure that is lower than the pressure of the coolant supplied to the energy delivery system allows the collapsible and expandable cooling member to be formed of thinner, more compliant materials, that would be otherwise impractical if the cooling member were to be maintained at the pressures necessary to maintain rigidity in the energy delivery system. Advantageously, utilizing a thinner walled expandable member can, among other benefits, improve the delivery profile of the expandable member, improve heat transfer between the coolant circulated in the expandable member and tissue of the airway wall, and improve compliance of the expandable member to the contours of the airway wall. Improved compliance and heat transfer have a direct effect on cooling efficiency.

In another aspect the pulmonary treatment system includes a collapsible fluid supply channel and an expandable member. The fluid supply channel includes an energy delivery portion. In a deployed state, the fluid supply channel extends circumferentially around the expandable member. The fluid supply channel is formed of a non-deformable, but collapsible material that does not plastically deform at a first pressure. The expandable member is formed of a compliant material that plastically deforms at a second pressure that is lower than the first pressure.

It has been recognized that inducing turbulent flow along the surface of the cooling member improves the efficiency with which the cooling member transports heat away from an airway wall at a treatment site. In one aspect, the differential pressure system can include a throttle positioned between the energy delivery system and an expandable member. The throttle creates a high pressure zone in the energy delivery system and a low pressure zone in the expandable member. The throttle can be configured to improve coolant flow in the expandable member, and thereby improve the cooling efficacy of the cooling member.

In one example, the position, orientation, and/or shape of the throttle induces eddies and turbulent flow along the surface of the cooling member, which improves the efficiency with which the cooling member transports heat away from an airway wall of the patient at a treatment site.

In another aspect, a gas is injected into the cooling system that circulates a liquid to and from an expandable member of a cooling system of the pulmonary treatment system. The injected gas generates bubbles in the expandable member that disrupt laminar flow along the walls of the expandable member and thereby improves the efficiency with which heat is transported from the portion of the expandable member in contact with airway tissue at the treatment site.

In another example, the collapsible and expandable cooling member includes a small, longitudinally extending, axial support. The support can be a centrally located axial shaft that includes a shape memory material. The axial support can aid in pushability of the cooling member while allowing the cooling member to be formed of a lightweight, highly compliant material.

In another aspect, the cooling system includes co-axial supply and return lumens. In one example, the supply lumen is positioned within the return lumen. The supply lumen may be supplied with a high pressure cooling media, and the return lumen may receive the cooling media at a reduced pressure. Advantageously, locating the supply lumen within the return lumen reduces the delivery size of the pulmonary treatment system and reduces thermal losses in the supply lumen.

In another aspect, the cooling system includes supply and return lumens that share a common wall within an elongate member of the pulmonary treatment system.

In another aspect, the pulmonary treatment system includes an elongate member and a treatment device. A supply lumen and a return lumen extend in the elongate member and are in fluid communication with the treatment device. The junction between the elongate member and the treatment device can include skived portions for passage of the supply lumen and the return lumen. In another aspect, the supply lumen and the return lumen include serial bond joints between the elongate member and the treatment device. Advantageously, the use of skiving and serial bonding can reduce the delivery size of the pulmonary treatment device.

In one aspect, a method of treating a subject includes positioning an energy delivery device in an airway of the subject; then apposing the energy delivery device against an inner surface of an airway wall such that an energy delivery portion is positioned relative to two adjacent cartilage rings; then applying a treatment to the subject with the energy delivery device.

Applying the treatment to the subject can include treating substantially an entire circumference of the airway wall with a single energy application from the energy delivery device. Applying the treatment can include delivering ultrasound energy to the airway wall to disrupt nerve activity in nerves that extend along the airway wall. Applying the treatment can include delivering microwave energy to the airway wall to disrupt nerve activity in nerves that extend along the airway wall. Applying the treatment can include delivering radiofrequency energy to the airway wall to disrupt nerve activity in nerves that extend along the airway wall.

Applying the treatment includes delivering energy to target tissue in or along an airway wall of the airway. The energy can be delivered so as to reduce airway resistance in a distal airway that is a higher generation airway than the airway. The target tissue can include nerve tissue located at least 3 mm outward from an inner surface of the airway wall.

The target tissue can include a nerve trunk disposed along an outer wall of the airway. Applying the treatment can include protecting tissue in the airway wall located between the target tissue and the inner surface of the airway wall. Protecting the tissue can include circulating a liquid coolant that is cooled external to the subject through the energy delivery device.

In another aspect, a method of treating a subject includes positioning an ablation assembly of a delivery device within an airway; delivering energy from the ablation assembly to damage nerve tissue of a nerve trunk such that nervous system signals transmitted to a portion of the bronchial tree are attenuated; and thermodynamically cooling the airway wall by subjecting a fluid to the Joule-Thomson effect.

Thermodynamically cooling the airway wall can include a phase transition from a liquid to a gas. Thermodynamically cooling the airway wall can include delivering a gas at high pressure to an inner tube and forcing the gas through a throttle into an expansion chamber. Thermodynamically cooling the airway wall can include cooling the airway wall to non-freezing temperatures that are above those typically used to cryogenically injure tissue or cause programmed cell death. Thermodynamically cooling the airway wall includes reducing temperatures of the electrode to less than 5° C. and greater than −2° C.

The method can further include passively cooling an inflatable element arranged adjacent the ablation assembly.

The ablation assembly can include at least one electrode configured to delivery radio frequency energy to the airway wall. The ablation assembly can include at least one transducer configured to delivery ultrasound energy to the airway wall. The ablation assembly can include at least one antenna configured to delivery microwave energy to the airway wall.

In another aspect, a pulmonary treatment system includes a nerve modification assembly configured to assume a reduced profile for passage through a lumen of an elongate device and positioning in an airway of a patient, the lumen having a diameter in the range of about 1.0 millimeters to about 6.0 millimeters. The nerve modification assembly includes an energy delivery portion configured to generate heat energy at a power density ranging from 0.1 to 2 $W/mm^2$ in an airway wall of the airway; and a cooling portion configured to remove heat energy at a power density ranging from about 0.1 to about 0.4 $W/mm^2$ from the airway wall during activation of the energy delivery portion.

The energy delivery portion can include at least one electrode configured to delivery radio frequency energy to the airway wall. The energy delivery portion can include at least one transducer configured to delivery ultrasound energy to the airway wall. The energy delivery portion includes at least one antenna configured to delivery microwave energy to the airway wall.

The cooling portion can include a thermodynamic cooling mechanism. The cooling portion can include an inflatable member that is in fluid communication with a source of chilled fluid. The cooling portion can include an inflatable member includes an inflatable member and a fluid delivery conduit that extends at least partially around a circumference of the inflatable member.

The energy delivery member can include at least one collapsible and expandable electrode coupled to a portion of a fluid supply conduit. The electrode can be a film or coating directly coupled to an external surface of the fluid supply conduit.

The energy delivery member can include at least one transducer coupled to a portion of a fluid supply conduit. The transducer can be configured to delivery ultrasound energy to the airway wall is a collapsible and expandable electrode.

The energy delivery portion can be configured to generate heat energy at a power density ranging from 0.3 to 1.0 $W/mm^2$ in an airway wall of the airway. The energy delivery portion can be configured to generate heat energy at a power density ranging from 0.48 to 0.64 $W/mm^2$ in an airway wall of the airway.

The cooling portion can be configured to remove heat energy at a power density ranging from about 0.025 to about 1.0 $W/mm^2$ from the airway wall during activation of the energy delivery portion. The cooling portion can be configured to remove heat energy at a power density ranging from about 0.1 to about 0.4 $W/mm^2$ from the airway wall during activation of the energy delivery portion.

In another aspect, a pulmonary treatment system includes an expandable member, and two axially offset electrodes extending circumferentially around the expandable member on opposites side of the expandable member.

The electrodes overlap when viewed along a longitudinal axis of the expandable member. The electrodes can be narrow bands that each respectively fit between offset sets of adjacent cartilage rings when the expandable member is expanded against an airway wall of a patient. The expandable member can include raised portions directly below the electrodes that aid in seating the electrodes between the sets of adjacent cartilage rings.

The pulmonary treatment system can further include a coolant supply in fluid communication with the expandable member to circulate a coolant therein.

The electrodes can be spaced from each other such that one of the electrodes is positioned to treat a lateral wall of the right main bronchus of a patient without affecting the corina located on the medial side of the right main bronchus of the patient while the other electrode is simultaneously positioned to treat the medial wall of the right main bronchus without affecting the upper lobe bronchus located on the lateral side of the right main bronchus.

In another aspect, a method of treating a subject includes positioning an ablation assembly of a delivery device within an airway at a first location; delivering energy from the ablation assembly to only a first side of the airway wall to damage nerve tissue of a nerve trunk such that nervous system signals transmitted to a portion of the bronchial tree are attenuated; positioning that ablation assembly of the delivery device within the airway at a second location; delivering energy from the ablation assembly to only a second side of the airway wall to damage nerve tissue of a nerve trunk such that nervous system signals transmitted to a portion of the bronchial tree are attenuated. The second side of the airway is an opposite side of the airway from the first side of the airway.

The second side of the airway can include a thin walled septum of the airway at the first location. The airway can be a right main bronchus. The first treatment location can be in the right main bronchus proximal of an upper lobe bronchus and the first side is the lateral wall of the right main bronchus. The second treatment location can be the right main bronchus distal of the carina and the second side wall is the medial wall of the right main bronchus. The delivering energy at the first and second location can create lesions in the first and second locations that overlap when viewed along the airway so that, when taken together, the lesions form a pair of offset lesions that disrupt nerve activity around an entire circumference of the airway wall.

BRIEF DESCRIPTION OF THE DRAWINGS

The drawings discussed in the detailed description are described briefly as follows, in which:

FIG. 21B is a partial, longitudinal cross-sectional view of the pulmonary treatment system of FIG. 21A in an airway.

FIG. 21C is a partial, cross-section view of the pulmonary treatment system taken along lines 21C-21C of FIG. 21A.

DETAILED DESCRIPTION

I. Overview

Figure 16:
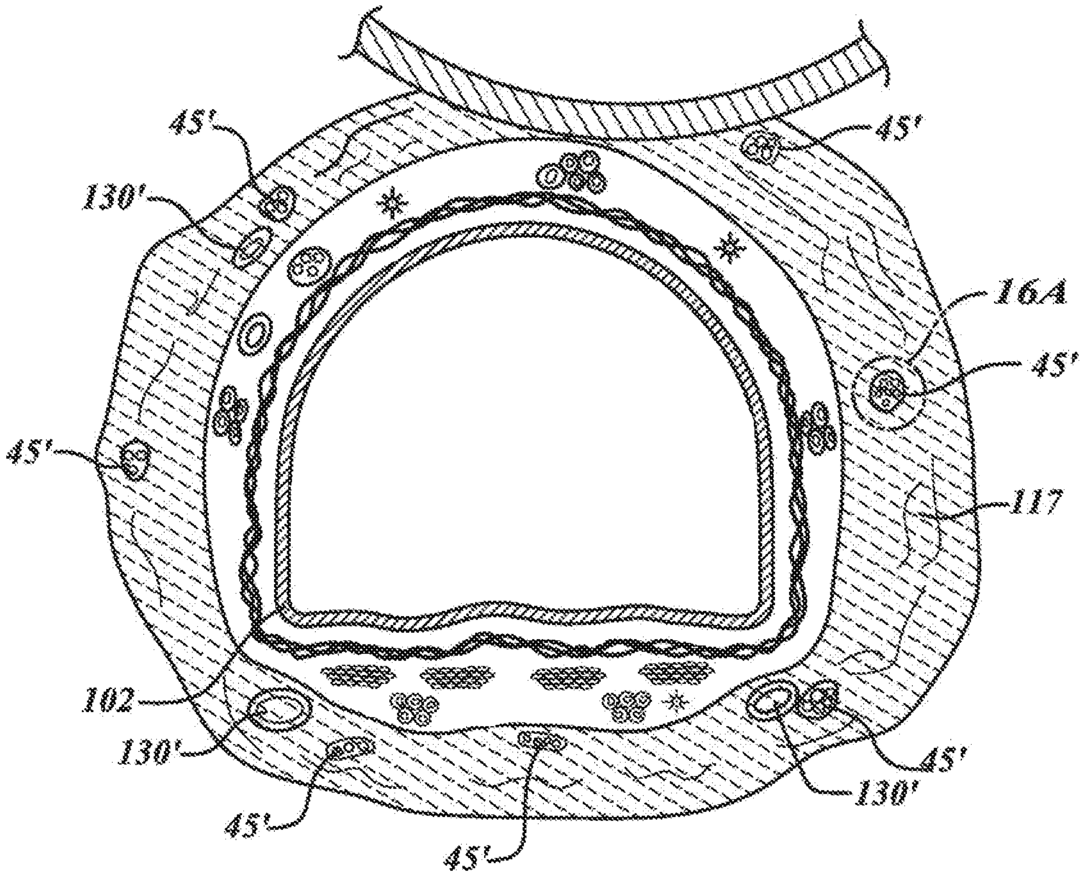
FIG. 16 is the cross-sectional view of the main stem bronchus of FIG. 12 following a complete circumferential treatment.
Figure 17:
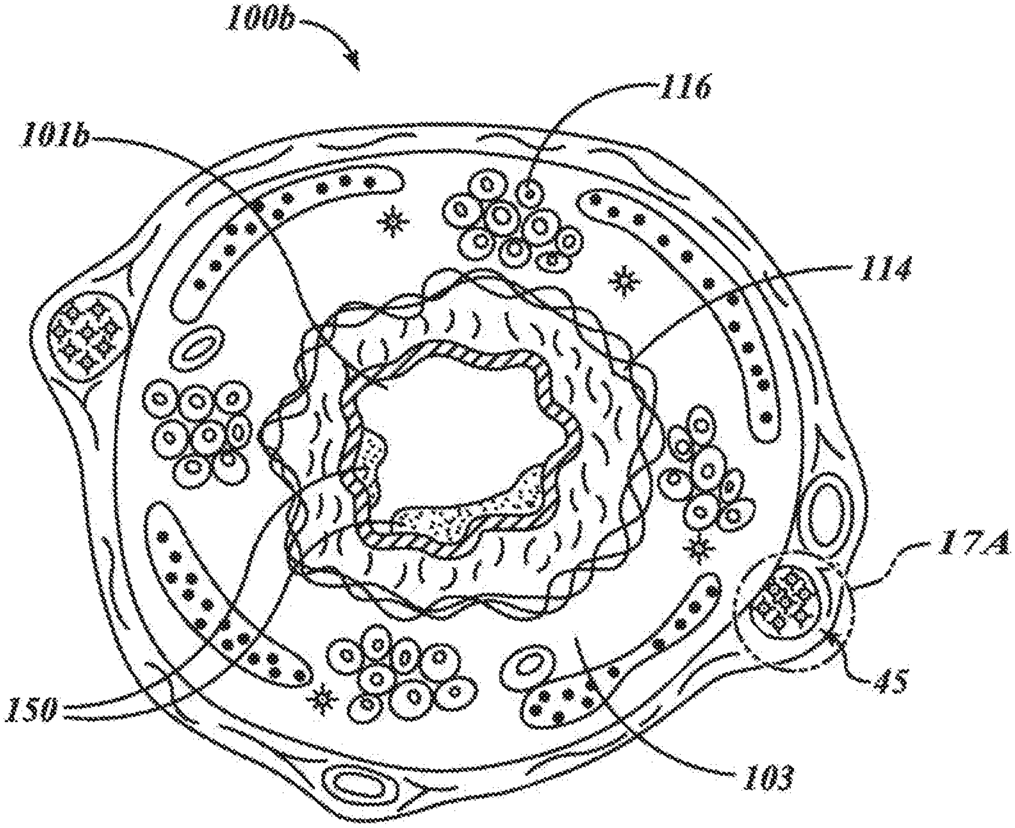
FIG. 17 is a cross-sectional view of a distal airway in the lung prior to treatment, taken along line 17-17 of FIG. 11.

FIGS. 1-6 provide an overview of human lung function and the role the nervous system can play in a diseased lung. FIGS. 7-15 provide an overview of an example treatment applied to the pulmonary system according to one aspect of the present disclosure. FIGS. 16 and 17 provide an overview of the effects of the treatment illustrated in FIGS. 7-15.

Figure 1:
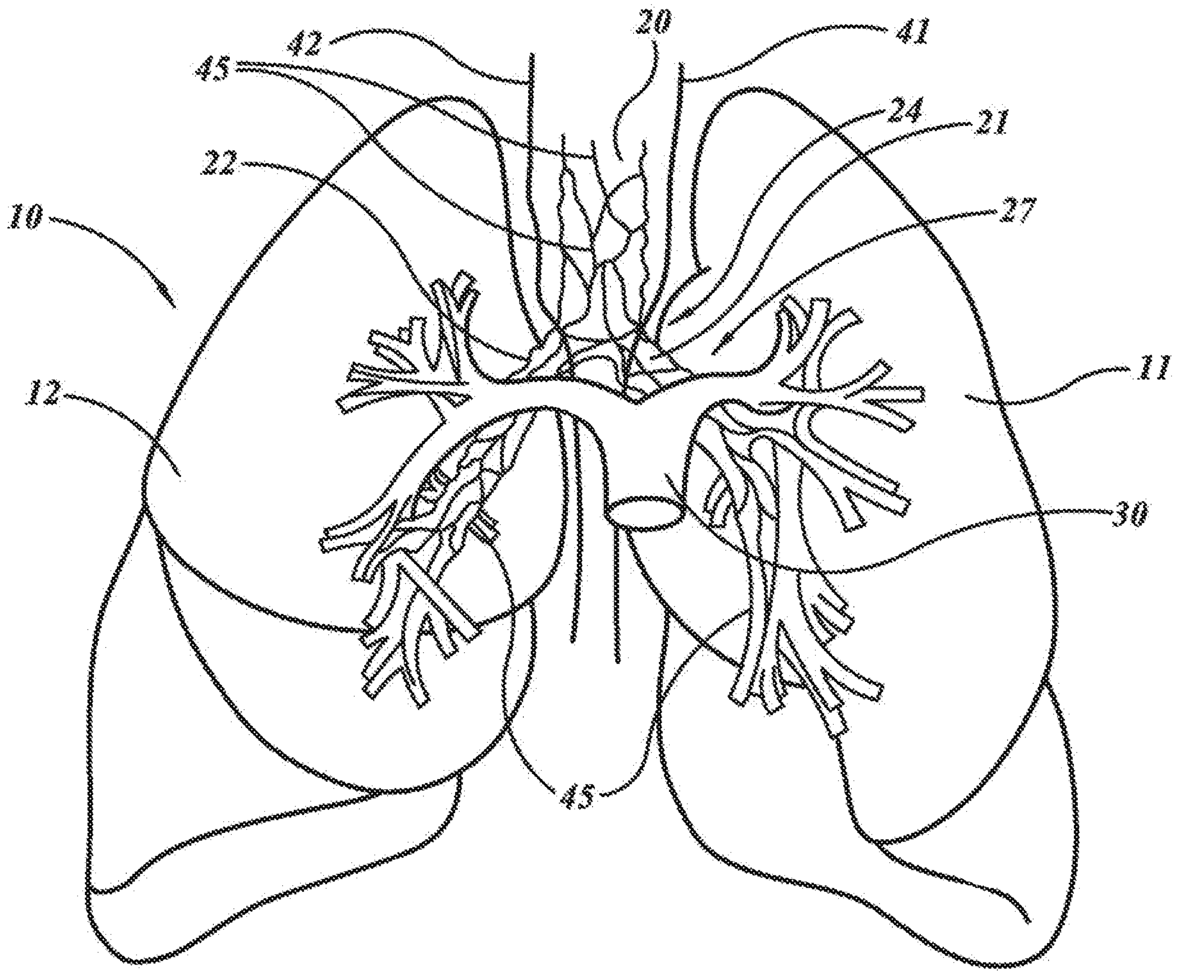
FIG. 1 is an anterior view of the lungs, blood vessels, and nerves near to and in the lungs.

FIG. 1 illustrates human lungs 10 having a left lung 11 and a right lung 12. A trachea 20 extends downwardly from the nose and mouth and divides into a left main bronchus 21 and a right main bronchus 22. The left main bronchus 21 and right main bronchus 22 each branch to form lobar, segmental bronchi, and sub-segmental bronchi, which have successively smaller diameters and shorter lengths in the outward direction (i.e., the distal direction). A main pulmonary artery 30 originates at a right ventricle of the heart and passes in front of a lung root 24. At the lung root 24, the artery 30 branches into a left and a right pulmonary artery, which in turn branch to form a network of branching blood vessels. These blood vessels can extend alongside airways of a bronchial tree 27. The bronchial tree 27 includes the left main bronchus 21, the right main bronchus 22, bronchioles, and alveoli. Vagus nerves 41, 42 extend alongside the trachea 20 and branch to form nerve trunks 45.

The left and right vagus nerves 41, 42 originate in the brainstem, pass through the neck, and descend through the chest on either side of the trachea 20. The vagus nerves 41, 42 spread out into nerve trunks 45 that include the anterior and posterior pulmonary plexuses that wrap around the trachea 20, the left main bronchus 21, and the right main bronchus 22. The nerve trunks 45 also extend along and outside of the branching airways of the bronchial tree 27. Nerve trunks 45 are the main stem of a nerve, comprising a bundle of nerve fibers bound together by a tough sheath of connective tissue.

The primary function of the lungs 10 is to exchange oxygen from air into the blood and to exchange carbon dioxide from the blood to the air. The process of gas exchange begins when oxygen rich air is pulled into the lungs 10. Contraction of the diaphragm and intercostal chest wall muscles cooperate to decrease the pressure within the chest to cause the oxygen rich air to flow through the airways of the lungs 10. For example, air passes through the mouth and nose, the trachea 20, then through the bronchial tree 27. The air is ultimately delivered to the alveolar air sacs for the gas exchange process.

Oxygen poor blood is pumped from the right side of the heart through the pulmonary artery 30 and is ultimately delivered to alveolar capillaries. This oxygen poor blood is rich in carbon dioxide waste. Thin semi-permeable membranes separate the oxygen poor blood in capillaries from the oxygen rich air in the alveoli. These capillaries wrap around and extend between the alveoli. Oxygen from the air diffuses through the membranes into the blood, and carbon dioxide from the blood diffuses through the membranes to the air in the alveoli. The newly oxygen-enriched blood then flows from the alveolar capillaries through the branching blood vessels of the pulmonary venous system to the heart. The heart pumps the oxygen-rich blood throughout the body. The oxygen spent air in the lung is exhaled when the diaphragm and intercostal muscles relax and the lungs and chest wall elastically return to the normal relaxed states. In this manner, air can flow through the branching bronchioles, the bronchi 21, 22, and the trachea 20 and is ultimately expelled through the mouth and nose.

The nervous system provides communication between the brain and the lungs 10 using electrical and chemical signals. A network of nerve tissue of the autonomic nervous system senses and regulates activity of the respiratory system and the vasculature system. Nerve tissue includes fibers that use chemical and electrical signals to transmit sensory and motor information from one body part to another. For example, the nerve tissue can transmit motor information in the form of nervous system input, such as a signal that causes contraction of muscles or other responses. The fibers can be made up of neurons. The nerve tissue can be surrounded by connective tissue, i.e., epineurium. The autonomic nervous system includes a sympathetic system and a parasympathetic system. The sympathetic nervous system is largely involved in "excitatory" functions during periods of stress. The parasympathetic nervous system is largely involved in "vegetative" functions during periods of energy conservation. The sympathetic and parasympathetic nervous systems are simultaneously active and generally have reciprocal effects on organ systems. While innervation of the blood vessels originates from both systems, innervation of the airways are largely parasympathetic in nature and travel between the lung and the brain in the right vagus nerve 42 and the left vagus nerve 41.

Some of the nerve tissue in the network of nerve trunks 45 coalesce into other nerves (e.g., nerves connected to the esophagus, nerves though the chest and into the abdomen, and the like). Some fibers of anterior and posterior pulmonary plexuses coalesce into small nerve trunks which extend along the outer surfaces of the trachea 20 and the branching bronchi and bronchioles as they travel outward into the lungs 10. Along the branching bronchi, these small nerve trunks continually ramify with each other and send fibers into the walls of the airways, as discussed in connection with FIGS. 3 and 4.

Vagus nerve tissue includes efferent fibers and afferent fibers oriented parallel to one another within a nerve branch. The efferent nerve tissue transmits signals from the brain to airway effector cells, mostly airway smooth muscle cells and mucus producing cells. The afferent nerve tissue transmits signals from airway sensory receptors, which respond to irritants, and stretch to the brain. While efferent nerve tissue innervates smooth muscle cells all the way from the trachea 20 to the terminal bronchioles, the afferent fiber innervation is largely limited to the trachea 20 and larger bronchi. There is a constant, baseline tonic activity of the efferent vagus nerve tissues to the airways which causes a baseline level of smooth muscle contraction and mucous secretion.

Figure 2:
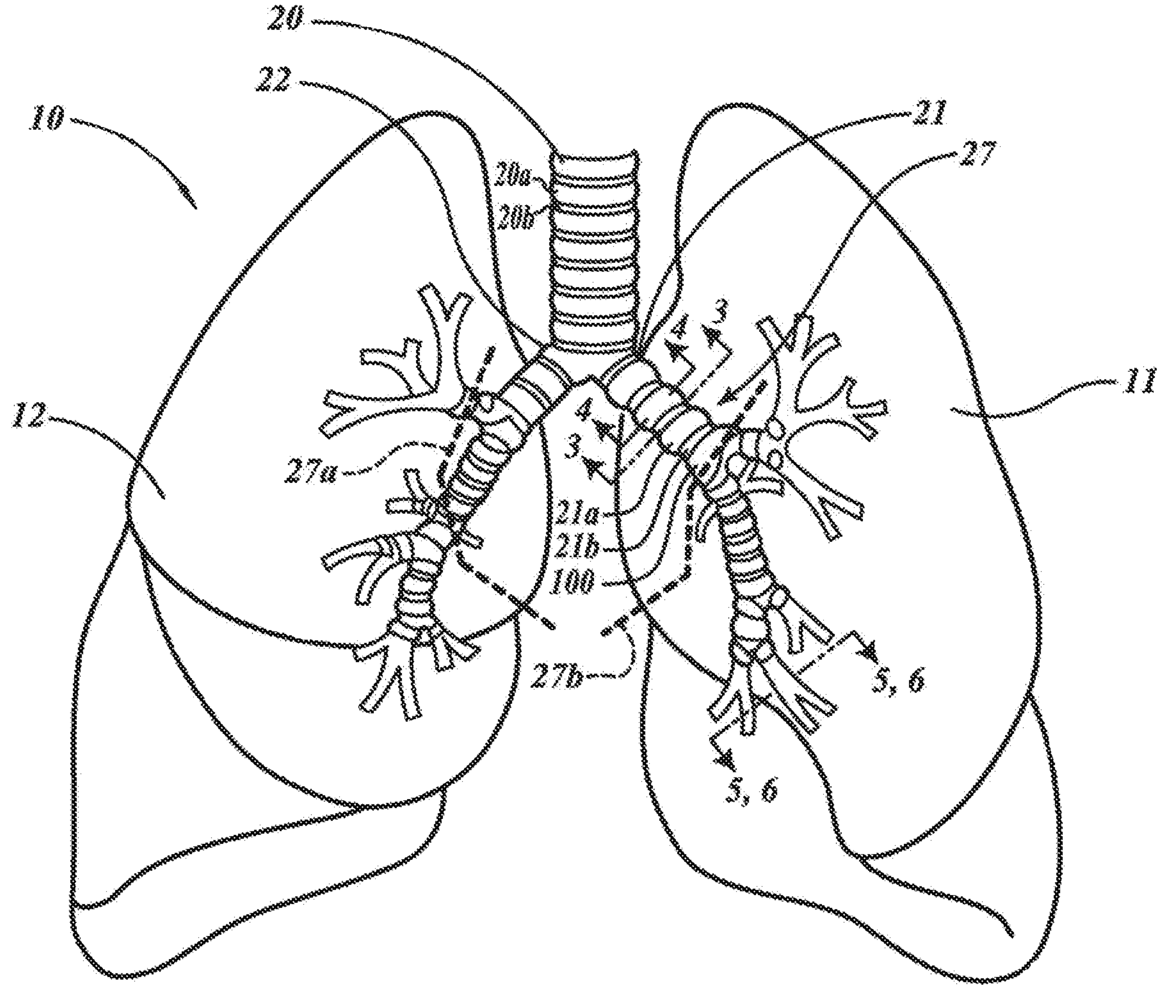
FIG. 2 is a further anterior view of the lungs in FIG. 1.

FIG. 2 is an anterior view of the lungs 10, 11; the trachea 20; and the bronchial tree 27. FIG. 2 includes a generalized illustration of the structure imposed by cartilage rings on the trachea 20 and bronchial tree 27. Portion 20*a* of the trachea 20 in FIG. 2 represents a portion of the trachea 20 that includes a cartilage ring, and portion 20*b* represents a portion of the trachea 20 between adjacent cartilage rings. Likewise, portion 21*a* represents a portion of the left main bronchus 21 that includes a cartilage ring, and portion 21*b* represents a portion of the left main bronchus 21 between adjacent cartilage rings. For ease of representation, the number of cartilage rings has been reduced and the spacing between the cartilage rings has been increased.

Notably, cartilage rings in the trachea do not extend around the entire circumference of the trachea, but instead are discontinuous on a posterior side of the trachea, which faces the esophagus. The discontinuity of the cartilage rings accommodates expansion of the esophagus into the tracheal space, for example, as food is swallowed. The shape of cartilage rings contributes to the cross-sectional shape of the trachea. Studies of the trachea have revealed a diversity of cross-sectional shapes in different patients, including elliptical, C-shaped, U-shaped, D-shaped, triangular, and circular. In addition, the cross-sectional shape of the trachea can change during the respiratory cycle from, for example, an elliptical shape during inspiration to, for example, a horseshoe shape during exhalation.

Figure 3:
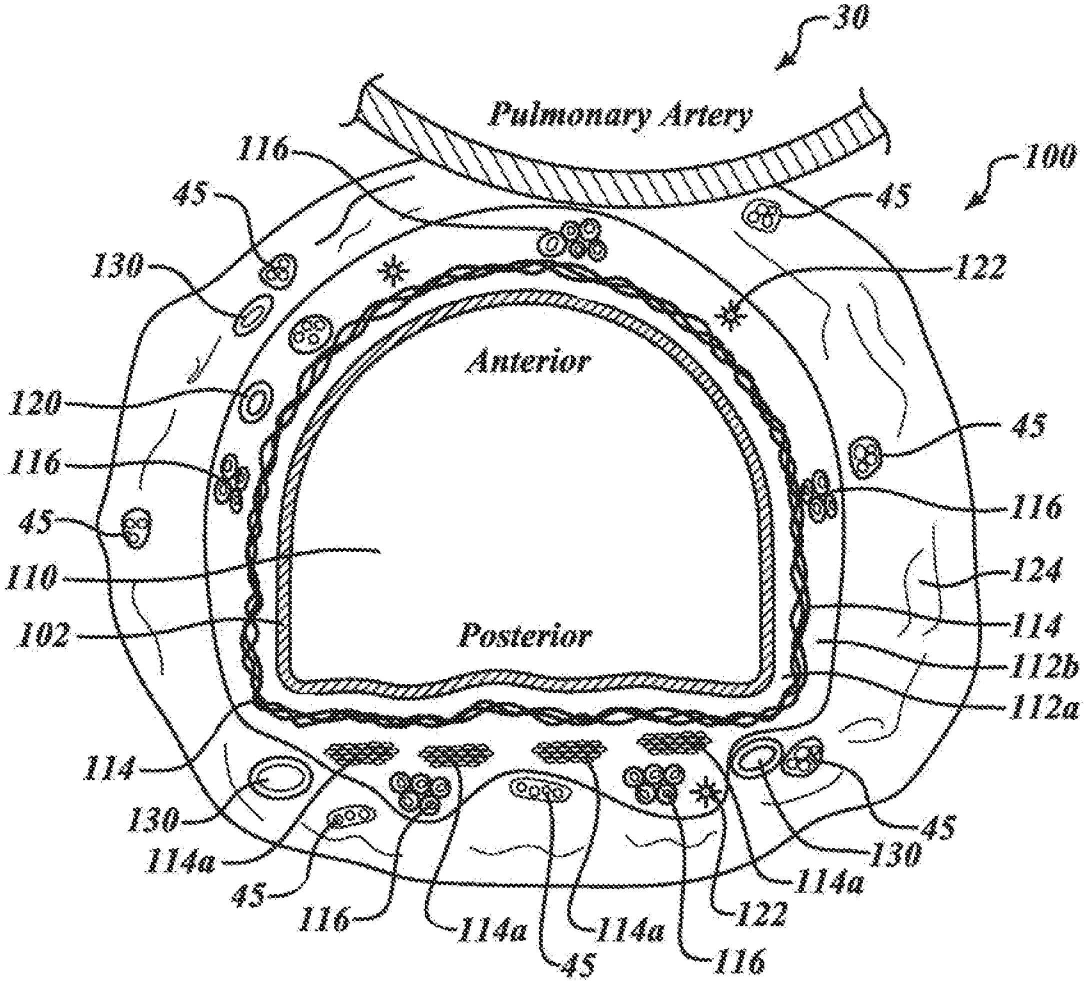
FIG. 3 is a cross-sectional view of a main stem bronchus between two adjacent cartilage rings, taken along line 3-3 of FIG. 2.
Figure 4:
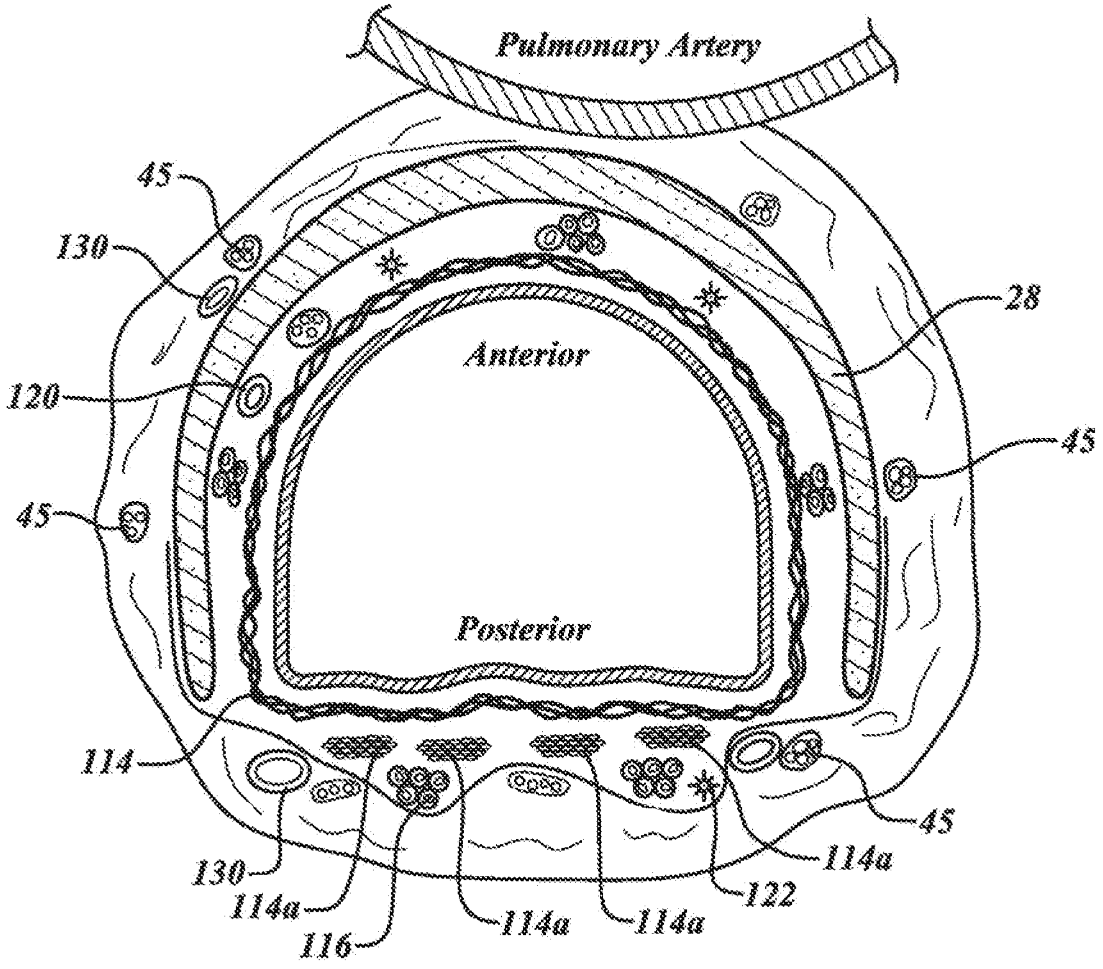
FIG. 4 is a cross-sectional view of a main stem bronchus through one of the cartilage rings, taken along line 4-4 of FIG. 2.

The cartilage rings in the left and right main bronchus are also incomplete. FIG. 3 is a cross-sectional view of a portion of an airway 100 in the left main bronchus 21 that is located between adjacent cartilage rings. FIG. 4 is a cross-sectional view of the airway 100 in portion of the left main bronchus 21 that includes a cartilage ring 28. In this example, the C-shaped cartilage ring 28 contributes to the D-shaped cross-sectional shape of the illustrated portion of the left main bronchus 21. The pulmonary artery 30 extends along an anterior side of the airway 100.

The airway 100 includes a lumen 101 defined by an inner surface 102 of the airway 100. The illustrated inner surface 102 is defined by a folded layer of epithelium 110 surrounded by stroma 112*a*. A layer of smooth muscle tissue 114 surrounds the stroma 112*a*. A layer of stroma 112*b* is between the muscle tissue 114 and connective tissue 124. Mucous glands 116, blood vessels 120, and nerve fibers 122 are within the stroma layer 112*b*. Smooth muscle bands 114*a* extend longitudinally along the posterior side of the airway 100, which is relatively loose when compared to the other portions of the airway 100 that are supported by the cartilage rings 28. Bronchial artery branches 130 and nerve trunks 45 are exterior to a wall 103 of the airway 100. The illustrated arteries 130 and nerve trunks 45 are within the connective tissue 124 surrounding the airway wall 103 and can be oriented generally parallel to the airway 100. In FIG. 1, for example, the nerve trunks 45 originate from the vagus nerves 41, 42 and extend along the airway 100 towards the air sacs. The nerve fibers 122 are in the airway wall 103 and extend from the nerve trunks 45 to the muscle tissue 114. Nervous system signals are transmitted from the nerve trunks 45 to the muscle 114 and mucous glands 116 via the nerve fibers 122. Additionally, signals are transmitted from sensory receptors (e.g., cough, irritant, and stretch) through the nerve trunks 45 to the central nervous system.

Figure 5:
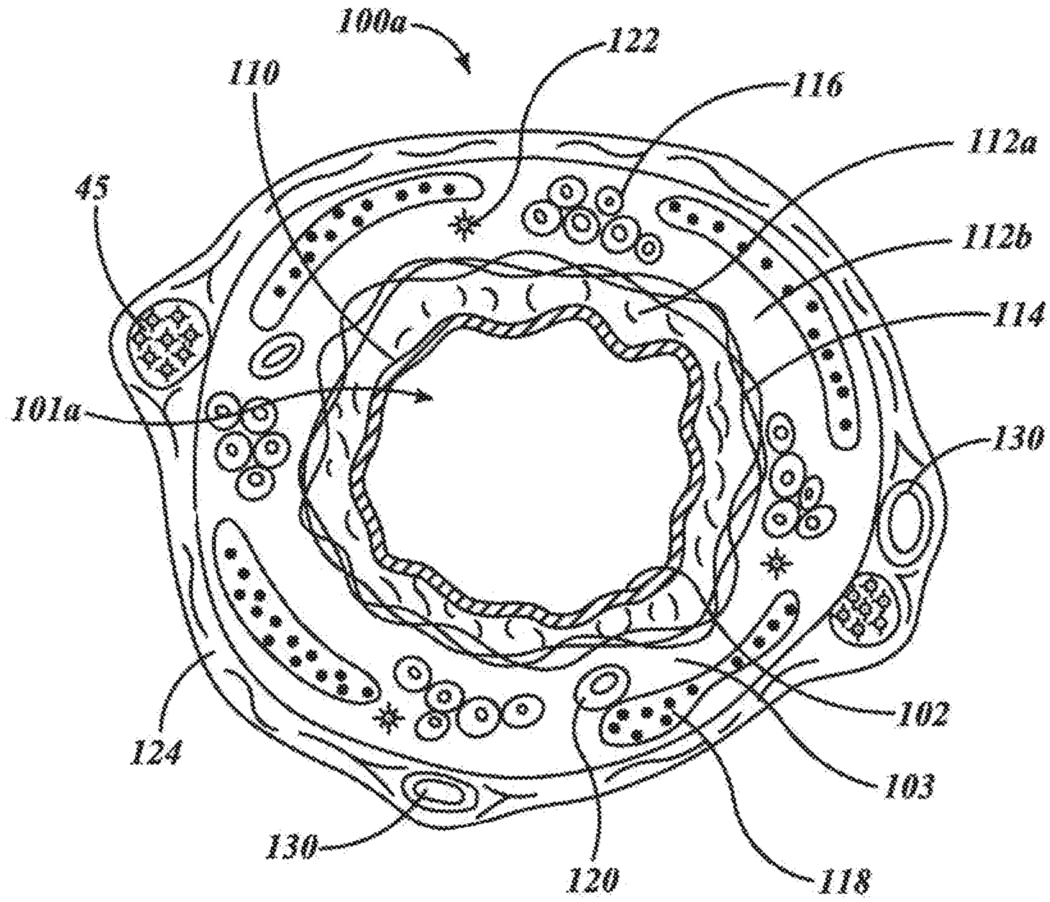
FIG. 5 is a cross-sectional view of a healthy distal airway in the lung, taken along line 5-5 of FIG. 2.
Figure 6:
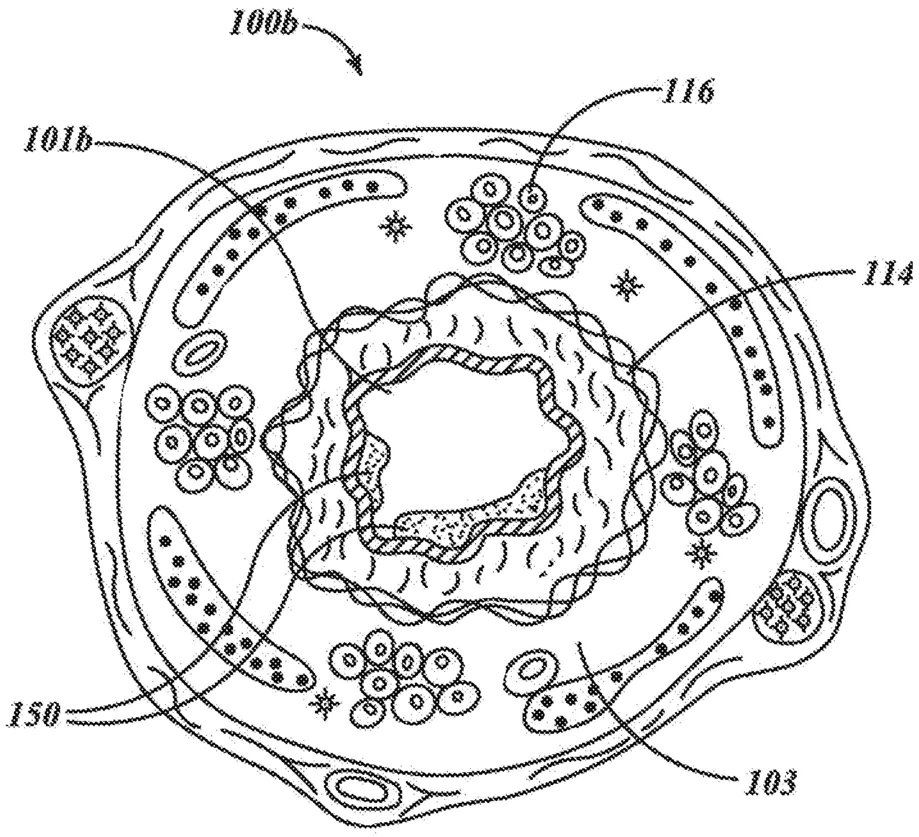
FIG. 6 is a cross-sectional view of the distal airway in FIG. 5 in which the airway is in an unhealthy constricted state, and mucus is in an airway lumen.

FIGS. 5 and 6 illustrate cross-sectional views of higher generation airways in healthy and diseases lungs, respectively. For the purpose of this disclosure, airway branches are numbered in generations starting down from the main stem at generation 0, continuing to the main bronchi at generation 1, and on to the more distal branches at generation 2 and higher. FIG. 5 is a cross-sectional view of a distal airway 100*a* of the bronchial tree 27 in a healthy lung. FIG. 6 is a cross-sectional view of a distal airway 100*b* that is affected by a pulmonary disease. The representation in FIGS. 5 and 6 is a generalized view that is intended to be representative of airways distal of the dashed lines 27*a* and 27*b* in FIG. 2. The example airways 100*a* and 100*b* include cartilage plates 118 rather than cartilage rings 28.

The lumen 101*b* of the airway 100*b* in FIG. 6 is significantly narrower than the lumen 101*a* of the healthy airway 100*a*, and is partially blocked by excess mucus 150. Depending on the patient, the reduced size of the lumen 101*b* can be attributable to variety of ailments, including, for example, inflammation of the airway wall 103, constriction of the smooth muscle tissue 114, or excessive intraluminal mucus or edema fluid, or both.

FIGS. 7-15 provide an overview of one example method and system that can be used to treat diseased airways such as the one shown in FIG. 6. It has been found that attenuating the transmission of signals traveling along the vagus nerves 41, 42 can alter airway smooth muscle tone, airway mucus production, airway inflammation, and the like in airways distal to the treatment site. Attenuation can include, without limitation, hindering, limiting, blocking, and/or interrupting the transmission of signals. For example, the attenuation can include decreasing signal amplitude of nerve signals or weakening the transmission of nerve signals.

Figure 7:
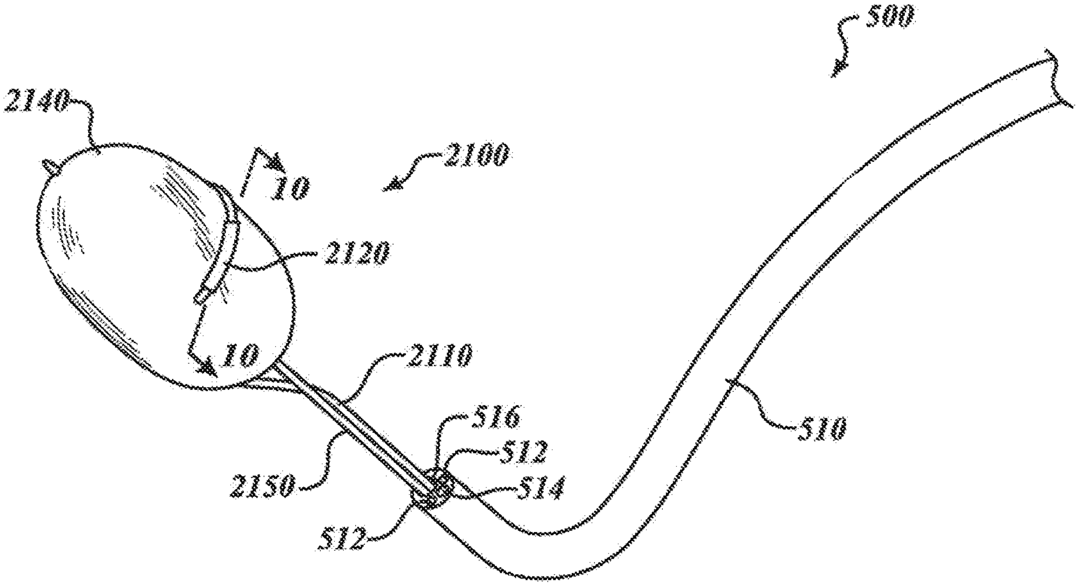
FIG. 7 is an isometric view of a pulmonary treatment system that is deployed from a working channel of a flexible bronchoscope according to one aspect of the present disclosure.

According to one aspect of the present disclosure, a thermodynamically cooled pulmonary treatment system is used to attenuate the transmission of signals traveling along the vagus nerve. FIG. 7 illustrates a thermodynamically cooled pulmonary treatment system 2100 deployed from a working channel 516 of a flexible bronchoscope 500. The pulmonary treatment system 2100 is configured to be positioned at a treatment site within an airway of a patient to deliver energy to target tissue while protecting airway tissue located between the pulmonary treatment system 2100 and the target tissue. In this example, the pulmonary treatment system 2100 includes a thermodynamically cooled treatment wand 2110, an electrode 2120, and an expandable member 2140. FIG. 7 illustrates the pulmonary treatment system 2100 in a fully deployed state, in which the expandable member 2140 is fully inflated and the treatment wand 2110 extends circumferentially around a portion of the expandable member 2140. In this example, the electrode 2120 extends around an entire circumference of the treatment wand 2110 near a distal end of the treatment wand 2110. In other examples, the electrode can extend only partially around a circumference of the treatment wand 2110. In this example, the electrode 2120 is adapted to deliver radio frequency (RF) energy to the target tissue.

The pulmonary treatment system 2100 shown in FIG. 7 is compatible with the working channel 516 of a flexible bronchoscope 500. In one example, the working channel 516 defines a lumen having a diameter in the range of about 1.0 millimeters to about 6.0 millimeters. In other examples, the working channel 516 defines a lumen having a diameter in the range of about 1.0 millimeters to about 4.0 millimeters. In other examples, the working channel 516 defines a lumen having a diameter in the range of about 1.2 millimeters to about 3.2 millimeters. As noted above, utilizing the working channel of a flexible bronchoscope to deliver a pulmonary treatment system to a patient's airway has numerous benefits, including obviating the need to separately navigate the bronchoscope and the pulmonary treatment system to the treatment site, providing a repeatable delivery location for the pulmonary treatment system, and improving visualization of the delivery and treatment. In this example, the flexible bronchoscope 500 includes an insertion tube 510, two light guides 512, and an objective lens 514. Other aspects relating to the compact delivery of the pulmonary treatment system 2100 will be discussed in greater detail below.

Figure 8:
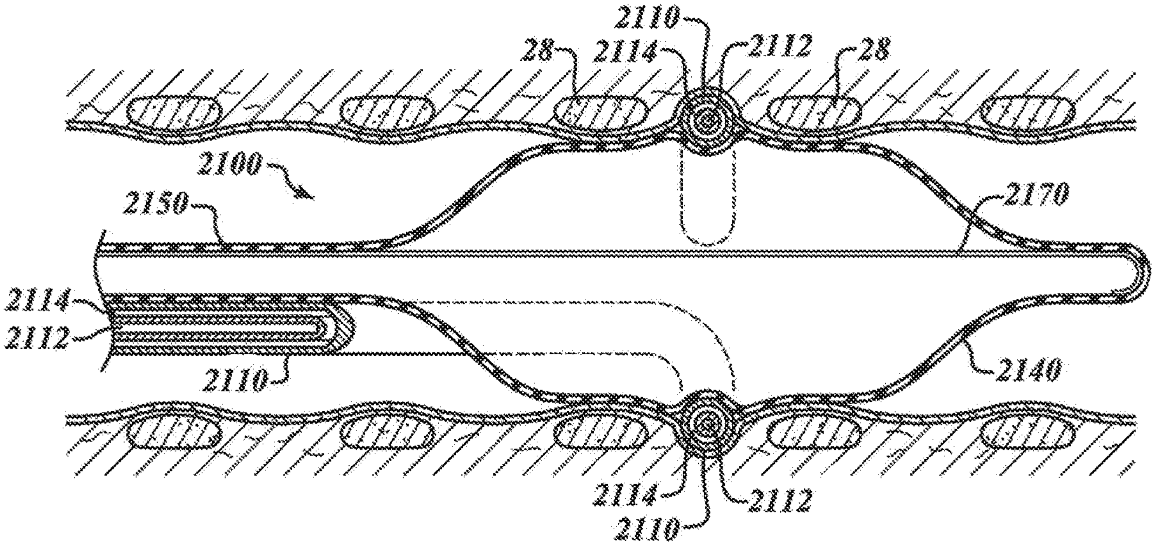
FIG. 8 is a partial cross-sectional view of the pulmonary treatment system of FIG. 7 positioned within an airway during treatment.

FIG. 8 is a partial cross-sectional view of the pulmonary treatment system 2100 in a deployed configuration within an airway of a patient. The treatment wand 2110 extends partially around a circumference of the expandable member 2140. The expandable member 2140 conforms to the shape of the treatment wand 2110 and holds the treatment wand 2110 in close appositional contact with the airway wall between adjacent cartilage rings 28. In this example, the expandable member is supplied with a fluid for expansion via an elongate member 2150. A rigid member 2170 aids in the stiffness and pushability of the expandable member 2140 in a deflated state.

Figure 9:
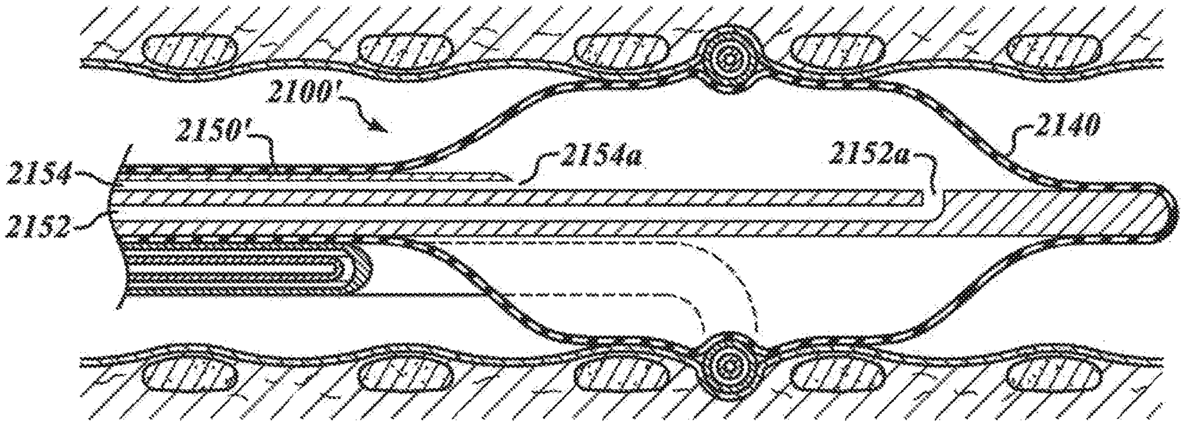
FIG. 9 is a partial cross-sectional view of pulmonary treatment system according to another aspect.

In another example, shown in FIG. 9, the expandable member 2140 is configured for continuous circulation of fluid. An elongate member 2150' includes a supply lumen 2152 and a return lumen 2154. Fluid enters the expandable member 2140 at one end thereof through an opening **2152*a* in the supply lumen 2152, and exits the expandable member 2140 into the return lumen at another end thereof at the opening 2154*a* of the return lumen 2154**.

The pulmonary treatment system 2100 is thermodynamically cooled by a fluid, such as $NO_2$, undergoing expansion through a throttle positioned within the treatment wand 2110. For the purposes of the present disclosure, the phrase "thermodynamic cooling" is intended to encompass temperature drops that are attributable to one or both of (i) a fluid undergoing a phase change from a liquid to a gas; and/or (ii) a rapid transition of a compressible fluid (e.g. gas) from a high pressure to a lower pressure, independent of any phase change.

Figure 10:
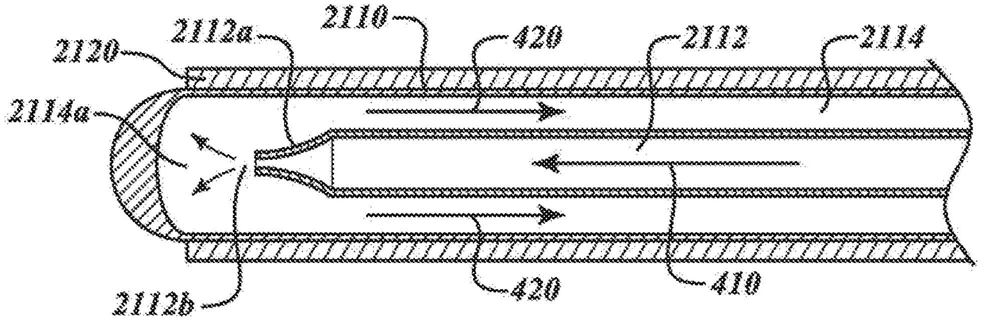
FIG. 10 is a partial cross-sectional view of a thermodynamically cooled treatment wand and electrode of the pulmonary treatment system of FIG. 7.

As shown in FIGS. 8-10, the treatment wand 2110 includes a supply lumen 2112, a return lumen 2114, and a nozzle **2112*a*. FIG. 10 is a partial cross-sectional view of the treatment wand 2110 and the electrode 2120. The treatment wand 2110 includes a supply lumen 2112 and a return lumen 2114 arranged co-axially around the supply lumen 2112. A distal end of the supply lumen 2112 terminates in a nozzle 2112*a*. The nozzle 2112*a* is a constriction formed at a distal end of the supply lumen 2112. The nozzle can take a variety forms, including a stepped down profile, a longitudinal taper, or an abrupt end of the lumen 2112** with a small opening. The cross-sectional area of the opening defined by the nozzle can be significantly reduced when compared to the cross-sectional area of the supply lumen in order to create the requisite change in pressure, described in greater detail below.

The return lumen 2114 defines an expansion chamber **2114*a* around and distal of the nozzle 2112*a*. In this example, $NO_2$ is delivered at high pressure to the supply lumen 2112, as shown by the arrow 410. The $NO_2$ passes through the nozzle 2112*a* and is released into the expansion chamber 2114*a* through an opening 2112*b* in the nozzle 2112*a*. Coolant may be delivered to the supply lumen 2112 in either a gaseous or liquid state. If delivered in gaseous form, the $NO_2$ quickly expands and undergoes a pressure and temperature drop (the Joule-Thomson effect), cooling the chamber expansion chamber 2114*a* and the return lumen 2114. If delivered in a liquid state, the $NO_2$ may undergo a phase change to gas, further dropping its temperature. The gaseous $NO_2$ is then withdrawn through the return lumen 2114, as shown by arrows 420**.

A Joule-Thomson throttle can recover work energy from the expansion of a fluid resulting in a lower downstream temperature. For example, when the coolant supplied to the pulmonary treatment system 2100 is an $NO_2$ gas, the $NO_2$ gas enters the inner lumen 2112 at a first, high pressure $P_1$; passes through the throttle **2112*a*; and enters the expansion chamber 2114*a***, where the pressure of the $NO_2$ gas drops to $P_2$. The drop in pressure from $P_1$ to $P_2$ leads to a drop in temperature of the gas from $T_1$ to $T_2$. The magnitude of the temperature change generally be understood by the following relationship:

$$T_1-T_2=\mu(P_1-P_2) \qquad \text{Equation 1}$$

where

T is the temperature of the gas;

P is the pressure of the gas;

μ is the is the Joule-Thomson coefficient of the gas;

Subscript 1 denotes a high pressure condition; and

Subscript 2 denotes a low pressure condition.

Equation 1 demonstrates that the drop in temperature is affected by the relative change in pressure from $P_1$ to $P_2$. As will be explained in greater detail below, the pulmonary treatment system 2100 is thermodynamically cooled to protect tissue in an airway wall of a patient located between tissue targeted for treatment and the electrode 2110. Accordingly, when using a fluid such as $NO_2$ in the pulmonary treatment system 2100, it is important to control the relative drop in pressure so as not to lower the temperature to a point that would result in damage to tissue in the airway wall. For example, dropping the temperature too low may result in crystallization or desiccation of the tissue the thermodynamic cooling is intended to protect. Ideally, the pulmonary treatment system 2100 will cool tissue to non-freezing temperatures that are above those typically used to cryogenically injure tissue or cause programmed cell death. For example, the pulmonary treatment system 2100 will preferably cool tissue within 4 mm of the electrode 2120, measured longitudinally along an airway wall, to less that 20° C. and above −5° C., more preferably to less than 10° C. and above −2° C., and ideally to less than 5° C. and greater than 0° C. One way to control the temperature drop includes controlling the pressure of the delivered $NO_2$ as well as the back pressure in the expansion chamber **2114*a*** so as to control the pressure drop across the throttle.

FIGS. 11-15 illustrate an example treatment sequence with the pulmonary treatment system 2100. The pulmonary treatment system 2100 is coupled to a steering mechanism 2000, a control portion 2200, and a coolant portion 2300. The coolant portion can include separate coolant supplies for the coolant supplied to the thermodynamically cooled treatment wand and the expandable member 2140.

The control portion 2200 may include, without limitation, one or more processors, microprocessors, digital signal processors (DSPs), field programmable gate arrays (FPGA), and/or application-specific integrated circuits (ASICs), memory devices, buses, power sources, and the like. For example, the control portion 2200 can include a processor in communication with one or more memory devices. Buses can link an internal or external power supply to the processor. The memories may take a variety of forms, including, for example, one or more buffers, registers, random access memories (RAMs), and/or read only memories (ROMs). The control portion 2200 may also include a display, such as a screen, and an input device. The input device can include a keyboard, touchpad, or the like and can be operated by a user to control the pulmonary treatment system 2100.

The control portion 2200 can store different programs. A user can select a program that accounts for the characteristics of the tissue and desired target region. For example, an air-filled lung can have relatively high impedance, lymph nodes can have medium impedance, and blood vessels can have relatively low impedance. The control portion 2200 can determine an appropriate program based on the impedance. A differential cooling program can be executed to deliver different temperature coolants through the expandable member 2140 and the treatment wand 2110. The temperature difference can be at least 10° C. For example, the expandable member can be supplied with a coolant at room temperature of 20° C. while the coolant in the treatment wand is driven as low as −5° C., resulting a difference of approximately 25° C. In other examples, various combinations of chilled or non-chilled coolant supplied to the expandable member and a coolant supplied to the treatment wand result in temperature differences of between 10° C. and 25° C. Performance can be optimized based on feedback from sensors that detect temperatures, tissue impedance, or the like. For example, the controller can control operation of the pulmonary treatment system 2100 based on a surface temperature of the tissue to which energy is delivered. If the surface temperature becomes excessively hot, cooling can be increased and/or electrode power decreased in order to produce deep lesions while protecting surface tissues. The control portion 2200 can also be programmed to control the amount of energy delivered from a power source to the energy emitter to injure targeted tissue and promote the formation of scar tissue. Different programs can be used to generate overlapping lesions, spaced-apart lesions, adjust lesion density, or the like.

The internal power supply can supply energy to the electrode 2120 and can be an energy generator, such as a radiofrequency (RF) electrical generator. RF energy can be outputted at a desired frequency. Example frequencies include, without limitation, frequencies in a range of about 50 KHZ to about 1,000 MHZ. When the RF energy is directed into tissue, the energy is converted within the tissue into heat causing the temperature of the tissue to be in the range of about 40° C. to about 99° C. The RF energy can be applied for about 1 second to about 120 seconds. In some embodiments, the RF generator has a single channel and delivers approximately 1 to 25 watts of RF energy and possesses continuous flow capability. Other ranges of frequencies, time intervals, and power outputs can also be used. Alternatively, the internal power supply can be an energy storage device, such as one or more batteries. Electrical energy can be delivered to the electrode 2120, which converts the electrical energy to RF energy or another suitable form of energy. Other forms of energy that may be delivered include microwave, ultrasound, direct current, or laser energy.

The expandable member 2140 optionally can include a sensor (not depicted) that is communicatively coupled to the control portion 2200. The control portion 2200 can command the catheter based on signals from the sensor (e.g., a pressure sensor, a temperature sensor, a thermocouple, a contact sensor, or the like). Sensors can also be positioned on or in proximity to the electrode 2120. The control portion 2200 can be a closed loop system or an open loop system. For example, in a closed loop system, the electrical energy is delivered to the electrode based upon feedback signals from one or more sensors configured to transmit (or send) one or more signals indicative of one or more tissue characteristics, energy distribution, tissue temperatures, or any other measurable parameters of interest. Based on those readings, the control portion 2200 adjusts operation of the electrode 2120 and/or the coolant supply 2300. Alternatively, in an open loop system, the operation of the electrode and the coolant supply 2300 are set by user input. For example, the user can observe tissue temperature or impedance readings and manually adjust the power level delivered to the electrode 2120 and/or the pressure and/or flow rate of coolant supplied from the coolant supply 2300. Alternatively, the power and coolant supplies can be set to fixed values. In yet other embodiments, a user can repeatedly switch between a closed loop system and an open loop system.

Figure 11:
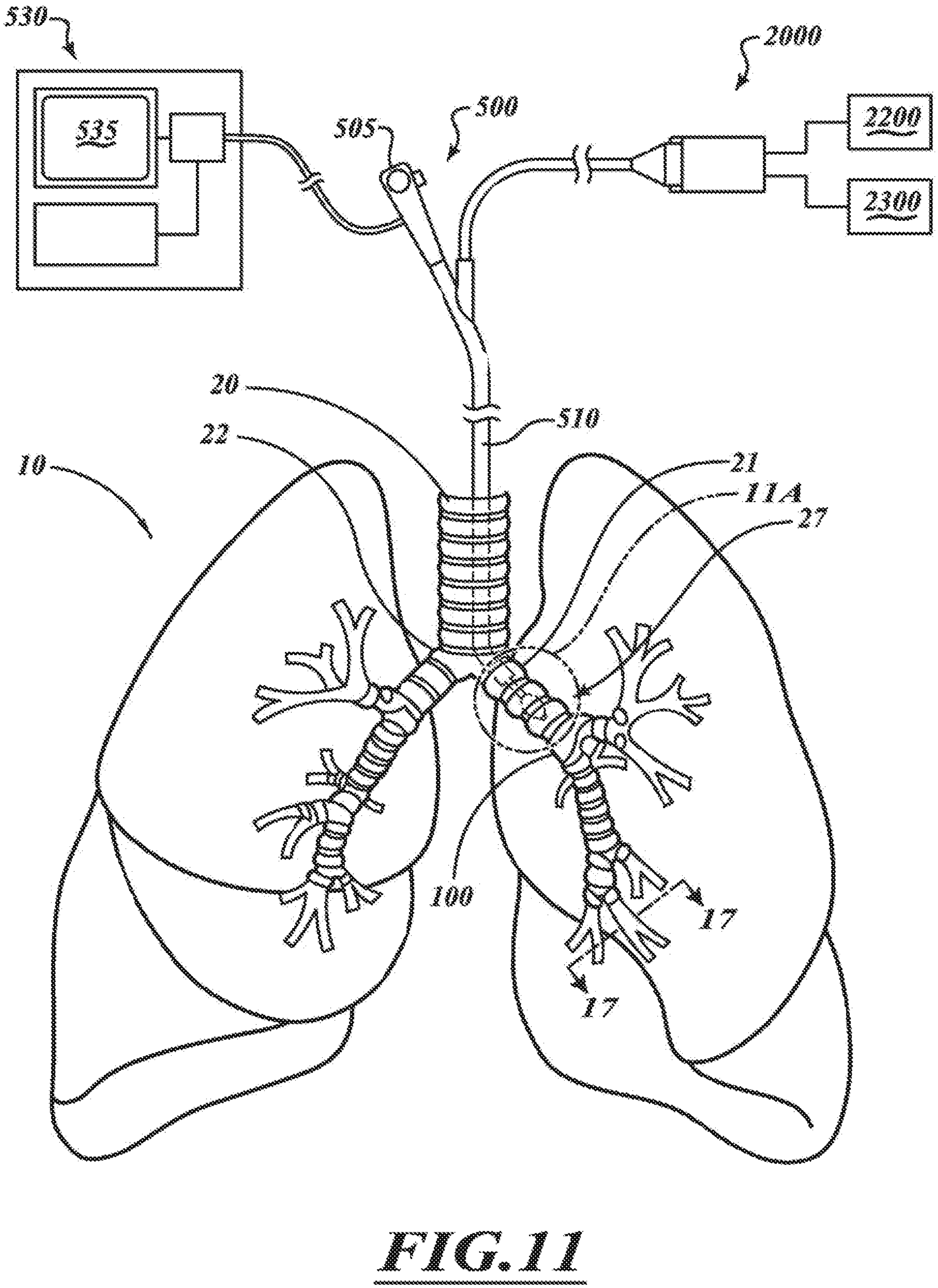
FIG. 11 is a schematic illustration of a pulmonary treatment system during a treatment session according to one aspect.
Figure 11A:
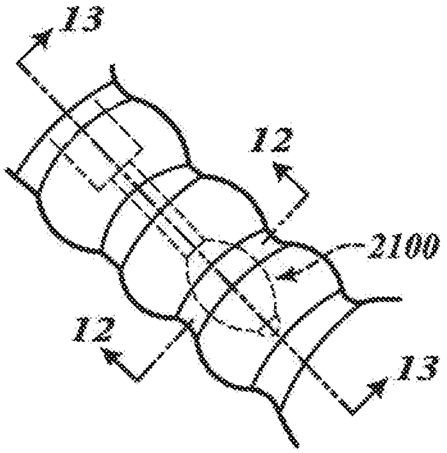
FIG. 11A is a schematic illustration of the pulmonary treatment system of FIG. 11 positioned within a left main bronchus according to one aspect.

FIGS. 11 and 11A illustrate the pulmonary treatment system 2100 positioned within the left main bronchus 21 of a patient for a treatment session. In this example, the pulmonary treatment system 2100 is delivered to the treatment site via a flexible bronchoscope 500. FIG. 11 illustrates an insertion tube 510 of the bronchoscope extending from a control section 505 external to the patient body, through the trachea 20, and to a treatment site within the left main bronchus 21. The bronchoscope 500 can be coupled to a video system 530, which allows a practitioner to observe progress of the insertion tube 510 through the patient on a monitor 535 as the insertion tube 510 is steered with the assistance of the control section 505.

Although the pulmonary treatment system 2100 is positioned in the left main bronchi in this example, the pulmonary treatment system 2100 can be positioned in other locations outside the lung, such as within the right main bronchi, the lobar bronchi, and bronchus intermedius. The bronchus intermedius is the portion of the right main bronchus between the upper lobar bronchus and the origin of the middle and lower lobar bronchi. The pulmonary treatment system 2100 can also be positioned in higher generation airways (e.g., airway generations >2) to affect remote distal portions of the bronchial tree 27. The pulmonary treatment system 2100 can be navigated through tortuous airways to perform a wide range of different procedures, such as, for example, denervation of a portion of a lobe, an entire lobe, multiple lobes, or one lung or both lungs. In some embodiments, the lobar bronchi are treated to denervate lung lobes. For example, one or more treatment sites along a lobar bronchus may be targeted to denervate an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat one lobe. Based on the effectiveness of the treatment, the physician can concurrently or sequentially treat additional lobe(s). In this manner, different isolated regions of the bronchial tree can be treated.

Figure 12:
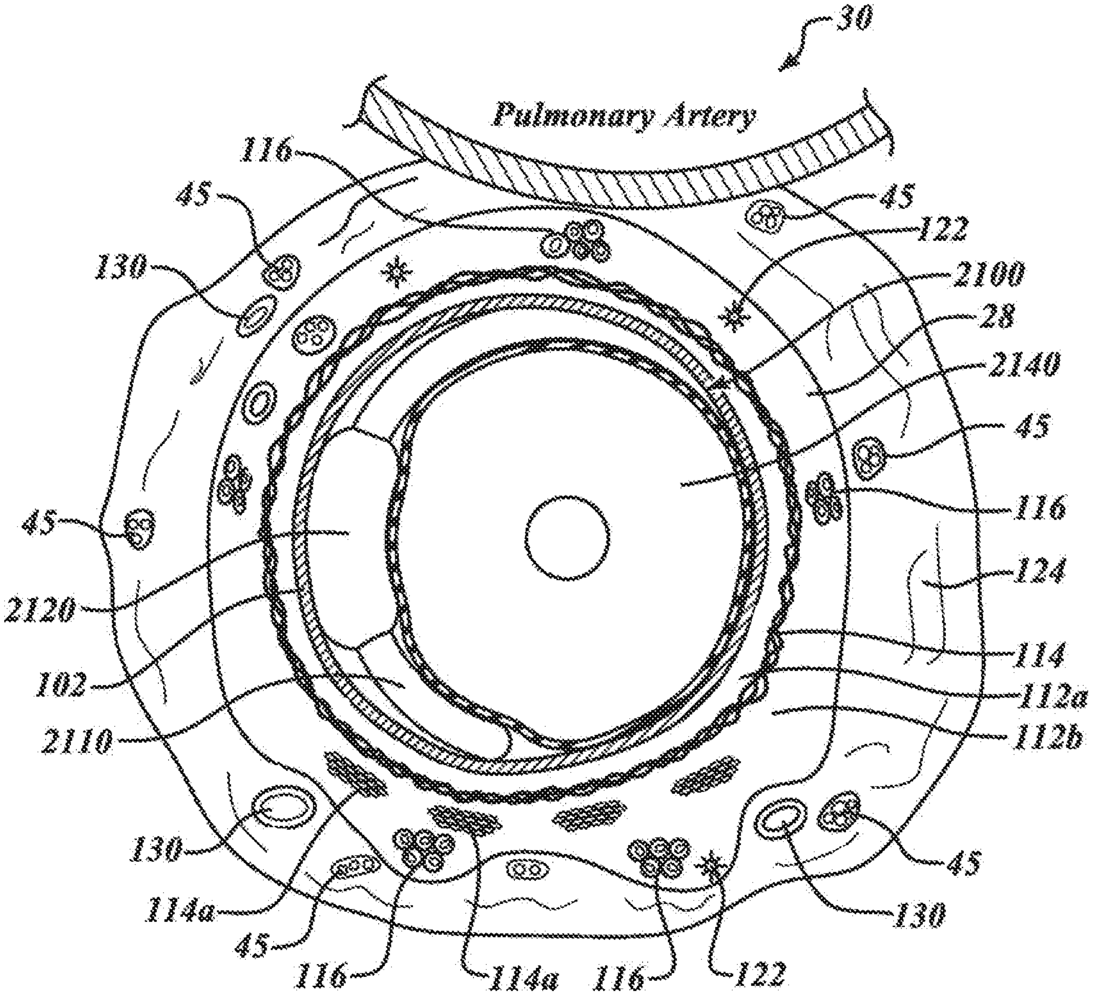
FIG. 12 is a cross-sectional view of a main stem bronchus taken between two adjacent cartilage rings with an energy delivery apparatus positioned in the airway lumen and the device inflated, taken along line 12-12 of FIG. 11.

FIG. 12 is a cross-sectional view, taken along line 12-12 of FIG. 11, of the left main stem bronchus 21 taken between two adjacent cartilage rings. This figure illustrates the pulmonary treatment system 2100 positioned in the airway lumen with the expandable member 2140 inflated. For ease of understanding, the pulmonary treatment system 2100 is not shown in cross section in this view. Inflating the expandable member 2140 apposes the electrode 2120 against the inner surface 102 of the airway wall 103. Notably, the force of contact between the expandable member and the inner surface 102 of the airway wall 103 stretches and thins the airway wall in multiple dimensions all the way around the circumference of the airway, including on the posterior side that includes the longitudinally extending smooth muscle bands. The electrode 2120 further thins and distends airway wall tissue and, depending on the size of the electrode, can act to spread the cartilage rings between which the electrode 2120 is seated. As noted above with reference to FIG. 3, the posterior side of the airway 100 is relatively loose when compared to the other portions of the airway 100 because the cartilage rings do not extend entirely around a circumference of the airway in this portion of the left main bronchus. Stretching the airway wall 103 with a preferential stretching in the location of the electrode can contribute to consistent energy delivery around the circumference of the airway wall.

Figure 13:
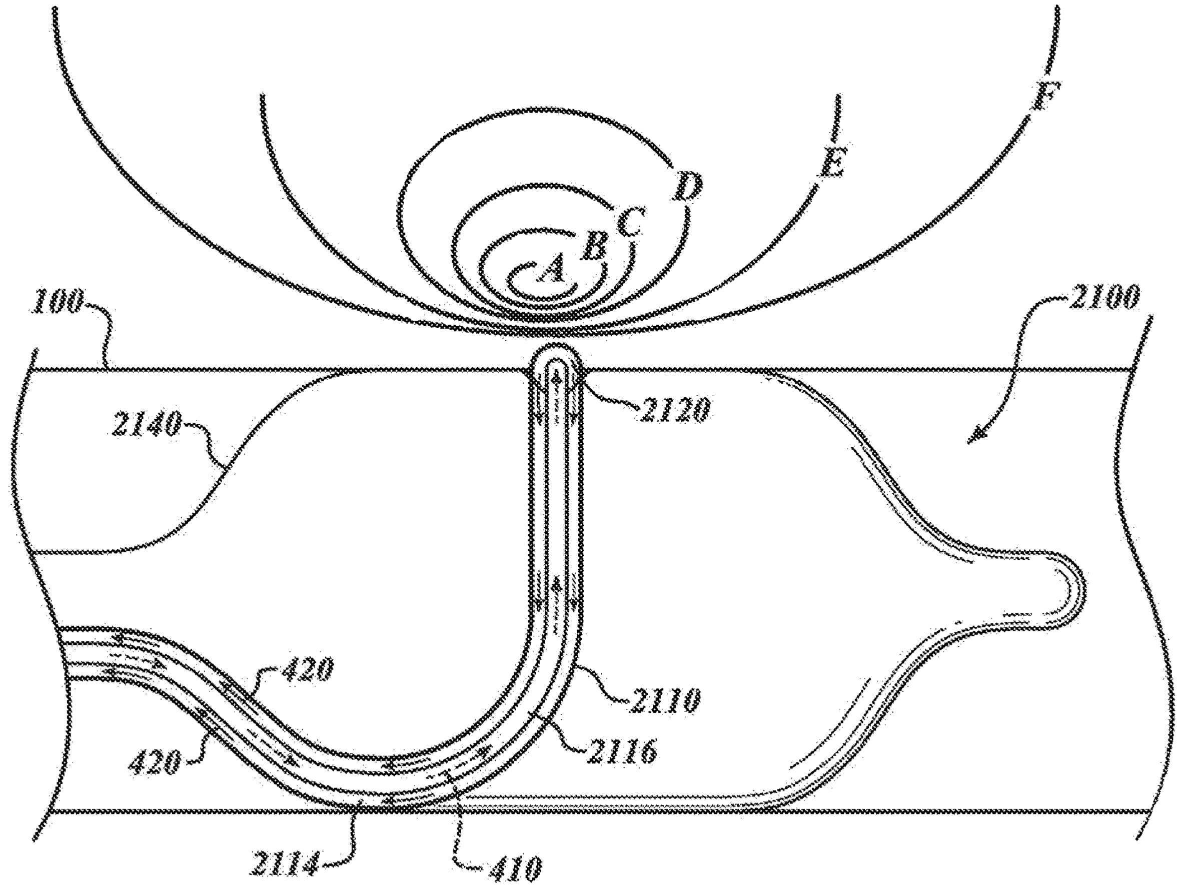
FIG. 13 is a side elevation view of a pulmonary treatment system in an airway illustrating example isotherms, taken along line 13-13 of FIG. 11A.
Figure 14:
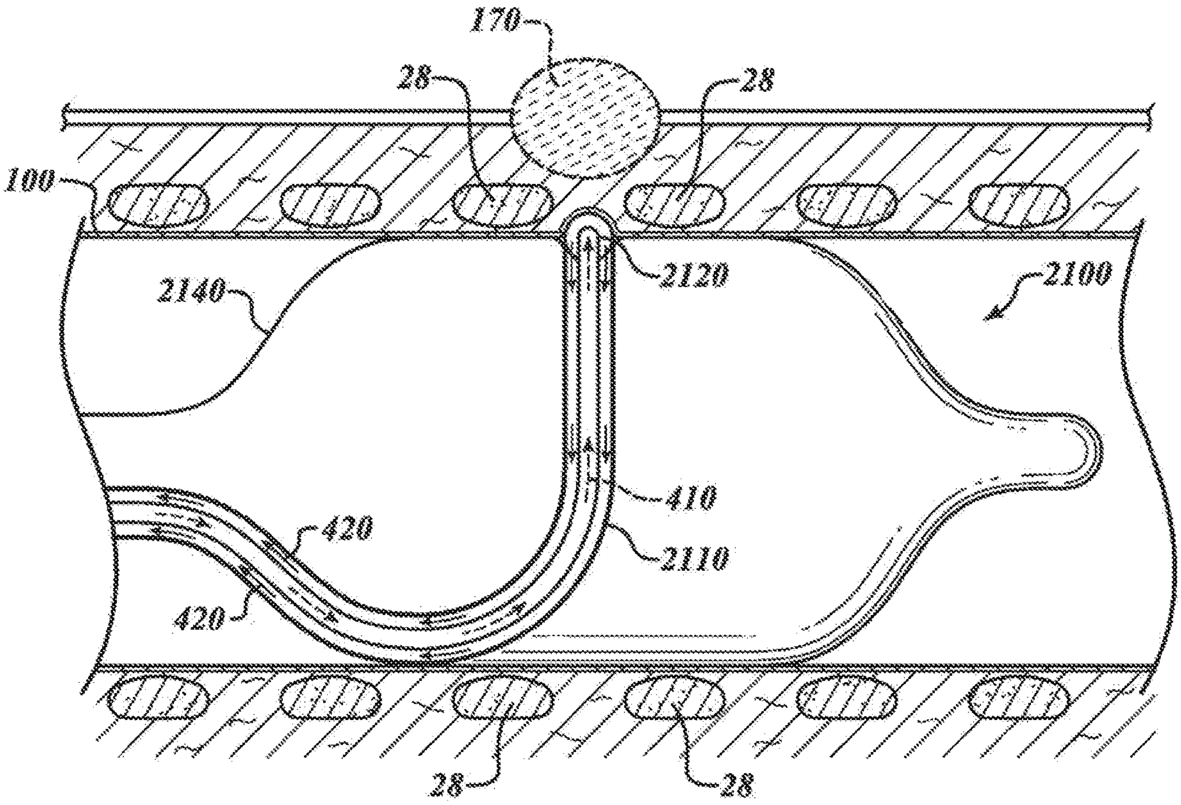
FIG. 14 is a side elevation view of a pulmonary treatment system in an airway illustrating the creation of a lesion, taken along line 13-13 of FIG. 11A.

FIGS. 13 and 14 are side elevation views, taken along line 13-13 of FIG. 11A, of the pulmonary system 2100 in the left main stem bronchus 21. FIG. 13 illustrates example isotherms generated during treatment. FIG. 14 illustrates the creation of a lesion 170 in an airway wall. For ease of representation, many structures (e.g., nerve branches, vessels, etc.) are not shown in FIGS. 13 and 14.

The isothermal curves in FIG. 13 show the temperatures that are reached at different depths into the airway wall 100 from an electrode-tissue interface when power is applied to the electrode 2120 and the pulmonary treatment system 2100 is thermodynamically cooled. As previously described with reference to FIG. 14, the pulmonary treatment system 2100 is thermodynamically cooled by expanding a coolant within the treatment wand. Arrows 410 in FIGS. 13 and 14 depict the coolant being supplied in the supply lumen 2114 of the treatment wand prior to expansion, and arrows 420 depict the coolant returning via the return lumen 2114 of the treatment wand 2110.

By adjusting the rate of power delivery to the electrode 2120, the pressure at which the coolant is supplied to the delivery lumen 2112 of the treatment wand 2110, the back pressure applied to the expansion chamber 2114*a* of the return lumen 2114, and the size of the expandable member 2140, the exact contour and temperature of the individual isotherms can be modified. For example, by selecting the proper pressures and the rate of power delivery to the electrode, it is possible to achieve temperatures in which isotherm A=60° C., B=55° C., C=50° C., D=45° C., E=40° C., and F=37° C. To form the lesion 170 in FIG. 14, the electrode 2120 can receive and output about 10 watts to about 30 watts for about 30 seconds to about 240 seconds. In some procedures, about 15 watts to about 25 watts can be delivered to the electrode 2120 for about 60 seconds to about 80 seconds. The total energy dosage, in some procedures, can be about 300 Joules to about 7,200 Joules.

The amount of power delivered from the electrode to achieve the desired lesion densities, shapes, and locations can range from, for example, 3 watts to 65 watts. In some examples, it is beneficial to create a power density ranging from 0.1 to 2 W/$mm^2$ in the airway wall. In other examples, a power density of from 0.3 to 1.0 W/$mm^2$ is generated in the airway wall. In one preferred example, delivering 15-20 watts through an electrode that is cylindrical in shape, 9.5 mm long and 2.1 mm in diameter with about half of the electrode in contact with the airway wall can result in a power density of 0.48 To 0.64 W/$mm^2$. In this example, energy can be delivered from the electrode for about 120 seconds. However, in other examples, energy can be applied for periods ranging from 10 seconds to 600 seconds, and preferably for a period ranging from 60 to 180 seconds. The position of the electrode(s) and the total energy dosage can be adjusted to obtain lesions of different densities, shapes, and locations.

Although the above noted energy densities are discussed in the context of the application of electrical energy that is delivered to the electrode 2120, which converts the electrical energy to RF energy, the above-noted energy densities are also applicable to other forms of energy, such as microwave energy delivered from one or more antenna(e), ultrasound energy delivered from one or more transducers, direct current delivered from one or more electrodes, or laser energy delivered from one or more light sources.

In order to achieve the desired lesion at the desired depth while protecting the intervening tissue, the amount of energy delivered to the tissue by an RF energy source is balanced against the amount of energy that can be effectively removed by cooling. For example, using a higher wattage energy output may result in a shorter dwell time and, thus, a shorter overall treatment time. However, if the tissue is heated too quickly, the impedance of the tissue increases as liquid is driven out of the tissue. This may impair the ability to create a lesion at a desired depth. On the other hand, applying a lower amount of energy may require less cooling, but a longer dwell time. Further, the active cooling works against rapid delivery of heat to a target location, causing the time required to achieve a particular temperature at a particular depth to increase.

Regardless of the modality used to generate the above-noted energy densities, it is desirable to remove heat energy from the airway wall and, in some cases, the energy source (such as an electrode) during energy application through the various types of cooling disclosed herein in order to protect a region of tissue between an interior wall of an airway and a target treatment region that is located within the airway wall and radially spaced from the interior wall of the airway. In one example, about 0.1 to about 0.4 W/$mm^2$ is removed by cooling during activation of one or more electrode(s) or other energy sources, such as one or more microwave antennae or one or more ultrasonic transducers. In other examples, between about 0.025 and about 1.0 W/$mm^2$ of heat energy is removed by cooling during treatment. In other examples, it is desirable to remove between about 0.1 and about 0.4 W/$mm^2$ of energy during treatment. The cooling employed to remove heat energy from the airway wall is not limited to thermodynamic cooling, but can be any combination of thermodynamic cooling, cooling from circulating an externally chilled coolant through a pulmonary treatment system, and/or cooling generated by a chemical reaction.

Airway wall tissue may continue to rise in temperature even after the electrode stops delivering energy as energy flux within the tissue, itself, continues for a period of time after the electrode is de-energized. As such, removing the cooling aspects of the treatment system from the treatment site immediately following energy delivery may result in a sudden rise in tissue temperature. To avoid this detrimental heating, in one example, a treatment at a particular location may include a period of in-place cooling immediately after cessation of energy delivery to avoid a sudden rise in tissue temperature. The dwell time at the treatment site following energy delivery can range from, for example, a few seconds to 90 seconds. In some examples, the post-energy delivery cooling time can be around 30 seconds.

Further adjustments make it possible to achieve temperatures where isotherm A=50° C., B=47.5° C., C=45° C., D=42.5° C., E=40° C., and F=37° C. Only those areas contained within the 50° C. isotherm will be heated enough to induce cell death. In some procedures, tissue at a depth of about 2 mm to about 8 mm in the airway wall can be ablated while other non-targeted tissues at a depth less than 2 mm in the airway wall are kept at a temperature below at temperature that would cause cell death.

In some aspects, the expandable member 2140 can be filled with a liquid coolant that is independent from the coolant supplied to the treatment wand 2110. The liquid coolant can be continuously circulated in the expandable member 2140 or pulsed into and out of the expandable member 2140. In other aspects, the expandable member is filled and remains static, without further fluid flow, during energy delivery. In each of these cases, the high rate of cooling achieved in the thermodynamically cooled treatment wand 2110 acts to passively cool the expandable member 2140. The expandable member 2140 then absorbs energy from the tissue wall 100 while the expandable member 2140 holds the electrode 2120 against the airway 100. In a still further aspect, the return lumen 2114 is in fluid communication with an interior of the expandable member 2140. In this example, as the expandable member 2140 includes a larger volume than the return lumen 2114, the expandable member 2140 experiences a rapid drop in temperature when the coolant passes from the return lumen 2114 into the expandable member 2140.

As shown in FIG. 14, the electrode 2120 is positioned entirely within a space between adjacent cartilage rings 28 along the airway 100 when the pulmonary treatment system 2100 is in the fully deployed configuration. In some examples, the electrode 2120 has a length of at least about 2 mm up to about 3 mm, and a width (or diameter if cylindrical) no larger than the width of the spaces between the cartilage rings. In some aspects, the electrode width is from 0.1 mm to about 3 mm. Airway cartilage rings or cartilage layers typically have a significantly larger electrical resistance than airway soft tissue (e.g., smooth muscle or connective tissue). Airway cartilage impedes energy flow (e.g., electrical radiofrequency current flow) and makes the formation of therapeutic lesions with radiofrequency electrical energy to affect airway nerve trunk(s) challenging when the electrode is next to cartilage. Further, as discussed above, it can be beneficial to stretch the airway wall tissue in an area of treatment. The airway wall tissue is more flexible in the regions that do not include cartilage rings.

Figure 15:
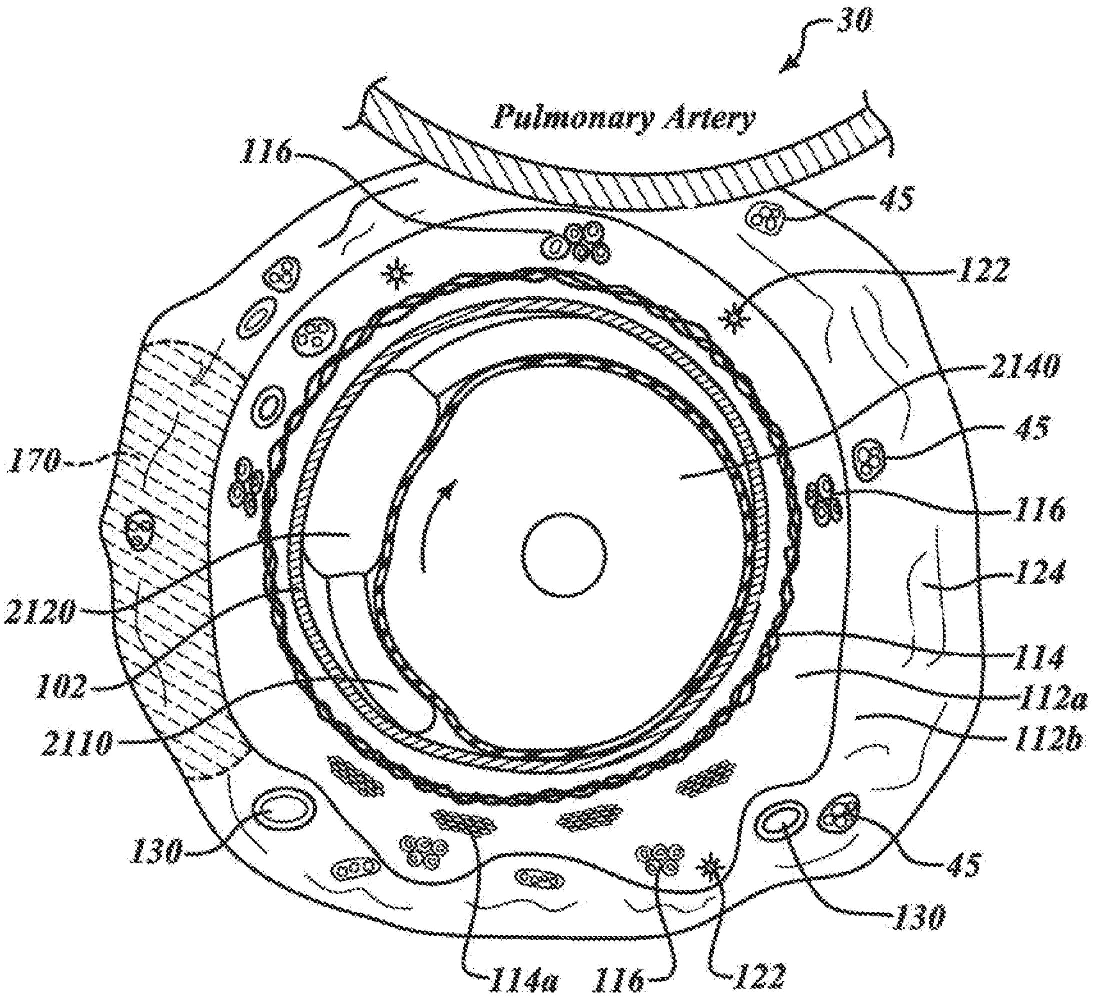
FIG. 15 is a cross-sectional view of the main stem bronchus with the energy delivery apparatus rotated into a second position relative to FIG. 12.

After the lesion 170 is formed, the pulmonary treatment system 2100 is rotated ⅛$^{th}$ of a turn to the location shown in FIG. 15. In one example, the cartilage rings are used as a guide as the pulmonary treatment system is rotated. For example, following the first application of energy in the location shown in FIG. 12, a fluid supply to the expandable member 2140 can be reduced or interrupted without fully deflating the expandable member 2140. In this state, the expandable member 2140 continues to bias the treatment wand 2110 between adjacent cartilage rings, but allows the pulmonary system 2100 to be rotated. The adjacent cartilage rings act as guide during rotation, and the electrode 2120 can be moved to the next treatment location in a more repeatable manner. Once the electrode 2120 reaches the second treatment location shown in FIG. 15, the fluid supply the expandable member 2040 can be returned to a level appropriate to achieve full apposition. The treatment sequence is then repeated to create second lesion adjacent, and possibly overlapping, the lesion 170. The process is repeated to create a completely circumferential zone of ablation 117, as shown in FIG. 16.

The pulmonary treatment system can be positioned to avoid branching points in the bronchial tree to avoid applying excess heat and creating unwanted damage to a thin walled portion of the airway, such as a septum between adjacent airways. In one example, the left lung can be treated by positioning the pulmonary treatment system in the left distal main stem bronchus with a tip of the pulmonary treatment system located just in the orifice of the left lower lobe bronchus and the electrode 2120 positioned spaced distally from the main carina. In one example, the electrode 2120 is positioned at least 10 millimeters from the main carina.

In another example, the right lung can be treated by positioning the pulmonary treatment system in the right distal main stem bronchus such that the electrode 2120 is proximal to the orifice of the right upper lobe bronchus on the lateral wall and spaced from the main carina on the medial wall. In one example, electrode 2120 is positioned at least 4 millimeters proximal to the orifice of the right upper lobe bronchus on the lateral wall and at least 10 millimeters from the main carina on the medial wall.

Longitudinally and circumferentially offset treatment patterns can be used to avoid narrow portions of the airway. In one such example, the right lung is treated by applying energy at two offset locations along the main stem bronchus to avoid the carina and the upper lobe bronchus. The first treatment location is in the right main bronchus proximal to the branching point of the upper lobe bronchus. The electrode 2120 is rotated or otherwise positioned at the first treatment location to treat the lateral wall of the right main bronchus without affecting the carina located on the medial side of the right main bronchus. As with the treatment discussed above, the electrode 2120 can be positioned between adjacent cartilage rings in the first treatment position. Depending on the length of the electrode 2120, a single or multiple treatments can be applied at the first location to create a lesion around a portion of the circumference on at least the lateral side of the right main bronchus without creating a lesion on the carina.

The second treatment location is further into the right main bronchus than the first treatment location, distal of the carina. The electrode 2120 is rotated or otherwise positioned at the second treatment location to treat the medial wall of the right main bronchus without affecting the upper lobe bronchus located on the lateral side of the right main bronchus. As with the treatment discussed above, the electrode 2120 can be positioned between adjacent cartilage rings in the second treatment position. Depending on the length of the electrode 2120, a single or multiple treatments can be applied at the second location to create a lesion around a portion of the circumference on at least the medial side of the right main bronchus without creating a lesion on the upper lobe bronchus.

The lesions created in the first and second locations can overlap circumferentially when viewed down the longitudinal axis of the airway so that, when taken together, they form a pair of offset lesions that disrupt nerve activity around an entire circumference of the airway wall. This technique avoids the need to create a single, continuous lesion around the airway that could, in some circumstances, cause undesired damage tissue to thin walled portions of the airway, such as near the carina or other branch in the bronchial tree.

Figure 16A:
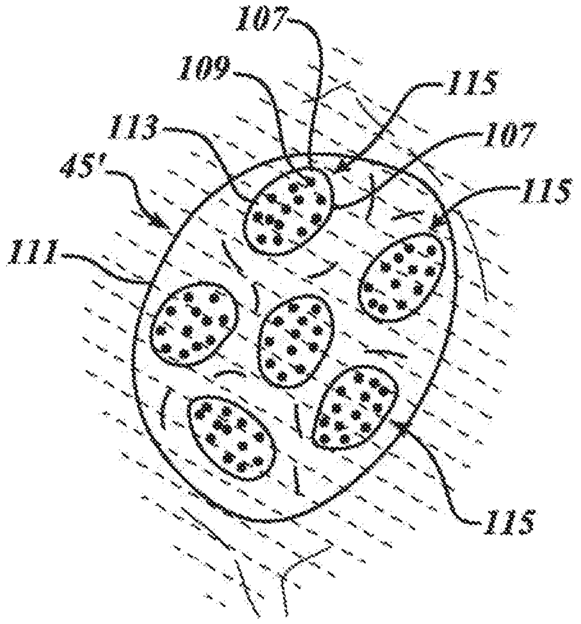
FIG. 16A is the detail view of a nerve trunk shown in FIG. 16.

FIG. 16A is an enlarged cross-section of a nerve trunk 45' that is within the zone of ablation in FIG. 16. The nerve trunk 45' includes fascicles 115 protected by an epineurium 111. The fascicles 115 include nerve fibers 109 and a perineurium 107 surrounding the fibers 109. The nerve fibers 109 have axons, myelin that surrounds and insulates each of the axons, and endoneurium 113.

The nerve trunk 45' has the ability to regenerate. Neuroregeneration may include, for example, remyelination and formation of new neurons, glia, axons, myelin, and/or synapses. If axons are damaged, the axons can retract and neurons can undergo a relatively short dormant phase. The neurons can then be activated for axon regeneration. Severe injuries, such as a Type 3 injury or greater as discussed below, can inhibit reinnervation.

Type 1 nerve injuries involve neurapraxia that typically involves demyelination with an intact nerve. There is no interruption of axonal or connective tissue continuity. Remyelination can occur resulting in about 100% recovery.

Type 2 nerve injuries involve axonotmesis that is often characterized by axonal disruption with intact connective tissue sheaths. Endoneurial microstructure is maintained, often resulting in complete functional regeneration of axons. There is about 90% recovery.

Type 3 nerve injuries are characterized by discontinuity of endoneurial microstructures including injuries to axons, and may involve endoneurial scarring. There is generally no injury to the perineurium. Recovery from such an injury may be dependent upon the extent of the injury. A relatively long lesion formed by a Type 3 injury may prevent functional regeneration of nerve tissue. Scar tissue can form to help prevent reinnervation. There is often less than 60% recovery.

A Type 4 nerve injury is a complete injury to nerve fibers and often involves significant scarring contained within the epineurium 113. Regeneration of axons is difficult because substantially the entire population of axons within a fascicle are blocked by scar tissue. A fourth degree injury involves injury to the axon, myelin, endoneurium, and perineurium. There is often less than about 10% to about 20% recovery.

A Type 5 injury occurs when nerve fiber and axons in all connective tissue elements are divided or severed. A complete transection is a Type 5 injury. Nerves typically do not regenerate after complete transection. Thus, there is typically no functional recovery.

The methods and systems of at least some embodiments of the present disclosure enable the selection of the desired type of injury based on various factors including the power level, lesion size, lesion location, number of lesions, and lesion composition to achieve a desired effective length of treatment. By way of example, lesion 170 can be a Type 3 or greater nerve injury that involves disruption of axon sheaths and the formation of scar tissue in the endoneurium. This alters respiratory function of a region of the lung distal to the injury site for a significant length of time (for example, at least about 6 months). In some procedures, substantially all of the axons of the fascicle 115, myelin, and endoneurium 113 are destroyed. Scar tissue replaces the destroyed tissue. In some procedures, all of the axons of the fascicle 115, the myelin, and endoneurium 113 are ablated and replaced by scar tissue. Denervation can include targeting efferent parasymthetic nerves, afferent parasympathetic nerves, c-fibers, or other nerve tissue to denervate airways of one or both lungs. The system can inhibit afferent c-fiber reinnervation, without or without efferent reinnervation.

In addition to damaging nerves, delivering energy from the pulmonary treatment system 2110 may occlude at least one bronchial artery 130' within the zone of ablation 117. It is believed that occluding a bronchial artery that extends along a first airway may reduce inflammation in a second airway that is a higher generation airway of the first airway. For example, it is has been found that occluding a bronchial artery along the first airway can result in backfilling the occluded artery and lowering blood pressure in the occluded artery at the second airway. This may result in a decrease in the supply of blood that feeds inflammation at the second airway, thereby reducing inflammation at the second airway. In addition, the decrease in nutrient supply to the mucosa and smooth muscle would result in decreased cellular function. A lower pressure gradient further results in lower interstitial fluid buildup, thereby decreasing the hydrostatic pressure gradient.

Figure 17A:
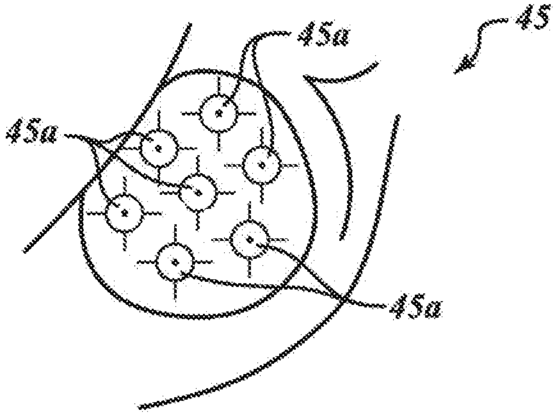
FIG. 17A is a detail view of the nerve axons of a nerve trunk associated with the airway of FIG. 17.

Further effects of the example treatment described above on distal airways will now be discussed with reference to FIGS. 17 and 18. FIG. 17 is a cross-sectional view of a distal airway in the lung, taken along line 17-17 of FIG. 11, prior to treatment. FIG. 16 is a cross-sectional view of the same airway after. FIGS. 17A and 18A provide detailed views of nerve axons of a nerve trunk associated with the distal airway before and after the treatment, respectively.

As shown in FIG. 17, prior to treatment, the lumen 101*b* of the airway 100*b* narrow and is partially blocked by excess mucus 150. Depending on the patient, the reduced size of the lumen 101*b* can be attributable to variety of ailments, including, for example, inflammation of the airway wall 103, constriction of the smooth muscle tissue 114, or excessive intraluminal mucus or edema fluid, or both.

Figure 18:
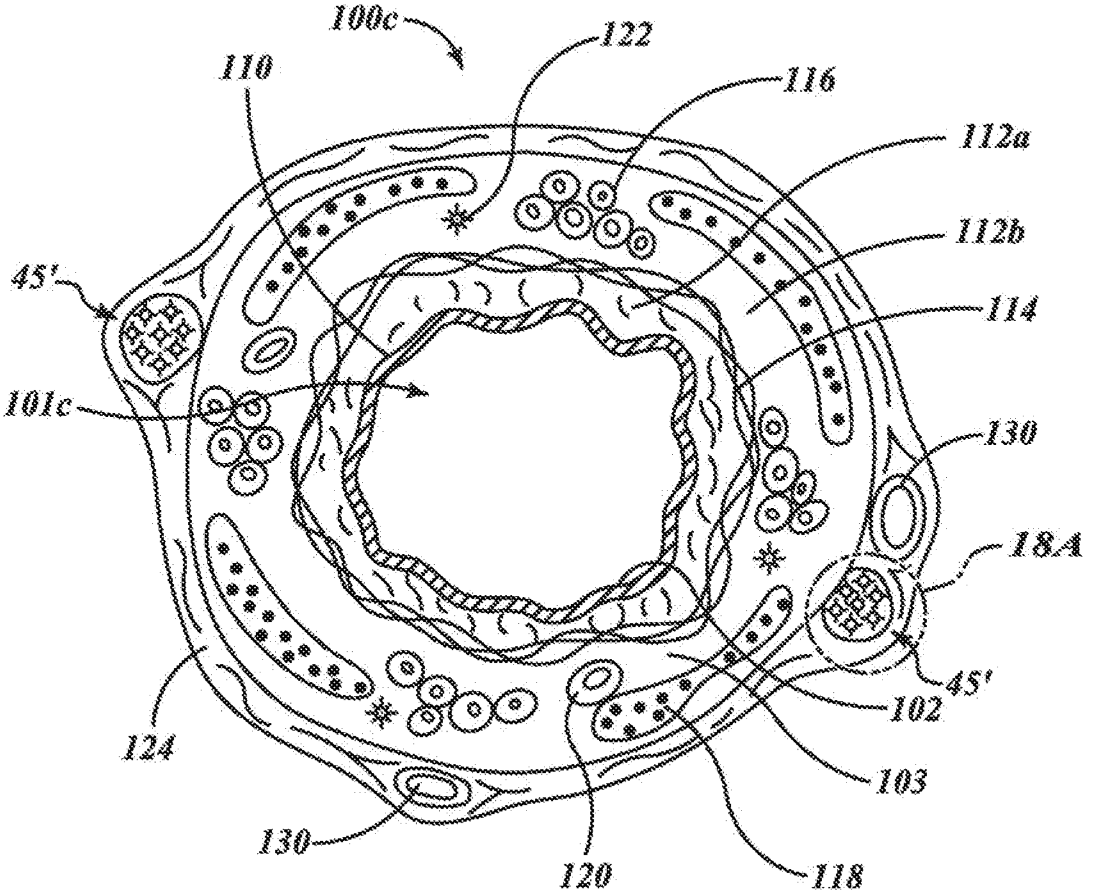
FIG. 18 is a cross-sectional view of the distal airway of FIG. 17 after a treatment.
Figure 18A:
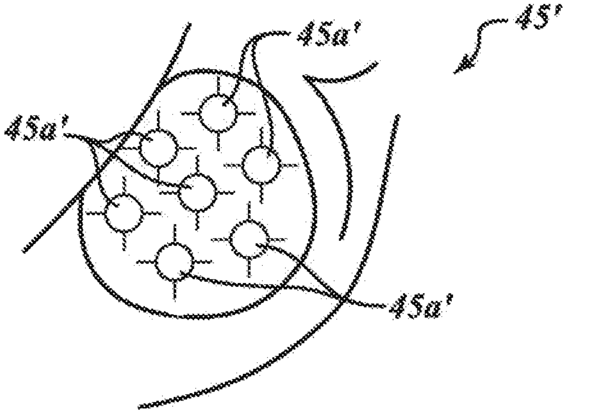
FIG. 18A is a detail view of the destroyed nerve axons of the nerve trunk associated with the airway of FIG. 18.

Following treatment, as shown in FIG. 18, the lung lumen 101*c* has opened a significant amount, and mucus production is greatly reduced. Notably, the nerve axons that are present in FIG. 17A, are no longer present in FIG. 18A. Nevertheless, the function of other tissue or anatomical features, such as the mucous glands, cilia, smooth muscle, body vessels (e.g., blood vessels), and the like can be maintained even though the nerve tissue is injured.

As a result of the treatment, the nerve supply along a section of the bronchial tree can be cut off. When the signals are cut off, the distal airway smooth muscle can relax, which can lead to the airway dilation seen in FIG. 18. Cutting the nervous system signals can also causing mucous cells to decrease mucous production leading to the reduced amount of mucous in the lumen 101*c* of FIG. 18. The treatment may also cause inflammatory cells to stop producing airway wall swelling and edema. For example, the occurrence of acetylcholine receptors may be increased, while inflammatory cells, inflammatory cytokines, and other markers in the distal airway may be reduced.

All of these changes reduce airflow resistance so as to increase gas exchange in the lungs 10, thereby reducing, limiting, or substantially eliminating one or more symptoms, such as breathlessness, wheezing, chest tightness, and the like. Tissue surrounding or adjacent to the targeted nerve tissue may be affected but not permanently damaged. In some embodiments, for example, the bronchial blood vessels along the treated airway can deliver a similar amount of blood to bronchial wall tissues and the pulmonary blood vessels along the treated airway can deliver a similar amount of blood to the alveolar sacs at the distal regions of the bronchial tree 27 before and after treatment. These blood vessels can continue to transport blood to maintain sufficient gas exchange. In some embodiments, airway smooth muscle is not damaged to a significant extent. For example, a relatively small section of smooth muscle in an airway wall which does not appreciably impact respiratory function may be reversibly altered. If energy is used to destroy the nerve tissue outside of the airways, a therapeutically effective amount of energy does not reach a significant portion of the non-targeted smooth muscle tissue.

In addition to the near-term benefits, interrupting nervous system signal communication with distal airways has the long term effect of remodeling previously constricted airways beyond simply relaxing the smooth muscle tissue or reducing mucous production. For example, without nervous signals causing them to contract, the smooth muscle will begin to atrophy over time. Eventually, smooth muscle and muscle gland mass will decrease. In addition, there will be a decrease in airway wall fluid, such as edema and interstitial tissue fluid. As such, unlike temporary treatments that block nervous system signals for discrete periods of time, it is expected that the amount of obstruction in distal airways will continue to decrease over time following a treatment with the pulmonary treatment systems of the present disclosure.

Additional aspects of the present disclosure, including aspects relating to thermodynamically cooled treatment systems, improved electrodes, apposition members, and liquid cooled pulmonary treatment systems, will be discussed in greater detail below.

II. Thermodynamically Cooled Pulmonary Treatment System

FIGS. 19-21 illustrate various example aspects of thermodynamically cooled pulmonary treatment systems according to the present disclosure.

Advantageously, employing thermodynamic cooling in the pulmonary treatment system 2100 discussed above not only increases the cooling efficacy of pulmonary treatment systems, but also decreases the delivery size of the pulmonary treatment system. For example, thermodynamically cooling the energy delivery system at the treatment site eliminates the need to cool a liquid cooling media outside of the patient's body and then transport it to the treatment site. Accordingly, the size of a supply lumen of a cooling media can be reduced without regard to thermal losses during transport to the treatment site. In addition, as noted above, using gas for a cooling media instead of a liquid further reduces the size requirements of the supply and return lumens of the cooling system.

However, although the thermodynamically cooled pulmonary treatment systems described herein advantageously allow for a compact design that facilitates compatibility with the working channel of a flexible bronchoscope, the aspects described herein are not so limited. For example, as will be readily apparent to one of ordinary skill in the art upon a complete review of the present disclosure, the aspects disclosed in FIGS. 19-21 are also scalable to be compatible with larger working lumens that may or may not be associated with a bronchoscope. Notably, the present disclosure is not limited solely to systems that are delivered via the working channel of a bronchoscope, but also encompasses systems delivered by other means, such as an independent sheath and/or delivery catheter.

Further, although treatment wands and expandable members in the various examples that follow are shown being deployed from the same working channel, the treatment wand and the expandable member may be arranged to be positioned at a treatment site independent of each other, through separate working channels or via a separate delivery catheters. Specifically, by decoupling the treatment wand from the expandable member they may be introduced separately from each other, allowing the pulmonary treatment system to be introduced through very small-diameter passageways. This is particularly useful to allow the pulmonary treatment system to be inserted through a working channel of a bronchoscope. First, the treatment wand may be collapsed and introduced through the working channel (with or without a sheath), then the expandable member can be introduced. The combined apparatus may then be assembled within the airway outside the working channel.

FIGS. 19A-19F illustrate the thermodynamically cooled pulmonary treatment system 2100 discussed above being deployed from and then withdrawn into a working channel of a flexible bronchoscope. For ease of representation, only the working channel 516 of the bronchoscope is shown in FIGS. 19A-19F.

Figure 19A:
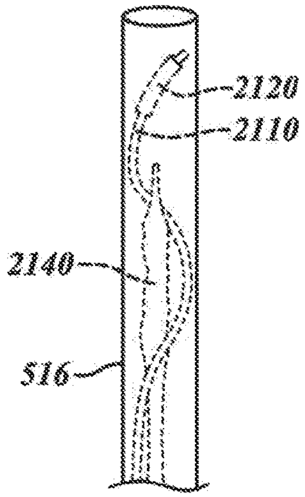
FIG. 19A is a pictorial view of a pulmonary treatment system ready to be deployed from a delivery apparatus.

FIG. 19A illustrates the treatment wand 2110, which includes the electrode 2120, arranged around the expandable member 2140 within the working channel 516. For example, the treatment wand 2110 can have a slight bend as depicted in FIG. 19A such that the wand 2110 surrounds the expandable member 2140 to aid in the advancement of the expandable member 2140 through fictional engagement during advancement through the working channel 516. The working channel 516 of the bronchoscope can have a working channel in the range of 500 to 650 millimeters. An overall working length of the pulmonary treatment system can be less than 800 mm, preferably about 760 mm. Further both the treatment wand 2110 and the expandable member 2140 have sufficient flexibility enough to accommodate a bending radius of 3.1 mm or less or, in some examples, 2.7 mm or less. Although not depicted in this example, the pulmonary treatment system 2100 could be slidably positioned within and deployed from a separate sheath that is advanced through the working channel 516.

Figure 19B:
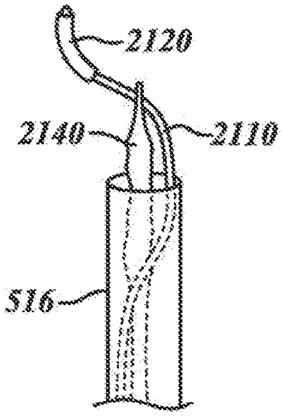
FIG. 19B is a pictorial view of the pulmonary treatment system of FIG. 19A in a partially deployed state.
Figure 19C:
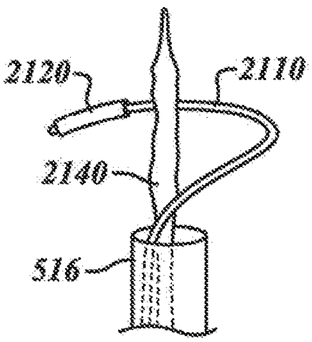
FIG. 19C is a pictorial view of the pulmonary treatment system of FIG. 19A in a deployed state prior to inflation of an apposition member.
Figure 19D:
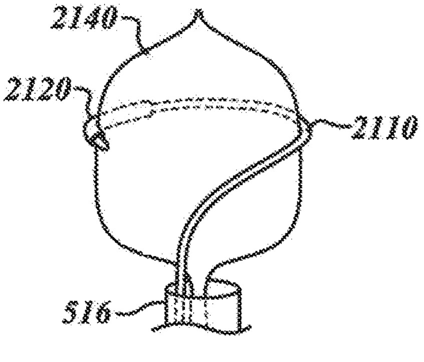
FIG. 19D is a pictorial view of the pulmonary treatment system of FIG. 19A in the deployed state with the apposition member inflated.

The expandable member 2140 and the treatment wand 2110 are then advanced together out of the working channel 516 at the same time, as shown in FIGS. 19B and 19C. As the treatment wand 2110 is deployed, it can take on a predetermined shape around the expandable member 2140. The treatment wand 2110 can include a shape memory material. Shape memory materials include, for example, shape memory metals or alloys (e.g., Nitinol), shape memory polymers, ferromagnetic materials, combinations thereof, and the like. In the partially deployed state illustrated in FIG. 17B, the treatment wand 2110 contracts towards the working channel 516 as it simultaneously bends and takes on a larger profile in a direction transverse to the working channel 516. In this state, the profile of the treatment wand 2110 is larger than a diameter of the working channel. In FIG. 19C, the treatment wand 2110 is in a fully deployed state, in which the treatment wand takes a circular or spiral orientation suitable for apposition with an airway wall. The expandable member 2140 is then inflated, as shown in FIG. 19D, to bring the electrode 2120 on the treatment wand 2110 in apposition with an airway wall. In this state, the expandable member 2140 and the treatment wand 2110 are in close appositional contact such that, as discussed above, the expandable member 2140 could also serve as a passively cooled element during energy delivery.

Figure 19E:
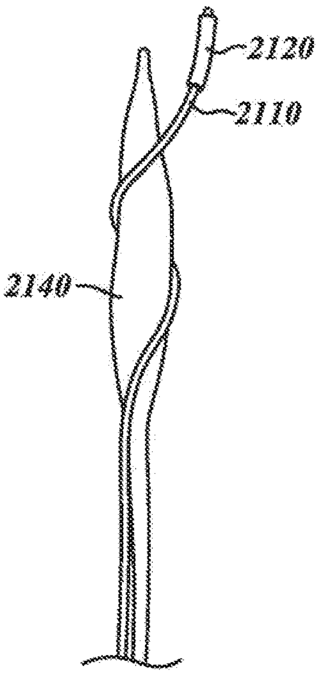
FIG. 19E is a pictorial view of the pulmonary treatment system of FIG. 19A in a deployed state prior to prior to withdrawal of the pulmonary treatment system into the delivery apparatus.
Figure 19F:
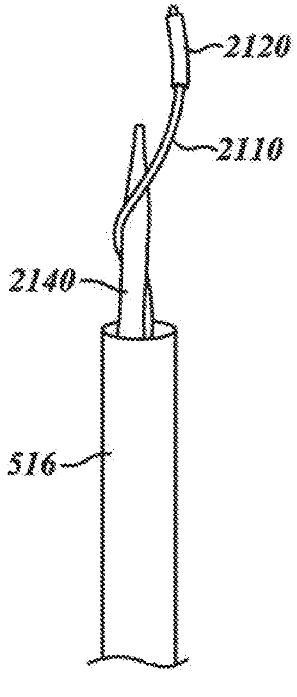
FIG. 19F is a pictorial view of the pulmonary treatment system of FIG. 19A in partially withdrawn state.

Following treatment, the expandable member 2140 can be deflated and the treatment wand 2110 can be returned to its delivery configuration. In some cases, the shape of the treatment wand 2110 can be temperature dependent, such that activating the thermodynamic cooling system can assist the treatment wand 2110 in returning to a delivery configuration for ease of withdrawal through the working channel 516, as shown in FIGS. 19E and 19F. Specifically, the expandable member 2140 is deflated and, either subsequently or concurrently, the thermodynamic cooling system is activated, thereby lowering the temperature of the treatment wand 2110 such that the treatment wand takes on a more compliant state and reduced profile shape, similar to that during initial advancement through the working channel 516. As seen in FIG. 19E, the profile of the treatment wand 2110 in a direction transverse to the working channel is once again reduced. Then, as shown in FIG. 19F, both the treatment wand 2110 and the expandable member 2140 can be withdrawn into the working channel, as the combined diameters of both these components is less than, in some cases 3.1 millimeters, or, preferably, less than 2.7 millimeters.

In another aspect, FIGS. 20A-20D illustrate a pulmonary treatment system 3100 in which a thermodynamically cooled treatment wand is arranged axially in line with, and distal of, an expandable member during delivery. Advantageously, locating the treatment wand distal of the expandable member rather than proximal of the expandable member allows a practitioner to optically couple a visualization device, such as a bronchoscope, to the deployable member without the treatment wand obscuring the view. This configuration also contributes to a compact delivery configuration, as the treatment wand can be arranged axially in line with the deployable member in the delivery state.

Figure 20A:
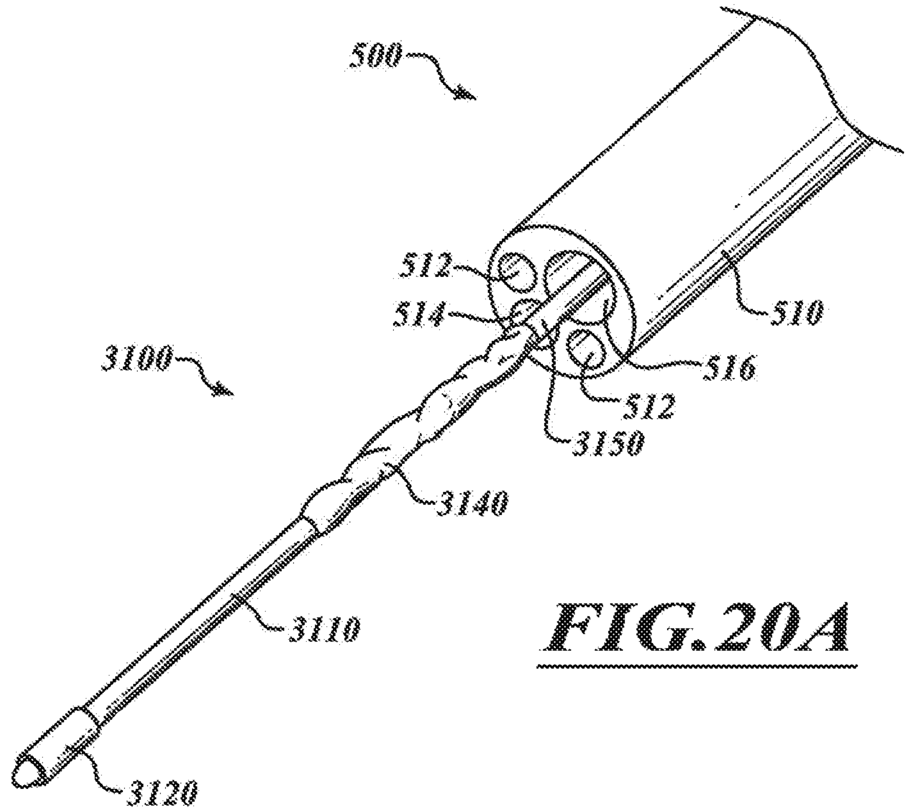
FIG. 20A is an isometric view of another aspect which provides easy coupling of the bronchoscope optics to the proximal portion of an apposition member which is configured to allow direct visualization of the energy emitter.

FIG. 20A illustrates the pulmonary treatment system 3100 that includes a thermodynamically cooled treatment wand 3110, an electrode 3120, and an expandable member 3140, and a fluid delivery conduit 3150. FIG. 20A illustrates the pulmonary treatment system 3100 in an initial state of deployment, in which the treatment wand 3110 is axially aligned with the expandable member 3140. In particular, the expandable member 3140 from a distal end of the fluid delivery conduit 3150, the thermodynamically cooled treatment wand 3110 extends from a distal end of the expandable member 3140, and the electrode 3120 is arranged around a distal portion of the thermodynamically cooled treatment wand 3110. This compact design contributes to the compact delivery size of the pulmonary treatment system 3100. In this example, the pulmonary treatment system 3100 is deployed from a working channel 516 of a flexible bronchoscope 500. In this example, the flexible bronchoscope 500 also includes an insertion tube 510, two light guides 512, and an objective lens 514.

Figure 20B:
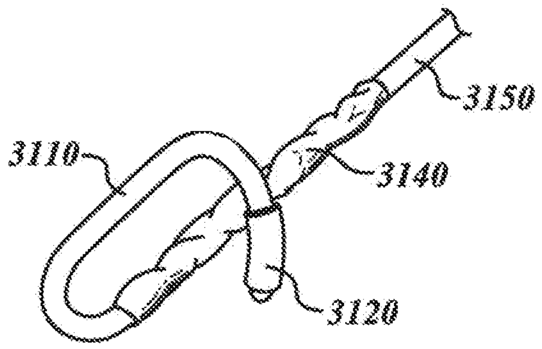
FIG. 20B is an isometric view of the pulmonary treatment system of FIG. 20A in a partially deployed state, prior to inflation of the apposition member.

FIG. 20B illustrates the treatment wand 3110 taking a spiral shape and bending rearward around the expandable member 3140. For example, the treatment wand 3100 can be preshaped so as to have a first bend distal to the expandable member about an axis perpendicular to the longitudinal axis, a generally straight section extending proximally in the axial direction along the expandable member, and a curved section with a curvature about an axis generally parallel to the longitudinal axis and generally corresponding to the curvature of the airway wall.

Figure 20C:
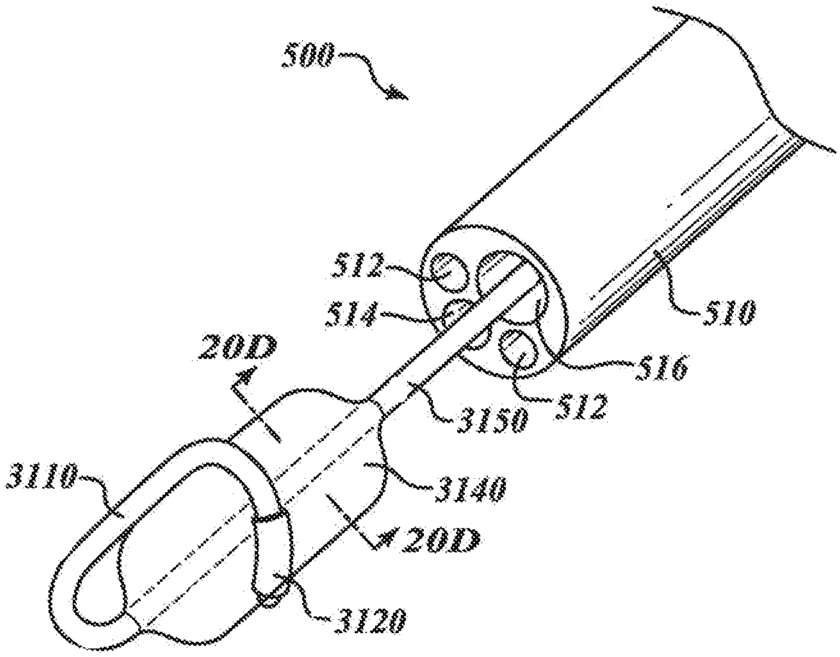
FIG. 20C is an isometric view of the pulmonary treatment system of FIG. 20A in a fully deployed state.

The expandable member 3140 is then inflated, as shown in FIG. 20C. In this state, the expandable member 3140 presses into close contact with the treatment wand 3110 to bring the electrode 3120 into close apposition with the airway wall for treatment. Further, as the expandable member inflates, it draws up and around the treatment wand 3110 and conforms to the shape of the portions of the treatment wand 3110 it contacts such that there is no air gap between the expandable member, the electrode 3120, and the airway wall. The insertion tube 510 of the bronchoscope 500 is advanced up to the back of the expandable member 3140 to optically couple the bronchoscope 500 to the expandable member 3140. In particular, the objective lens 514 is pressed against expandable member 3140. In this example, the expandable member is made of a transparent or semi-transparent material. With this technique, a practitioner can better visualize the treatment site through the balloon.

Figure 20D:
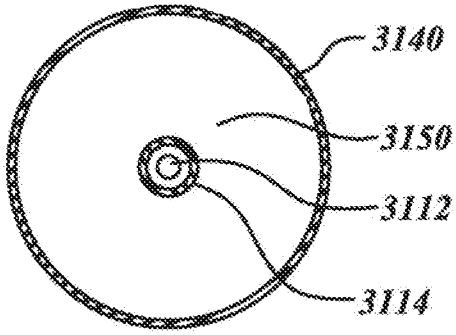
FIG. 20D is a cross-sectional view of the pulmonary treatment system of FIG. 20C, taken along lines 20D-20D of FIG. 20C.

FIG. 20D is a cross-sectional view of the pulmonary treatment system 3100 taken along lines 20D-20D of FIG. 20C. As shown in FIGS. 20C and 20D, a fluid delivery conduit 3150 extends through the expandable member 3140 to the thermodynamically cooled treatment wand 3110. The fluid delivery conduit 3150 includes a supply lumen 3112 and return lumen 3114 coaxial with the supply lumen 3112, each in fluid communication with corresponding lumens in the treatment wand 3110. Specifically, the fluid supply lumen 3112 terminates in a nozzle positioned in the electrode 3120 in a manner similar to the nozzle depicted in FIG. 10, and the return lumen corresponds to the return lumen 2114 described above with reference to FIG. 10. Advantageously, as treatment wand 3110 and the delivery conduit 3150 are more rigid than the expandable member 3140, this configuration allows the combination of the delivery conduit 3150 and the treatment wand 3110 to act as a push rod to advance the expandable member 3140 in its flimsy, deflated state through the working conduit 516 of the flexible bronchoscope 500 to a treatment site.

In the present example, the expandable member 3140 is coupled to a coolant supply that is independent of the coolant supplied to the thermodynamically cooled energy delivery system via the fluid delivery conduit 3150. Advantageously, this configuration decouples actuation of the expandable member 3140 from coolant flow to the treatment wand 3110.

In addition, if the fluid supplied to the expandable member 3140 is a liquid coolant, the expandable member 3140 can be passively cooled from two sides: (i) externally from the treatment wand 3110 as it extends circumferentially around the expandable member; and (ii) internally from the return lumen 3114 of the fluid delivery conduit 3150. For example, a high pressure gas can be initially supplied to the throttle (not depicted) in the electrode 3120 via the fluid supply lumen 3112. The fluid supply lumen 3112, and thus the high pressure gas, passes through the fluid delivery conduit 3150, then through the portion of the thermodynamically cooled treatment wand 3110 that extends through the inside of the expandable member 3140, then through the portion of the thermodynamically cooled treatment wand 3110 that extends outside of and around the exterior surface of the expandable member 3140, and then terminates in the nozzle in the portion of the thermodynamically cooled treatment wand 3110 that includes the electrode 3120. Following expansion and rapid cooling caused by passing through the throttle, the now-chilled fluid, in either a liquid or gaseous phase at this point, returns through the return lumen 3114, taking the reverse of the route to that taken by the supply lumen 3112. Specifically, the now chilled fluid initially passes through the portion of the thermodynamically cooled treatment wand 3110 that extends outside of and around the exterior surface of the expandable member 3140. The portions of the treatment wand directly contact an outside of the expandable member 3140 serve to cool the expandable member 3140 from the outside through this close, direct contact between the expandable member 3140 and the external surface of the thermodynamically cooled treatment wand 3110. The chilled fluid in the return lumen 3114 passes then further through the thermodynamically cooled treatment wand 3110, and back through the center of the expandable member 3140. The liquid coolant within the expandable member 3140 is, at this stage, further chilled by direct contact with the portion of the external surface of the thermodynamically cooled treatment wand 3110 that extends within the expandable member 3140.

In another example, the expandable member 3140 is in fluid communication with the energy system return lumen 3114, and is inflated when coolant is supplied to the treatment wand 3110. In another example, the expandable member 3140 is actively cooled by a continuously circulated coolant supply that is independent from the coolant supply associated with the thermodynamically cooled treatment wand 3110.

Thermodynamically cooling the energy delivery system at the treatment site at the distal end of the pulmonary treatment system results in far higher temperature drops than are possible by solely circulating an externally cooled liquid through the pulmonary treatment system. This increase in cooling efficiency allows for greater flexibility in the size, shape, and treatment role of structures in the energy delivery system such as apposition members and dedicated cooling members.

Figure 21A:
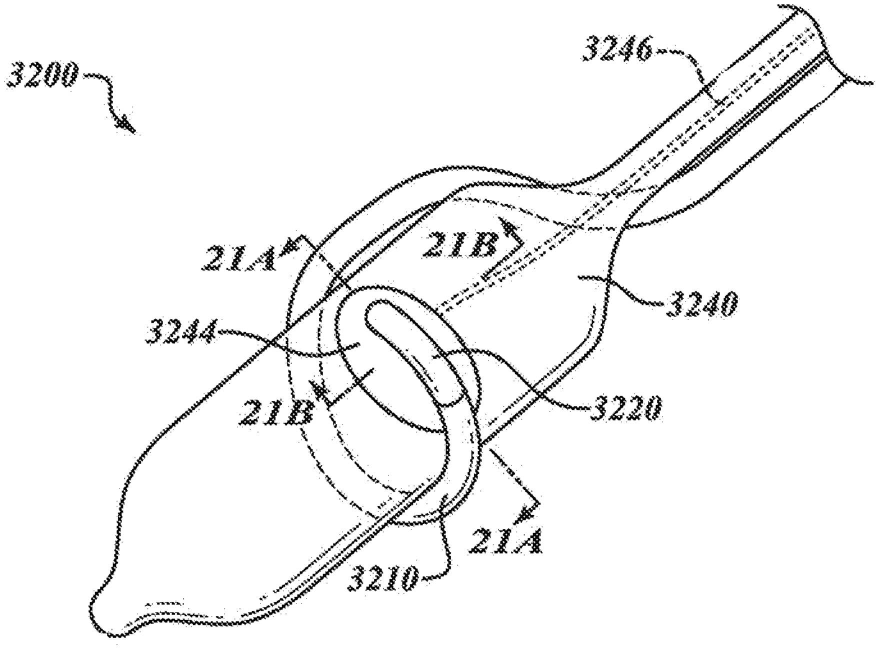
FIG. 21A is an isometric view of a pulmonary treatment system according to another aspect.

For example, FIGS. 21A-21C illustrate a pulmonary treatment system that includes a secondary cooling bladder in addition to an expandable member.

FIG. 21A illustrates a pulmonary treatment system 3200 in a fully deployed state. The pulmonary treatment system 3200 includes an expandable member 3240, a secondary cooling bladder 3244, and a thermodynamically cooled treatment wand 3210. A distal portion of the thermodynamically cooled treatment wand 3210 extends partially around a circumference of the expandable member 3240. A distal end of the distal portion of the thermodynamically cooled treatment wand 3210 includes an electrode 3220. The secondary cooling bladder 3244 is arranged around and between the electrode 3220 and the expandable member 3240. As such, although portions of the expandable member 3240 are in close direct contact with the distal portion of the thermodynamically cooled treatment wand 3210, the secondary cooling bladder 3244 wraps closely around the portion of the thermodynamically cooled treatment wand 3210 that includes the electrode 3220.

The cooling bladder 3244 is supplied with a coolant via a tube 3246. In some embodiments treatment wand 3210 will be straightenable and positionable distally of expandable member 3240 during delivery as described above, and in such cases, tube 3246 will be configured with sufficient flexibility and dimensions to allow cooling bladder 3244 to move with the treatment wand into such a delivery configuration. In some embodiments, tube 3246 may be adhered to the outside of the shaft of treatment wand 3210, or may be a lumen integrally formed within such shaft. FIG. 21B is a partial cross-sectional view of the pulmonary treatment system 3200 during a treatment session. The depiction in FIG. 21B provides further detail on how the secondary cooling bladder 3244 extends around a portion of the circumference of the electrode 3220. Cooling bladder 3244 is configured to conform closely to the electrode such that the airway tissue along the edges of the electrode are directly contacted by the bladder and cooled therewith. The expandable member 3240 may assist the positioning of secondary cooling bladder 3244 into close, conforming contact with both the electrode 3220 and the airway wall 100.

As best seen in FIGS. 21B and 21C, the treatment wand 3210 includes a thermodynamic cooling system that includes a supply lumen 3212, a nozzle 3212*a*, and a return lumen 3214. With this arrangement, the secondary cooling bladder 3244, is passively cooled by the thermodynamic cooling system of the treatment wand 3120. In this example, rather than cooling the entire expandable member 3240, the secondary cooling bladder 3244 is sized and shaped to extend a short distance from the edges of electrode 3220 such that only the areas adjacent the electrode 3220 that are desired to be cooled are cooled by the thermodynamic cooling system.

This results in a more efficient use of the cooling generated by the treatment wand 3210. Additionally, this configuration allows the expandable member 3240 to be purely dedicated to the task of apposition, and thus be supplied with a gas, such with air. As shown in FIG. 21B, a lesion 173 can be created in the airway wall 100 at a desired depth without damaging tissue between the targeted area and the pulmonary treatment system 3200.

In the example pulmonary treatment system illustrated in FIGS. 22A-22D, the thermodynamically cooled treatment wand provides sufficient apposition for the electrode and cooling elements, and no additional apposition member is needed. This not only reduces the size of the pulmonary treatment system for delivery, but also vastly improves airway ventilation during treatment.

Figure 22A:
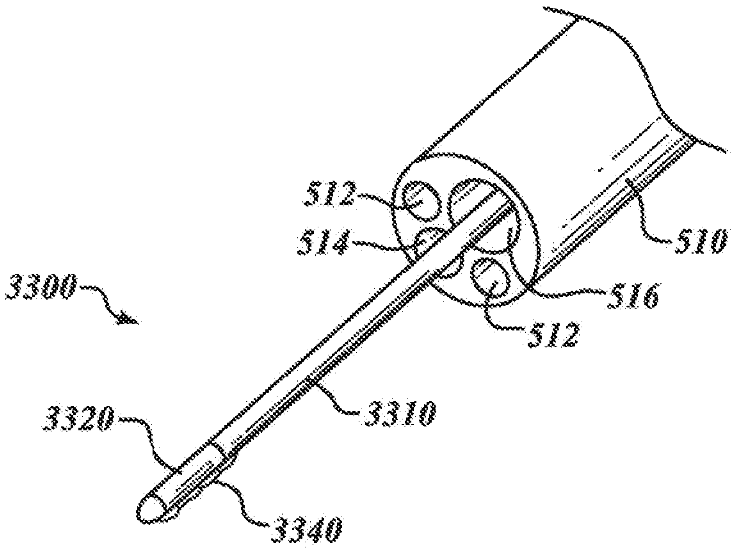
FIG. 22A is an isometric view of another aspect which includes a deployable cooling element located adjacent to an energy emitter assembly in a partially deployed state.

The pulmonary treatment system 3300 shown in FIG. 22A includes a thermodynamically cooled treatment wand 3310. An electrode 3320 and a cooling member 3340 are arranged on the treatment wand 3340. The cooling member can be fixedly attached to the cooling wand, or can be a separate, non-attached element that is arranged to be brought into close contact with the cooling wand during operation of the pulmonary treatment system 3300. A fluid supply lumen (not shown) extends through the shaft of treatment wand 3310 and communicates with the interior of cooling member 3340 for delivery of fluid thereto. As can be seen in FIG. 22A, this configuration is very compact for delivery, and can be deployed linearly out from a working channel 516 of a flexible bronchoscope.

Figure 22B:
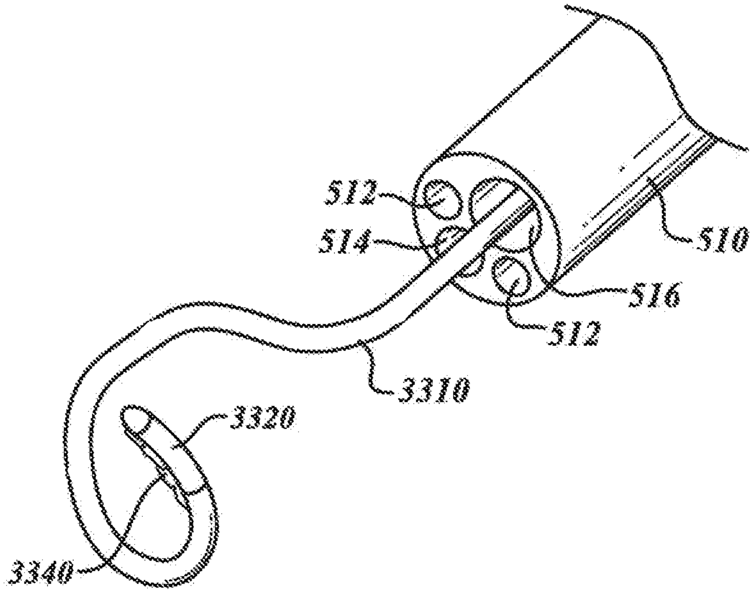
FIG. 22B is an isometric view of the pulmonary treatment system of FIG. 22A in a partially deployed state in which a shaft of the pulmonary treatment system or a bronchoscope is deployed to provide apposition.
Figure 22C:
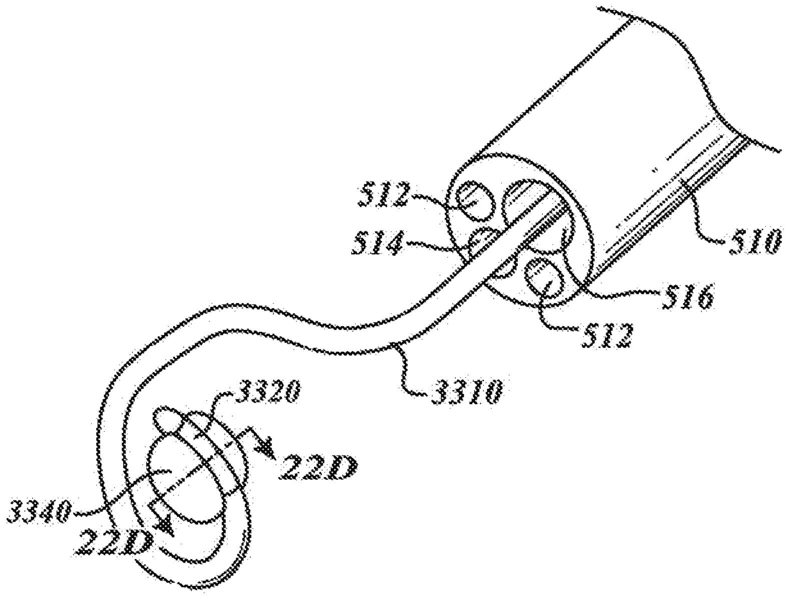
FIG. 22C is an isometric view of the pulmonary treatment system of FIG. 22A with both the energy emitter assembly and the cooling element fully deployed in a manner that reduces obstruction of the airway by the pulmonary treatment system.

FIG. 22B illustrates a second stage of deployment, in which the treatment wand 3310 is placed in a treatment configuration, and the cooling member 3340 remains deflated. The treatment wand 3310 can be made of a shape memory or self-conforming material that takes shape immediately upon deployment. In another example, the treatment wand 3310 can be actively shaped in the treatment configuration by shaping mechanisms such as pull wires or the hydraulic pressure of the thermodynamic cooling system within the treatment wand. Due to the absence of an expandable member to provide apposition of the electrode with the airway wall, the stiffness of the treatment wand is selected such that the shaped distal portion is firmly apposed to the airway wall in the deployed configuration, but may be straightened to a more compact configuration for delivery through the bronchoscope. FIG. 22C illustrates the cooling member 3340 in an expanded state. In the expanded state, the cooling member 3340 extends around electrode 3320 in order to engages tissue adjacent the electrode 3320 without air pockets.

Figure 22D:
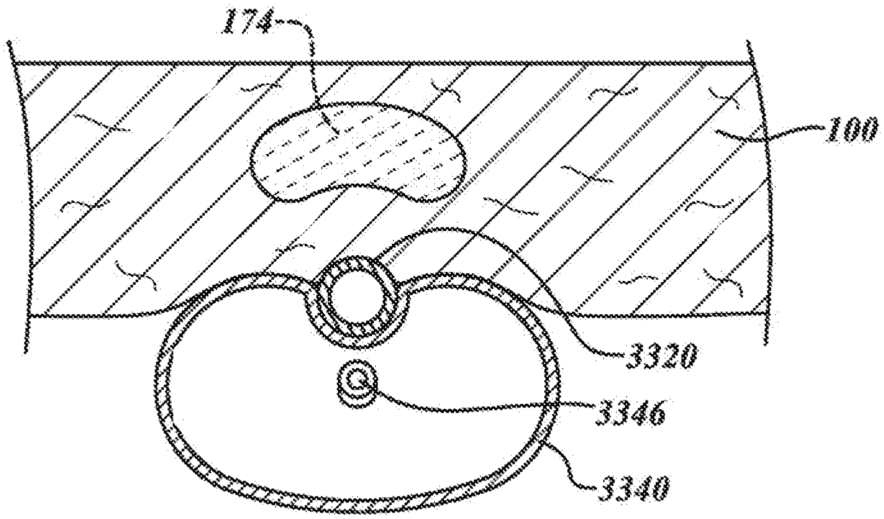
FIG. 22D is a partial, cross-section view of the pulmonary treatment system of FIG. 22A taken along lines 22D-22D of FIG. 22C.

FIG. 22D is a cross-sectional view of the pulmonary treatment system 3300 applying a treatment to an airway wall. For ease of representation, the supply lumen of the thermodynamic cooling system is omitted from this depiction. The cooling member 3340 includes an inlet 3346 through which a coolant can be introduced. The coolant can be continuously circulated or placed statically in the cooling member 3340 and cooled solely by passive cooling from the electrode 3320. The treatment wand 3310 provides good apposition with the airway wall 100. Such apposition may be assisted by active mechanisms in the treatment wand such as pull wires, push rods, or fluid lumens into which fluid may be introduced at high pressure, to urge the treatment wand into the desired curvature. Cooling member 3340 closely conforms to the exterior of electrode 3320 so as to directly engage and cool tissue adjacent to the edges of the electrode, minimizing any air gaps. With only the combination of the thermodynamic cooling with the passively cooled member 3340, the pulmonary treatment system 3300 is able to create a lesion 174 that is spaced from the pulmonary treatment system 3300.

III. Electrodes

FIGS. 23-47 illustrate various aspects of electrodes that may be applicable to the pulmonary treatment systems disclosed herein.

Although the electrodes disclosed herein are described with reference to either thermodynamically cooled energy delivery or energy delivery systems that employ liquid cooling systems, the electrodes described herein may be applicable to either system and are generally not limited to one or the other. Further, in some instances, the electrodes described herein are also applicable to systems that do not include cooling. In addition, the electrodes disclosed herein may also be applicable to other types of treatment, outside of the pulmonary system, such as in the esophagus, intestines, and or stomach to treat the digestive system; or the blood vessels or heart to treat the cardiovascular system.

In addition to the benefits discussed above, thermodynamically cooling an energy delivery device of a pulmonary treatment system can, in some instances, obviate the need for an additional cooling member. In particular, thermodynamic cooling can be combined with an electrode with a specifically tailored contact area to generate lesions in a target area that is remote from the electrode-tissue interface while protecting tissue located between the target are and an inner wall of the airway. This concept is shown in FIGS. 23-27, which illustrate various configurations of shielded and unshielded electrodes with various types of cooling, and the resulting effects on lesion formation.

Figure 23:
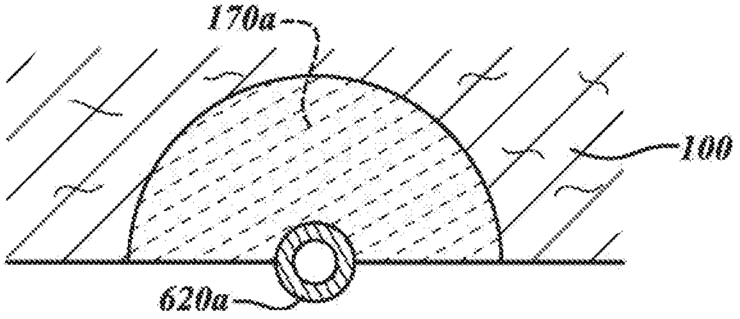
FIG. 23 is a longitudinal sectional view of a pulmonary treatment system creating a lesion in an airway. The pulmonary treatment system in this depiction includes an unshielded electrode with modest cooling.

FIG. 23 demonstrates what lesion formation would look like if an unshielded electrode applied energy with minimal to no cooling. In particular, FIG. 23 is a cross-sectional view of an unshielded electrode 620*a* in apposition with an airway wall 100. The electrode 620*a* is electrically and thermally conductive around its entire circumference, without shielding or insulation. The lesion 170*a* illustrated in FIG. 23 is representative of the type of lesion that would be formed when the electrode 620*a* is energized with RF energy and minimal to no cooling is applied to either the electrode 620*a* or the airway wall 100. For example, only a minimal amount of liquid is circulated through an interior of the electrode 620*a* and no additional cooling member, such as an actively or passively cooled expandable member, is applied to the airway wall 100 or the electrode 620*a*. As would be expected, the lesion 170*a* extends radially outward from the electrode 620*a*, with tissue damage extending from the airway wall and diminishing in size deeper into the tissue.

Figure 24:
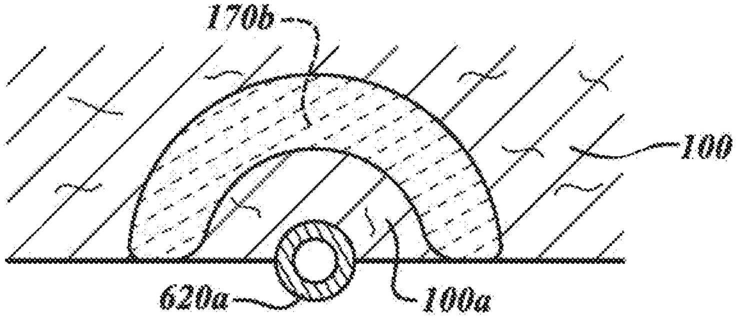
FIG. 24 is a longitudinal sectional view of a pulmonary treatment system creating a lesion in an airway and a protected area adjacent to the electrode of the pulmonary treatment system. The pulmonary treatment system in this depiction includes the same electrode as in FIG. 23, but has enhanced cooling relative to the cooling in FIG. 23.

FIG. 24 is another cross-sectional view of the unshielded electrode 620*a*. As with FIG. 23, the electrode 620*a* is electrically and thermally conductive around its entire circumference. The lesion 170*b* illustrated in FIG. 24 is representative of the type of lesion that would be formed when the electrode 620*a* is energized with RF energy and a high cooling rate is applied to the electrode 620*a*. For example, the electrode 620*a* can be subjected to thermodynamic cooling. As in FIG. 23, no additional cooling member, such as an actively or passively cooled expandable member, is applied to either the airway wall 100 or the electrode 620*a*. Thermodynamically cooling the electrode 620*a* makes it possible to lower the temperature of the airway wall at the electrode-tissue interface low enough to protect tissue from damage due to excessive heating, but not so low as to permanently damage tissue cryogenically. This cooling creates a protected region 100*a* in the airway wall between the lesion 170*b* and the electrode 620*a*.

Notably, the protected region 100*a* in FIG. 24 extends right up to the edge of the electrode 620*a*. As will be discussed in greater detail below, the region of the airway wall directly on either side of the electrode-tissue interface can be difficult to protect in non-thermodynamically cooled pulmonary treatment systems that create a protection region in the airway wall by circulating a liquid coolant through an energy delivery system and an expandable cooling member. In particular, it has been found that inadequate compliance and/or apposition of an expandable cooling member in such a system can result, in some cases, in tissue damage immediately along either side of the electrode. As is readily apparent from the protected region 100*a* in FIG. 24, thermodynamically cooling the electrode 620*a* addresses this issue.

Figure 25:
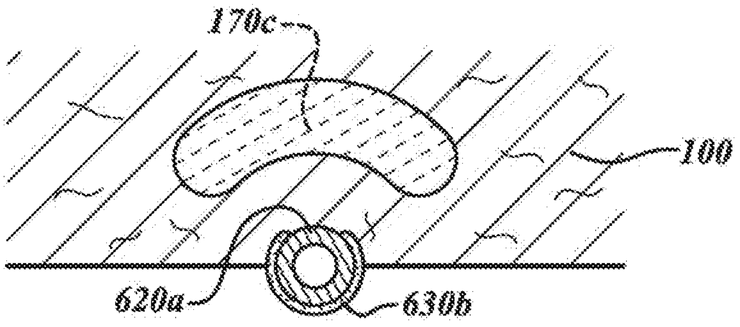
FIG. 25 is a longitudinal sectional view of an pulmonary treatment system creating a lesion in an airway and an enhanced protected area adjacent to the electrode of the pulmonary treatment system. The pulmonary treatment system in this depiction includes an electrode with shielding that is not present in the electrodes of FIGS. 23 and 24, and the enhanced cooling shown in FIG. 24.

It has been found that shielding the edge of the electrode can further improve surface protection of the airway wall during treatment. For example, FIG. 25 is a cross-sectional view of an electrode 620*b* that is partially shielded with a layer 630*a* of electrically insulating, thermally conductive material. The layer 630*a* extends partially around a circumference of the electrode 620*b* so as to cover all of the portions of the electrode 620*b* that are not in contact with the airway wall 100, as well as a selected amount of surface area that is in contact with the airway wall 100. Depending on the desired lesion shape, the shielding may cover as little as 180 degrees of the electrode surface, to as much as 340 degrees. Preferably, 30 to 45 degrees of the surface of the electrode 620*b* are not covered by the layer 630*a*. The lesion 170*c* illustrated in FIG. 25 is representative of the type of lesion that would be formed when the electrode 620*b* is energized with RF energy and a high cooling rate, such as by thermodynamic cooling, is applied to the electrode 620*b*. As with the previous examples, no additional cooling member is applied to either the airway wall 100 or the electrode 620*b*. Electrically shielding the edges of the electrode 620*b* with the layer 630*a* prevents unwanted heating in surface portions of the airway wall 100, while the thermal conductivity of the layer 630*a* allows the thermodynamic cooling to reach tissue immediately adjacent the electrode 620*b*. The resulting lesion 170*c* is spaced from the surface of the airway wall 100 in its entirety.

Thus, an energy delivery system that combines thermodynamic cooling with a selectively shielded RF electrode can generate a lesion within a target region of an airway wall while maintaining a protected region in which a majority of the airway wall tissue is not permanently damaged between the target region and the inner surface of the airway. Advantageously, this protection can be achieved without requiring a secondary cooling member.

Figure 26:
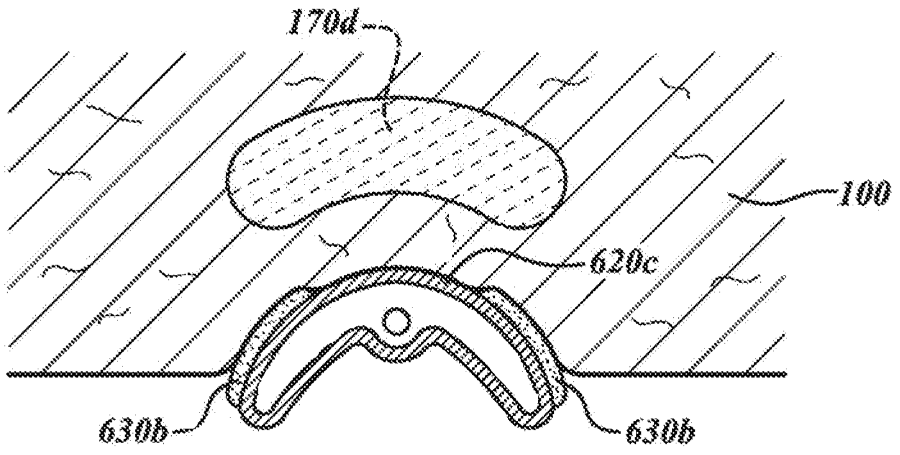
FIG. 26 is a longitudinal sectional view of another aspect of a pulmonary treatment system creating a lesion in an airway and an enhanced protected area adjacent to the electrode of the pulmonary treatment system.

FIG. 26 is a cross-sectional view of a partially shielded electrode according to another aspect. The electrode 620*c* includes two regions of masking 630*b* in which electrode 620*c* is covered with a thermally conductive, electrically insulating material. This creates an exposed electrically conductive region of limited area between the masking regions 630*b*. By thermodynamically cooling the electrode 620*c* during energy delivery, it is possible to generate the lesion 170*d*, that, like the lesion 17*c* of FIG. 25, is spaced from the surface of the airway wall 100 in its entirety. Unlike the electrode 620*b* in FIG. 25, the electrode 620*c* is flexible and/or deformable so that it can be moved from a collapsed, delivery configuration (not depicted), to the deployed configuration shown in FIG. 26. As will be discussed in greater detail below, this configuration reduces a delivery size of the electrode 620*c* while maintaining the contact area of the electrode 620*a* that is available at an electrode-tissue interface of the airway 100 during energy delivery. Advantageously, this contributes to a compact delivery profile of the pulmonary treatment system.

Figure 27:
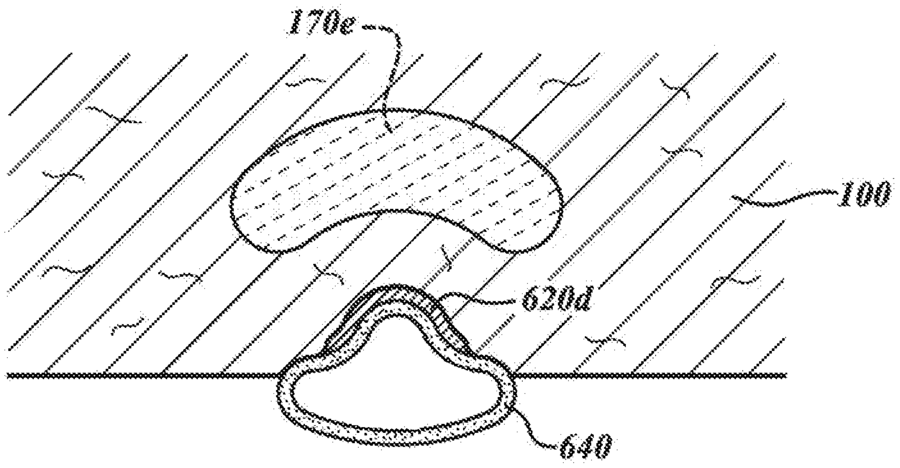
FIG. 27 is a longitudinal sectional view of another aspect of a pulmonary treatment system creating a lesion in an airway and an enhanced protected area adjacent to the electrode of the pulmonary treatment system. The electrode in FIG. 27 is located on the outside of a thermally conductive, electrically insulated cooling member.

FIG. 27 is a cross-sectional view of an energy delivery portion of a pulmonary treatment system that includes a flexible electrode 620*d* applied to a surface of an expandable member 640. The expandable member 640 can be, for example, a thermodynamically cooled inflatable member such as a balloon. In this example, the expandable member 640 is thermally conductive and electrically insulating. Simultaneous cooling and energy generation with this configuration results in a lesion 170*e* that is spaced from the surface of the airway wall 100 in its entirety. Advantageously, the collapsible nature of the electrode 620*d* and the expandable member 640 allow for a compact delivery size.

Notably, although no separate apposition member is illustrated in FIGS. 24-27, the aspects shown in FIGS. 24-27 can be achieved with or without a separate apposition member. For example, as discussed in the previous section, a thermodynamically cooled treatment wand can include a shape-memory material that allows the wand to appose the electrode of the pulmonary treatment system without the need for a further apposition member. On the other hand, as will be discussed below, various apposition or positioning members that do not perform cooling can be used in conjunction with a thermodynamically cooled pulmonary treatment system.

FIGS. 28 and 29 illustrate different aspects of a compact, thermodynamically cooled pulmonary treatment system that employs a collapsible, shielded electrode.

FIGS. 28A-28E illustrate a pulmonary treatment system that includes a compact design that is suitable for delivery via the working channel of a flexible bronchoscope. The pulmonary treatment system 3400 is similar to the pulmonary treatment system 3300 discussed above with reference to FIGS. 22A-22D, in that no separate apposition member is required.

Figure 28A:
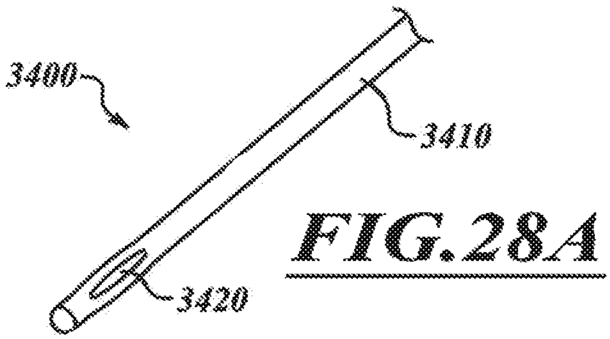
FIG. 28A is an isometric view of an electrode portion of an ablation wand according to another aspect in a partially deployed state.
Figure 28B:
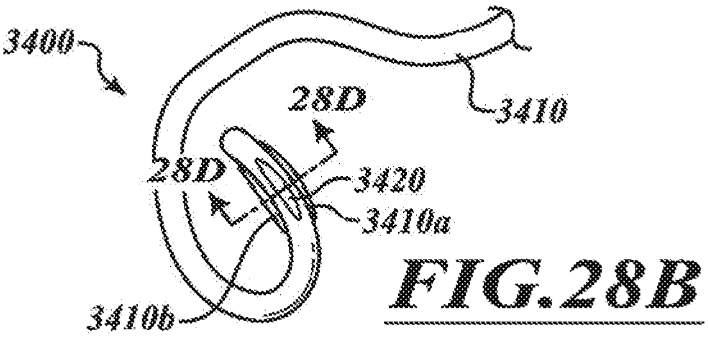
FIG. 28B is an isometric view of the electrode portion of a thermodynamically cooled treatment wand of FIG. 28A with the wand deployed for apposition the cooling member in a non-deployed state.
Figure 28C:
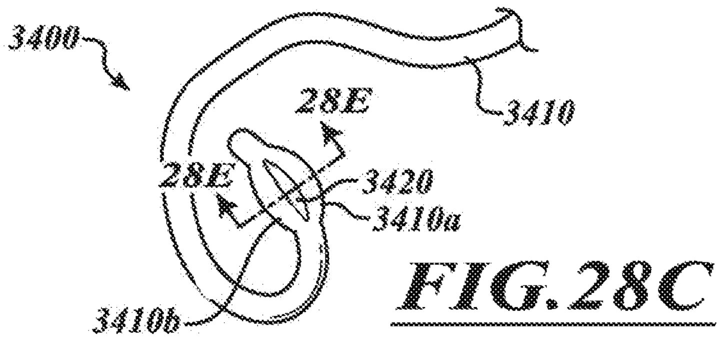
FIG. 28C is an isometric view of the electrode portion of the thermodynamically cooled treatment wand of FIG. 28A with the wand deployed for apposition and the cooling member deployed.
Figure 28D:
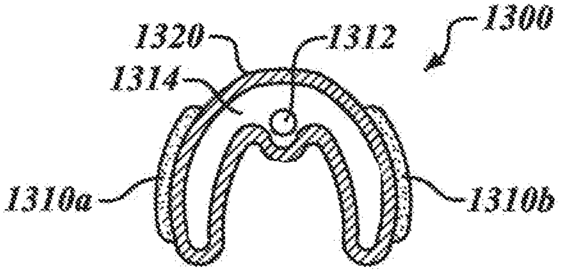
FIG. 28D is a cross-sectional view of the electrode in FIG. 28B, taken along line 28D-28D.
Figure 28E:
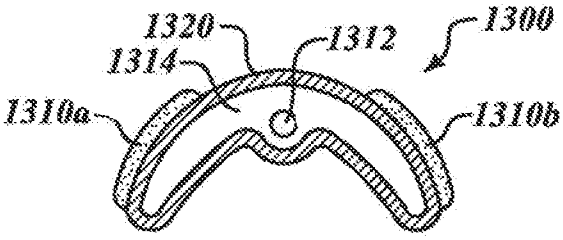
FIG. 28E is a cross-sectional view of the electrode in FIG. 28C, taken along line 28E-28E.

The pulmonary treatment system 3400 includes a thermodynamically cooled treatment wand 3410 that includes a partially shielded, collapsible electrode 3420. FIG. 28A shows the treatment wand 3410 in an initial state of deployment in which the electrode 3420 is in a compact, collapsed state, and the treatment wand 3410 extends in a generally straight configuration. In FIG. 28B, the treatment wand 3410 takes on a treatment configuration by any of the ways discussed above with respect the treatment wand 3310. As shown in the cross-section view of FIG. 28D, the electrode 3420 is in a compact, collapsed state that is advantageous for delivery to a treatment site. The electrode 1320 includes two regions 1310*a* and 1310*b* of masking with a thermally conductive, electrically insulating material. As discussed above, such masking can protect the tissue at the airway wall during energy delivery. The fully deployed state of the pulmonary treatment wand 1310 is shown in FIGS. 28C and 28E. In this example, the electrode can be deployed by inflating the electrode or activating a shape memory material in the electrode. In the deployed state, the full contact area of the electrode 1320 is available for electrode-tissue interface of the airway 100 during energy delivery, even though a much smaller profile was presented in the delivery configuration shown in FIGS. 28A-28C.

Figure 29A:
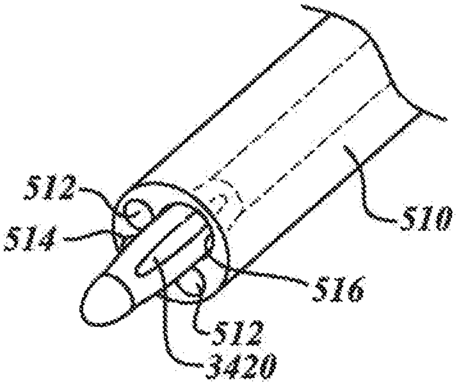
FIG. 29A is an isometric view of electrode portion of a thermodynamically cooled treatment wand according to another aspect in a partially deployed state.
Figure 29B:
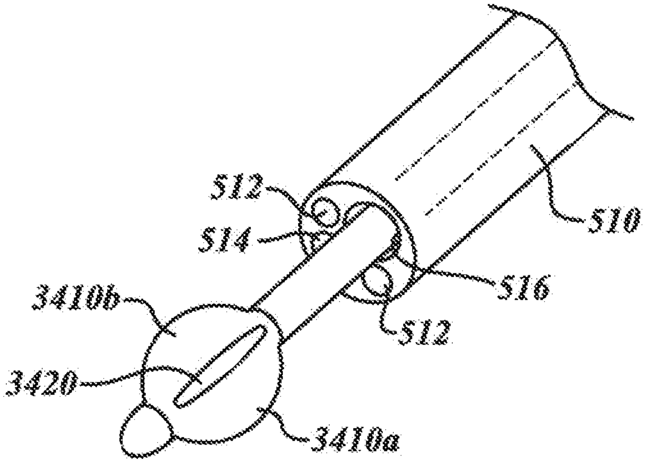
FIG. 29B is an isometric view of the electrode portion of the thermodynamically cooled treatment wand of FIG. 29A in a deployed state.
Figure 30:
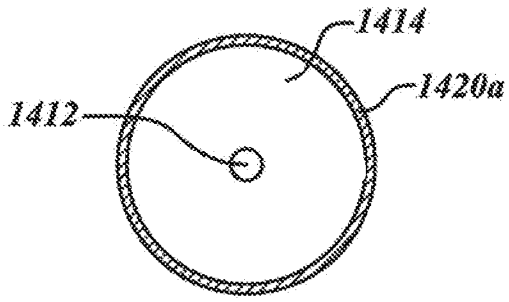
FIG. 30 is a cross-sectional view of an electrode with a cylindrical cross section.

FIGS. 29A and 29B illustrate a variation on the collapsible electrode 1320, in which the electrode 1320 resiliently expands upon being deployed from the working channel 516 of a flexible bronchoscope 500.

Figure 31:
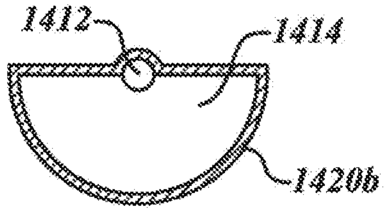
FIG. 31 is a cross-sectional view of an electrode according to another aspect.
Figure 32:
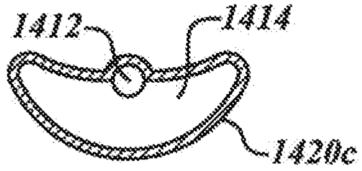
FIG. 32 is a cross-sectional view of an electrode according to another aspect.
Figure 33:
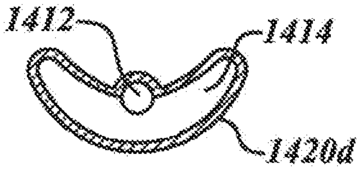
FIG. 33 is a cross-sectional view of an electrode according to another aspect.
Figure 34:
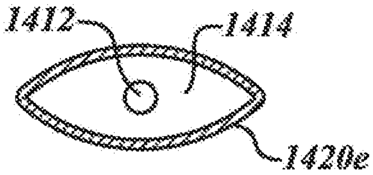
FIG. 34 is a cross-sectional view of an electrode according to another aspect.
Figure 35:
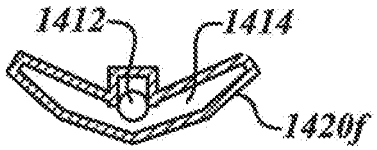
FIG. 35 is a cross-sectional view of an electrode according to another aspect.

FIGS. 30-35 illustrate electrodes with various shapes. Each of the cross-sectional views shows that the electrodes include a supply lumen 1412 and a return lumen 1414 for thermodynamic cooling. The electrode in FIG. 30 has a circular cross-sectional shape. The electrodes in FIGS. 31-35 other cross-sectional shapes create a reduced profile for delivery and while maintaining surface area availability for contact with the tissue wall at an electrode-tissue interface during energy delivery. For example, FIG. 31 illustrates an electrode 1420 with a semi-circular cross-section; FIGS. 32 and 33 illustrate electrodes 1420*c* and 1420*d*, respectively, that each have a "smile" or crescent-shaped cross-section. FIG. 34 illustrates an electrode 1420*e* with an ovoid cross-section. FIG. 35 illustrates an electrode 1420*f* with an angular smile cross-section.

FIGS. 36-39 illustrate various aspects of electrodes in combination with a thermodynamically cooled treatment wand. The electrodes in FIGS. 36-39 advantageously maintain a single, large area configured to fit in the space between adjacent cartilage rings for lesion without increasing the size of the thermodynamically cooled treatment wand over its entire length.

Figure 36A:
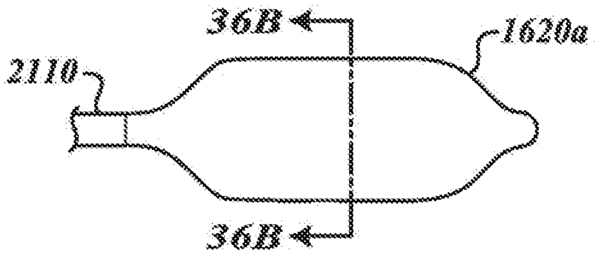
FIG. 36A is a side-elevation view of an electrode and a thermodynamically cooled treatment wand according to another aspect.
Figure 36B:
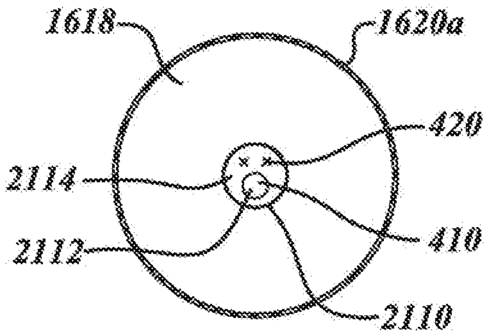
FIG. 36B is a cross-sectional view of the electrode and the thermodynamically cooled treatment wand of FIG. 36A, taken along line 36B-36B of FIG. 36A.

FIG. 36A illustrates an inflatable, polymer electrode 1620*a* in combination with the thermodynamically cooled treatment wand 2110, and FIG. 36B is a cross-sectional view of the same. The thermodynamically cooled treatment wand 2110 includes a return lumen 2114 arranged circumferentially around a supply lumen 2112. A cooling fluid 410 is supplied to the supply lumen 2112. The expanded cooling fluid 420 returns through the return lumen 2114. The polymer electrode 1620*a* is depicted in an inflated state in FIGS. 36A and 36B, and includes a space 1618 between the polymer electrode 1620*a* and the thermodynamically cooled treatment wand 2110.

Figure 37A:
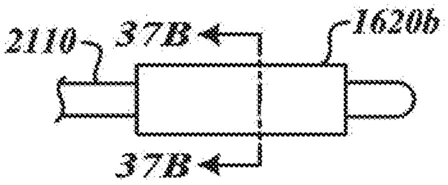
FIG. 37A is a side-elevation view of an electrode and a thermodynamically cooled treatment wand according to another aspect.
Figure 37B:
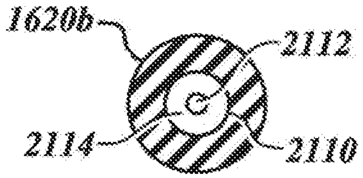
FIG. 37B is a cross-sectional view of the electrode and the thermodynamically cooled treatment wand of FIG. 37A, taken along line 37B-37B of FIG. 37A.

FIG. 37A illustrates a rigid electrode 1620*b* in combination with the thermodynamically cooled treatment wand 2110, and FIG. 37B is a cross-sectional view of the same. The rigid electrode 1620*b* can be formed of a polymer of a conductive plastic.

Figure 38A:
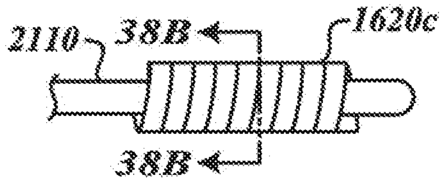
FIG. 38A is a side-elevation view of an electrode and a thermodynamically cooled treatment wand according to another aspect.
Figure 38B:
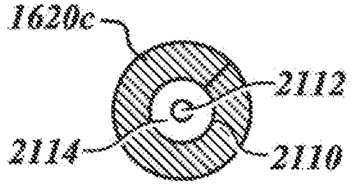
FIG. 38B is a cross-sectional view of the electrode and the thermodynamically cooled treatment wand of FIG. 38A, taken along line 38B-38B of FIG. 38A.

FIG. 38A illustrates a flexible coil 1620*c* in combination with the thermodynamically cooled treatment wand 2110, and FIG. 38B is a cross-sectional view of the same. The flexible coil allows for easier maneuverability of the thermodynamically cooled treatment wand 2110.

Figure 39A:
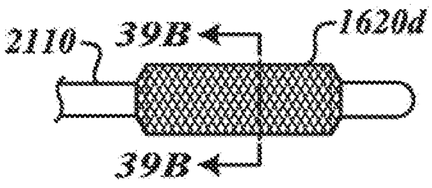
FIG. 39A is a side-elevation view of an electrode and a thermodynamically cooled treatment wand according to another aspect.
Figure 39B:
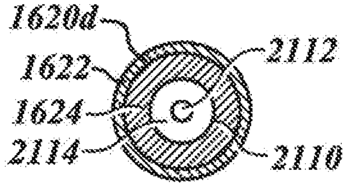
FIG. 39B is a cross-sectional view of the electrode and the thermodynamically cooled treatment wand of FIG. 39A, taken along line 39B-39B of FIG. 39A.

FIG. 39A illustrates a flexible mesh electrode 1620*d* in combination with the thermodynamically cooled treatment wand 2110, and FIG. 39B is a cross-sectional view of the same. In this example, the flexible mesh electrode 1620*d* includes a conductive mesh braid 1622 arranged over a polymer portion 1624.

Figure 40:
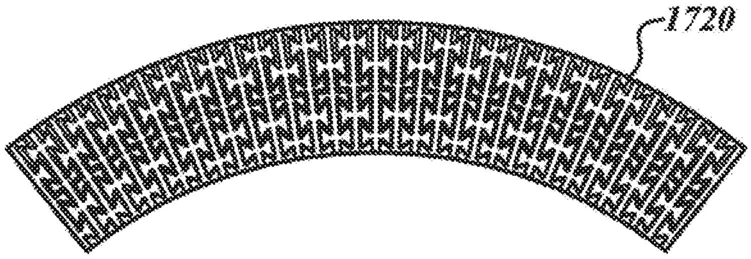
FIG. 40 is a partial side elevation view of an electrode according to one aspect.

FIG. 40 illustrates a flexible electrode 1720 according to another aspect. The electrode 1720 is formed of a laser cut material, preferably a flexible metal such as Nitinol or other suitable conductive material, in order to improve flexibility.

Figure 41:
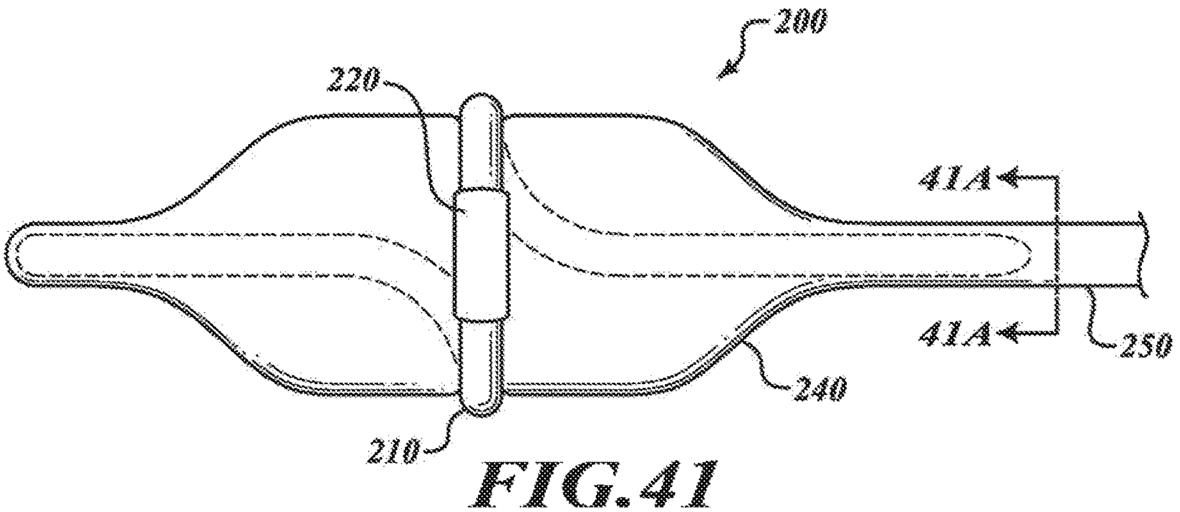
FIG. 41 is a side elevation view of a pulmonary treatment system that includes a cooling system that circulates a liquid coolant serially through an energy delivery portion and an expandable member.
Figure 41A:
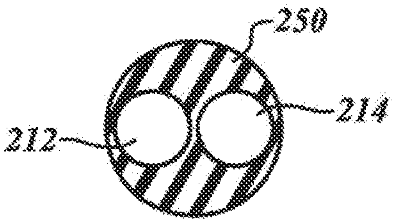
FIG. 41A is a cross-sectional view of an elongate member of the pulmonary treatment system of FIG. 41, taken along line 41A-41A in FIG. 41.
Figure 42:
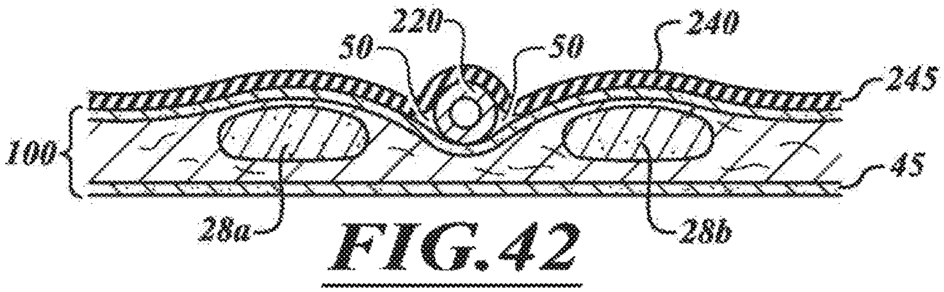
FIG. 42 is a partial cross-sectional view of the pulmonary treatment system of FIG. 41 apposed against an airway wall.
Figure 43:
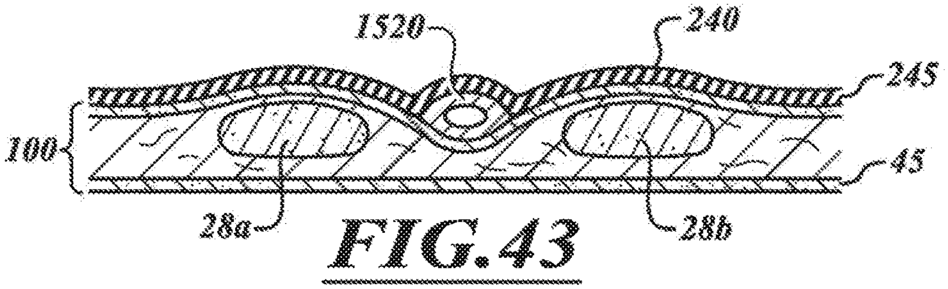
FIG. 43 is a partial cross-sectional view of the pulmonary treatment system of FIG. 41 with a modified electrode, apposed against an airway wall.

FIGS. 41-43 illustrate the effects of electrode shape on the quality of apposition of a cooling member immediately adjacent an electrode-tissue interface. The effectiveness of apposition of the cooling member in the area immediately adjacent an electrode-tissue interface has an important effect on cooling in this region for pulmonary treatment systems that are cooled by circulating a liquid coolant. FIG. 41 is a side elevation view of a distal portion of one such liquid-cooled pulmonary treatment system 200 in a fully deployed state. The pulmonary treatment system 200 includes an expandable member 240 that extends from a distal end of an elongate member 250. As shown in FIG. 41A, the elongate member 250 includes a supply lumen 212 and a return lumen 214. A liquid coolant supply channel 210 also extends from the distal end of the elongate member and around a portion of the circumference of the expandable member 240. A proximal end of the liquid coolant supply channel 210 is in fluid communication with the supply lumen 212, and a distal end of the liquid coolant supply channel 210 is in fluid communication with the interior of the expandable member 240. The return lumen 214 is in fluid communication with the interior of the expandable member 240 at a proximal end of the expandable member 240. An electrode 220 surrounds a portion of the liquid coolant supply channel 210.

During energy delivery from the electrode 220, a liquid coolant is circulated serially from the supply lumen 212, through the liquid coolant supply channel 210, into the expandable member 240, and then out the return lumen 214. Ideally, liquid coolant circulating through the electrode 220 and the expandable member act to protect a region of tissue between an interior wall of an airway and a target treatment region that is located within the airway wall and radially spaced from the interior wall of the airway.

FIG. 42 is a partial cross-sectional view of the pulmonary treatment system of FIG. 41 apposed against an airway wall 100. The electrode 220 is positioned between two adjacent cartilage rings 28*a* and 28*b*. In this example, the expandable member 240 is a conformable balloon that can be made, in whole or in part, of a highly compliant material. Highly compliant materials include, without limitation, silicon, rubber, polyethylene, polyvinyl chloride, or other materials capable of undergoing large deformation. A sidewall 245 of the balloon 240 contacts the airway wall 100 with a relatively high amount of surface contact. This provides rapid and effective cooling of tissue on and near the airway wall surface while a deeper target region, which includes the nerve trunk 45, can be damaged. Nevertheless, gaps 50 occur on either side of the electrode 220 between the balloon 240 and the airway wall 100. The gaps 50 are the result of the shape of the electrode 220. The act as a region of insulation for the cooling, can result in railroad track shaped pattern of tissue damage consisting of damaged tissue extending immediately along either side of the electrode.

FIG. 43 illustrates a configuration in which the electrode 220 is replaced with an electrode 1520 with an ovoid or eye-shaped cross-sectional shape. The gaps 50 on either side of the electrode-tissue interface have been substantially eliminated. As a result, more uniform, and effective cooling can be achieved, and the risk of unintentional tissue damage on either side of the electrode-tissue interface can be significantly reduced.

Figure 44:
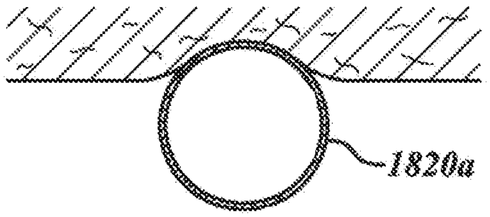
FIG. 44 is a side-elevation view of an electrode according to another aspect.
Figure 45:
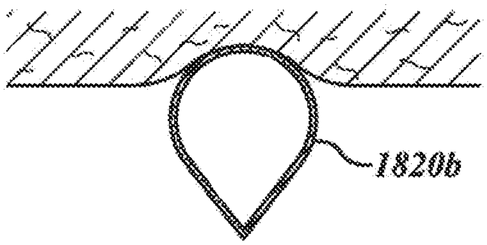
FIG. 45 is a side-elevation view of an electrode according to another aspect.
Figure 46:
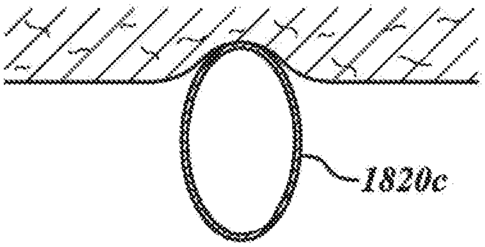
FIG. 46 is a side-elevation view of an electrode according to another aspect.
Figure 47:
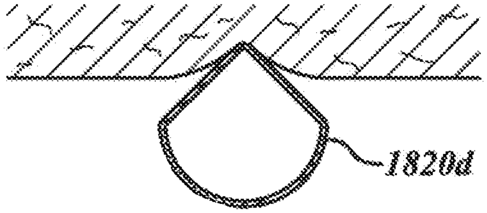
FIG. 47 is a side-elevation view of an electrode according to another aspect.

FIGS. 44-47 further illustrate the effects of various electrode shapes on the amount of force and pressure that can be applied to an airway wall. FIG. 44 illustrates an electrode with a circular cross-sectional shape. FIG. 45 illustrates an electrode with a teardrop cross-sectional shape. FIG. 46 illustrates an electrode with an ovoid cross-sectional shape. FIG. 47 illustrates an electrode with a hybrid triangular-semicircular cross-sectional shape. Each cross-sectional shape provides a different amount of surface area at the electrode-tissue interface. As a result, the amount of pressure exerted on the tissue wall will vary if the same amount of force is applied in each instance. A higher pressure at the electrode-tissue interface will cause the airway wall tissue to thin, enabling the creation of a deeper lesion without adjusting the amount of energy or cooling that is delivered. Further, as increasing the amount of pressure exerted on the tissue wall at the electrode-tissue interface increases the amount of deflection in the tissue wall, and an increased apposition pressure may aid in accurately positioning a thermodynamically cooled treatment wand between adjacent cartilage rings. A more consistent apposition pressure allows for better energy delivery and improved surface protection.

IV. Apposition Members

Thermodynamically cooling the energy delivery system at the treatment site at the distal end of the pulmonary treatment system results in far higher temperature drops than are possible by solely circulating an externally cooled liquid through the pulmonary treatment system. This increase in cooling efficiency allows for greater flexibility in the size, shape, and treatment role of structures in the energy delivery system such as apposition members and dedicated cooling members.

For example, the expandable member 240 of the liquid-cooled pulmonary treatment system 200 discussed above with reference to FIG. 41 typically will fill an entire diameter of an airway in order to achieve adequate apposition for uniform cooling, As such, the airway of the patient is entirely blocked during treatment.

Further, the size of the expandable member 240 also contributes to increasing the delivery size of the pulmonary treatment system 200, thereby affecting the compatibility of a pulmonary treatment system with a working channel of a flexible bronchoscope.

In addition, apposition members can be specifically tailored to provide targeted apposition for a more uniform cooling profile.

Figure 48:
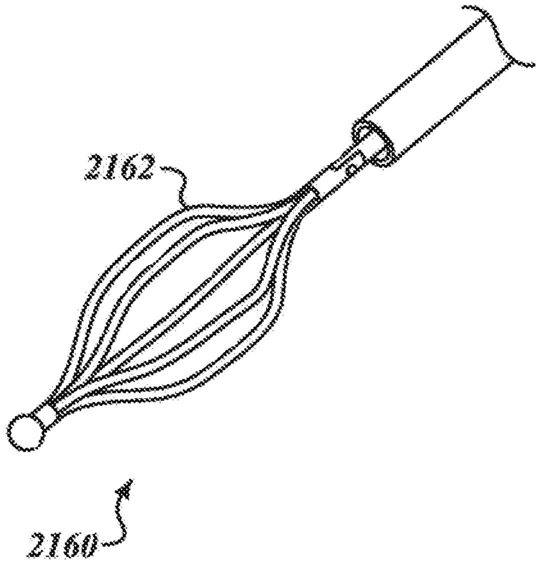
FIG. 48 is an isometric view of an apposition member according to one aspect.

Thermodynamic cooling makes it possible to employ ventilated apposition or positioning members that may or may not perform cooling. For example, an apposition member can be a stent, or a deployable basket 2160, as shown in FIG. 48. The deployable basket 2160 has an elongate shape and includes a plurality of elongated arms or struts 2162. When deployed, a thermodynamically cooled treatment wand can extend circumferentially around the elongated arms or struts 2162. In other aspects, the basket 2160 can be generally spherical, ovoid, or can have any other suitable configuration. Advantageously, air can pass through the basket 2160 to maintain ventilation and visibility.

Other possible apposition members can include an S-shaped member with a natural spring shape. This member can be self-expand upon deployment to appose a thermodynamically cooled treatment wand. In another example, a coil-shaped member, similar in shape to a watch spring, can be used to bias a thermodynamically cooled treatment wand against an airway wall.

In addition, due to the wide range of temperatures that are achievable with the thermodynamic cooling system, electrodes and treatment wands made of a nickel-titanium shape memory alloy may experience softening during cooling. In this state, the nickel-titanium shape memory alloy would be shifted from an austenitic phase into a martensitic phase (soft and malleable). When this occurs, the apposition member, such as a balloon or some other mechanical reinforcement, that forces the electrode and/or the treatment wand to stay in shape and in contact with the airway wall become more important. Additionally, since the electrode and/or treatment wand is more flexible in this state, the electrode can achieve better contact with the airway wall and avoid the gaps that may result in damage to surface tissue.

V. Compact, Liquid Cooled Pulmonary Treatment System

FIGS. 49-60 will now be discussed in connection with a pulmonary treatment system that is both compatible with a working channel of a flexible bronchoscope and also includes a cooling system that circulates an externally chilled, liquid coolant to an energy delivery assembly positioned in an airway of a patient. The inventors hereof have succeeded in creating a system of unexpectedly compact delivery size through a unique combination of features and characteristics, including fluid delivery lumen arrangement and design; lumen connection design; the creation of differential pressure zones between an energy delivery portion and an expandable cooling member; a collapsible and expandable energy delivery portion; a thin walled, highly compliant coolant member; an axial support element; and other elements and methods to induce a flow pattern in the cooling member that improve heat transport from the airway wall.

Although the liquid cooled pulmonary treatment systems described herein advantageously allow for a compact profile that facilitates compatibility with the working channel of a flexible bronchoscope, the aspects described herein are not so limited. For example, as will be readily apparent to one of ordinary skill in the art upon a complete review of the present disclosure, the aspects disclosed in FIGS. 49-60 are also scalable to be compatible with larger working lumens that may or may not be associated with a bronchoscope. Notably, the present disclosure is not limited solely to systems that are delivered via the working channel of a bronchoscope, but also encompasses systems delivered by other means, such as an independent sheath and/or delivery catheter.

Figure 49:
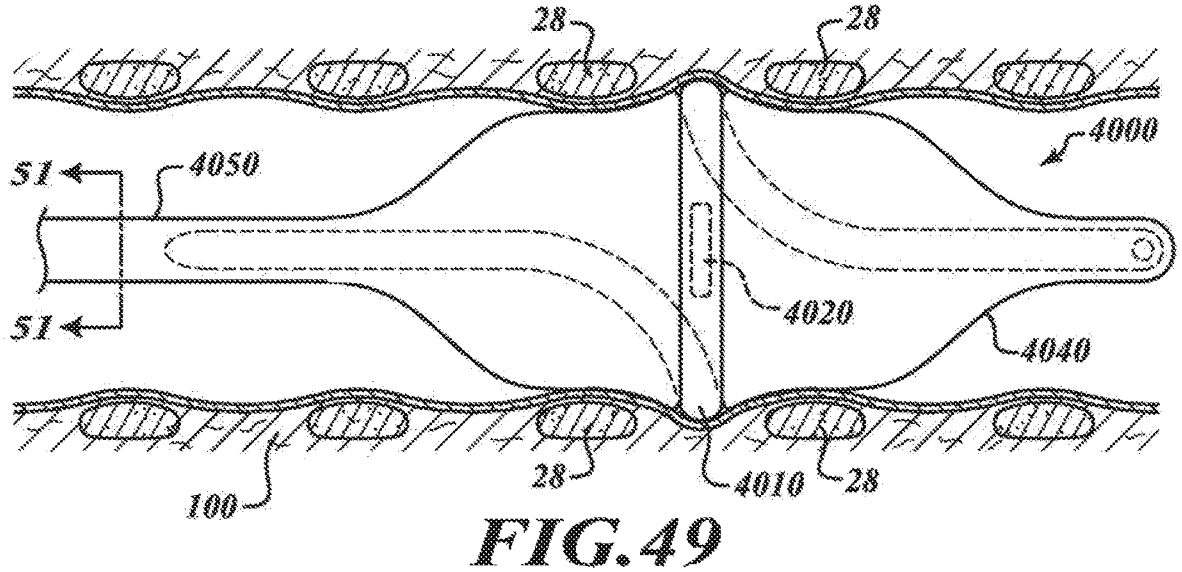
FIG. 49 is a side view of a pulmonary treatment system according to another aspect.
Figure 51:
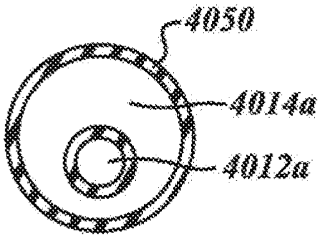
FIG. 51 is a cross-sectional view of the delivery and return lumens of the pulmonary treatment system of FIG. 49, taken along lines 51-51 of FIG. 49.

FIG. 49 is a side elevation view of a distal portion of a pulmonary treatment system 4000 in a fully deployed state. The pulmonary treatment system 4000 includes an expandable member 4040 that extends from a distal end of an elongate member 4050. As shown in FIG. 51, the elongate member 4050 includes a supply lumen **4012*a* and a return lumen 4014*a*. A liquid coolant supply channel 4010 also extends from the distal end of the elongate member 4050, around a portion of the circumference of the expandable member 4040, to a distal end of the expandable member 4040. A proximal end of the liquid coolant supply channel 4010 is in fluid communication with the supply lumen 4012*a*, and a distal end of the liquid coolant supply channel 4010 is in fluid communication with the interior of the expandable member 4040. The return lumen 4014 is in fluid communication with the interior of the expandable member 4040 at a proximal end of the expandable member 4040. An electrode 4020 is applied to an outside surface of the liquid coolant supply channel 4010**.

The overall working length of the pulmonary treatment system can range from 300 to 1000 millimeters in length, depending on the location of the bronchial tree where treatment is to be performed and, in some instances, the working length of the working channel of the flexible bronchoscope. Flexible bronchoscopes typically include a working length of 600 mm, but can range in length from 300 mm to 1000 mm. The pulmonary treatment system 4000 can have a working length suitable for treatment of airways up to the and including the main stem bronchi, or a working length for treatment of airways up to the and including the lobar bronchi. Working lengths up to 1000 mm are also within the scope of the present disclosure for treatment of airways distal the lobar bronchi. In one example, a pulmonary treatment system with a working length of about 760 millimeters facilitates access to and treatment of the main stem bronchus.

The pulmonary treatment system 4000 can be flexible enough to accommodate a working channel with a bending radius of 3.1 mm or less, or, in some examples, 2.7 mm or less. Further the pulmonary treatment system 4000, in a collapsed delivery state, can be advanced through a working channel having a diameter in the range of about 1.0 millimeters to about 6.0 millimeters, in one example. In other examples, the pulmonary treatment system 4000, in a collapsed delivery state, can be advanced through a working channel having a diameter in the range of about 1.0 millimeters to about 4.0 millimeters. In other examples, the pulmonary treatment system 4000, in a collapsed delivery state, can be advanced through a working channel having a diameter in the range of about 1.2 millimeters to about 3.2 millimeters.

A liquid coolant is circulated through the pulmonary treatment system 4000 during energy delivery. For example, a liquid coolant is circulated serially from the supply lumen **4012*a*, through the liquid coolant supply channel 4010, into the expandable member 4040, and then out the return lumen 4014*a*. Liquid coolant circulating through the liquid coolant supply channel 4010 and the expandable member 4040** protect a region of tissue between an interior wall of an airway and a target treatment region that is located within the airway wall and radially spaced from the interior wall of the airway.

The amount of power delivered from the electrode to achieve the desired lesion densities, shapes, and locations can range from, for example, 3 watts to 65 watts. In some examples, it is beneficial to create a power density ranging from 0.1 to 2 W/mm$^2$ in the airway wall. In other examples, a power density of from 0.3 to 1.0 W/mm$^2$ is generated in the airway wall. In one preferred example, delivering 15-20 watts through an electrode that is cylindrical in shape, 9.5 mm long and 2.1 mm in diameter with about half of the electrode in contact with the airway wall can result in a power density of 0.48 To 0.64 W/mm$^2$. In this example, energy can be delivered from the electrode for about 120 seconds. However, in other examples, energy can be applied for periods ranging from 10 seconds to 600 seconds, and preferably for a period ranging from 60 to 180 seconds.

In order to protect a region of tissue between an interior wall of an airway and a target treatment region that is located within the airway wall and radially spaced from the interior wall of the airway, it is desirable in some examples, to remove about 0.1 to 0.4 W/mm$^2$ from the airway wall during activation of the electrode 4020 by circulating a coolant through the liquid coolant supply channel 4010 and the expandable member 4040. For the above-noted example, in which 15-20 watts is passed through a cylindrical electrode for about 120 seconds, about four to six watts, in total, can be removed from the airway wall by circulating a coolant through the liquid coolant supply channel 4010 and the expandable member 4040 during activation of the electrode. In other examples, between about 0.025 and about 1.0 W/mm$^2$ of heat energy are removed from the airway wall during treatment. In other examples, it is desirable to remove between about 0.1 and about 0.4 W/mm$^2$ of energy from the airway wall during treatment.

In general, it has been found that for a mass flow rate of 60 ml/min of coolant (water or a 5% dextrose intravenous solution), each change in temperature of 1° C. from baseline can result in approximately 4.125 watts of heat energy being carried away from the treatment site. Notably, this coolant removes heat not just from an area next to the electrode, but also the airway wall that is in contact with the entire expandable member 4040.

The return lumen **4014*a* surrounds the supply lumen 4012*a* in the elongate member 4050. As will be discussed in greater detail below, the cooling fluid in the supply lumen 4012a is both at a higher pressure and a lower temperature than the cooling fluid in the return lumen 4014a. Advantageously, locating the supply lumen 4012a within the return lumen 4014a reduces the delivery size of the pulmonary treatment system 4000 and reduces thermal losses in the supply lumen 4012a. In effect, the return lumen 4014a jackets the supply lumen 4012**a to provide an additional layer of protection from heat losses.

Figure 50:
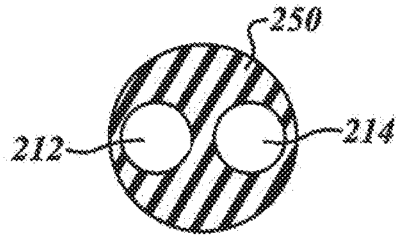
FIG. 50 is a cross-sectional view of the delivery and return lumens of a conventional pulmonary treatment system.

By contrast, a conventional arrangement, in which an elongate member includes separate, independent supply and return lumens is shown in FIG. 50. The elongate member 250 includes a supply lumen 212 that is the same size as a separate return lumen 214. This arrangement is not only a less efficient use of space, but it also does not account for the different pressure needs of each lumen or provide for the same amount of thermal efficiency as the arrangement in FIG. 51.

Figure 52:
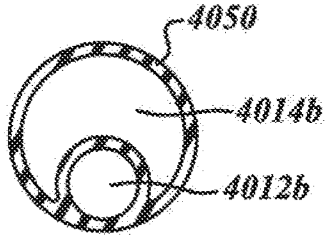
FIG. 52 is a cross-sectional view of the delivery and return lumens of another example pulmonary treatment system.
Figure 53:
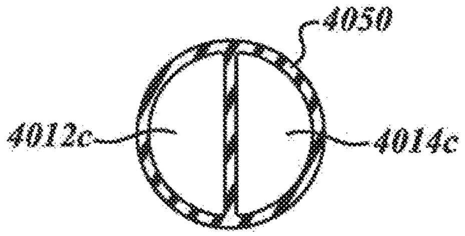
FIG. 53 is a cross-sectional view of the delivery and return lumens of another example pulmonary treatment system.

Other beneficial lumen arrangements are shown in FIGS. 51 and 53. In FIG. 52, the supply lumen 4012a and the return lumen 4014a are replaced with a supply lumen 4012b and a return lumen 4014b. In this example, the supply lumen 4014a is not entirely surrounded by the return lumen 4014b, but instead shares a wall with the elongate member 4050. In FIG. 53, the supply lumen 4012a and the return lumen 4014a are replaced with a supply lumen 4012c and a return lumen 4014c. In this example, the supply lumen 4014c shares a single, common wall with the return lumen 4014c. This configuration is also more space efficient than the configuration in FIG. 50. Although the supply lumen 4012c and the return lumen 4014c are depicted as having similar cross-sectional areas, other relative cross-sectional areas are also within the scope of the present disclosure.

As will be described in greater detail below, it is advantageous to supply the coolant to the liquid coolant supply channel 4010 at a much higher pressure than the expandable member 4040. As shown in FIGS. 51 and 52, it may be beneficial to size the supply lumen significantly smaller than the return lumen. In what is sometimes referred to as the Law of LaPlace, a cylinder with an increased radius requires increased wall thickness of to accommodate a stable wall tension. Thus, decreasing the diameter of the higher pressure supply lumen will require a thinner lumen wall, despite the large pressure. As will be readily apparent, the thickness of the wall, and therefore the compactness for delivery, can then be balanced against the flow resistance created by restricting the size of the supply lumen.

Further, as discussed below, it is beneficial to maintain the expandable member 4040 at a significantly lower pressure than the supply channel 4010. Accordingly, it is beneficial to size the return lumen to be quite large compared to the supply lumen so as to reduce back pressure on the expandable member 4040.

Any of the above-described configurations can employ barriers to heat transfer around the lumens or the elongate member. For example, polymers, air, or foam can be employed to insulate the return and supply lumens as well as the elongate member.

Figure 54:
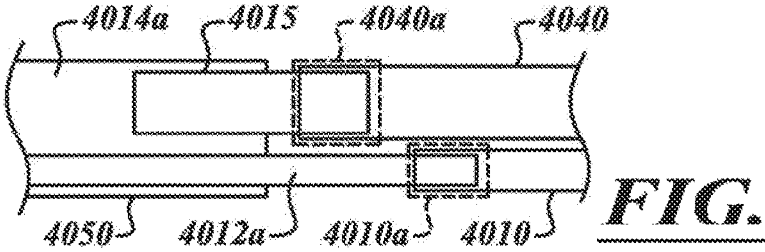
FIG. 54 is a schematic view of serially bonded joints in a pulmonary treatment system.
Figure 55:
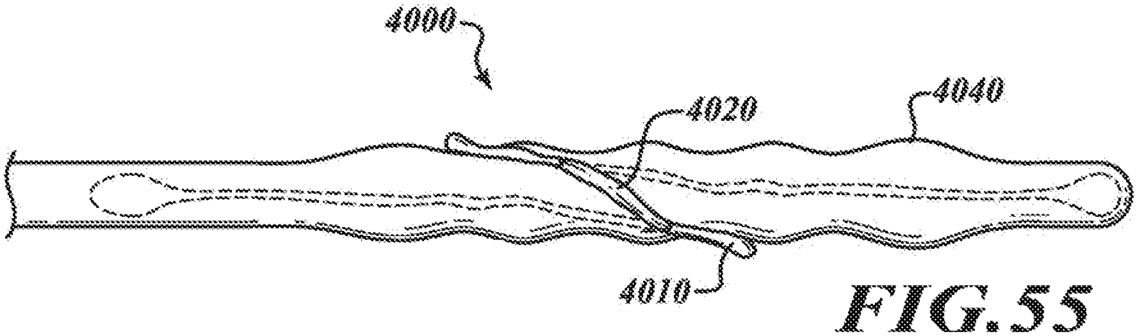
FIG. 55 is a side elevation view of the pulmonary treatment system of FIG. 49 in a collapsed state.

The junctions between the various fluid delivery lumens can also drive the delivery size of the pulmonary treatment system. Forming these junctions by skiving the elongate member or using serial bonding can reduce the delivery size of the pulmonary treatment system. FIG. 54 is a schematic view of serially bonding connections in a pulmonary treatment system. In FIG. 54, the supply lumen 4012a is connected to the liquid coolant supply channel 4010 at a bond joint 4010a. The return lumen is connected to the expandable member 4040 via a transition element 4015 at a bond joint 4040a. The bond joints 4040a and 4010a are serial bond joints in that they are offset from each other in a longitudinal direction and do not overlap. Accordingly, the increase in diameter associated with the bond joints can be spread out along a length of the pulmonary treatment system rather than additively stacked at a single longitudinal location.

In another aspect, adding lubricious coatings to the pulmonary treatment system 4000 can further aid in advancing the pulmonary treatment system through a compact channel, such as the working channel of a flexible bronchoscope. For example, a silicone or hydrophilic coating can be applied to the elongate member 4050 proximal of the expandable member 4040. In another example, the electrode 4020 can be masked, and portions of the expandable member 4040, the liquid coolant supply channel 4010, and the elongate member 4050 could all be coated with the lubricious coating. In a further example, a portion of the expandable member 4040 could also be masked so only the distal and proximal portions of the expandable member 4040 and the elongate member 4050 would be coated.

FIGS. 55-58 illustrate the collapsibility of the pulmonary treatment system 4000. In this example, the liquid coolant supply channel 4010 is a flexible conduit and the electrode 4020 is a conductive epoxy applied to an outside surface of the conduit. Other materials and configurations are also possible for the electrode 4020, including other coatings, thin foils, films, or other electrically conductive materials. Different types of coating, plating or fabrication techniques can be used to form the electrode 4020. For example, the electrode 4020 can include one or more a films or coatings that can be made of metal, conductive polymers, or other suitable materials formed by a deposition process (e.g., a metal, such as gold or silver, deposition process), coating process, etc., and can comprise, in whole or in part, silver ink, silver or gold epoxy, combinations thereof, or the like.

The length of the electrode 4020 can be chosen based on the length of the lesion that is desired from a treatment session. For example, if it is desired to create a lesion around an entire circumference of an airway, the length of the electrode 4020 can be selected based on several factors, including: the size of the airway wall when expanded by the pulmonary treatment system 4000, a desired amount of overlap in lesions, a desired number of energy applications to create a circumferential lesion, the desired amount of energy application. As an example, an electrode of 8.5 to 9.5 millimeters in length can be used to create circumferential lesion in with eight energy applications in a main stem bronchus of an adult human. Other lengths of electrodes could be used to reduce the required number of energy applications to create a circumferential lesion from eight to, for example, four, three, two, or even a single energy application.

Further, although the present example illustrates only a single electrode 4020, multiple electrodes 4020 could be included along the liquid coolant supply channel. The number and spacing of the multiple electrodes can reduce the amount of time and number of energy applications needed to create a desired lesion pattern.

In one aspect, the pulmonary treatment system 4000 maintains coolant delivered to the liquid coolant supply channel 4010 at a high pressure and coolant delivered to the expandable member 4040 at a low pressure. For example, the differential pressure can be maintained by a throttle positioned between the liquid coolant supply channel 4010 and the expandable member 4040.

Figure 56:
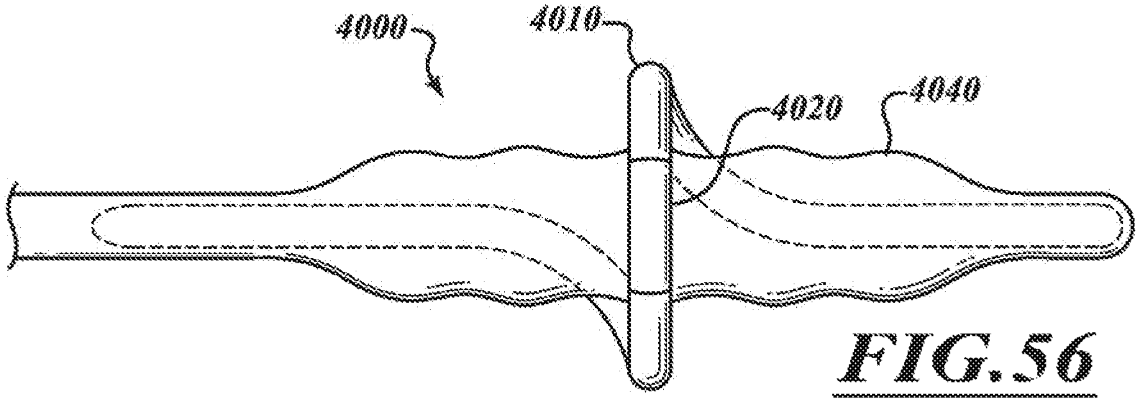
FIG. 56 is a side elevation view of the pulmonary treatment system of FIG. 49 in a partially inflated state.

The different functions of the liquid coolant supply channel 4010 and the expandable member 4040 a best suited to different pressures. For example, although rigidity in an electrode is not always a favorable feature for compact delivery to a treatment site, electrode rigidity can be very important for consistent energy delivery at the treatment site. Accordingly, it can be advantageous to inflate the liquid coolant supply channel 4010, and thereby the electrode, with a high fluid pressure so that the electrode remains inflexible during energy delivery. FIG. 56 illustrates how backpressure caused by a throttle (which is not depicted in FIG. 56, but will be discussed below with reference to two examples depicted in FIGS. 59 and 60) makes the liquid coolant supply channel 4010 and the electrode 4020 rigid prior to the complete inflation of the expandable member 4040. Preferably, the liquid supply channel 4010 will be made of a material, such as a heat treated polyethylene terephthalate (PET), that will expand to a repeatable shape each time it is inflated to a relatively high operational pressure without deforming. Other possible materials for the liquid supply channel 4010 include, but are not limited to, nylon, polyethylene (PE), or polyether block amide (Pebax). In particular, it is desirable that the liquid supply channel 4010 be capable of collapsing for delivery, but not deform beyond a predetermined size when inflated. If the liquid supply channel were to either plastically deform or otherwise elastically deform in an inconsistent manner when inflated, the electrode 4020 could be adversely affected. Nevertheless, it is preferable that the liquid supply channel 4010 remain somewhat bendable in a fully inflated state so as to be conformable to the inside surface of an airway surface. For example, although the diameter of the supply channel will, preferably, not expand beyond a certain size under high pressures, the liquid supply channel 4010 will be conformable in airways that range from, for example about 10 millimeters in diameter to 20 millimeters in diameter.

Advantageously, the combined size of the electrode 4020 and the liquid supply channel 4010 includes an outside width or diameter in the fully inflated state that aids in seating between adjacent cartilage rings in the airways. For example, the liquid supply channel 4010 can have a width (or diameter if cylindrical) no larger than the width of the spaces between the cartilage rings, preferably in some embodiments being about 1.5 millimeters to about 3 mm. In one example, the liquid supply channel 4010 is inflatable to about 2 mm.

For compact delivery, the liquid supply channel 4010 is collapsible to the combined double wall thickness of the liquid supply channel 4010 and the thickness of the electrode 4020. In one example, the total thickness of the liquid supply channel 4010 and the electrode 4020 in the collapsed state is in the range of about 0.03 millimeters to 0.07 millimeters.

Figure 57:
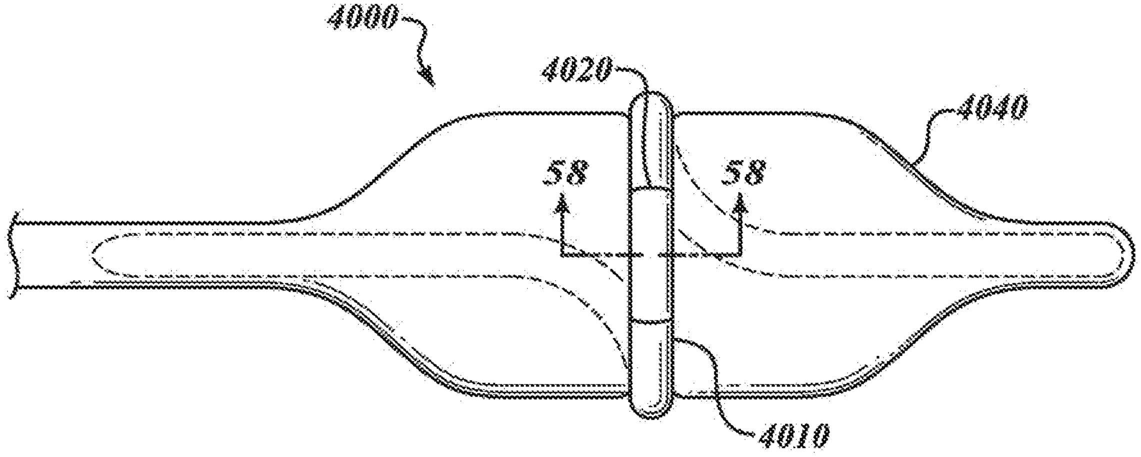
FIG. 57 is a side elevation view of the pulmonary treatment system of FIG. 49 in a completely inflated state.
Figure 58:
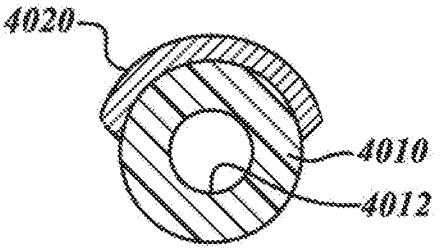
FIG. 58 is a cross-sectional view of the electrode and fluid delivery conduit of FIG. 57, taken along line 58-58 of FIG. 57.

FIG. 57 illustrates a fully expanded state, and FIG. 58 provides a cross-sectional view of the electrode 4020 and the liquid coolant supply channel 4010 in a rigid state with a fluid supply lumen 4012 for passage of the liquid coolant.

On the other hand, it can be advantageous for the expandable member 4040 to remain somewhat flexible to achieve a more conformable apposition with the tissue of the airway wall. In addition, by supplying a low pressure to the expandable member 4040, the expandable member can be a thin-walled balloon made of a highly compliant material. The diameter of the deflated expandable member 4040 can be relatively small. For example, a maximum diameter of the balloon can be in a range of about 1 mm to about 3 mm when the expandable member 4040 is fully collapsed. To treat a bronchial tree of a human, the diameter of the expandable member 4040 can be in a range of about 10 mm to about 20 mm. For enhanced treatment flexibility, the inflated expandable member 4040 diameter may be in a range of about 7 mm to about 25 mm. Of course, the expandable member 4040 can be other sizes to treat other organs or tissue of other animals. The balloon can conform to irregularities on the airway surface (e.g., cartilaginous rings, side branches, etc.) and can be made, in whole or in part, of a distensible material, such as polyurethane (e.g., low durometer polyurethane) or other type of highly conformable material such as nylon, polyether block amide (Pebax), or polyethylene terephthalate (PET), that may be transparent, semi-transparent, or opaque. The balloon can have different inflated shapes, including a hot dog shape, an ovoid shape, a cylindrical shape, or the like. Using a thin walled, distensible material for the expandable member 4040 has numerous benefits, including: (1) a decreased delivery profile, (2) increased efficiency in heat transfer, and (3) increase compliance with the airway wall. Improved compliance and heat transfer have a direct effect on cooling efficiency, thereby further reducing the volume of coolant that needs to be supplied. Reducing the volume of coolant also reduces the required size of the delivery lumens, which directly impacts the delivery profile of the pulmonary treatment system.

Thus, it is beneficial to use non-deformable, but collapsible material for the supply channel 2010 and a highly compliant material for the expandable member 2040. For example, the supply channel 2010 is preferably made of a material that will not deform at pressures around 75 psi, whereas the expandable member 2040 is preferably made of a material that will plastically deform at pressures less than 30 psi.

Further, by using differential pressures between the expandable member 4040 and the liquid supply channel 4010, and by using a sufficiently non-deformable material for the liquid supply channel 4010 and a compliant material for the expandable member 4040, the expandable member 4040 and the liquid supply channel 4010 can work together to seat the electrode between adjacent cartilage rings.

It order to supply cooling fluid to the liquid coolant supply channel 4010 and the expandable member 4040 at the single pressure that will achieve the appropriate rigidity in the electrode 4020 without also over expanding or rupturing the expandable member 4040, it would be necessary to use a less compliant material, such as polyethylene terephthalate (PET), and thicker walls for the expandable member 4040. However, the expandable member 4040 would be less compliant and require a higher flow rate of coolant to achieve the same amount of cooling. Thus, the size of the delivery lumens would need to increase to accommodate the increase in fluid volume.

Figure 59:
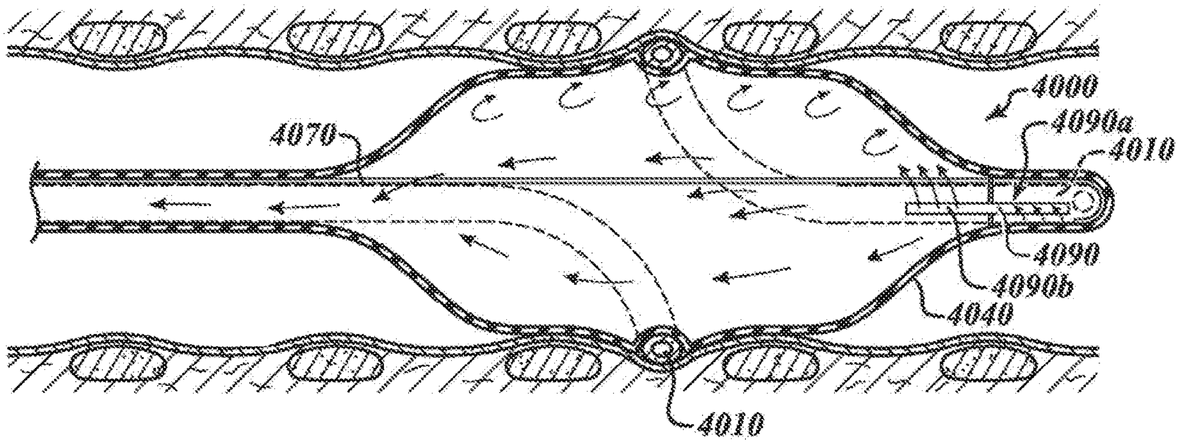
FIG. 59 is a cross-sectional view of a pulmonary treatment system according to one aspect.
Figure 60:
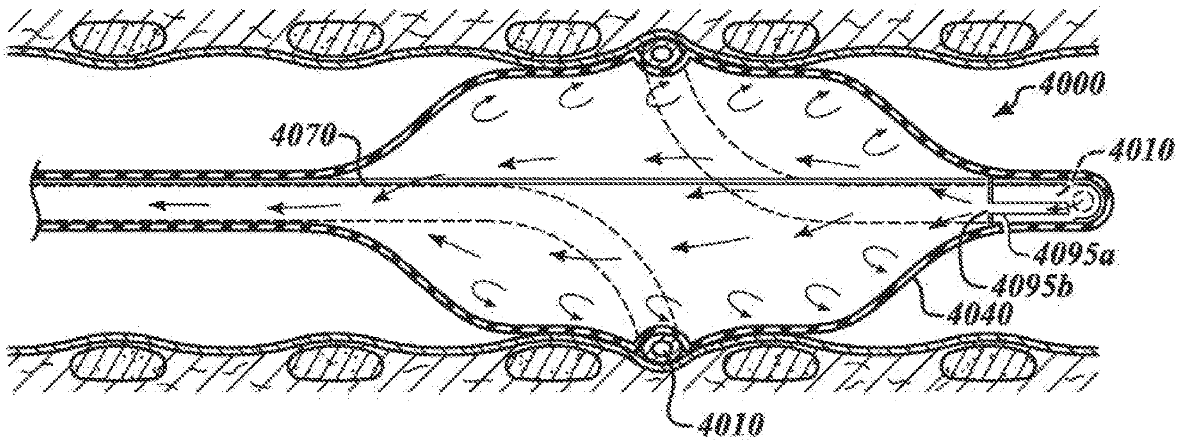
FIG. 60 is a cross-sectional view of a pulmonary treatment system according to another aspect.

FIGS. 59 and 60 are cross-sectional views of the pulmonary treatment system 4000, each having a different configuration of throttle between the liquid coolant supply channel 4010 and the expandable member 4040. The throttle 4090 in FIG. 59 includes several inlets **4090*a* in the liquid coolant supply channel 4010, and several outlets 4090*b* in the expandable member 4040. The throttle 4095 in FIG. 60 includes a channel 4095*a* that leads to a single, restrictive opening 4095*b* between the liquid coolant supply channel 4010 and the expandable member 4040. In one non-limiting example, the opening 4095*b* is 0.26" in diameter. The pressure differential created by the throttles can be significant, creating a pressure differential of at least 20 psi with values greater than 50 psi on the liquid coolant supply channel 4010 side, and less than 30 psi on the expandable member 4040. In another example, the pressure differential is at least 45 psi with coolant pressure greater than 60 psi on the liquid coolant supply channel 4010 side, and less than 15 psi on the expandable member 4040 side. In one example, the pressure differential is at least 72 psi, with pressure approximately 75 psi on the liquid coolant supply channel 4010 side, and approximately 3 psi on the expandable member 4040** side.

It has been recognized that inducing turbulent flow along the surface of the expandable member 4040 improves the efficiency with which the expandable member 4040 transports heat away from an airway wall at a treatment site. In addition to creating a pressure differential in the coolant supply system, the throttle of the pulmonary treatment system 4000 can be configured to improve coolant flow in the expandable member 4040, and thereby improve the cooling efficacy of the expandable member 4040. The position, orientation, and/or shape of the throttle can be configured to induce eddies and turbulent flow along the surface of the cooling member, which improves the efficiency with which the cooling member transports heat away from an airway wall of the patient at a treatment site.

For example, the outlets 4090*b* of the throttle 4090 in FIG. 59 are directed to a treatment side of the expandable member 4040 to induce eddies along the wall of the expandable member 4040. In another example, the opening 4095*b* in the throttle 4095 creates a Jacuzzi jet effect throughout the expandable member 4040, thereby improving heat transport and cooling efficiency of the expandable member 4040.

In another aspect, a gas is injected into liquid coolant supply. The injected gas generates bubbles in the expandable member 4040 that disrupt laminar flow along the walls of the expandable member 4040 and thereby improve the efficiency with which heat is transported from the portion of the expandable member 4040 in contact with airway tissue at the treatment site.

In another example, the expandable cooling member 4040 includes a small, longitudinally extending, axial support 4070. In the examples in FIGS. 59 and 60, the support 4070 is a centrally located axial shaft that includes a shape memory material. The axial support can aid in pushability of the cooling member while allowing the cooling member to be formed of a lightweight, highly compliant material.

Additionally, although the examples above describe an electrode 4020, other types of ablation elements can be used instead of or in addition to the electrode 4020. For example, one or more electrodes operable to output electrical energy, and/or radiofrequency (RF) energy, and/or one or more transducers operable to output ultrasonic energy can be used in conjunction with the aspects discussed above that contribute, either alone or in combination with each other, to the compact delivery size of this system. For example, the above described aspects relating to fluid delivery lumen arrangement and design; lumen connection design; the creation of differential pressure zones between an energy delivery portion and an expandable cooling member; a collapsible and expandable energy delivery portion; a thin walled, highly compliant coolant member; an axial support element; and other elements and methods to induce a flow pattern in the cooling member that improve heat transport from the airway wall can be used with a variety of other energy delivery modalities, including, for example, microwave, ultrasound, direct current, or laser energy.

In one example, the electrode 4020 can be replaced with one or more ultrasonic transducers coupled to the liquid coolant supply channel 4010. These transducer(s) may be arranged within the coolant supply channel 4010, outside the coolant supply channel 4010, or as a portion defining the coolant supply channel 4010.

Further, less than all of the aspects discussed above that contribute to the compact delivery size of this system may be combined with any of the above-noted energy delivery modalities to achieve the joint benefits of compact delivery size and improved airway wall cooling. For example, a pulmonary treatment system that includes an ultrasonic transducer can employ all or only some of the combined aspects of a thin walled, a highly compliant coolant member; an axial support element; and elements to induce a flow pattern in the cooling member that improve heat transport from the airway wall. Such a system may not include an external liquid supply channel but, instead, include supply and return lumens that open directly into an interior of the expandable member. In such as system, the ultrasonic transducer could be positioned within the expandable member. The outlet of the supply lumen could include a nozzle positioned and dimensioned to induce eddies along the wall of the expandable member, thereby improving coolant circulation within the expandable member and heat transport from the airway wall during application of ultrasonic energy. Such a system can be configured for the transmission of focused or unfocused ultrasonic energy.

Microwave energy has found increasing uses over the past few years and may be used in embodiments of the present invention as an alternative energy system. Principally, microwave energy is delivered through an antenna. There are a number of different types of microwave antennae. With suitable modifications based on the teachings of the instant disclosure, some the basic microwave antenna forms may be incorporated into devices designed for modulating or modifying pulmonary nerves as described herein. Of particular use for the application of catheter based microwave energy within the pulmonary system is the family of antenna based upon coaxial wire leads. There are a number of different designs using the coaxial leads. These types of antennae come in many different configurations—monopole, dipole, slot, capped, choked, cap-choke, sleeved, etc. Each antenna variation is intended to either shift the field orientation, to improve the efficiency of energy delivery, or both. Wave guide antennae are another known antennae for microwave applications. Wave guide antennae are typically a metal jacketed dielectric, which is fed with a coaxial cable inserted into a side hole in the device.

Figure 61:
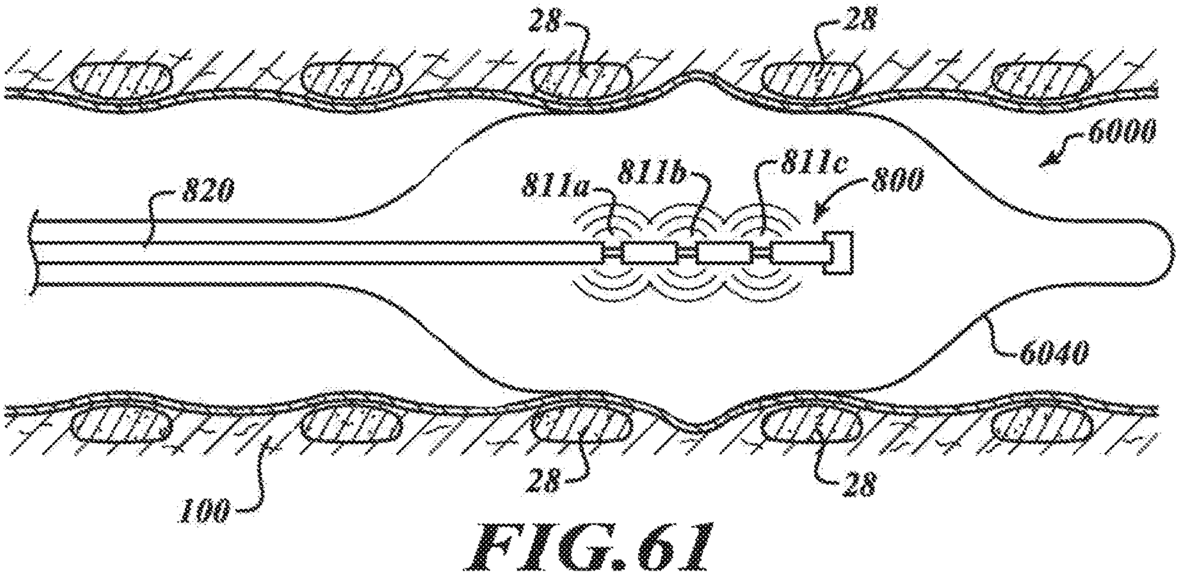
FIG. 61 is a partial cross-sectional view of the pulmonary treatment system that includes a microwave antenna.

In one exemplary embodiment, an antenna that may be particularly effective in pulmonary applications for microwave energy delivery is a multi-slot coaxial antennae such as the multi-slot coaxial antennae 800 of the pulmonary treatment system 6000 shown FIG. 61. In this embodiment, in addition to a slot near the tip, a plurality of additional slots 811*a*, 811*b*, 811*c*, are positioned at appropriate distances down the shaft of the device, with the distances being determined by wavelengths of operation, desired specific absorption rate (SAR) pattern, etc. Specific absorption rate, or SAR, is a proxy for energy delivery to the tissue, or heating profiles of the tissue, and are the standard way in which antenna designs are evaluated and optimized. In addition to the extra slots 811*a*, 811*b*, 811*c*, and hence extra treatment zones spaced longitudinally down a catheter shaft 820, the spiral design may have partial-circumferential shielding (device not shown). The position of the shielding would vary by position along the length of the catheter. For example, a multi-slot design providing four treatment areas longitudinally could be shielded from 12-3 o'clock in longitudinal segment 1, 3-6 o'clock in longitudinal segment 2, 6-9 o'clock in longitudinal segment 3, and 9-12 o'clock in the final longitudinal segment. Thus, it is possible with a single energy application that an entire spiral-shaped energy deposition is made.

The pulmonary treatment system 6000 can include one or more of the aspects discussed above that contribute, either alone or in combination with each other, to the compact delivery size of this system. For example, the pulmonary treatment system 6000 can include one or more of the above described aspects relating to: fluid delivery lumen arrangement and design; lumen connection design; a thin walled, highly compliant coolant member; an axial support element; and other elements and methods to induce a flow pattern in the cooling member that improve heat transport from the airway wall.

In this embodiment, an expandable member 6040 surrounds the antenna 800 and couples with substantially the entire circumference of the airway 100. The expandable member 6040 cools at least a portion of the non-target tissue in the airway wall 100 while the microwave antenna 800 delivers the microwave energy. The wall of the expandable member 6040 is positioned between the microwave antenna 800 and the wall of the airway. The microwave energy can pass through the expandable member 6040 and penetrate the airway wall to a depth of the target tissue with an intensity sufficient to alter the tissue. Optionally, shielding may be built into the expandable member 6040 or other part of the pulmonary treatment system 6000 to block transmission on a portion of the circumference to protect that portion from treatment. In other embodiments, the shielding can absorb the microwave energy. This shielding could be used to protect the esophagus, for example.

Figure 62A:
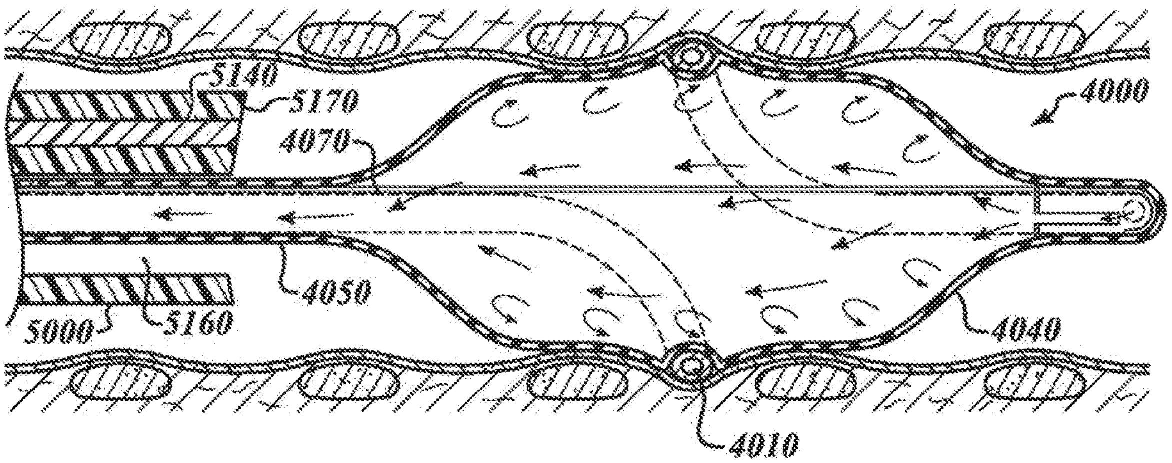
FIG. 62A is a cross-sectional view of a pulmonary treatment system extending from a working channel of a flexible bronchoscope.
Figure 62B:
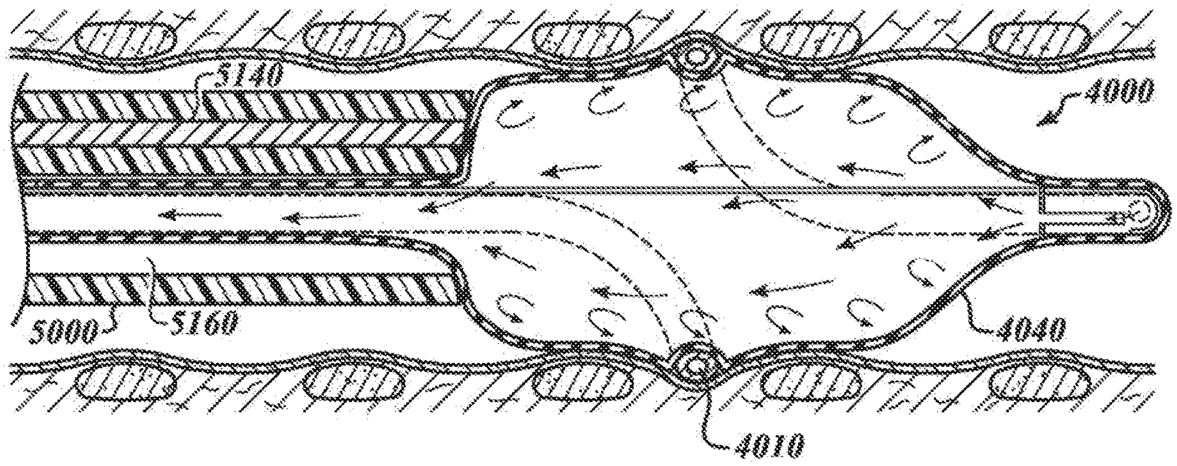
FIG. 62B is a cross-sectional view of the flexible bronchoscope of FIG. 62A optically coupled to an expandable member of the pulmonary treatment system of FIG. 62A.

FIGS. 62A and 62B illustrate optically coupling a flexible bronchoscope 5000 to the expandable member 4040 to assist with visualization of the position of the various components of the pulmonary treatment system 4000. FIG. 62A shows the pulmonary treatment system 4000 extending out a distal end of a working channel 5160 of a flexible bronchoscope 5000. The elongate member 4050 extends through the working channel 5160. An optical element 5140 can be used to view and position the flexible bronchoscope 5000 for appropriate placement in the airways for treatment. The expandable member 4040 can be transparent or semi-transparent.

The flexible bronchoscope 5000 includes optical element 5140. FIG. 62B shows a distal end 5170 of the flexible bronchoscope 5000 optically coupled to a proximal wall of the expandable member 4040. The distal end 5170 of the flexible bronchoscope 5000 is pressed against the conformable, expandable member 4040's proximal surface to provide optical coupling. During use, the user may view the electrode 4020 or other components or anatomical features through the wall of the expandable member 4040 and the fluid within the expandable member 4040. The compliance of the expandable member 4040 may aid in the optical coupling. In other examples, the proximal wall of the expandable member 4040 has a geometry selected to enable optical coupling; e.g. the proximal wall may be disposed at a relatively steep angle near 90 degrees relative to the elongate member 4050 so to have a matching or near matching profile to that of the distal end 5170 of the flexible bronchoscope 5000.

Depending on the level of transparency of the expandable member 4040 and the coolant circulated therein, physical contact between the expandable member 4040 and the optical element 5140 may not be necessary to view components of the pulmonary treatment system 4000 or anatomical features through the wall of the expandable member 4040. However, the quality of the visualization will be somewhat reduced relative to that achieved with physical contact between the optical element 5140 and the bronchoscope 5000.

In other embodiments, the flexible bronchoscope 5000 is replaced with a sheath with fiber optics having lenses, light sources, cameras, or the like. In certain embodiments, the optical element 5140 is integrated or coupled to the expandable member 4040. This prevents mucous or other unwanted substances from obscuring the user's view.

As noted above, the expandable member geometry, specifically the angle of the proximal expandable member wall, may be selected to optimize optical coupling with the optical element 5140. For example, if the expandable member 4040 is replaced with an expandable member formed of a more rigid, non-compliant material, such as such as a heat treated polyethylene terephthalate (PET), the proximal wall of the expandable member can have a section which can be aligned with the optical element 5140 and which is substantially flat, smooth, transparent, and which is generally parallel to the plane of the distal end 5170 of the flexible bronchoscope 5000, preferably in some embodiments being disposed at an angle of about 75 degrees to about 105 degrees relative to the longitudinal axis of the elongate member 4050. The material of the proximal expandable member wall may be selected to optimize visibility and transparency, e.g. with a refractive index which is compatible with the optical element 5140 and/or fluid within the expandable member.

FIGS. 63 to 66 illustrate examples of expandable members with an integrated liquid supply channel. These examples provide for even further size savings for compact delivery by reducing the amount of material needed to form the separate flow paths of the liquid supply channel and the expandable member.

Figure 63A:
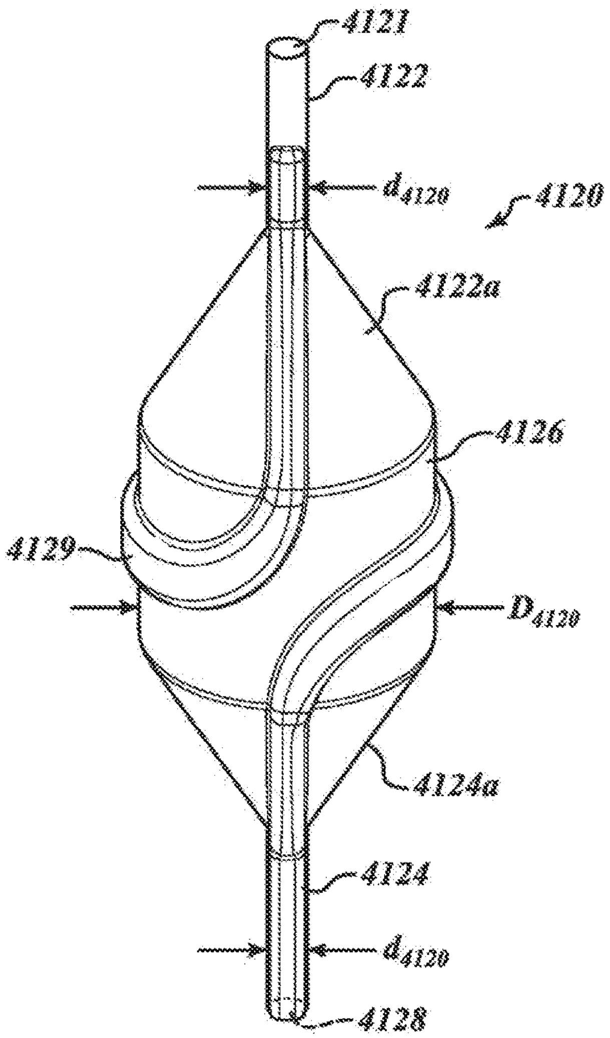
FIG. 63A is a pictorial view of an external balloon of a pulmonary treatment system that includes an external, integrated fluid supply conduit.
Figure 63B:
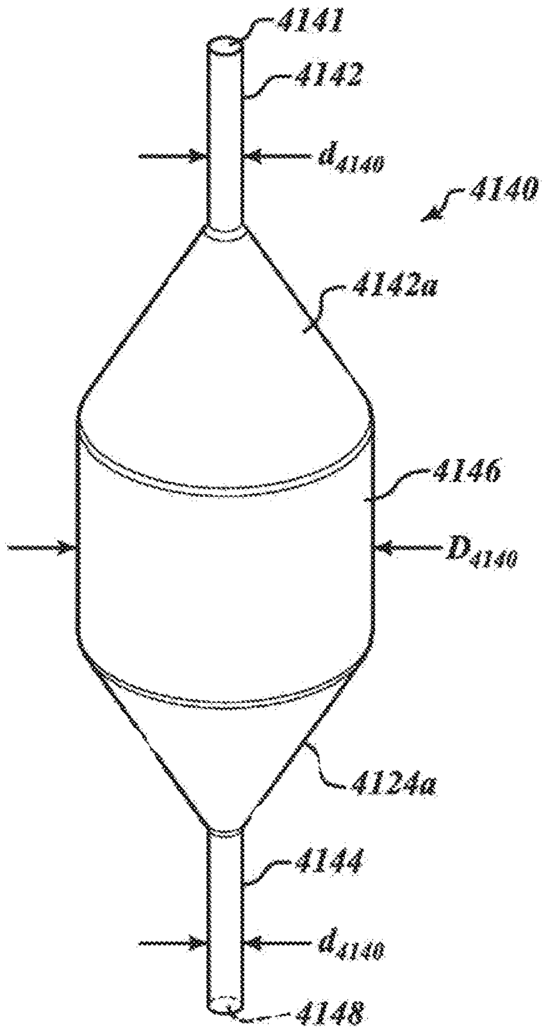
FIG. 63B is a pictorial view of an internal balloon of a pulmonary treatment system that includes an external, integrated fluid supply conduit.
Figure 64:
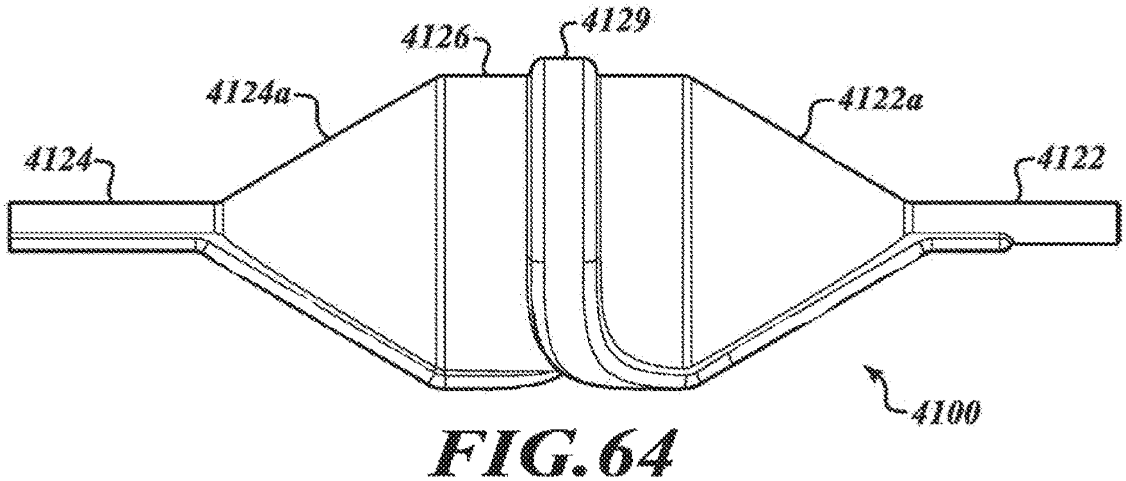
FIG. 64 is a side view of the pulmonary treatment system formed by combining the balloons in FIGS. 63A and 63B.

FIG. 64 illustrates a pulmonary treatment system 4100 that includes an external, integrated fluid supply conduit formed by combining the balloons 4120 and 4140 respectively in FIGS. 63A and 63B.

FIG. 63A illustrates the external balloon 4120. The external balloon 4120 extends from a first end 4128 to a second end 4121. The first end 4128 includes a first conduit 4124 that has a conduit diameter $d_{4120}$. A tapered portion 4124*a* extends away from the first conduit 4124 to a main body portion 4126. In this example, the first tapered portion 4124*a* increases linearly in diameter from the first conduit 4124 to a main body portion 4126. The main body portion 4126 has a main body diameter $D_{4120}$ that is greater than the conduit diameter $d_{4120}$. A second tapered portion 4122*a* extends from the main body portion 4126 to a second conduit 4122. In this example, the second tapered portion 4122*a* decreases linearly in diameter from the main body portion 4126 to the second conduit 4122. The second conduit 4122 also has a conduit diameter $d_{4120}$. The external balloon 4120 includes an integrated fluid supply conduit 4129 that extends from the first end 4128 to the second conduit 4122. The integrated fluid supply conduit 4129 is a raised profile portion of the external balloon 4120 that, when the external balloon 4120 is combined with the internal balloon 4140, will form an integrated fluid supply conduit. In this example, the integrated fluid supply conduit 4129 extends along the first conduit 4124, up the first tapered portion 4124*a*, along and circumferentially around the main body portion 4126, down the second tapered portion 4122*a*, and along the second conduit 4122. In this example, the fluid supply conduit 4129 ends short of the second end 4121. The external balloon 4120 can be made of a medical-grade thermoplastic elastomer, such as Pebax.

FIG. 63B illustrates the internal balloon 4140. The internal balloon 4140 extends from a first end 4148 to a second end 4141. The first end 4148 includes a first conduit 4144 that has a conduit diameter $d_{4140}$. A tapered portion 4144*a* extends away from the first conduit 4144 to a main body portion 4146. In this example, the first tapered portion 4144*a* increases linearly in diameter from the first conduit 4144 to a main body portion 4146. The main body portion 4146 has a main body diameter $D_{4140}$ that is greater than the conduit diameter $d_{4140}$. A second tapered portion 4142*a* extends from the main body portion 4146 to a second conduit 4142. In this example, the second tapered portion 4142*a* decreases linearly in diameter from the main body portion 4146 to the second conduit 4142. The second conduit 4142 also has a conduit diameter $d_{4140}$. The external balloon 4120 can be made of a flexible material, such as nylon 12.

FIG. 64 illustrates the external balloon combined 4120 with the internal balloon 4140. The diameters $D_{4140}$ and $d_{4140}$ of the internal balloon are sized so that the first conduit 4144 of the internal balloon 4120 forms a close fit inside of the first conduit 4124, the second conduit 4142 of the internal balloon 4120 forms a close fit inside of the first conduit 4122, and the main body 4146 of the internal balloon 4120 forms a close fit inside of the main body 4126. These close fitting surfaces can be bonded together. Because the integrated fluid supply conduit 4129 is a raised profile portion of the external balloon 4120, combining the external balloon 4120 with the internal balloon 4140 forms an integrated fluid supply conduit between the integrated fluid supply conduit 4129 and portions of the external surface of the internal balloon 4140. The internal surfaces of the internal balloon 4140 then define a larger lumen that is in serial fluid communication with the integrated fluid supply conduit. One or more flexible electrodes can be applied to an external surface of the integrated fluid supply conduit to create a pulmonary treatment 4100 that is readily collapsible for delivery, and expandable for energy delivery and treatment.

Figure 65A:
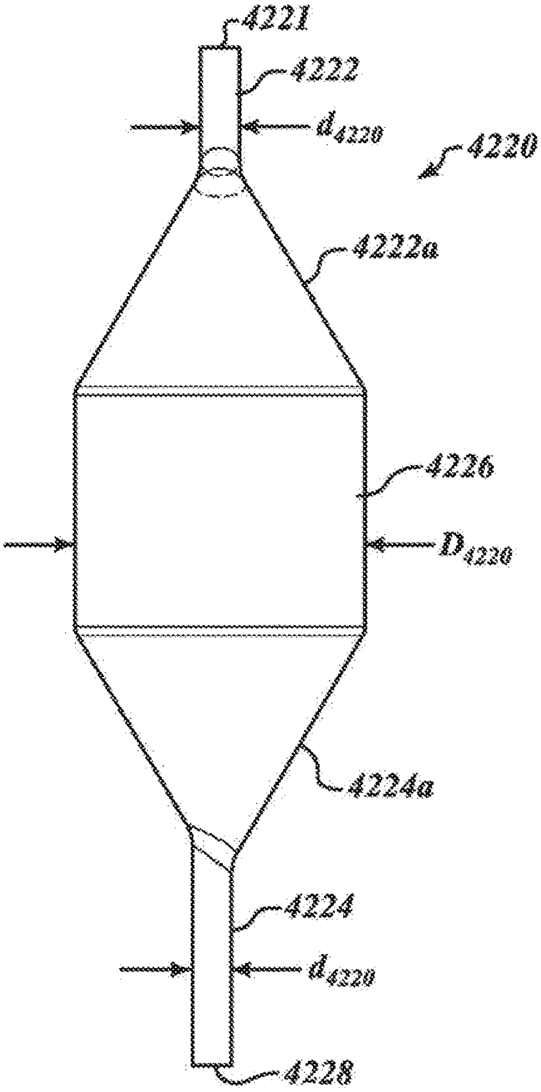
FIG. 65A is a pictorial view of an external balloon of a pulmonary treatment system that includes an internal, integrated fluid supply conduit.
Figure 65B:
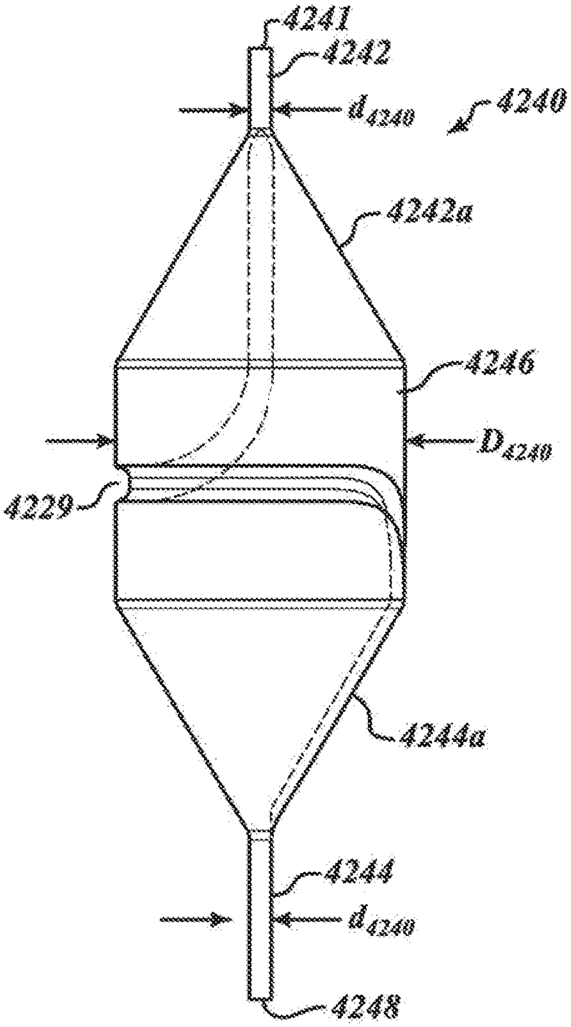
FIG. 65B is a pictorial view of an internal balloon of a pulmonary treatment system that includes an internal, integrated fluid supply conduit.
Figure 66:
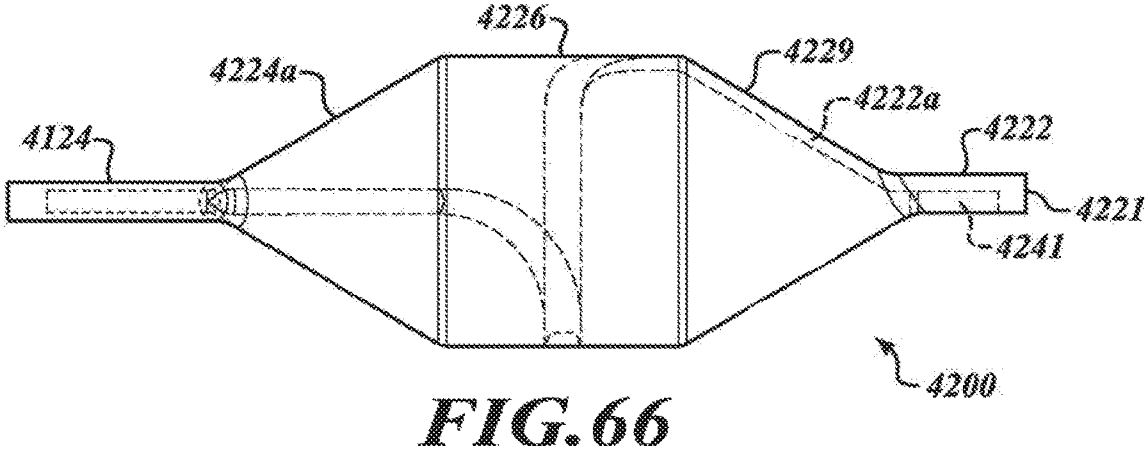
FIG. 66 is a side view of the pulmonary treatment system formed by combining the balloons in FIGS. 65A and 65B.

FIG. 66 illustrates a pulmonary treatment system 4200 that includes an external, integrated fluid supply conduit formed by combining the balloons 4220 and 4240 respectively in FIGS. 65A and 65B.

FIG. 65A illustrates the external balloon 4220. The external balloon 4220 extends from a first end 4228 to a second end 4221. The first end 4228 includes a first conduit 4224 that has a conduit diameter $d_{4220}$. A tapered portion 4224*a* extends away from the first conduit 4224 to a main body portion 4226. In this example, the first tapered portion 4224*a* increases linearly in diameter from the first conduit 4224 to a main body portion 4226. The main body portion 4226 has a main body diameter $D_{4220}$ that is greater than the conduit diameter $d_{4220}$. A second tapered portion 4222*a* extends from the main body portion 4226 to a second conduit 4222. In this example, the second tapered portion 4222*a* decreases linearly in diameter from the main body portion 4226 to the second conduit 4222. The second conduit 4222 also has a conduit diameter $d_{4220}$.

FIG. 65B illustrates the internal balloon 4240. The external balloon 4240 extends from a first end 4248 to a second end 4241. The first end 4248 includes a first conduit 4244 that has a conduit diameter $d_{4240}$. A tapered portion 4244*a* extends away from the first conduit 4244 to a main body portion 4246. In this example, the first tapered portion 4244*a* increases linearly in diameter from the first conduit 4244 to a main body portion 4246. The main body portion 4246 has a main body diameter $D_{4240}$ that is greater than the conduit diameter $d_{4240}$. A second tapered portion 4242*a* extends from the main body portion 4246 to a second conduit 4242. In this example, the second tapered portion 4242*a* decreases linearly in diameter from the main body portion 4246 to the second conduit 4242. The second conduit 4242 also has a conduit diameter $d_{4240}$. The internal balloon 4240 includes an integrated fluid supply conduit 4229 that extends from a junction between the first tapered portion 4244*a* and the first conduit 4244 to a junction between the second conduit 4242 and the second tapered portion 4242*a*. The integrated fluid supply conduit 4129 is a recessed profile portion of the internal balloon 4240 that, when the external balloon 4220 is combined with the internal balloon 4240, will form an integrated fluid supply conduit. In this example, the integrated fluid supply conduit 4229 extends up the first tapered portion 4244*a*, along and circumferentially around the main body portion 4246, and down the second tapered portion 4142*a*.

FIG. 64 illustrates the external balloon combined 4220 with the internal balloon 4240. The diameters $D_{4240}$ and $d_{4240}$ of the internal balloon are sized so that the first conduit 4244 of the internal balloon 4220 is significantly smaller than an inside diameter of the first conduit 4224, the second conduit 4242 of the internal balloon 4120 is significantly smaller than an inside diameter of the first conduit 4222, and the main body 4246 of the internal balloon 4220 forms a close fit inside of the main body 4226. The close fitting surfaces can be bonded together. Because the integrated fluid supply conduit 4229 is a recessed profile portion of the internal balloon 4240, combining the external balloon 4220 with the internal balloon 4240 forms an integrated fluid supply conduit between the integrated fluid supply conduit 4229 and portions of the internal surface of the external balloon 4220. The internal surfaces of the internal balloon **4*s*40 then define a larger lumen that is in serial fluid communication with the integrated fluid supply conduit. One or more flexible electrodes can be applied to an external surface of the integrated fluid supply conduit to create a pulmonary treatment 4200** that is readily collapsible for delivery, and expandable for energy delivery and treatment.

Figure 67:
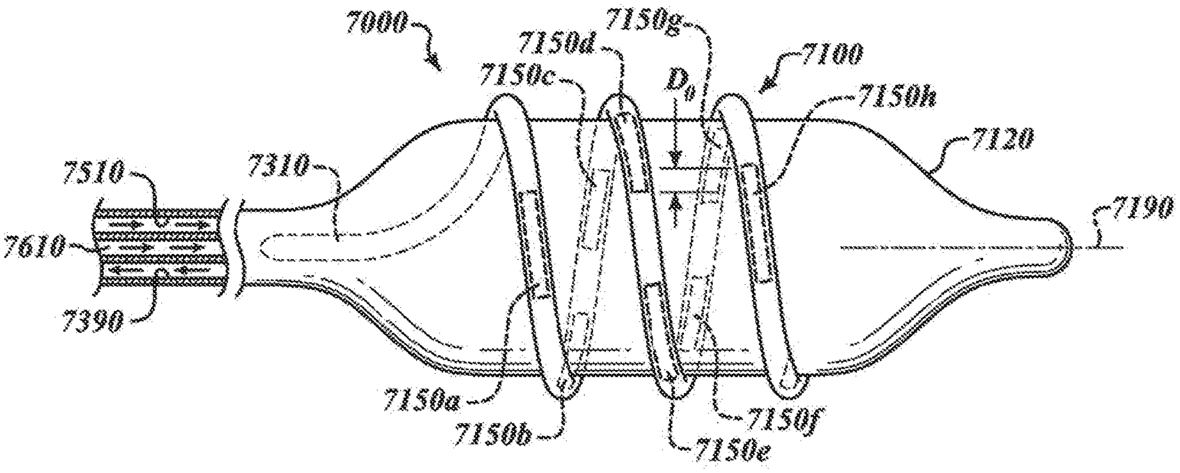
FIG. 67 is a side view of pulmonary treatment system configured for compact delivery and energy delivery from multiple, spirally arranged electrodes.

The compact design features disclosed above can be applied to pulmonary treatment systems that include multiple electrodes that extend spirally around an expandable member. FIG. 67 illustrates a pulmonary treatment system 7000 that includes an energy emitter in the form of an electrode assembly 7100 wrapped about an expandable member 7120. The electrode assembly 7100 includes a conduit 7310 and a plurality of electrodes 7150*a-h* (collectively "7150"). The electrodes 7150 can simultaneously or sequentially form lesions. The conduit 7310 delivers coolant (saline or other coolant) serially through the electrodes 7150.

Separate wire pairs can be electrically coupled to each electrode 7150. Each electrode 7150 can be operated independently. In other embodiments, the electrodes 7150 are bipolar and arranged in pairs of opposite polarity. As discussed with respect to previous embodiments, the electrodes 7150 can be oriented and positioned with respect to one another to form lesions within inter-collagenous spaces. Electrodes 7150*a-h* are arranged along the helical conduit 7310 such that they create lesions which are circumferentially offset from one another, albeit with some overlap, and which are axially offset from one another. An imaginary line drawn in the axial direction (parallel to axis 7190) through each of electrodes 7150*a-h* will intersect another of electrodes 7150*a-h* to ensure that the entire circumference of the airway is treated. Advantageously, the electrodes are spaced apart along the helical conduit 7310 such that the lesions they create are longitudinally separated along the airway, thus reducing the chance that stenosis will result.

Advantageously, activation of all of the electrodes 7150 at the same time can generate a lesion pattern that affects nerve around an entire circumference of the airway with a single shot.

The pulmonary treatment system 7000 can include some or all of the aspects discussed above with reference to FIGS. 49-60 that contribute to the joint benefits of compact delivery size and improved airway wall cooling.

For example, the return lumen 7510 surrounds the supply lumen 7610 in the elongate member 7390. The cooling fluid in the supply lumen 7610 can be both at a higher pressure and a lower temperature than the cooling fluid in the return lumen 7510.

The supply lumen 7610 and return lumen 7510 can, in other examples, employ the other beneficial lumen arrangements shown in FIGS. 51 and 53. Further, the size the supply lumen 7610 can be significantly smaller than the return lumen 7510. The pulmonary treatment system 7000 can employ barriers to heat transfer around the lumens or the elongate member. For example, polymers, air, or foam can be employed to insulate the return and supply lumens as well as the elongate member.

The junctions between the various fluid delivery lumens of the pulmonary treatment system 7000 can be formed by skiving the elongate member or using serial bonding can reduce the delivery size of the pulmonary treatment system, as discussed above with reference to FIG. 54.

The pulmonary treatment system 7000 can also be collapsible in a manner similar to the pulmonary treatment system 4000 as shown in FIGS. 55-58. In this example, the helical conduit 7310 is a flexible conduit and the electrodes 7150 are a conductive epoxy applied to an outside surface of the conduit 7310. Other materials and configurations are also possible for the electrode 7150, including other coatings, thin foils, films, or other electrically conductive materials. Different types of coating, plating or fabrication techniques can be used to form the electrode 7150.

Further, the pulmonary treatment system 7000 can maintain coolant delivered to the helical conduit 7310 at a high pressure and coolant delivered to the expandable member 7120 at a low pressure. For example, the differential pressure can be maintained by a throttle positioned between the helical conduit 7310 and the expandable member 7120.

In one aspect, the helical conduit 7310 is be made of a material, such as a heat treated polyethylene terephthalate (PET), that will expand to a repeatable shape each time it is inflated to a relatively high operational pressure without deforming, while the expandable member 7120 is formed of a thin-walled balloon made of a highly compliant material. The balloon can conform to irregularities on the airway surface (e.g., cartilaginous rings, side branches, etc.) and can be made, in whole or in part, of a distensible material, such as polyurethane (e.g., low durometer polyurethane) or other type of highly conformable material that may be transparent, semi-transparent, or opaque. The balloon can have different inflated shapes, including a hot dog shape, an ovoid shape, a cylindrical shape, or the like. In effect, this example includes a non-deformable, but collapsible material for the helical conduit 7310 and a highly compliant material for the expandable member 7120. For example, the helical conduit 7310 is preferably made of a material that will not deform at pressures around 75 psi, whereas the expandable member 7120 is preferably made of a material that will plastically deform at pressures around 10 psi.

Further, the pulmonary treatment system 7000 can include either of the different configurations of throttles shown in FIGS. 59 and 60 between the liquid coolant supply channel helical conduit 7310 and the expandable member 7120. Such a throttle can be positioned, oriented, and/or shaped to induce eddies and turbulent flow along the surface of the cooling member, which, as discussed above with reference to FIGS. 59 and 60, improves the efficiency with which the cooling member transports heat away from an airway wall of the patient at a treatment site.

In another aspect, a gas can be injected into the liquid coolant supply of the pulmonary treatment system 700 to disrupt laminar flow along the walls of the expandable member 7120 and thereby improve the efficiency with which heat is transported from the portion of the expandable member 7120 in contact with airway tissue at the treatment site.

In another example, the expandable cooling member 7120 can include a small, longitudinally extending, axial support, such as that shown in FIGS. 59 and 60, to aid in pushability of the cooling member while allowing the cooling member to be formed of a lightweight, highly compliant material.

Figure 68:
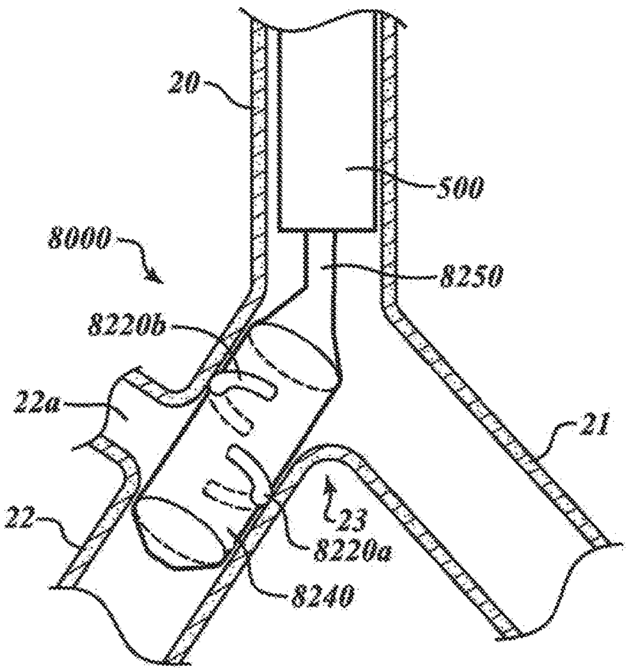
FIG. 68 is a pictorial view of a pulmonary treatment system with offset electrodes that avoid thin wall portions of the airway when positioned in the right main bronchus.

FIG. 68 illustrates a pulmonary treatment system 8000 that can, in some examples, treat an entire circumference of the right main bronchus without requiring the treatment catheter to be repositioned while also avoiding thin walled portions of the right main bronchus at the carina on the medial wall and areas adjacent the upper lobe bronchus on the lateral wall. In this example, two axially offset electrodes are activated, either simultaneously, in sequence, or with partially overlapping activation periods, to treat opposite sides of the right main bronchus. In other examples, the pulmonary treatment system 8000 could be rotated or otherwise repositioned between activation periods of the two electrodes. Further, the pulmonary treatment system 8000 is not limited to use in the right main bronchus, and could be used in airways other than the right main bronchus to achieve, for example, offset first and second lesions that overlap when viewed along the airway.

The pulmonary treatment system 8000 includes an expandable member 8240 that extends from a distal portion of an elongate member 8250. In one example, the expandable member 8240 can be a balloon made, in whole or in part, of polyurethanes, nylon, polyether block amide (Pebax), polyethylene terephthalate (PET), silicone, other polymers, other plastics, rubber, polyethylene, polyvinyl chloride, chemically inert materials, non-toxic materials, electrically insulating materials, combinations thereof, or the like. The expandable member 8240 can be formed to a desired shape and size by blowing according to conventional techniques. To enhance heat transfer, the balloon sidewall can comprise one or more conductive materials with a high thermal conductivity. For example, conductive strips (e.g., metal strips) can extend along the expandable member 8240 to help conduct thermal energy away from hot spots, if any. The expandable member 8240 can conform to irregularities on the airway surface (e.g., cartilaginous rings, side branches, etc.) and can be made, in whole or in part, of a distensible material, such as polyurethane (e.g., low durometer polyurethane) or other type of highly conformable material that may be transparent, semi-transparent, or opaque. The expandable member 8240 can have different inflated shapes, including a hot dog shape, an ovoid shape, a cylindrical shape, or the like.

The pulmonary treatment system 8000 includes two axially offset electrodes 8220*a* and 8220*b* coupled to the expandable member 8240. The electrodes 8220*a* and 8220*b* can be films or coatings that can be made of metal, conductive polymers, or other suitable materials formed by a deposition process (e.g., a metal, such as gold or silver, deposition process), coating process, etc., and can comprise, in whole or in part, silver ink, silver or gold epoxy, combinations thereof, or the like. The electrodes 8220*a* and 8220*b* are operably coupled to a controller configured to pass power through the electrodes 8220*a* and 8220*b* to the airway wall during treatment.

The electrodes 8220*a* and 8220*b* extend around a portion of the circumference of the expandable member 8240 on opposite sides thereof. In one example, the electrodes 8220*a* and 8220*b* each extend more than 180 degrees around the expandable member 8240 and are positioned so as to overlap when viewed along a longitudinal axis of the expandable member 8240. In other example, the electrodes 8220*a* and 8220*b* form overlapping arcs on the surface expandable member 8240 when viewed along a longitudinal axis of the expandable member 8240 with one electrode being significantly longer than the other. For example, the electrode 8220*a* may extend less between 90 and 120 around the expandable member 8240 electrode 8220*a* between 280 degrees and 250 degrees around the expandable member 8240.

In one example, the electrodes 8220*a* and 8220*b* are narrow bands that each respectively fit between offset sets of adjacent cartilage rings when the expandable member 8240 is expanded against the airway wall. For example, the electrodes 8220*a* and 8220*b* can be between 1.0 millimeters and 3.0 millimeters wide. In one example, the electrodes 8220*a* and 8220*b* are about 2.0 millimeters wide. Further, the expandable member 8240 can include raised portions directly below the electrodes 8220*a* and 8220*b* that aid in seating the electrodes 8220*a* and 8220*b* between adjacent cartilage rings.

In one example, a coolant is supplied to the expandable member 8240 and circulated therein to actively cool both the electrodes 8220*a* and 8220*b* and the airway wall during energy application. The flow within the expandable member 8240 can be altered and directed by one or more throttles or the location of inlet and outlet lumens of the elongate member 8250 to further enhance the cooling effects.

FIG. 68 illustrates a pulmonary treatment system 8000 extending out of a flexible bronchoscope 500 and positioned in the right main bronchus. The electrodes 8220*a* and 8220*b* are positioned to avoid narrow portions of the airway. Specifically, the electrode 8220*b* is positioned to treat the lateral wall of the right main bronchus without affecting the carina located on the medial side of the right main bronchus; and the 8220*a* is positioned to treat the medial wall of the right main bronchus without affecting the upper lobe bronchus located on the lateral side of the right main bronchus. Depending on the lengths of the electrodes 8220*a* and 8220*b* a single energy application from each electrode can create a first lesion around a portion of the circumference on at least the lateral side of the right main bronchus without creating a lesion on the carina, and a second lesion around a portion of the circumference on at least the medial side of the right main bronchus without creating a lesion on the upper lobe bronchus.

The first and second lesions can overlap when viewed along the airway so that, when taken together, they form a pair of offset lesions that disrupt nerve activity around an entire circumference of the airway wall. By activating the 8220*a* and 8220*b* simultaneously, it is possible to treat the entire right lung with a single energy application period.

VI. Cooling by Endothermic Reaction

In another aspect, cooling can be achieved through an endothermic reaction. This can be used in place of the thermodynamic or externally chilled cooling systems discussed above. For example, a chemical reaction can created to remove energy in a therapeutic procedure. More particularly, a cooled fluid may be circulated in an open or closed circuit to a targeted therapeutic area with the cooling achieved by endothermic reaction at the site or remote from it.

In one example, an endothermic reaction provides close to 0° C. coolant and potentially obviates a large equipment need with reagents placed in disposables (cartridge, capsule, etc.). Sodium Bicarbonate and Citric Acid are biocompatible substances which may be mixed to create an endothermic reaction:

$$C_6H_8O_7+3NaHCO_3 \rightarrow Na_3C_6H_5O_7+3H_2O+3CO_2$$

Sodium Bicarbonate and Citric Acid both come in powdered forms that could be placed in capsules within a closed disposable circuit upstream of a targeted therapeutic area. Upon addition of room temperature water circulating through capsules, the reagents can mix to lower the liquid temperature (~4° C.) by drawing energy from surroundings. The disposables, or the reagents themselves, can be positioned at a distal end of an energy treatment device to allow localized cooling without losses associated by transport of a chilled fluid through a catheter to the treatment site. For example, a treatment catheter can include both an energy delivery source and a quantity of reagent at a distal end thereof. By circulating a liquid to the distal end of the catheter while it is positioned in an airway of a patient, the resulting endothermic reaction can remove energy generated by the energy source to protect the portions of an airway wall located between the energy delivery source and targeted nerves that run along the airway. Such a system can be disposable or reusable. For example, the reagents can be preloaded in a disposable device, or reloaded into a reusable device. In another example, this type of cooling can also be used for therapeutic hypothermia.

VII. Additional Aspects

Although the pulmonary treatment systems and various aspects thereof described herein advantageously allow for a compact design that facilitates compatibility with the working channel of a flexible bronchoscope, the aspects described herein are not so limited. For example, as will be readily apparent to one of ordinary skill in the art upon a complete review of the present disclosure, the aspects disclosed herein are also scalable to be compatible with larger working lumens that may or may not be associated with a bronchoscope. Notably, the present disclosure is not limited solely to systems that are delivered via the working channel of a bronchoscope, but also encompasses systems delivered by other means, such as an independent sheath and/or delivery catheter.

Further, although the phrase "pulmonary treatment system" is used throughout the present disclosure, the devices disclosed herein may also be used to treat the digestive system, nervous system, vascular system, or other systems. For example, as will be readily apparent to one of ordinary skill in the art upon a complete review of the present disclosure, treatment systems, elongate assemblies, intraluminal catheters, and delivery devices disclosed herein can be delivered through the esophagus, intestines, and or stomach to treat the digestive system. Treatments system can target tissue within a vessel wall, tissue adjacent to vessel walls (e.g., tissue contacting a vessel wall), or tissue spaced apart from a vessel wall. The target tissue can be nerve tissue, tissue of a hollow vessel (e.g., a blood vessel, duct, or the like), cardiac tissue (e.g., tissue of a blood vessel, tissue forming a chamber of a heart, or the like), or vessels through which fluid flows. In certain aspects, a treatment system can be positioned in one hollow vessel to injure another hollow vessel.

The treatment systems and its components disclosed herein can also be used as an adjunct during another medical procedure, such as minimally invasive procedures, open procedures, semi-open procedures, or other surgical procedures (e.g., lung volume reduction surgery) that provide access to a desired target site. Various surgical procedures on the chest may provide access to lung tissue, cardiovascular tissue, respiratory tissue, or the like. Access techniques and procedures used to provide access to a target region can be performed by a surgeon and/or a robotic system. Those skilled in the art recognize that there are many different ways that a target region can be accessed.

The delivery devices disclosed herein can be used with guidewires, delivery sheaths, optical instruments, introducers, trocars, biopsy needles, or other suitable medical equipment. If the target treatment site is at a distant location in the patient (e.g., a treatment site near the lung root 24 of FIG. 1), a wide range of instruments and techniques can be used to access the site. The flexible elongated assemblies can be easily positioned within the patient using, for example, steerable delivery devices, such as endoscopes and bronchoscopes, as discussed above, for example, with reference to side-by side delivery of treatment devices and a flexible bronchoscope and delivery through the working channel of a rigid bronchoscope.

Semi-rigid or rigid elongated assemblies can be delivered using trocars, access ports, rigid delivery sheaths using semi-open procedures, open procedures, or other delivery tools/procedures that provide a somewhat straight delivery path. Advantageously, the semi-rigid or rigid elongated assemblies can be sufficiently rigid to access and treat remote tissue, such as the vagus nerve, nerve branches, nerve fibers, and/or nerve trunks along the airways, without delivering the elongated assemblies through the airways. The aspects and techniques disclosed herein can be used with other procedures, such as bronchial thermoplasty.

The various embodiments and aspects described above can be combined to provide further embodiments and aspects. These and other changes can be made to the embodiments in light of the above-detailed description. The aspects, embodiments, features, systems, devices, materials, methods and techniques described herein may, in some embodiments, be similar to any one or more of the embodiments, features, systems, devices, materials, methods and techniques described in U.S. Pat. No. 8,088,127, PCT Application No. PCT/US2010/056424 filed Nov. 11, 2010 (Publication No. WO 2011/060200), U.S. application Ser. No. 12/913,702 filed on Oct. 27, 2010, U.S. application Ser. No. 12/944,666 filed Nov. 11, 2010, U.S. application Ser. No. 13/081,406 filed on Apr. 6, 2011, and U.S. Provisional Application No. 61/543,759. Further the systems disclosed herein can employ any of the cooling systems described in U.S. Provisional Patent Application Ser. No. 61/779,371, filed on Mar. 13, 2013. Each of these applications is incorporated herein by reference in its entirety. In addition, the aspects, embodiments, features, systems, devices, materials, methods and techniques described herein may, in certain embodiments, be applied to or used in connection with any one or more of the embodiments, features, systems, devices, materials, methods and techniques disclosed in the above-mentioned applications and patents.

Unless the context requires otherwise, throughout the specification and claims which follow, the word “comprise” and variations thereof, such as “comprises” and “comprising” are to be construed in an open, inclusive sense, that is, as “including but not limited to.”

In general, in the following claims, the terms used should not be construed to limit the claims to the specific embodiments and aspects disclosed in the specification and the claims, but should be construed to include all possible embodiments and aspects along with the full scope of equivalents to which such claims are entitled. Accordingly, the claims are not limited by the disclosure.

What is claimed is:

1. A pulmonary treatment system, comprising:

a nerve modification assembly configured to assume a reduced profile for passage through a lumen of an elongate device and positioning in an airway of a patient, the lumen having a diameter less than about 6.0 millimeters, and configured to assume a treatment configuration for treatment of the airway, the nerve modification assembly including:

an energy delivery portion configured to generate heat energy in an airway wall of the airway to ablate nerve tissue along the airway, and a cooling portion configured to remove heat energy from the airway wall while heat energy is generated in the airway wall by the energy delivery portion, wherein the cooling portion includes an inflatable member and a fluid delivery conduit that extends at least partially around a circumference of the inflatable member when the nerve modification assembly is in the treatment configuration, wherein the energy delivery member includes an elongate electrode coupled to a portion of the fluid delivery conduit, the electrode being arcuate and flexible, the electrode including:

a tissue facing side, the tissue facing side being convex and electrically conductive, an inflatable member facing side joined to the tissue facing side, and an electrically insulating mask adhered to, partially covering, and confined to the tissue facing side, the electrically insulating mask being convex and flexible, the electrically insulating mask thereby defining at least one electrically conductive tissue contact region along the tissue facing side, and at least one electrically insulating tissue contact region bound within the tissue facing side of the energy delivery member.

2. The pulmonary treatment system of claim 1, wherein the electrode is configured to deliver radio frequency energy to the airway wall.

3. The pulmonary treatment system of claim 1, wherein the cooling portion includes a thermodynamic cooling mechanism.

4. The pulmonary treatment system of claim 1, wherein the inflatable member and the fluid delivery conduit are in fluid communication with a source of chilled fluid.

5. The pulmonary treatment system of claim 1, wherein the energy delivery portion is configured to generate heat energy at a power density ranging from 0.3 to 1.0 $W/mm^2$ in an airway wall of the airway.

6. The pulmonary treatment system of claim 5, wherein the electrode comprises a collapsible and expandable electrode coupled to a portion of the fluid delivery conduit.

7. The pulmonary treatment system of claim 1, the cooling portion is configured to remove heat energy at a power density ranging from about 0.025 to about 1.0 $W/mm^2$ from the airway wall while heat energy is generated in the airway wall by the energy delivery portion.

8. The pulmonary treatment system of claim 1, wherein the energy delivery portion is configured to heat nerve tissue at a depth of at least 2 mm in the airway wall to a temperature of at least 50° C.

9. The pulmonary treatment system of claim 1, wherein the cooling portion is configured to cool airway wall tissue disposed between the energy delivery portion and the nerve tissue to a temperature of less than 50° C.

10. The pulmonary treatment system of claim 1, wherein the electrically insulating mask is a first electrically insulating mask, a second electrically insulating mask is also adhered to, partially covering, and confined to the tissue facing side, and the at least one electrically conductive tissue contact region extends along the longitudinal axis of the conduit and is bounded between the first electrically insulating mask and the second electrically insulating mask.

11. The pulmonary treatment system of claim 1, further comprising:

an elongated shaft having proximal and distal ends and a fluid delivery lumen, wherein the cooling portion is coupled to the elongate shaft near the distal end and is fluidly coupled to the fluid delivery lumen such that a coolant may be circulated through the cooling portion so as to remove heat energy from the airway wall while heat energy is generated in the airway wall by the energy delivery portion.

12. The pulmonary treatment system of claim 1, wherein the fluid delivery conduit is formed of a non-deformable, collapsible material that does not plastically deform at a first pressure.

13. The pulmonary treatment system of claim 12, wherein the inflatable member is formed of a compliant material that plastically deforms at a second pressure that is lower than the first pressure.

* * * * *